United States Patent
Bouchard et al.

(10) Patent No.: US 8,952,147 B2
(45) Date of Patent: Feb. 10, 2015

(54) CONJUGATES, PREPARATION THEREOF, AND THERAPEUTIC USE THEREOF

(75) Inventors: Hervé Bouchard, Paris (FR); Marie-Priscille Brun, Paris (FR); Alain Commercon, Paris (FR); Jidong Zhang, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/331,259

(22) Filed: Dec. 20, 2011

(65) Prior Publication Data

US 2012/0225089 A1 Sep. 6, 2012

Related U.S. Application Data

(63) Continuation of application No. PCT/FR2010/050986, filed on May 20, 2010.

(30) Foreign Application Priority Data

Jun. 29, 2009 (FR) ..................................... 09 03170
Nov. 25, 2009 (FR) ..................................... 09 05651

(51) Int. Cl.
   *C07D 223/00* (2006.01)
   *C07D 273/08* (2006.01)
(52) U.S. Cl.
   CPC .................................. *C07D 273/08* (2013.01)
   USPC ....................................................... 540/454
(58) Field of Classification Search
   None
   See application file for complete search history.

(56) References Cited

U.S. PATENT DOCUMENTS

| 2,719,170 | A | 9/1955 | Harris et al. |
| 5,208,020 | A | 5/1993 | Chari et al. |
| 7,230,101 | B1 | 6/2007 | Murthi et al. |
| 2007/0213511 | A1 | 9/2007 | Kunz et al. |

FOREIGN PATENT DOCUMENTS

| EP | 0306943 | 3/1989 |
| EP | 0496548 | 7/1992 |
| EP | 0830136 | 10/2004 |
| WO | 90/06774 | 6/1990 |
| WO | 98/08505 | 3/1998 |
| WO | 00/23429 | 4/2000 |
| WO | 00/34252 | 6/2000 |
| WO | 2004/016801 | 2/2004 |
| WO | 2004/043344 | 5/2004 |
| WO | 2004/103272 | 12/2004 |
| WO | 2005/009369 | 2/2005 |
| WO | 2005/077090 | 8/2005 |
| WO | 2005/082023 | 9/2005 |
| WO | 2005/116255 | 12/2005 |
| WO | 2006/042240 | 4/2006 |
| WO | 2006/061258 | 6/2006 |
| WO | 2006/069246 | 6/2006 |
| WO | 2006/096754 | 9/2006 |
| WO | 2006/110476 | 10/2006 |
| WO | 2007/085930 | 8/2007 |
| WO | 2007/102069 | 9/2007 |
| WO | 2007/127440 | 11/2007 |
| WO | 2007/144709 | 11/2007 |
| WO | 2008/010101 | 11/2007 |
| WO | 2008/047242 | 4/2008 |
| WO | 2009/002993 | 12/2008 |
| WO | 2009/016516 | 2/2009 |
| WO | 2009/026274 | 2/2009 |
| WO | 2009/126934 | 10/2009 |
| WO | 2009/134976 | 11/2009 |
| WO | 2009/134977 | 11/2009 |
| WO | 2010/014812 | 2/2010 |

OTHER PUBLICATIONS

Dumontet. Nature Reviews: Drug Discovery, 2010, 9, 790-803.*
Majoros. Biomacromolecules, 2006, 7, 572-79.*
Bioorganic and Medicinal Chemistry Letters, 1996, 6(10), 1111-16.*
Al-Awar et al., 'A convergent approach to Cryptophycin 52 analogues: Synthesis and biological evaluation of a novel series of fragment a epoxides and chlorohydrins,' J. Med. Chem., 46(14), 2003, pp. 2985-3007.
Al-Awar et al., 'Biological evaluation of cryptophycin 52 fragment a analogues: Effect of the multidrug resistance Atp binding cassette transporters on antitumor activity,' Mol. Cancer Ther. vol. 3, No. 9, 2004, pp. 1061-1067.
Appel, 'Tertiary Phosphane/Tetrachloromethane, a Versatile Reagent for Chlorination, Dehydration, and P—N. Linkage,' Angew. Chem. Int. Ed. Engl, 1975, Ch. 14, pp. 801-811.
Wessjohann et al., '1,4-Addition of (Diphenylmethylene)amine to Acceptor Substituted Olefins. A Versatile Synthesis of Protected Beta-Amino Acids, Nitriles, and Ketones,' Synthesis, vol. 5, 1989, pp. 359-363.
Boinpally et al., 'Pharmacokinetics and tissue distribution of cryptophycin 52 (C-52) epoxide and cryptophycin 55 (C-55) chlorohydrin in mice with subcutaneous tumors,' Cancer Chemoth. Pharm., vol. 52, 2003, pp. 25-33.
Bourdon et al., 'Protein thiolation and reversible protein-protein conjugation. N-Succinimidyl 3-(2-pyridyldithio) propionate, a new heterobifunctional reagent,' Biochem. J., vol. 173, 1978, pp. 723-737.
Burns et al., 'Selective Reduction of Disulfides by Tris(2-carboxyethyl) phosphine,' J. Org. Chem., vol. 56, No. 8, 1991, pp. 2648-2650.
Carter et al., 'Antibody-drug conjugates for cancer therapy,' Cancer Journal, 2008, vol. 14, 154-169.
Chari et al., 'Targeted Cancer Therapy: Conferring Specificity to Cytotoxic Drugs,' Accounts of Chemical Research, 2008, vol. 41, pp. 98-107.
Chen et al., Kumada Cross-Coupling of Aryl Grignard Reagents with Aryl Halides Catalyzed by an Immobilized Nickel Catalyst, Synthesis (2009), No. 14, pp. 2408-2412.
Chin et al., 'Addition of p-Azido-L-phenylalanine to the Genetic Code of *Escherichia coli*,' J. Am. Chem. Society, 2002, vol. 124, pp. 9026-9027.
Cromwell et al., 'Protein Aggregation and Bioprocessing,' AAPS Journal, 2006, vol. 8, No. 3, pp. E572-E579.

(Continued)

*Primary Examiner* — Noble Jarrell

(57) ABSTRACT

Provided herein are cryptophycin conjugates and compositions containing them. Methods of making and using such compounds also are provided.

39 Claims, 1 Drawing Sheet

(56) References Cited

OTHER PUBLICATIONS

Degraaf et al., 'Nonnatural Amino Acids for Site-Specific Protein Conjugation,' Bioconjugate Chem., vol. 20, No. 7, Jul. 2009, pp. 1281-1295.
Desmaris et al., 'Conversion of alcohols to bromides using a fluorous phospine,' Tetrahedron Letters, vol. 44, No. 41, 2003, pp. 7589-7591.
Drefahl et al.,'[4-Vinyl-styryl]-Aromaten,' Chem. Ber. (1961), 94, p. 2002-2010.
Edelman et al., 'Phase 2 study of cryptophycin 52 ( LY355703) in patients previously treated with platinum based chemotherapy for advanced non-small cell lung cancer,' Lung Cancer, vol. 39, 2003, pp. 197-199.
Eissler et al. 'The Synthesis of Cryptophycins,' Synthesis, 2006, vol. 22, pp. 3747-3789.
Faucher et al., 'tris(2-Carboxyethyl)phosphine (TCEP) for the Reduction of Sulfoxides, Sulfonylchlorides, N-Oxides, and Azides,' Synthetic Commun., vol. 33, 2003, pp. 3503-3511.
Garnett, 'Targeted drug conjugates: principles and progress,' Adv. Drug Deliver. Rev., 2001, vol. 53, pp. 171-216.
Hu et al., 'A Convenient Trimethylsilylthioxy-Dehalogenation Reaction for the Preparation of Functionalized Thiols,' J. Org.Chem, 1999, vol. 64, pp. 4959-4961.
Hughes, 'Progress in the Mitsunobu Reaction. A Review,' Org. Prep. Proced. Int., vol. 28, Issue 2, 1996, pp. 127-164.
Hughes, 'The Mitsunobu Reaction,' Organic Reactions, 1992, vol. 42, pp. 335-656.
Illa et al., 'Practical and Highly Selective Sulfur Ylide Mediated Asymmetric Epoxidations and Aziridinations Using an Inexpensive, Readily Available Chiral Sulfide. Applications to the Synthesis of Quinine and Quinidine,' J. Am. Chem. Soc. (2010), 132, pp. 1828-1830.
International Search Report for PCT/FR2010/050986 (WO2011/001052) as mailed on Nov. 30, 2010.
Junutula et al., 'Site-specific conjugation of a cytotoxic drug to an antibody improves the therapeutic index,' Nat. Biotechnol., vol. 26, 2008, pp. 925-932.
Liang et al., 'Cryptophycins-309, 249 and other cryptophycin analogs: Preclinical efficacy studies with mouse and human tumors,' Invest. New Drug., vol. 23, 2005, pp. 213-224.
Litzen et al., 'Separation and Quantitation of Monoclonal Antibody Aggregates by Asymmetrical Flow Field-Flow Fractionation and Comparison to Gel Permeation Chromatography,' Analytical Biochemistry, 1993, vol. 212, No. 2, pp. 469-480.
Matuszak et al., 'Synthesis and in Vitro Evaluation of N-Substituted Maleimide Derivatives as Selective Monoglyceride Lipase Inhibitors,' J. Of Med. Chem., vol. 52, 2009, pp. 7410-7420.
Mitsunobu, 'The Use of Diethyl Azodicarboxylae and Triphenylphosphine in Synthesis and Transformation of Natural Products,' Synthesis, 1981, pp. 1-28.
Mock et al., 'Catalysis by Cucurbituril. The Significance of Bound-Substrate Destabilization for Induced Triazole Formation,' J. Org. Chem., vol. 54, No. 22, 1989, pp. 5302-5308.
Monneret et al., 'Immunotargeting of antitumor drugs,' B. Cancer, 87(11), Nov. 2000, pp. 829-838.
Nevill et al., 'Triply-Convergent Synthesis of Two Sets of Homochiral Cyclopent[a]Indene Carbacyclin Analogs,' Bioorg. Med. Chem. Lett., vol. 1, No. 1, 1991, pp. 83-86.
Wu et al., 'Oxygen- and Sulfur-Containing Positively Charged Polycyclic Aromatic Hydrocarbons,' Organic Letters, vol. 11, 2009, pp. 5686-5689.
Patel et al., 'Novel cryptophycin antitumor agents: synthesis and cytotoxicity of fragment "B" analogues,' J. Med. Chem., vol. 42, No. 14, 1999, p. 2588-2603.
Pinnick et al., 'Oxidation of alpha,Beta-Unsaturated Aldehydes,' Tetrahedron, vol. 37, 1981, pp. 2091-2096.
Poeylaut-Palena et al., 'Solid-Supported Cross Metathesis and the Role of the Homodimerization of the Non-immobilized Olefin,' J. Org. Chem., vol. 73, 2008, pp. 2024-2027.
Potter et al., 'Synthesis of Heterosubstituted Hexaarylbenzenes via Asymmetric Carbonylative Couplings of Benzyl Halides ,' Organic Letters, vol. 9, No. 7, 2007, pp. 1187-1190.
Rej et al., 'Total Synthesis of Cryptophycins and Their 16-(3-Phenylacryloyl) Derivatives,' J. Org. Chem., vol. 61, 1996, pp. 6289-6295.
Ricart et al., 'Technology Insight: cytotoxic drug immunoconjugates for cancer therapy,' Nature Clinical Practice Oncology, vol. 4, pp. 245-255, 2007.
Richard et al., 'Internalization of a Peptide into Multilamellar Vesicles Assisted by the Formation of an alpha-Oxo Oxime Bond,' Chem. Eur. J.—vol. 11, No. 24, 2005, pp. 7315-7321.
Rostovtsev et al., A Stepwise huisgen Cycloaddition Process: Copper(I)-Catalyzed Regioselective "Ligation" of Azides and Terminal Alkynes, Angew. Chem. Int. Ed 2002, vol. 41, pp. 2596-2599.
Sakellariou et al., 'Novel peripherally functionalized seco-porphyrazines: characterization and synthesis, spectroscopic evaluation,' Tetrahedron vol. 59, 2003, pp. 9083-9090.
Salamonczyk et al., 'Total Synthesis of Cryptophycins via a Chemoenzymatic Approach,' J. Org. Chem., vol. 61, 1996, pp. 6893-6900.
Sessa et al., 'Phase I and pharmacological studies of the cryptophycin analogue LY355703 administered on a single intermittent or weekly schedule,' Eur. J. Cancer, vol. 38, 2002, pp. 2388-2396.
Shimomura et al., 'Synthesis and application of polytetrahydrofuran-grafted polystyrene (PS-PTHF) resin supports for organic synthesis,' Tetrahedron, vol. 61, 2005, pp. 12160-12167.
Taylor & Francis, CRC press book, ISBN=0-8493-1863-7, Anticancer agents from natural products, 'The isolation, characterization and development of a novel class of potent antimitotic macrocyclic depsipeptides: the cryptophycins,' Chapter 9, pp. 150,158 2005.
Tornoe et al., 'Peptidothazoles on Solid Phase: [1,2,3]-Triazoles by Regiospecific Copper(I)-Catalyzed 1,3-Dipolar Cycloadditions of Terminal Alkynes to Azides,' J. Org. Chem., vol. 67, No. 8, 2002 pp. 3057-3064.
Wang et al., 'Fractionation of monoclonal antibody aggregates using membrane chromatography,' J. Membrane Sci., 2008, vol. 318, pp. 311-316.

* cited by examiner

CONJUGATES, PREPARATION THEREOF, AND THERAPEUTIC USE THEREOF

CROSS-REFERENCE TO RELATED APPLICATIONS

This application is a continuation of International application No. PCT/FR2010/050986, filed May 20, 2010, which claims the benefit of priority of French Patent Application No. 0903170, filed Jun. 29, 2009 and French Patent Application No. 0905651, filed Nov. 25, 2009, all of which are incorporated herein by reference.

The present invention relates to cryptophycin conjugates, to compositions containing them and to their therapeutic use, especially as anticancer agents. The invention also relates to the process for preparing these compounds and to the cryptophycin derivatives themselves.

BACKGROUND

Cryptophycins are secondary metabolites belonging to the class of depsipeptide macrocycles produced by cyanobacteria of the genus *Nostoc*. Their name refers to the fact that they are highly cytotoxic towards yeasts of the genus *Cryptococcus*. The first representative of this class of molecules, cryptophycin-1 (C-1), was isolated in 1990 from cyanobacterium *Nostoc* sp (ATCC 53789) (see Eiβler S., et al., *Synthesis* 2006, 22, 3747-3789). The structure, the general formula and the numbering of the carbon atoms of these compounds, as described in WO 98/08505, are recalled below:

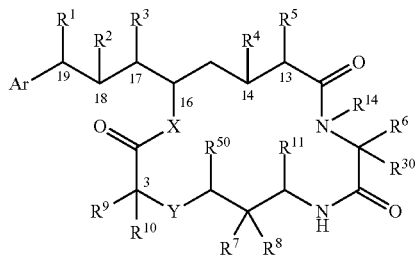

Cryptophycins C1 and C-52, which are characterized by an epoxide function represented below, have anticancer properties. Phase II clinical trials in lung cancer were conducted with C-52 (LY 355073): see Edelman M. J., et al., *Lung Cancer* 2003, 39, 197-199; Sessa C., et al., *Eur. J. Cancer* 2002, 38, 2388-96. Cryptophycin C-55, a prodrug of C-52, is itself characterized by a chlorohydrin function instead of the epoxide function (Bionpally R. R., et al., *Cancer Chemother Pharmacol* 2003, 52, 25-33). C-55 proved to be very active, but is not stable in solution. Derivatives of chlorohydrin glycinate type such as the compound C-55 Gly have also been described as gaining in stability (Liang J., et al., *Investigational New Drugs* 2005, 23, 213-224).

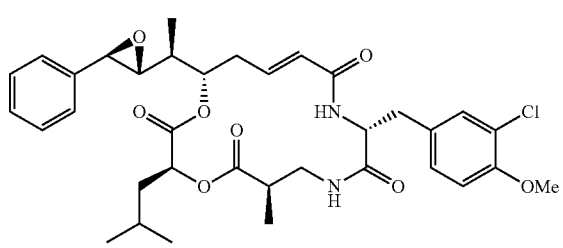

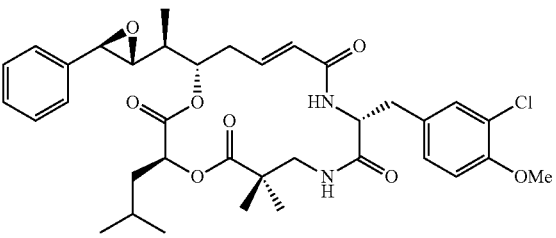

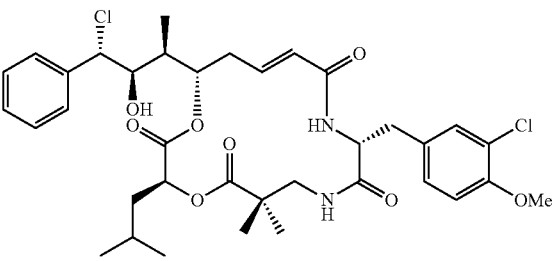

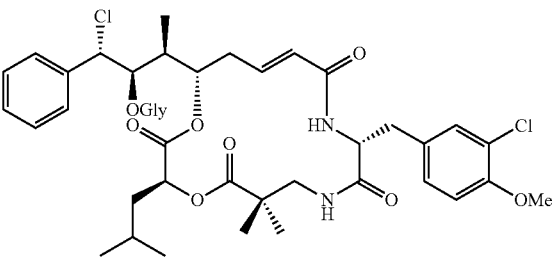

Conjugate chemistry has been known for many years and has been applied to several families of cytotoxic agents, for instance the maytansinoids (WO 04/103 272), taxanes (WO 06/061 258), tomaymycins (WO 09/016,516), leptomycins (WO 07/144,709), CC-1065 and analogues thereof (WO 2007/102 069); see also, with regard to conjugates, Monneret C., et al., *Bulletin du Cancer.* 2000, 87(11), 829-38; Ricart A. D., et al., *Nature Clinical Practice Oncology* 2007, 4, 245-255. However, it has not been applied to cryptophycin derivatives conjugated to antibodies or to other targeting agents.

The technical problem that the present invention intends to solve is that of proposing novel conjugates based on cryptophycin derivatives, and also novel cryptophycin derivatives that are suitable for being conjugated.

EP 0 830 136 and WO 98/08505 describe cryptophycin derivatives but do not describe cryptophycin conjugates. WO 98/08505 describes cryptophycin derivatives of formula (A):

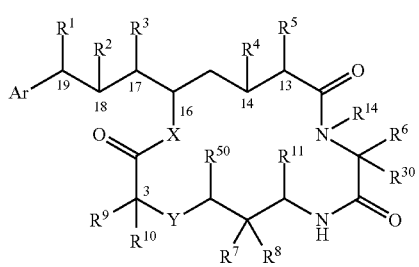

in which Ar may represent a group Ar' of formula:

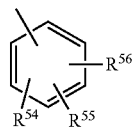

in which $R_{54}$ represents H, a group $(C_1-C_6)$alkyl, $(C_1-C_6)$alkyl$(R_{57}, R_{57}', R_{57}'')$, aryl, phenyl, heterocycloalkyl, a halogen atom, $COOR_{57}$, $PO_3H$, $SO_3H$, $SO_2R_{58}$, $NR_{59}R_{60}$, $NHOR_{61}$, $NHOR_{61}'$, CN, $NO_2$, $OR_{62}$, $CH_2OR_{62}'$, $CH_2NR_{96}R_{96}'$, $(C_1-C_6)$alkyl$OR_{100}$,

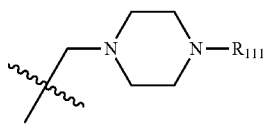

$SR_{63}$; $R_{55}$ and $R_{56}$ represent H, a group $(C_1-C_6)$alkyl, $C(R_{57}R_{57}'R_{57}'')$, aryl, phenyl, heterocycloalkyl, a halogen atom, $COOR_{57}$, $PO_3H$, $SO_3H$, $SO_2R_{58}$, $NR_{59}R_{60}$, $NHOR_{61}$, $NHCHR_{61}'$, CN, $NO_2$, $OR_{62}$, $CH_2OR_{62}'$, $CH_2OCOR_{95}$, $CH_2NR_{96}R_{96}'$, $(C_1-C_6)$alkyl$OR_{100}$, $(C_1-C_6)$alkyl$NR_{59}R_{60}$. WO 98/08505 especially describes the following compounds:

(Ex. 34)

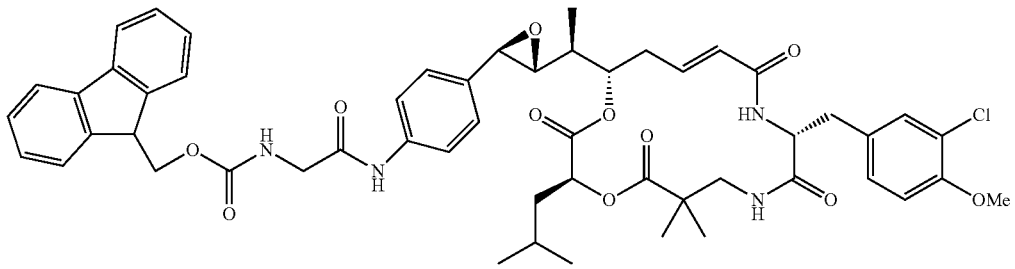

(compound 24, scheme 4)

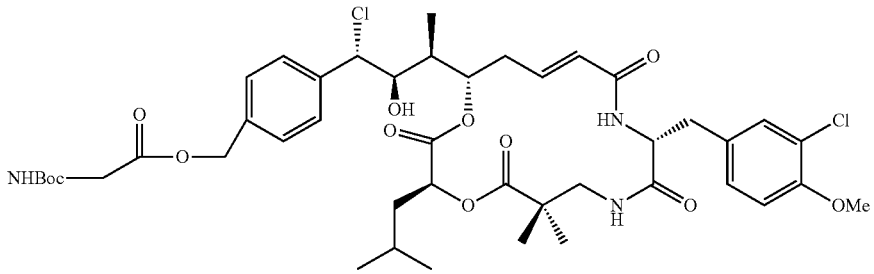

(compound 33, scheme 5)

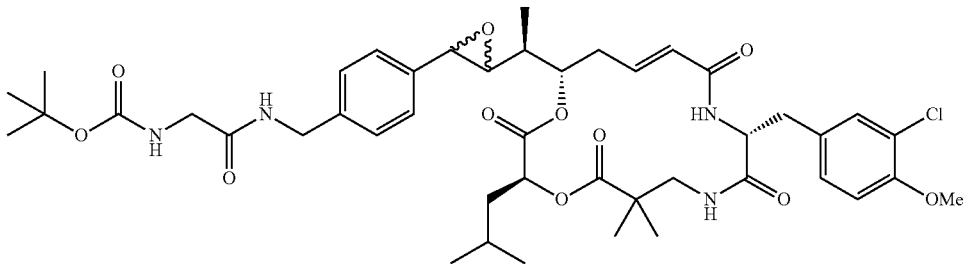

(Ex. 42)

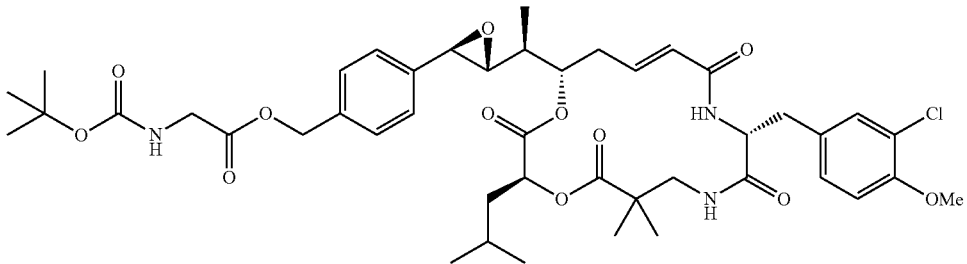

-continued

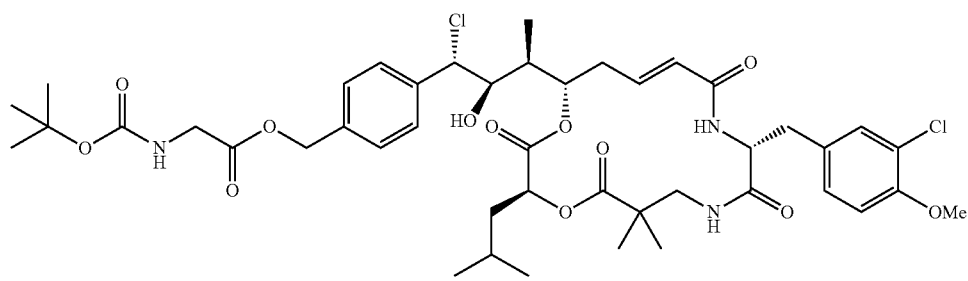
(Ex. 43)

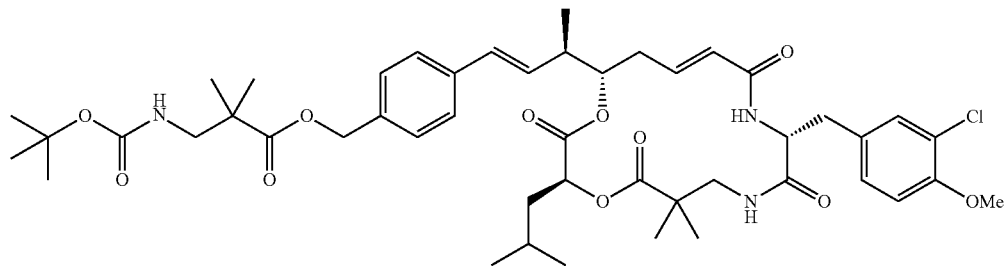
(Ex. 47)

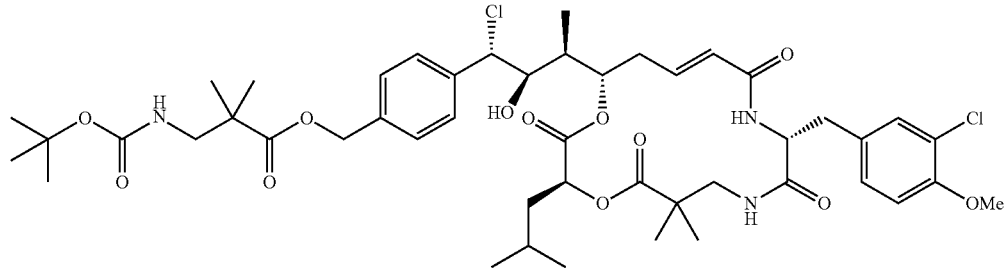
(Ex. 48)

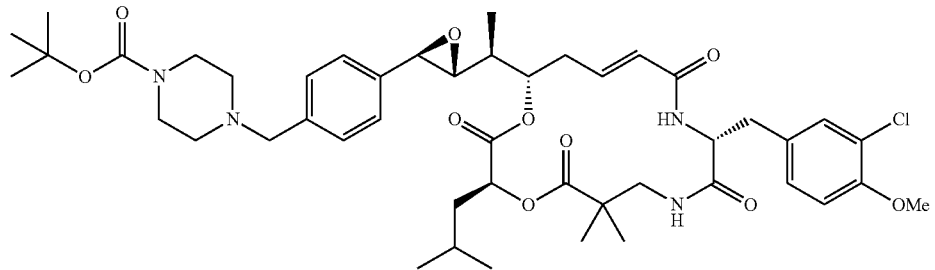
(Ex. 74)

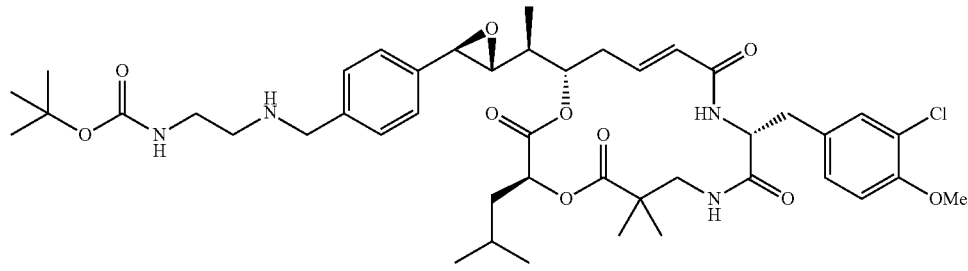
(Ex. 77)

which are characterized by the end group —NHC(=O)Ot-Bu. WO 98/08505 does not specify that these compounds are suitable for or intended to be conjugated.

US 2007/0 213 511 describes calicheamicin immunoconjugates. Among these, mention is made of Mylotarg® (or CMA-676), which is a calicheamicin immunoconjugate used in the treatment of AML (anti-CD33-calicheamicin). See also in respect of conjugates: WO 2006/042 240.

Al-awar R. S., et al., *J. Med. Chem.* 2003, 46(14), 2985-3007 and Al-awar R. S., et al., *Mol. Cancer Ther.* 2004, 3(9), 1061-1067 describe cryptophycin derivatives, and also their in vivo evaluations.

WO 08/010,101 describes an anti-EphA2 monoclonal antibody and also the corresponding conjugates comprising one or more molecules of a cytotoxic compound attached to the monoclonal antibody. WO 08/047,242 describes an anti-CD38 monoclonal antibody and also the corresponding conjugates comprising one or more molecules of a cytotoxic compound attached to the monoclonal antibody. The cytotoxic compound may be chosen from maytansinoids, taxanes, tomaymycins, leptomycins and CC-1065 and analogues thereof.

WO 2009/126 934 describes anti-CD70 antibodies and their conjugates with cytotoxic compounds; cryptophycin is mentioned among the cytotoxic agents. WO 2009/134 976 describes conjugates with an optimized degree of substitution for delivering the required amount of cytotoxic agent into the cell; cryptophycin is mentioned among the cytotoxic agents.

WO 2005/116 255 describes conjugates of aptamers and of a cytotoxic agent that may be a cryptophycin (see [0037] and Table 2), the linker possibly comprising a PEG chain ([0038]). More particularly, the cryptophycin Cryp-NH$_2$ is described:

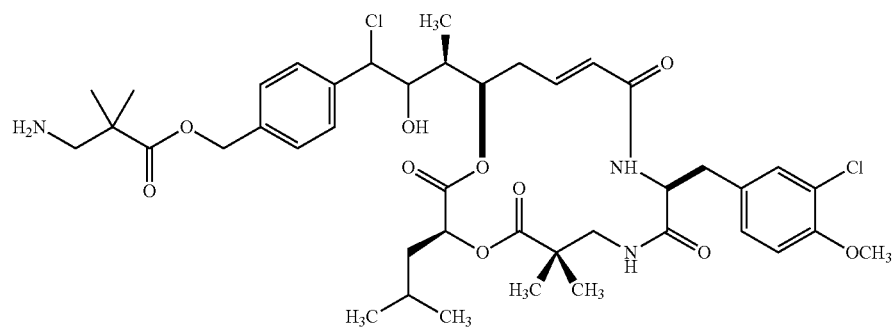

and also its conjugates of aptamers with the following linkers: NHS-PEG-erythritol, pNP-PEG-erythritol, NHS-PEG-octaPEG, pNP-PEG-octaPEG and PEG-comb (Tables 3 and 4). The nature of the sequence on the phenyl ring (—CH$_2$O—C(=O)—CMe$_2$-CH$_2$NH— ... ) is different from that which is envisaged in the present invention. WO 2006/096 754 also describes conjugates of aptamers and of a cytotoxic agent that may also be a cryptophycin.

WO 2009/002 993 describes cytotoxic conjugates of formula B-L-A comprising hydrophilic linkers, for example the linker of formula:

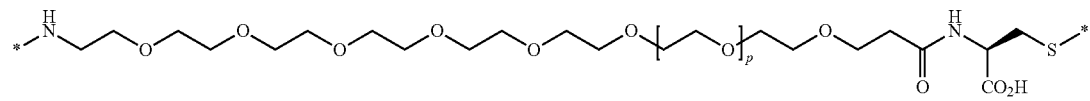

The cytotoxic agent may be a cryptophycin (page 46), but the point of attachment of the linker is not specified. An example of a conjugate is EC0262:

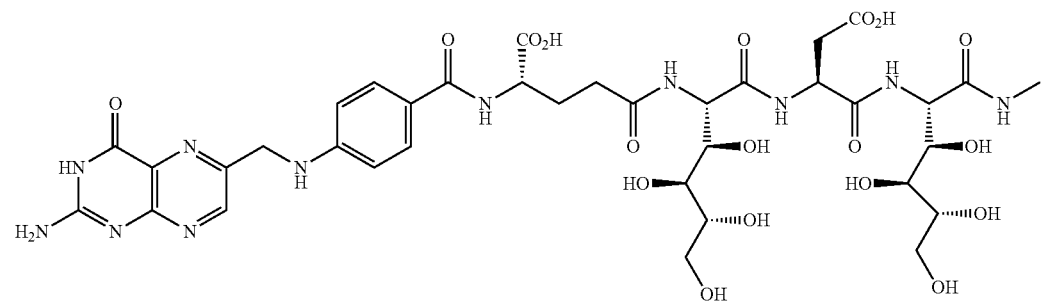

-continued

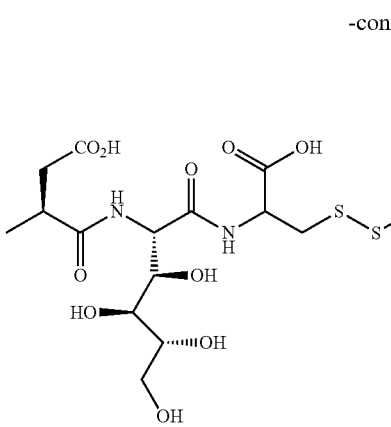
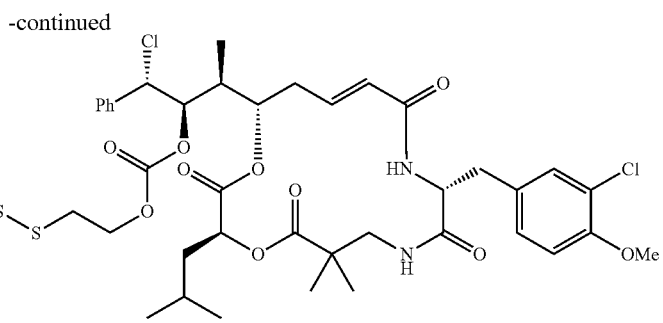

DEFINITIONS

Figure 1:
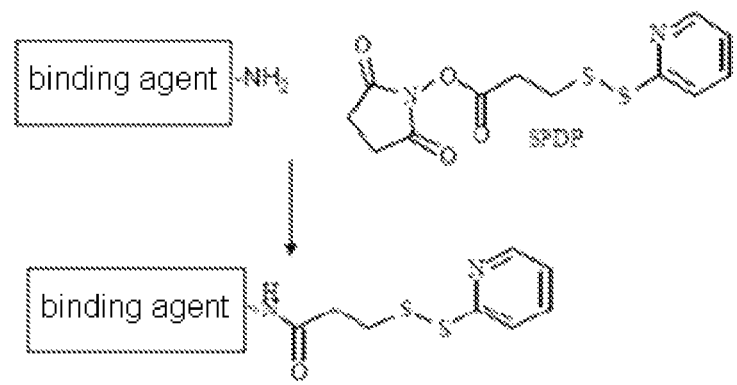
FIG. 1 illustrates the modification of an amino group of a binding agent with SPDP.

The following definitions apply:
conjugate: a cell binding agent to which is covalently attached at least one molecule of a cytotoxic compound;
cell binding agent: a molecule with affinity for a biological target: it may be, for example, a ligand, a protein, an antibody, more particularly a monoclonal antibody, a protein or antibody fragment, a peptide, an oligonucleotide or an oligosaccharide. The function of the binding agent is to direct the biologically active compound as a cytotoxic agent towards the biological target.
Preferably, the binding agent is not an aptamer;
biological target: an antigen (or group of antigens) preferably located at the surface of cancer cells or stromal cells associated with this tumour; these antigens may be, for example, a growth factor receptor, an oncogene product or mutated "tumour suppressant" gene product, an angiogenesis-related molecule, an adhesion molecule;
linker: a group of atoms that can covalently attach a cytotoxic compound to the binding agent;
alkyl group: a saturated aliphatic hydrocarbon-based group obtained by removing a hydrogen atom from an alkane. The alkyl group may be linear or branched. Examples that may be mentioned include methyl, ethyl, propyl, isopropyl, butyl, isobutyl, tert-butyl, pentyl, 2,2-dimethylpropyl and hexyl groups;
cycloalkyl group: a cyclic alkyl group comprising between 3 and 8 carbon atoms engaged in the cyclic structure. Examples that may be mentioned include cyclopropyl, cyclobutyl, cyclopentyl and cyclohexyl groups;
heterocycloalkyl group: a cycloalkyl group comprising at least one heteroatom (O, S or N) engaged in the ring and connected to the carbon atoms forming the ring;
alkoxy group: a group —O-alkyl, in which the alkyl group is as defined above;
alkanoyloxy group: a group —O—CO-alkyl, in which the alkyl group is as defined above;
alkylene group: a saturated divalent group of empirical formula —$C_nH_{2n}$—, obtained by removing two hydrogen atoms from an alkane. Examples that may be mentioned include methylene (—$CH_2$—), ethylene (—$CH_2CH_2$—), propylene (—$CH_2CH_2CH_2$—), butylene (—$CH_2CH_2CH_2CH_2$—) and hexylene (—$CH_2CH_2CH_2CH_2CH_2CH_2$—) groups or the following branched groups

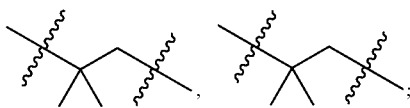

preferably, the alkylene group is of the formula —$(CH_2)_n$—, n representing an integer;
in the ranges of values, the limits are included (e.g. a range of the type "n ranging from 1 to 6" or "between 1 and 6" includes limits 1 and 6).

Abbreviations Used

EtOAc: ethyl acetate; ALK: ($C_1$-$C_{12}$)alkylene group, more particularly ($C_1$-$C_6$)alkylene, more particularly of the form —$(CH_2)_n$—, n being an integer from 1 to 12 and preferably from 1 to 6; aq.: aqueous; TLC: thin-layer chromatography; MSC: methanesulfonyl chloride; crypto denotes the unit of formula

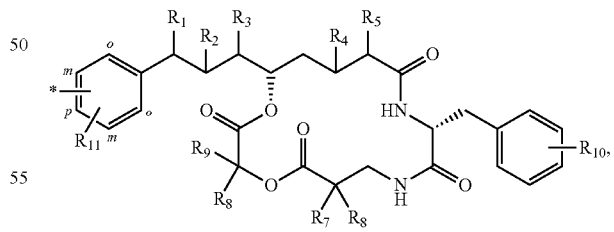

crypto especially denoting one of the $D_1$-$D_8$ cryptophycin derivatives described later or a cryptophycin derivative of an example; Rf: retention factor; DAR: degree of substitution (drug-antibody ratio); DBU: 1,8-diazabicyclo[5.4.0-]undec-7-ene; DCC: N,N'-dicyclohexylcarbodiimide; DCM: dichloromethane; DEAD: diethyl azodicarboxylate; DIC: N,N'-diisopropylcarbodiimide; DIPEA: N,N-diisopropylethylamine; DMA: dimethylacetamide; DMAP: 4-dimethylaminopyridine; DME: dimethoxyethane; DMF:

dimethylformamide; DMSO: dimethyl sulfoxide; EEDQ: 2-ethoxy-1-ethoxycarbonyl-1,2-dihydroquinoline; EDCl: N-(3-dimethylaminopropyl)-N'-ethylcarbodiimide; EDTA: ethylene-diaminetetraacetic acid; eq.: equivalent; Fmoc: fluorenylmethoxycarbonyl; HOBt: 1-hydroxybenzotriazole; HEPES: 4-(2-hydroxyethyl)-1-piperazineethanesulfonic acid; mCPBA: m-chloroperbenzoic acid; NHS: N-hydroxysuccinimide; NMP: N-methylpyrrolidinone; AP: atmospheric pressure; PABAC: "para-aminobenzyl alcohol carbonate"; RP: reduced pressure; SEC: steric exclusion chromatography; SPE: solid-phase extraction; RT: room temperature; TBDMS: tert-butyldimethylsilyl; TCEP: tris(2-carboxyethyl)phosphine hydrochloride; TEA: triethylamine; TFA: trifluoroacetic acid; TIPS: triisopropylsilyl; THF: tetrahydrofuran; $t_R$: retention time.

DETAILED DESCRIPTION OF THE INVENTION

The invention relates to a binding agent to which is attached at least one cryptophycin derivative of formula (I):

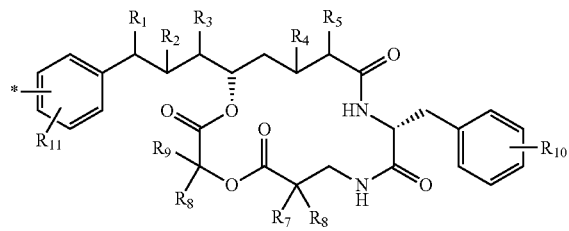

(I)

in which:

$R_1$ represents a halogen atom and $R_2$ represents a group —OH, an acyl group derived from an amino acid AA or a group $(C_1-C_4)$alkanoyloxy;

or alternatively $R_1$ and $R_2$ form an epoxide unit;

AA denotes a natural or unnatural amino acid;

$R_3$ represents a group $(C_1-C_6)$alkyl;

$R_4$ and $R_5$ both represent H or together form a double bond CH═CH between C13 and C14;

$R_6$ and $R_7$ represent, independently of each other, H or a group $(C_1-C_6)$alkyl;

$R_8$ and $R_9$ represent, independently of each other, H or a group $(C_1-C_6)$alkyl;

$R_{10}$ represents at least one substituent of the phenyl nucleus chosen from: H, a group —OH, $(C_1-C_4)$alkoxy, a halogen atom or a group $—NH_2$, $—NH(C_1-C_6)$alkyl or $—N(C_1-C_6)alkyl_2$;

$R_{11}$ represents at least one substituent of the phenyl nucleus chosen from H and a group $(C_1-C_4)$alkyl;

the binding agent and the cryptophycin derivative being covalently attached, the attachment being in the ortho (o), meta (m) or para (p) position of the phenyl nucleus bearing the unit $CR_1$.

Ortho (o), Meta (m) or Para (p) Positions:

$R_1$ represents a halogen atom, more particularly Cl, $R_3$ represents a group $(C_1-C_6)$alkyl, more particularly Me, $R_6$ and $R_7$ represent, independently of each other, H or a group $(C_1-C_6)$alkyl; more particularly, they represent, independently of each other, H or a group Me, $R_8$ and $R_9$ represent, independently of each other, H or a group $(C_1-C_6)$alkyl; more particularly, $R_8$ represents H and $R_9$ represents isobutyl.

$R_{10}$ represents at least one substituent of the phenyl nucleus chosen from H, a group OH, $(C_1-C_4)$alkoxy or a halogen atom. It may also be a group $—NH_2$, $—NH(C_1-C_6)$alkyl or $—N(C_1-C_6)alkyl_2$ such as, for example, $—NH_2$ or $—NMe_2$, preferably in position 3 or 4 on the phenyl nucleus. More particularly, the phenyl nucleus comprises two substituents in positions 3 and 4 on the phenyl nucleus. Preferably, it is 3-Cl and 4-methoxy. $R_{11}$ represents at least one substituent of the phenyl nucleus chosen from H and a group $(C_1-C_4)$alkyl; more particularly H.

More particularly, one of the substituents $R_1$ to $R_{11}$ may be chosen from those described in the examples. Each substituent $R_1$ to $R_{11}$, may also adopt one of the spatial configurations (e.g. R or S or alternatively Z or E) as described in the examples.

AA represents a natural or unnatural amino acid. It may be an α, β or γ amino acid. Mention may be made especially of the following amino acids: alanine (Ala), β-alanine, 2-amino-2-cyclohexylacetic acid, 2-amino-2-phenylacetic acid, arginine (Arg), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), valine (Val), γ-aminobutyric acid, α,α-dimethyl-γ-aminobutyric acid, β,β-dimethyl-γ-aminobutyric acid, ornithine (Orn), citrulline (Cit) and also the protected forms of the said amino acids (e.g. acetyl, formyl, tosyl, nitro). Preferably, it is a natural amino acid. More particularly, it is glycine.

$R_1$ and $R_2$ may also together form an epoxide unit.

The attachment between the cryptophycin derivative and the binding agent is produced by means of a linker L positioned in an ortho (o), meta (m) or para (p) position of the phenyl nucleus bearing the unit $CR_1$; thus, the cryptophycin derivative capable of conjugation has the formula (II):

(II)

The attachment to the binding agent takes place at the other end of the linker L on a reactive group present on the binding agent. Thus, L comprises at least one reactive chemical group (RCG1) that is reactive towards a reactive chemical group (RCG2) present on the binding agent. The reaction between RCG1 and RCG2 ensures the attachment of the compound of formula (II) to the binding agent by formation of a covalent bond. Thus, the cryptophycin derivative of formula (II) is able to be conjugated to a binding agent.

The cryptophycin derivatives of the present invention, including those that are illustrated, may exist in the form of bases or of acid-addition salts, especially of pharmaceutically acceptable acids.

Examples of RCG1 that may be mentioned include:
(i) the reactive group —$SZ_a$ for which $Z_a$ represents H or the group —$SR_a$ and $R_a$ represents a group $(C_1\text{-}C_6)$alkyl, $(C_3\text{-}C_7)$cycloalkyl, aryl, heteroaryl or $(C_3\text{-}C_7)$heterocycloalkyl;
(ii) the reactive group —C(=O)—$Z_bR_b$ for which $Z_b$ represents a single bond, —O— or —NH—, more particularly —O—, and $R_b$ represents H or a group $(C_1\text{-}C_6)$alkyl, $(C_3\text{-}C_7)$cycloalkyl, aryl, heteroaryl or $(C_3\text{-}C_7)$heterocycloalkyl;
(iii) one of the following reactive groups: —Cl, —$N_3$, —OH, —$NH_2$, the maleimido

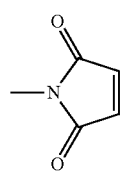

or haloacetamido

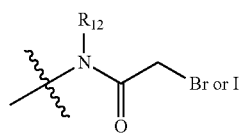

reactive group with $R_{12}$ representing H or a group $(C_1\text{-}C_6)$ alkyl, more particularly Me in the case of the compounds of formula (III):

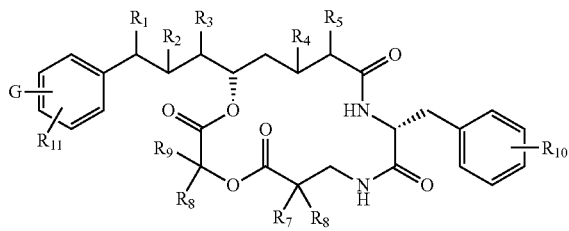

(III)

comprising the group G=—$(CH_2)_n$Y with Y=—Cl, —$N_3$, —OH, —$NH_2$,

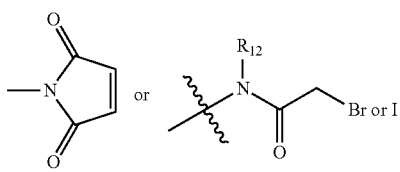

with $R_{12}$ representing H or a group $(C_1\text{-}C_6)$alkyl, more particularly Me;
(iv) the reactive group maleimido

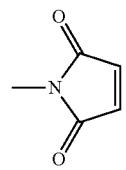

or haloacetamido

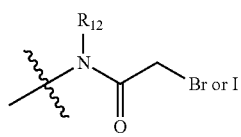

with $R_{12}$ representing H or a group $(C_1\text{-}C_6)$alkyl, more particularly Me.

More particularly, —$SZ_a$ may represent —SH or —$SS(C_1\text{-}C_6)$alkyl, especially —SSMe or —SS— heteroaryl, especially

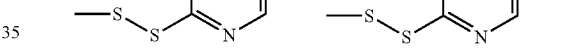

($X_1$ and $X_2$ being defined hereinbelow). More particularly, —$Z_bR_b$ may represent —OH, —$OCH_3$, —$OCH_2CH=CH_2$,

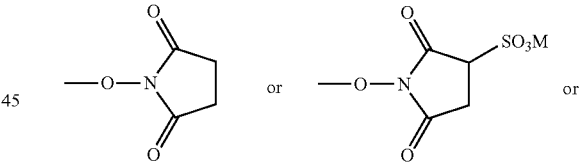

M = H or cation or the group

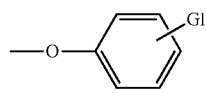

in which Gl represents at least one electroinductive group such as —$NO_2$ or -Hal, especially —F. They may be, for example, the following groups:

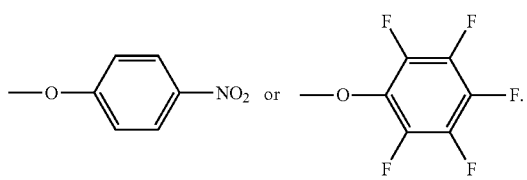

Another type of group —C(=O)$Z_bR_b$ is the following:

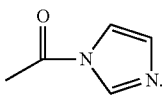

The reactive groups —SH and

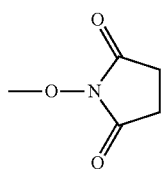

show good reactivity. More particularly, RCG1 may be chosen from one of those described in the examples.

Examples of RCG2 that may be mentioned include ε-amino groups of lysines borne by the side chains of the lysine residues that are present at the surface of an antibody, the saccharide groups of the hinge region or the thiols of cysteines by reducing intra-chain disulfide bonds (Garnett M. C., et al., *Advanced Drug Delivery Reviews* 2001, 53, 171-216). More recently, other approaches have been considered, for instance the introduction of cysteines by mutation (Junutula J. R., et al., *Nature Biotechnology* 2008, 26, 925-932; WO 09/026,274) or the introduction of unnatural amino acids allowing other types of chemistry (de Graaf A. J., et al., *Bioconjugate Chem.* 2009, Publication Date (Web): Feb. 3, 2009 (Review); DOI: 10.1021/bc800294a; WO 2006/069 246 and according to Chin J. W., et al., *JACS* 2002, 124, 9026-9027 (technology ReCode®)). These modes of attachment used with antibodies are applicable to all of the known binding agents as a function of their structure.

It is also possible to chemically modify the binding agent so as to introduce novel reactive chemical groups RCG2. Thus, it is well known to those skilled in the art how to modify an antibody with the aid of a modifying agent (see especially WO 2005/077 090 page 14). The modification makes it possible to improve the conjugation reaction and to use a wider variety of groups RCG1.

Modifying Agents for Introducing Disulfide Groups

The modifying agent may be an activated ester NHS of formula

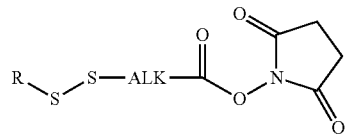

in which R represents a group ($C_1$-$C_6$)alkyl, aryl, heteroaryl, ($C_3$-$C_7$)cycloalkyl, ($C_3$-$C_7$)heterocycloalkyl and ALK represents a group ($C_1$-$C_6$)alkylene; for example, it is possible to use N-succinimidyl pyridyldithiopropionate (SPDP) or N-succinimidyl pyridyldithiobutyrate (SPDB or the N-hydroxy-succinimidyl ester of 4-(2-pyridyldithio)butanoic acid) so as to introduce dithiopyridyl reactive groups RCG2 (see Bourdon M. A., et al., *Biochem. J.* 1978, 173, 723-737; U.S. Pat. No. 5,208,020) which may then react with a reactive chemical group RCG1 of the type —SH present on the linker of the cryptophycin derivative so as to form a novel —S—S— bond (see Ex. 9 for a conjugate with a disulfide bond). The N-hydroxysuccinimide group preferentially reacts on the amino groups present on the antibody so as to form amide bonds. Another example of a modifying agent is described in WO 2004/016 801 of formula

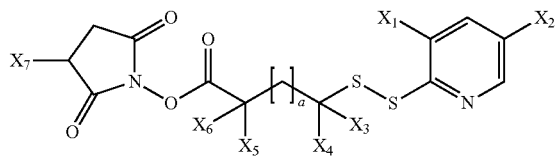

or a pegylated analogue of formula

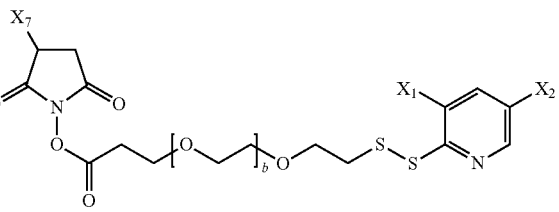

described in WO 2009/134 976 or a sulfonic analogue of formula

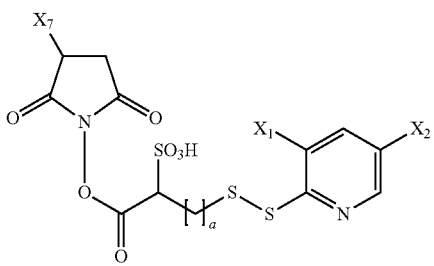

described in WO 2009/134 977 in which:
  $X_3$, $X_4$, $X_5$ and $X_6$ represent H or a ($C_1$-$C_6$)alkyl group,
  $X_1$ and $X_2$ represent —H, —CONX$_8$X$_9$, —NO$_2$, —X$_8$ and —X$_9$ representing H or a group ($C_1$-$C_6$)alkyl,
  $X_7$ represents —SO$_3^-$M$^+$ or H, or alternatively a quaternary ammonium group,
  a denotes an integer from 0 to 4 and b denotes an integer ranging from 0 to 2000 and preferably between 1 and 200; a and b may take all the values between, respectively, 0 and 4 or between 0 and 2000.

Modifying Agents for Introducing Maleimido Groups

Another example of a modifying agent is succinimidyl-4-(N-maleimidomethyl)cyclohexane-1-carboxylate (SMCC), a similar compound described in EP 0 306 943 or a sulfo-SMCC (sulfosuccinimidyl 4-(N-maleimidomethyl)cyclohexane-1-carboxylate). Other examples that may be mentioned include:

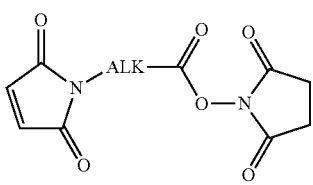

such as N-succinimidyl 3-maleimidopropanoate;

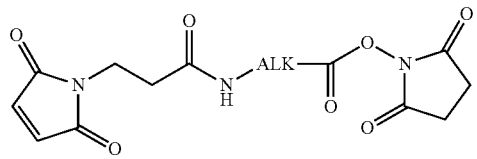

such as N-succinimidyl 6-(3-maleimidopropionamido)hexanoate;

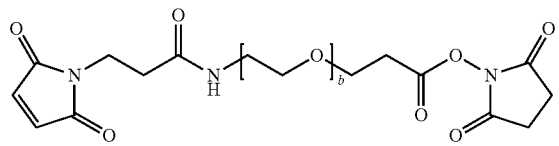

b being an integer between 0 and 2000 and preferably between 1 and 200 (b may take all the values between 0 and 2000), such as N-succinimidyl 3-(2-{2-[3-maleimidopropionylamino]ethoxy}ethoxy)propanoate or SM(PEG)$_2$;

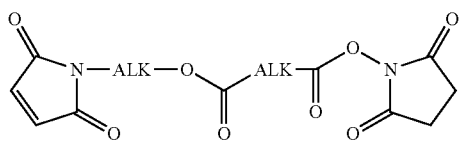

such as maleimidoethyl N-succinimidyl succinate;

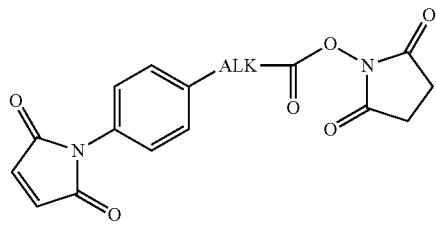

such as N-succinimidyl 4-(4-maleimidophenyl)butanoate, or

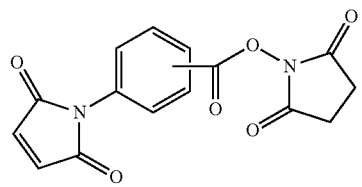

such as N-succinimidyl 3-maleimidobenzoate.

Modifying Agents for Introducing Thiol Groups

Another example of a modifying agent described in WO 90/06774 is of the formula

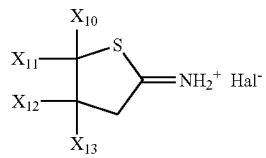

in which:

Hal represents a halogen atom;

$X_{10}$ represents a halogen atom or a group COOX$_{14}$, nitro, unsubstituted or halogenated (C$_1$-C$_8$)alkyl, unsubstituted or halogenated (C$_1$-C$_8$)alkoxy, unsubstituted or halogenated (C$_2$-C$_8$)alkenyl, unsubstituted or halogenated (C$_2$-C$_8$)alkynyl, unsubstituted (C$_3$-C$_8$)cycloalkyl, aryl that is unsubstituted or substituted with one to three substituents selected from amino, halogen atom, unsubstituted or halogenated (C$_1$-C$_8$)alkyl group, unsubstituted or halogenated (C$_1$-C$_8$)alkoxy;

each of the $X_{11}$, $X_{12}$ and $X_{13}$ independently represents a hydrogen atom or may represent $X_3$; or $X_{10}$ and $X_{11}$ together form a ring (C$_2$-C$_5$)alkylene, which is unsubstituted or substituted with one to five groups (C$_1$-C$_4$) alkyl;

or $X_{10}$ and $X_{11}$ form, together with $X_{12}$, a ring (C$_1$-C$_5$) alkylene, which is unsubstituted or substituted with one to five groups (C$_1$-C$_4$)alkyl;

and $X_{14}$ is —H or a group (C$_1$-C$_8$)alkyl.

Preferably, Hal represents a chlorine or bromine atom. The table below presents possibilities for $X_{10}$-$X_{13}$:

| $X_{10}$ | $X_{11}$ | $X_{12}$ | $X_{13}$ | Hal |
|---|---|---|---|---|
| Me | H | H | H | Cl |
| Ph | H | H | H | Cl |
| t-Bu | H | H | H | Cl |
| Me | Me | H | H | Cl |
| (—CH$_2$(CH$_2$)$_3$CH$_2$—) | | H | H | Cl |
| H | (—CH$_2$(CH$_2$)$_3$CH$_2$—) | | H | Cl |
| Et | H | H | H | Br |
| Et | Me | H | H | Cl |
| —CH—CH$_2$—CH— | H | H | H | Cl |
| Me | H | Me | H | Cl |
| H | H | Me | Me | Cl |
| Ph | Me | H | H | Cl |
| 4-ClPh | H | H | H | Cl |
| 3-furanyl | H | H | H | Cl |
| i-Pr | H | H | H | Cl |
| Me | Me | Me | Me | Cl |
| C$_6$H$_{11}$ | H | H | H | Cl |
| CH$_2$Br | H | H | H | Cl |
| CF$_3$ | H | H | H | Cl |
| CH=CH$_2$ | H | H | H | Cl |
| 2-NH$_2$Ph | H | H | H | Cl |

An example of a preferred iminothiolane is the following:

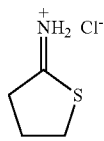

Modifying Agents for Introducing Haloacetamido Groups

Another example of a modifying agent is succinimidyl-4-(N-iodoacetyl)aminobenzoate

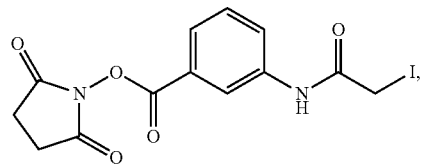
(SIAB)

or similar compounds, among which are succinimidyl-N-iodoacetate

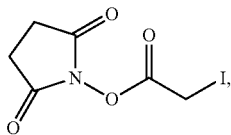
(SIA)

succinimidyl-N-bromoacetate (SBA), or succinimidyl-3-(N-bromoacetamido)propionate (SBAP) or a similar pegylated compound described in WO 2009/134 976

Figure 2:
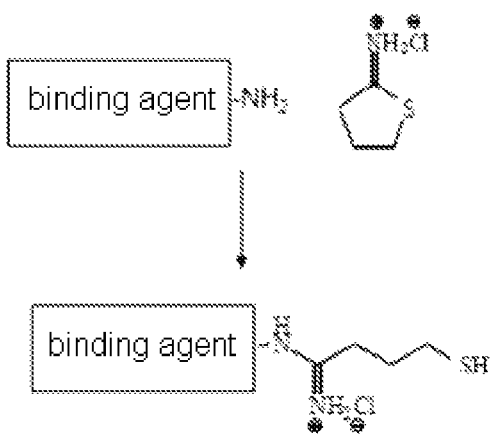
FIG. 2 illustrates the modification of an amino group of a binding agent with iminothiolane.

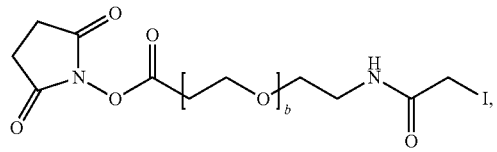

b being as described previously. FIGS. 1 and 2 illustrate the modification of an amino group of a binding agent with SPDP or with the preferred iminothiolane above.

Thus, it is possible to introduce onto the binding agent disulfide groups RCG2 (—SSR), especially of pyridyldisulfide type

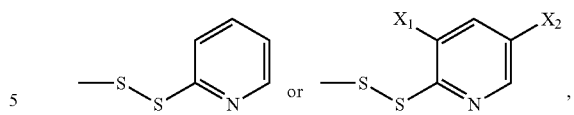

in the case where RCG1 represents —SH. Similarly, it is possible to introduce onto the binding agent thiol groups RCG2 (—SH), for example with an iminothiolane, in the case where RCG1 represents disulfide (i.e. RCG1=—$SZ_a$ with $Z_a \neq H$, for example $Z_a=$

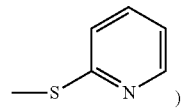
)

In both cases, the covalent bond that forms by reaction between RCG1 and RCG2 is a cleavable disulfide bond.

It is also possible, in the case where RCG1 represents —SH, to introduce onto the surface of the binding agent RCG2 groups of maleimido type (

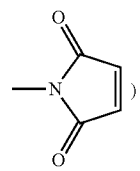
)

or haloacetamido type (e.g. bromo- or iodoacetamido

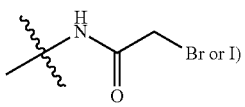

Reciprocally, it is possible to introduce onto the binding agent thiol groups RCG2 (—SH), for example with an iminothiolane, in the case where RCG1 represents

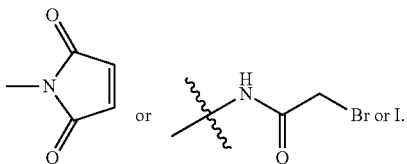

In this case, the covalent bond that forms by reaction between RCG1 and RCG2 is an uncleavable sulfide bond.

TABLE I examples of modifications of a binding agent when RCG1 = —SZ$_a$

| modifying agent | RCG2 at the surface of the binding agent | example after reaction of an amino group, especially lysine, of an antibody noted MAb |
|---|---|---|
| R—S—S—ALK | R—S—S—ALK (attached) | [R—S—S—ALK—NH]$_g$—MAb |
| SPDP | (2-pyridyl)-S-S-CH$_2$CH$_2$-C(O)- | [(2-pyridyl)-S-S-CH$_2$CH$_2$-C(O)-NH]$_g$—MAb |
| SPDB | (2-pyridyl)-S-S-CH$_2$CH$_2$CH$_2$-C(O)- | [(2-pyridyl)-S-S-CH$_2$CH$_2$CH$_2$-C(O)-NH]$_g$—MAb |
| SMCC | maleimide-CH$_2$-cyclohexyl-C(O)- | [maleimide-CH$_2$-cyclohexyl-C(O)-NH]$_g$—MAb |
| sulfo-SMCC | | |

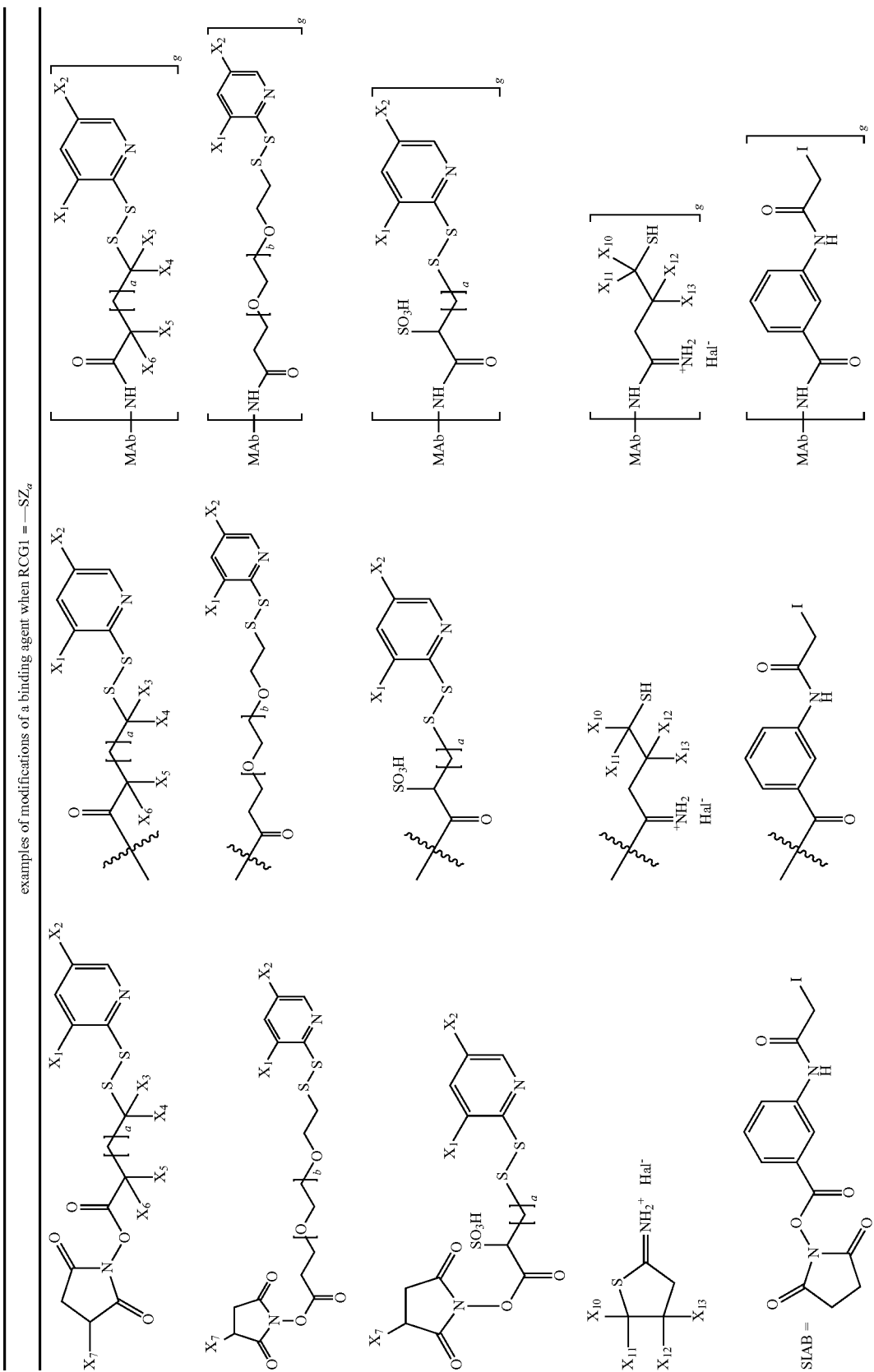

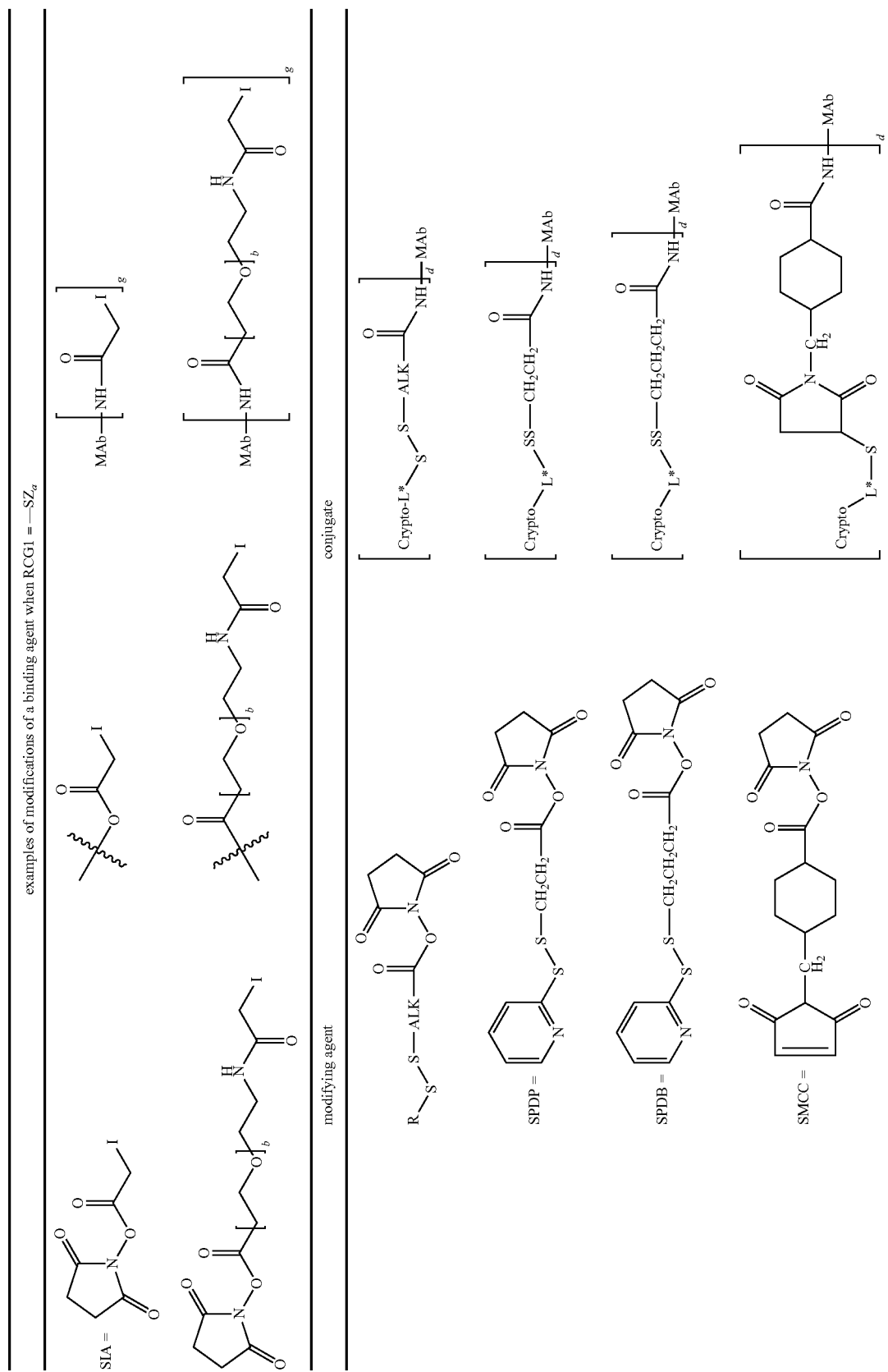

TABLE I-continued
examples of modifications of a binding agent when RCG1 = —SZ_a
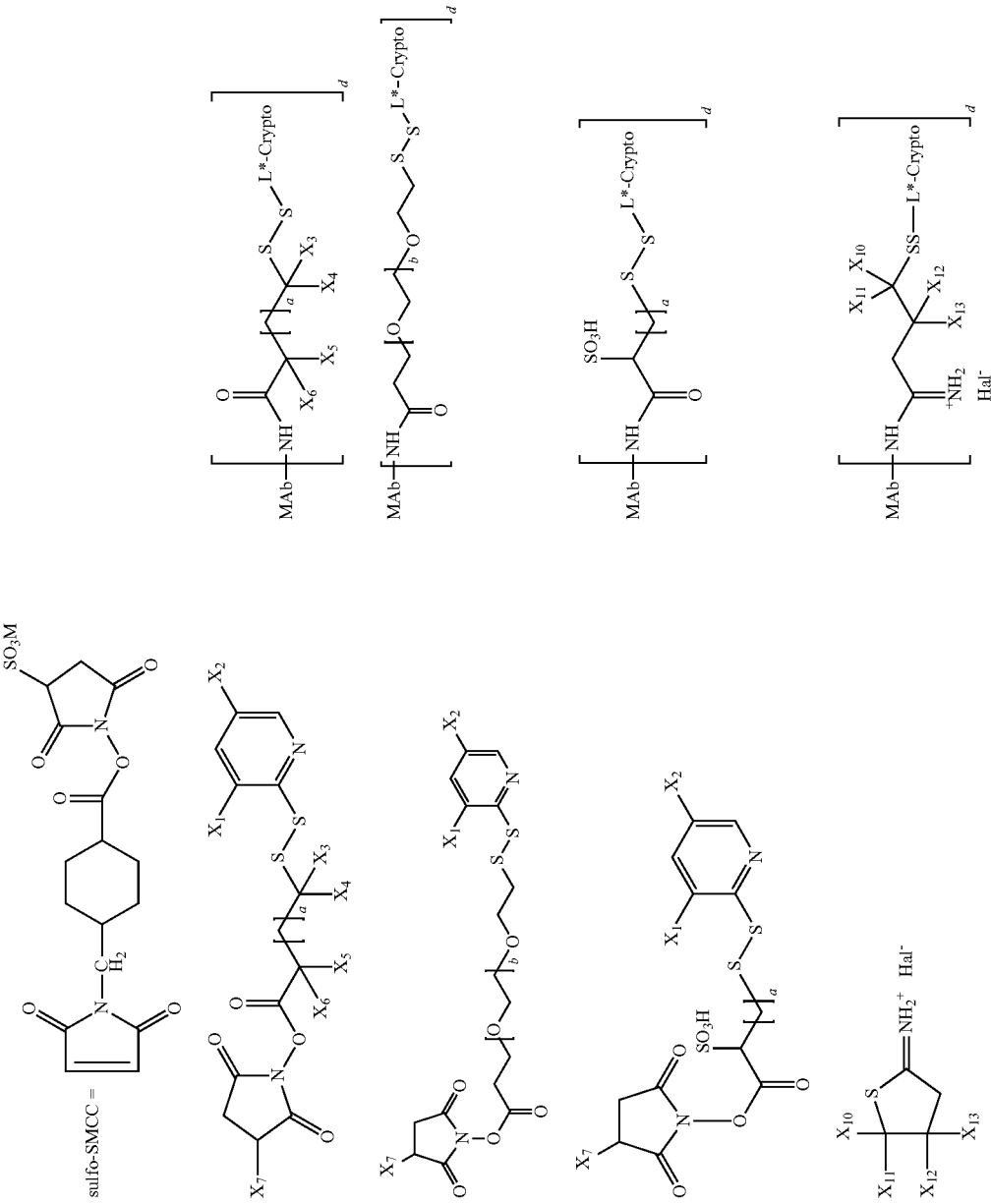

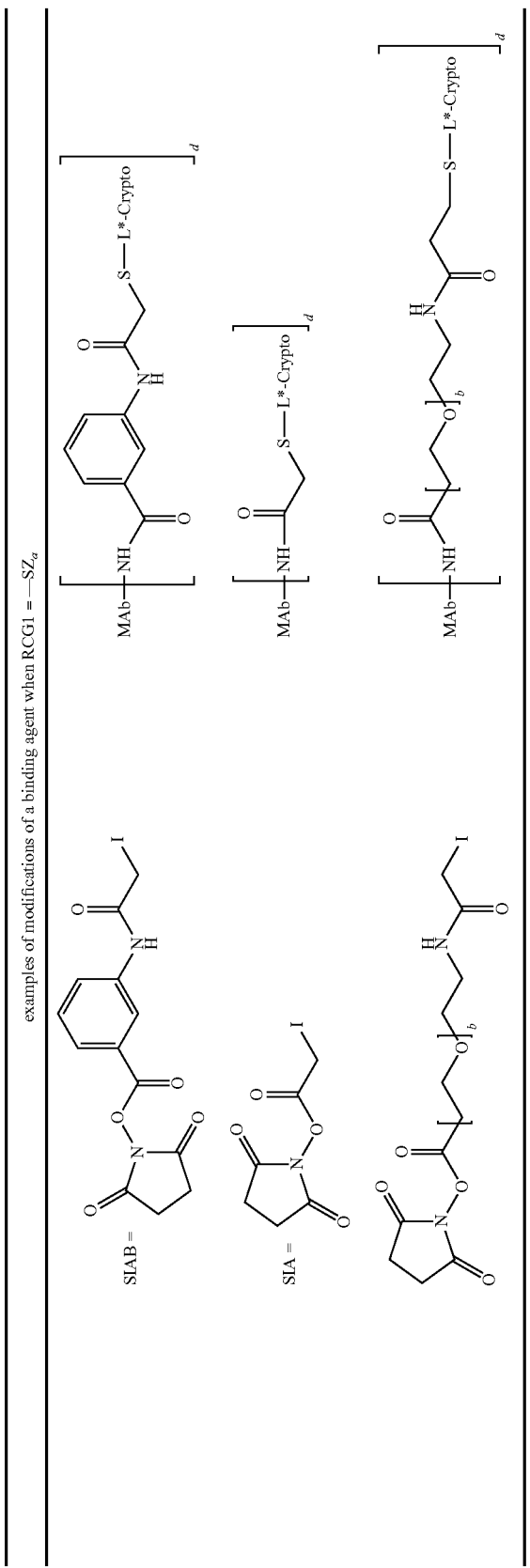
g: number of RCG2 functions on a modified binding agent;
d: number of cryptophycin derivatives on the binding agent MAb
L* = fragment of a linker L comprising RCG1 = —SZ_a and such that L = —L*SZ_a More particularly, in the case where RCG1 is of the type (iii) above, it is possible to chemically modify the binding agent using an adequate modifying agent or to introduce one or more unnatural amino acids so as to introduce the adequate functions RCG2. For example:

- with a function —$N_3$: RCG2 may be a group —C≡CH;
- with a function —OH or —$NH_2$: RCG2 may be a carboxylic acid function;
- with a function —Cl: RCG2 may be a group —SH.

In the case where RCG1 represents a maleimido

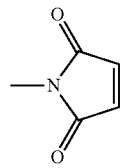

or haloacetamido

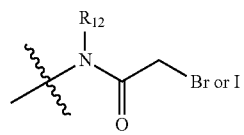

reactive group with $R_{12}$ representing H or ($C_1$-$C_6$)alkyl, more particularly Me, the cryptophycin derivative may be represented by the formula (IIa) or (IIb) below:

(IIa)

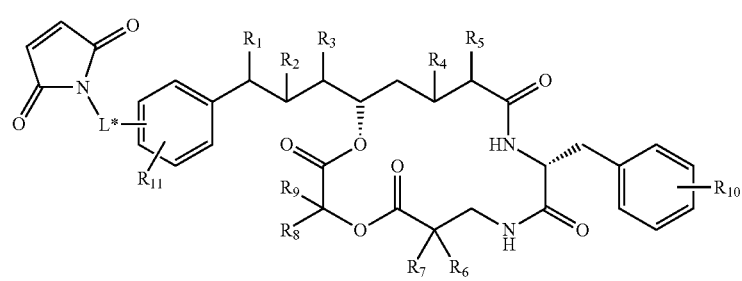

(IIb)

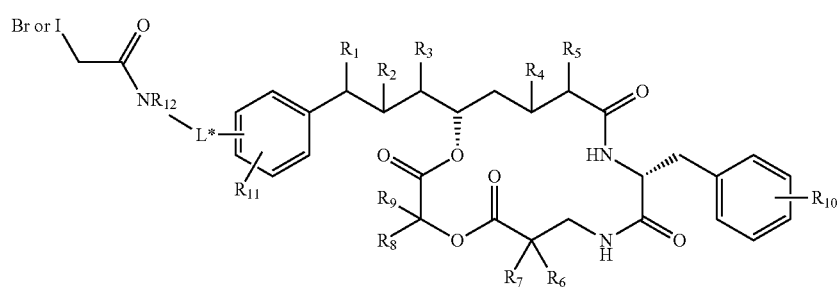

(L* represents a fragment of a linker L such that L=-L*-maleimido or L=-L*-haloacetamido)

The cryptophycin derivative may be, in the series C-52 and C-1, one of the following $D_1$-$D_8$:

$D_1$

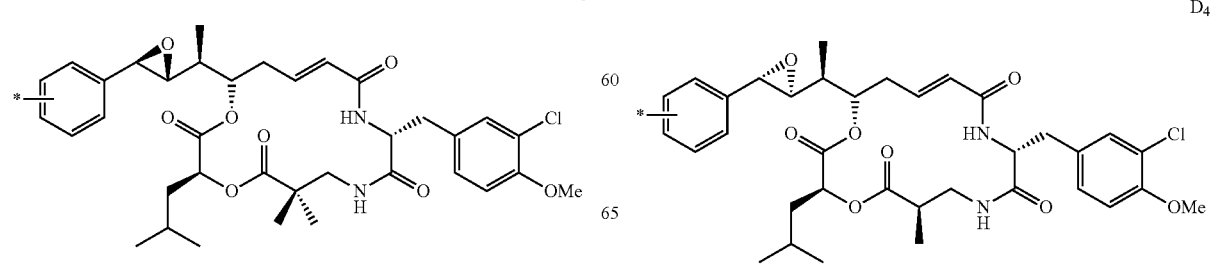

$D_2$

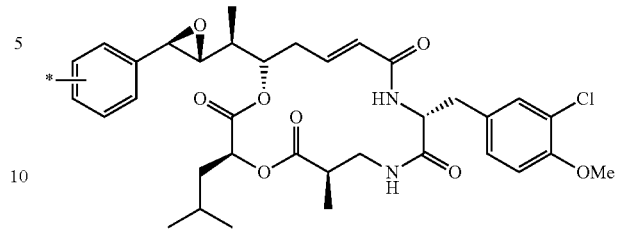

$D_3$

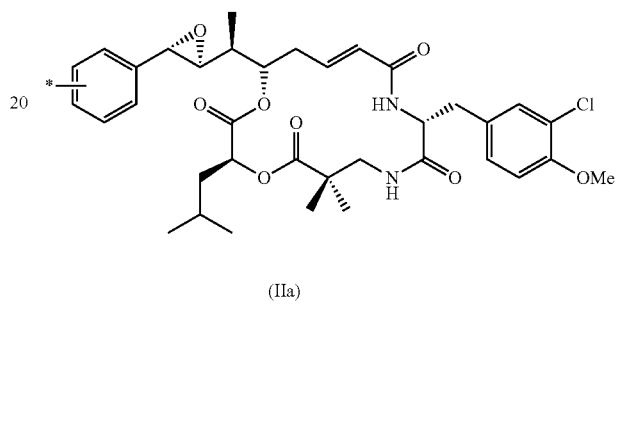

-continued $D_4$

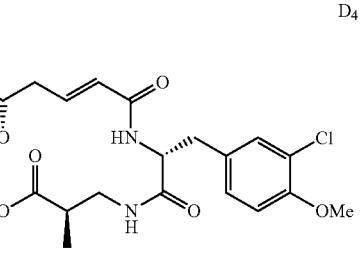

-continued

D₅

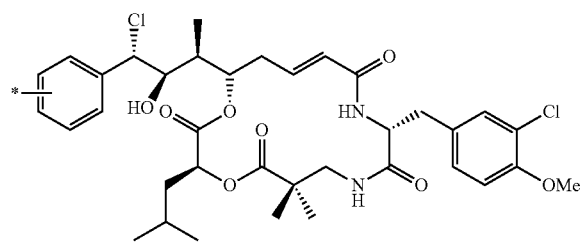

D₆

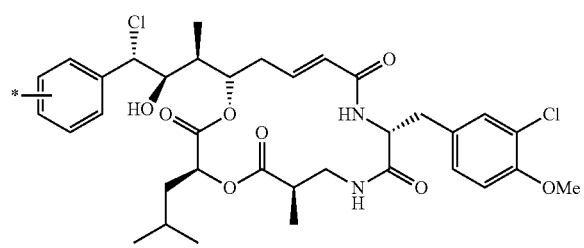

D₇

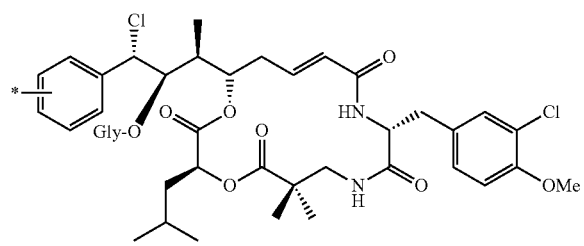
Gly = glycinate

D₈

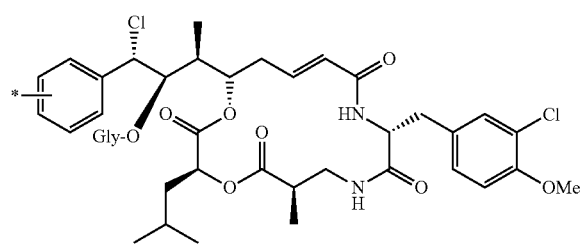
Gly = glycinate or an equivalent unit described in one of the examples.

More particularly, L is in the para position of the unit $RC_1$.

Process for Preparing the Cryptophycin Derivatives

The compounds of formula (II) are prepared according to Scheme 1 starting with a cryptophycin derivative of formula (III) and a linker precursor (LP):

Scheme 1

PL +

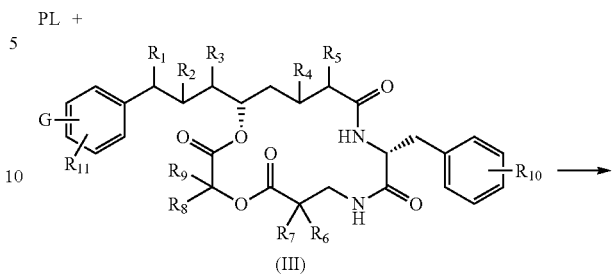

G represents the group —CH=CH₂, —(CH₂)ₙY or —(C₁-C₆)alkylene-Y with n being an integer ranging from 1 to 6 and Y representing —OH, —SH, —Cl, —OLG in which LG denotes a leaving group, for instance a mesylate (OMs) or tosylate group, or alternatively Y represents —N₃, —NH₂, —COON, —NR₁₂—CH₂—C≡CH in which R₁₂ represents H or a group (C₁-C₆)alkyl, more particularly a methyl group. The linker precursor LP has the function of introducing the linker L into the cryptophycin derivative after reaction between the group G and a chemical function present on LP.

G may also represent the group

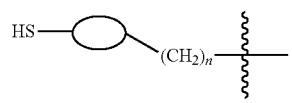

(i.e. Y represents the group

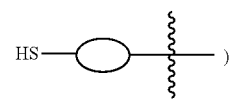
)

chosen from one of the following 9 groups (R₁₂ and R'₁₂ represent H or a group (C₁-C₆)alkyl):

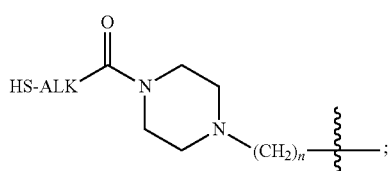

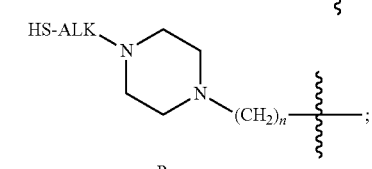

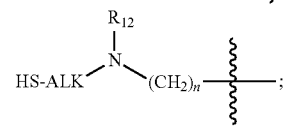

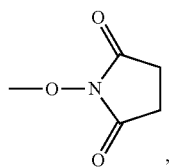

In Scheme 1, several steps and/or reactions may be necessary to arrive at the cryptophycin derivative (II) starting from the cryptophycin derivative (III). Thus, for example, in the case where $Z_a$=H, it is preferred to introduce a linker L for which $Z_a$=—S(C$_1$-C$_6$)alkyl using the corresponding linker precursor, and then to reduce the disulfide function —SS(C$_1$-C$_6$)alkyl to a thiol function —SH.

It is possible to use in order to do this, for example, TCEP: see in this respect Burns J. A., et al., *J. Org. Chem.* 1991, 56(8), 2648-2650. This conversion —SS(C$_1$-C$_6$)alkyl→—SH may apply, for example, to the linkers $L_{1-4}$ and $L_{21-23}$ of Table II.

Similarly, in the case where $Z_bR_b$=

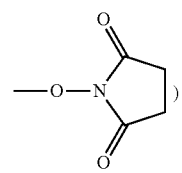

a linker L for which $Z_bR_b$=—O-allyl may be introduced using the corresponding linker precursor, followed by deprotecting the function —COOH and introducing

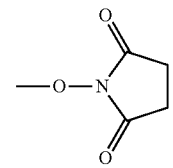

Deprotection may be performed by treatment with a palladium catalyst, for example Pd(PPh$_3$)$_4$ in the presence of a "scavenger" amine, for example morpholine; the activation may be performed with N,N'-disuccinimidyl carbonate in the presence of a base, for example DIPEA or with NHS in the presence of a coupling agent, for example DCC. This conversion of a group $Z_bR_b$ into another group $Z_bR_b$ (e.g. —O-allyl→

(image of O-N-succinimidyl group)

may be applied to obtain other groups $Z_bR_b$, especially those described above.

In the case where R$_1$ represents a halogen atom and R$_2$ represents an acyl group, it is preferred first to prepare a compound of formula (II) for which R$_2$ represents a group —OH (once the linker has been introduced), and then to introduce the acyl group using the corresponding acylating compound.

Schemes 1' and 1" similarly illustrate the preparation of a cryptophycin derivative comprising a linker comprising, respectively, a maleimido or haloacetamido group (L* represents a fragment of a linker such that L=-L*-maleimido or L=-L*-haloacetamido).

Scheme 1'

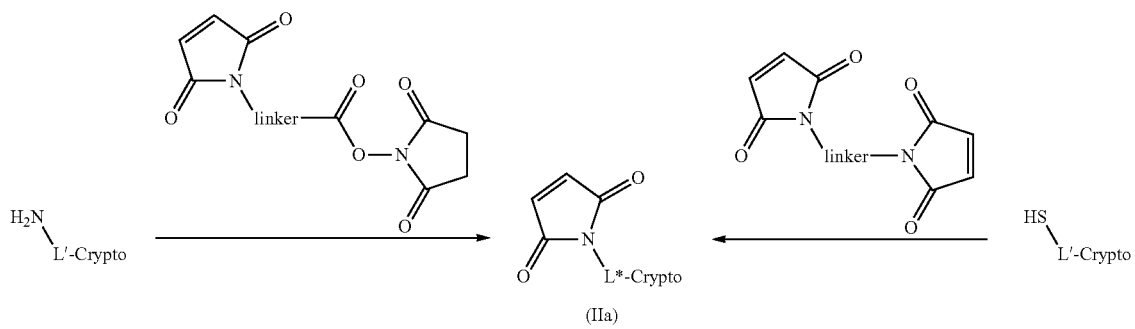

(IIa)

Scheme 1"

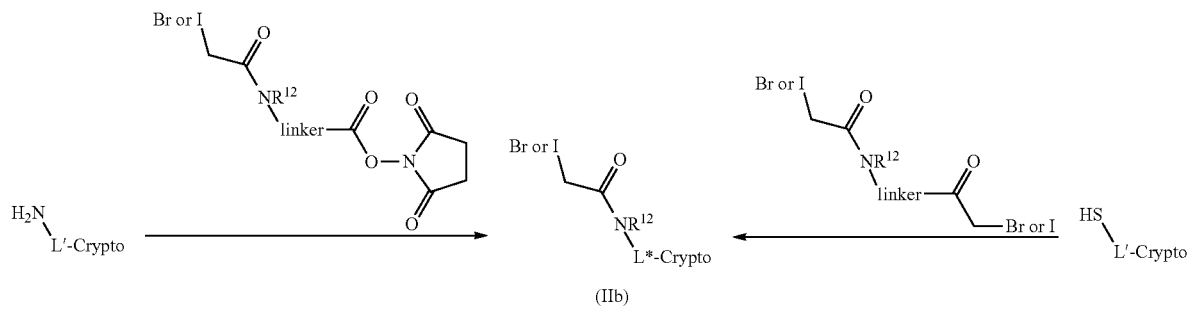

(IIb)

These derivatives are obtained by reaction between a cryptophycin derivative comprising a linker L' comprising an amino or thiol group and a modifying agent for introducing, respectively, a maleimido or haloacetamido group.

Examples of Reactions Between the Group G and a Chemical Function Present on LP

- nucleophilic substitution between a linker precursor LP bearing an amine function —NH— (an amine salt may also be suitable for use) and G=—(CH$_2$)$_n$Cl or —(CH$_2$)$_n$OMs (see, for example, Table II, LP$_{1-4}$, LP$_{7a}$, LP$_{8-10}$, LP$_{21-23}$): this reaction may be performed in a polar aprotic solvent in the presence of a base, for instance TEA or DIPEA. See Ex. 1, compound 7 or Ex. 15, compound 48;
- acylation between a linker precursor LP bearing a carbamoyl halide function and G=—(CH$_2$)$_n$OH (see, for example, Table II, LP$_5$): this reaction may be performed in a polar aprotic solvent in the presence of an amine base, for instance TEA.

According to one variant, it is also possible to react a linker precursor LP bearing an amine function —NH— and G=—(CH$_2$)$_n$O—C(=O)—O-(4-nitrophenyl) obtained from G=—(CH$_2$)$_n$OH and p-nitrophenyl chloroformate (activation of the alcohol in the form of carbonate) according to the scheme below (R$_{12}$=H or (C$_1$-C$_6$)alkyl):

—NHR$_{12}$+crypto-(CH$_2$)$_n$O—C(=O)—O-(4-nitrophenyl)→crypto-(CH$_2$)$_n$O—C(=O)—NR$_{12}$— the activation of an alcohol in the form of carbonate may also be used to react a linker precursor bearing a function —OH and G=—(CH$_2$)$_n$NH$_2$ or —(CH$_2$)$_n$OH to obtain, respectively, a carbamate function (—O—C(=O)—NH—) or carbonate (—O—C(=O)—O—) according to the following respective schemes:

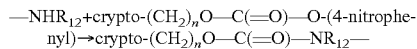

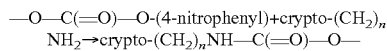
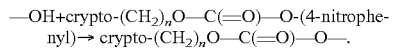

(see, for example, Table II, LP$_{6a-6b}$, LP$_{24-25}$)

- esterification between a linker precursor LP bearing an acid function —COOH and G=—(CH$_2$)$_n$OH (see, for example, Table II, LP$_{14b}$): this reaction may be performed in a polar aprotic solvent in the presence of an amine base, for instance DMAP and a coupling agent, for example DCC;
- amidation between a linker precursor LP bearing an acid function —COOH and G=—(CH$_2$)$_n$NH$_2$ (see, for example, Table II, LP$_{14a}$): this reaction may be performed in a polar aprotic solvent in the presence of a coupling agent, for example EDCl or HOBt;
- amidation between a linker precursor LP bearing a function —NH$_2$ and G=—(CH$_2$)$_n$COOH (see, for example, Table II, LP$_{7c}$): this reaction may be performed in a polar aprotic solvent in the presence of a coupling agent, for example EDCl or HOBt;
- 1,3-dipolar cycloaddition (also known as "click" chemistry) between a linker precursor LP bearing an alkyne terminal function and G=—(CH$_2$)—N$_3$ or alternatively a linker precursor LP bearing an azide function and G=—(CH$_2$)$_n$NR$_{12}$—CH$_2$C≡CH (see, for example, Table II, LP$_{15-18}$): this reaction may be performed in a polar solvent in the presence of Cu(I) as catalyst (see in this respect the Huisgen cycloaddition: Rostovtsev V. V., et al., *Angew. Chem. Int. Ed.* 2002, 41, 2596-2599; Tornoe C. W., et al., *J. Org. Chem.* 2002, 67, 3057-3064);
- metathesis between a linker precursor LP bearing an ethylenic end function and G=—CH=CH$_2$ (see Table II, LP$_{19}$, LP$_{20}$): this reaction may be performed in a polar aprotic solvent in the presence of a second-generation Grubbs catalyst (CAS No. 246047-72-3, see in this respect Poeylaut-Palena A. A., et al., *J. Org. Chem.* 2008, 73, 2024-2027).

As Regards the Linker L

The linker L may be chosen from one of the following:

-G' X (CR$_{13}$R$_{14}$)$_t$(OCH$_2$CH$_2$)$_y$(CR$_{15}$R$_{16}$)$_u$ Q RCG$_1$;
-G' X (CR$_{13}$R$_{14}$)$_t$(OCH$_2$CH$_2$)$_y$—Y'—(CR$_{15}$R$_{16}$)$_u$ Q RCG$_1$;
-G' X (CR$_{13}$R$_{14}$)$_t$(CR$_{17}$=CR$_{18}$)(CR$_{15}$R$_{16}$)$_u$(OCH$_2$CH$_2$)$_y$ Q RCG$_1$;
-G' X (CR$_{13}$R$_{14}$)$_t$(OCH$_2$CH$_2$)$_y$(CR$_{17}$=CR$_{18}$)(CR$_{15}$R$_{16}$)$_u$ Q RCG$_1$;
-G' X (CR$_{13}$R$_{14}$)$_t$-phenyl-(CR$_{15}$R$_{16}$)$_u$ Y' Q RCG$_1$; -G' X (CR$_{13}$R$_{14}$)$_t$-furyl-(CR$_{15}$R$_{16}$)$_u$ Y' Q RCG$_1$;
-G' X (CR$_{13}$R$_{14}$)$_t$-oxazolyl-(CR$_{15}$R$_{16}$)$_u$ Y' Q RCG$_1$; -G' X (CR$_{13}$R$_{14}$)$_t$-thiazolyl-(CR$_{15}$R$_{16}$)$_u$ Y' Q RCG$_1$;
-G' X (CR$_{13}$R$_{14}$)$_t$-thienyl-(CR$_{15}$R$_{16}$)$_u$ Y' Q RCG$_1$; -G' X (CR$_{13}$R$_{14}$)$_t$-imidazolyl-(CR$_{15}$R$_{16}$)$_u$ Y' Q RCG$_1$;
-G' X (CR$_{13}$R$_{14}$)$_t$-piperazinyl-CO(CR$_{15}$R$_{16}$)$_u$ Y' Q RCG$_1$; -G' X (CR$_{13}$R$_{14}$)$_t$-piperidyl-methyl-NR$_{12}$—CO(CR$_{15}$R$_{16}$)$_u$ Y' Q RCG$_1$; -G' X (CR$_{13}$R$_{14}$)$_t$-piperidyl-(CR$_{15}$R$_{16}$)$_u$ Y' Q RCG$_1$; -G' X (CR$_{13}$R$_{14}$)$_t$-piperidyl-NR$_{12}$—(CR$_{15}$R$_{16}$)$_u$ Y' Q RCG$_1$; -G' X (CR$_{13}$R$_{14}$)$_t$-triazolyl-(CR$_{15}$R$_{16}$)$_u$ Y' Q RCG$_1$; -G' X (CR$_{13}$R$_{14}$)$_t$-triazolyl-(CR$_{15}$R$_{16}$)$_u$ Y' Q RCG$_1$;
-G' X (CR$_{13}$R$_{14}$)$_t$-phenyl-(CR$_{15}$R$_{16}$)$_u$ Q RCG$_1$; -G' X (CR$_{13}$R$_{14}$)$_t$-furyl-(CR$_{15}$R$_{16}$)$_u$ Q RCG$_1$, -G' X (CR$_{13}$R$_{14}$)$_t$-oxazolyl-(CR$_{15}$R$_{16}$)$_u$ Q RCG$_1$; -G' X (CR$_{13}$R$_{14}$)$_t$-thiazolyl-(CR$_{15}$R$_{16}$)$_u$ Q RCG$_1$; -G' X (CR$_{13}$R$_{14}$)$_t$-thienyl-(CR$_{15}$R$_{16}$)$_u$ Q RCG$_1$; -G' X (CR$_{13}$R$_{14}$)$_t$-imidazolyl-(CR$_{15}$R$_{16}$)$_u$ Q RCG$_1$; -G' X (CR$_{13}$R$_{14}$)$_t$-piperazinyl-(CR$_{15}$R$_{16}$)$_u$ Q RCG$_1$; -G' X (CR$_{13}$R$_{14}$)$_t$-piperidyl-(CR$_{15}$R$_{16}$)$_u$ Q RCG$_1$; -G' X (CR$_{13}$R$_{14}$)$_t$-piperidyl-methyl- $NR_{12}$—$(CR_{15}R_{16})_u$ Q $RCG_1$; -G' X $(CR_{13}R_{14})_t$-piperidyl-$NR_{12}$—$(CR_{15}R_{16})_u$ Q $RCG_1$; -G' X $(CR_{13}R_{14})_t$-triazolyl-$(CR_{15}R_{16})_u$ Q $RCG_1$;
or
-G" Y $(CR_{13}R_{14})_t(OCH_2CH_2)_y(CR_{15}R_{16})_u$ Q $RCG_1$;
-G" Y $(CR_{13}R_{14})_t(OCH_2CH_2)_y$Y'—$(CR_{15}R_{16})_u$ Q $RCG_1$;
-G" Y $(CR_{13}R_{14})_t(CR_{17}=CR_{18})(CR_{15}R_{16})_u(OCH_2CH_2)_y$ Q $RCG_1$;
-G" Y $(CR_{13}R_{14})_t(OCH_2CH_2)_y(CR_{17}=CR_{18})(CR_{15}R_{16})_u$ Q $RCG_1$;
-G" Y $(CR_{13}R_{14})_t$-phenyl-$(CR_{15}R_{16})_u$ Y' Q $RCG_1$; -G" Y $(CR_{13}R_{14})_t$-furyl-$(CR_{75}R_{16})_u$ Y' Q $RCG_1$; -G" Y $(CR_{13}R_{14})_t$-oxazolyl-$(CR_{15}R_{16})_u$ Y' Q $RCG_1$; -G" Y $(CR_{13}R_{14})_t$-thiazolyl-$(CR_{15}R_{16})_u$ Y' Q $RCG_1$; -G" Y $(CR_{13}R_{14})_t$-thienyl-$(CR_{15}R_{16})_u$ Y' Q $RCG_1$; -G" Y $(CR_{13}R_{14})_t$-imidazolyl-$(CR_{15}R_{16})_u$ Y' Q $RCG_1$;
-G" Y $(CR_{13}R_{14})_t$-piperazinyl-$CO(CR_{15}R_{16})_u$ Y' Q $RCG_1$; -G" Y $(CR_{13}R_{14})_t$-piperidyl-methyl-$NR_{12}$—CO $(CR_{15}R_{16})_u$ Y' Q $RCG_1$; -G" Y $(CR_{13}R_{14})_t$-piperidyl-$(CR_{15}R_{16})_u$ Y' Q $RCG_1$; -G" Y $(CR_{13}R_{14})_t$-piperidyl-$NR_{12}$—$(CR_{15}R_{16})_u$ Y' Q $RCG_1$; -G" Y $(CR_{13}R_{14})_t$-triazolyl-$(CR_{15}R_{16})_u$ Y' Q $RCG_1$;
-G" Y $(CR_{13}R_{14})_t$-phenyl-$(CR_{15}R_{16})_u$ Q $RCG_1$; -G" Y $(CR_{13}R_{14})_t$-furyl-$(CR_{15}R_{16})_u$ Q $RCG_1$, -G" Y $(CR_{13}R_{14})_t$-oxazolyl-$(CR_{15}R_{16})_u$ Q $RCG_1$; -G" Y $(CR_{13}R_{14})_t$-thiazolyl-$(CR_{15}R_{16})_u$ Q $RCG_1$; -G" Y $(CR_{13}R_{14})_t$-thienyl-$(CR_{15}R_{16})_u$ Q $RCG_1$; -G" V $(CR_{13}R_{14})_t$-imidazolyl-$(CR_{15}R_{16})_u$ Q $RCG_1$; -G" Y $(CR_{13}R_{14})_t$-piperazinyl-$(CR_{15}R_{16})_u$ Q $RCG_1$; -G" Y $(CR_{13}R_{14})_t$-piperazinyl-$(CR_{15}R_{16})_u$ Q $RCG_1$; G" Y $(CR_{13}R_{14})_t$-piperidyl-$(CR_{15}R_{16})_u$ Q $RCG_1$; -G"Y $(CR_{13}R_{14})_t$-piperidyl-methyl-$NR_{12}$—$(CR_{15}R_{16})_u$ Q $RCG_1$; -G"Y $(CR_{13}R_{14})_t$-piperidyl-$NR_{12}$—$(CR_{15}R_{16})_u$ Q $RCG_1$; -G"Y $(CR_{13}R_{14})_t$-triazolyl-$(CR_{15}R_{16})_u$ Q $RCG_1$;

G' represents a group —CH=CH— or —$(CH_2)_n$—;
G" represents a group —$(CH_2)_n$—;
n represents an integer ranging from 1 to 6;
X represents a single bond or a group —CO—, —COO— or —$CONR_{12}$—, the group CO being attached to G';
Y represents a group —O—, —OCO—, —OCOO—, —$OCONR_{12}$—, —$NR_{12}$—, —$NR_{12}CO$—, —$NR_{12}CONR'_{12}$—, —$NR_{12}COO$— or —$S(O)_q$—, the atom O or the group $NR_{12}$ being attached to G";
Y' represents a group —O—, —OCO—, —OCOO—, —$OCONR_{12}$—, —$NR_{12}$—, —$NR_{12}COO$—, —$NR_{12}CONR'_{12}$—, —$NR_{12}COO$—, —$S(O)_q$—, —CO—, —COO—, or —$CONR_{12}$—;
$R_{12}$, $R'_{12}$, $R_{13}$, $R_{14}$, $R_{15}$ and $R_{16}$, $R_{17}$ and $R_{18}$ represent, independently of each other, H or a group ($C_1$-$C_6$)alkyl;
t, u and y represent integers that may range from 0 (in the case of the absent group) to 20 and such that t+u+y is greater than or equal to 1;
q represents an integer that may be 0, 1 or 2;
Q represents a single bond, a group ($C_1$-$C_{10}$)alkylene or a group $(OCH_2CH_2)_i$, i being an integer ranging from 1 to 20, more particularly from 1 to 10, even more particularly from 1 to 8 or from 1 to 6, and even more particularly from 2 to 5. i may take each of the values of these ranges, and may especially be 2, 3, 4 or 5.
In the case of the linker of formula -G" Y $(CR_{13}R_{14})_t$ $(OCH_2CH_2)_y$—Y'—$(CR_{15}R_{16})_u$ Q $RCG_1$, if y is 0 (no PEG group) and if Q represents a single bond, then u cannot be 0. More particularly, linkers comprising the terminal group —$NR_{12}$—C(=O)—O— (Y'=$NR_{12}$; u=0; Q=single bond and $RCG_1$=C(=O)$Z_bR_b$) are excluded.
y represents an integer ranging from 0 to 20, more particularly from 1 to 20, even more particularly from 1 to 10, from 1 to 8 or from 1 to 6, and even more particularly from 2 to 5. y may take each of the values of these ranges, and may especially be 2, 3, 4 or 5.

Some of these linkers have been described in patent applications WO 07/085,930 and WO 09/016,516.

The linker L may be chosen from one of those of formula (IV):

$$R_bZ_b-CO-ALK\underset{O}{\overset{O}{\|}}C-(AA)_w-D-(CH_2)_n-\xi \quad (IV)$$

in which:
$(AA)_w$ represents a sequence of w amino acids AA connected together via peptide bonds;
w represents an integer ranging from 1 to 12 and preferably from 1 to 6;
n represents an integer ranging from 1 to 6;
D represents one of the following units:

(D1)

—$NR_{12}$— structure with $V_1$, $V_2$, $R_{19}$, $R_{20}$, $R_{21}$, O—T (D2)

—$NR_{12}$— structure with $V_2=V_4$, $V_3$, $R_{20}$, $R_{21}$, O—T (D3)

—$NR_{12}$— structure with $V_2=V_4$, $V_5$, $V_2$, $R_{20}$, $R_{21}$, O—T for which:
$R_{12}$ represents H or a group ($C_1$-$C_6$)alkyl;
$R_{19}$, $R_{20}$, $R_{21}$ and $R_{22}$ represent, independently of each other, H, a halogen atom, —OH, —CN or a group ($C_1$-$C_4$)alkyl;
T attached to $(CH_2)_n$ represents $NR_{12}$ or O;
$V_1$ represents O, S or $NR_{12}$;
$V_2$ represents $CR_{22}$ or N;
$V_3$, $V_4$ and $V_5$ are chosen, independently of each other, from $CR_{22}$ and N.
An example of D2 is as follows:

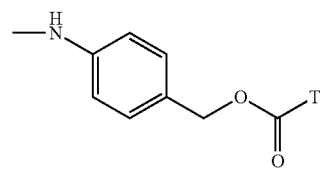

AA denotes a natural or unnatural amino acid, more particularly chosen from: alanine (Ala), β-alanine, 2-amino-2- cyclohexylacetic acid, 2-amino-2-phenylacetic acid, arginine (Arg), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), valine (Val), γ-aminobutyric acid, α,α-dimethyl-γ-aminobutyric acid, β,β-dimethyl-γ-aminobutyric acid, ornithine (Orn), citrulline (Cit).

The sequence $(AA)_w$ has the formula:

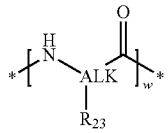

in which $R_{23}$ represents a residue of one of the amino acids described above. Examples of sequences are as follows: Gly-Gly, Phe-Lys, Val-Lys, Val-Cit, Phe-Phe-Lys, D-Phe-Phe-Lys, Gly-Phe-Lsy, Ala-Lys, Val-Cit, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Cit, Gly-Phe-Leu-Gly, Ala-Leu-Ala-Leu.

The linker precursors are those comprising the corresponding —OH units:

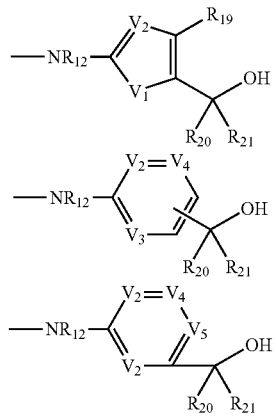

WO 2005/082 023 (see especially pages 61-64) describes how to obtain certain linker precursors. The preparations of the linker precursors LP25 and LP26 described below may also be used for obtaining other similar linker precursors comprising another sequence $(AA)_w$.

The linker L may also be chosen from one of those described in Table II or from the illustrated compounds. In all the formulae of linkers, $NR_{12}$ or $NR'_{12}$ more particularly represents NH or NMe.

Preparation of the Compounds of Formula (III)
In the Case where G=—$(CH_2)_n$OH or —CH=$CH_2$

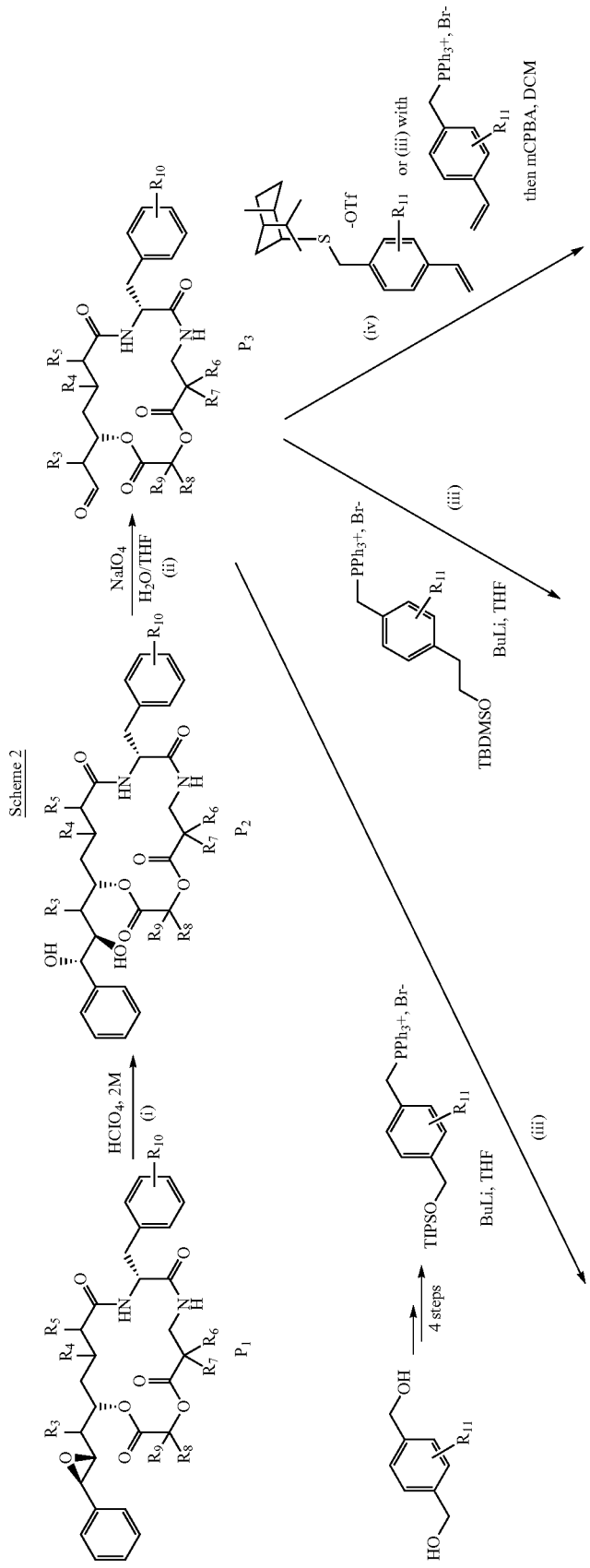

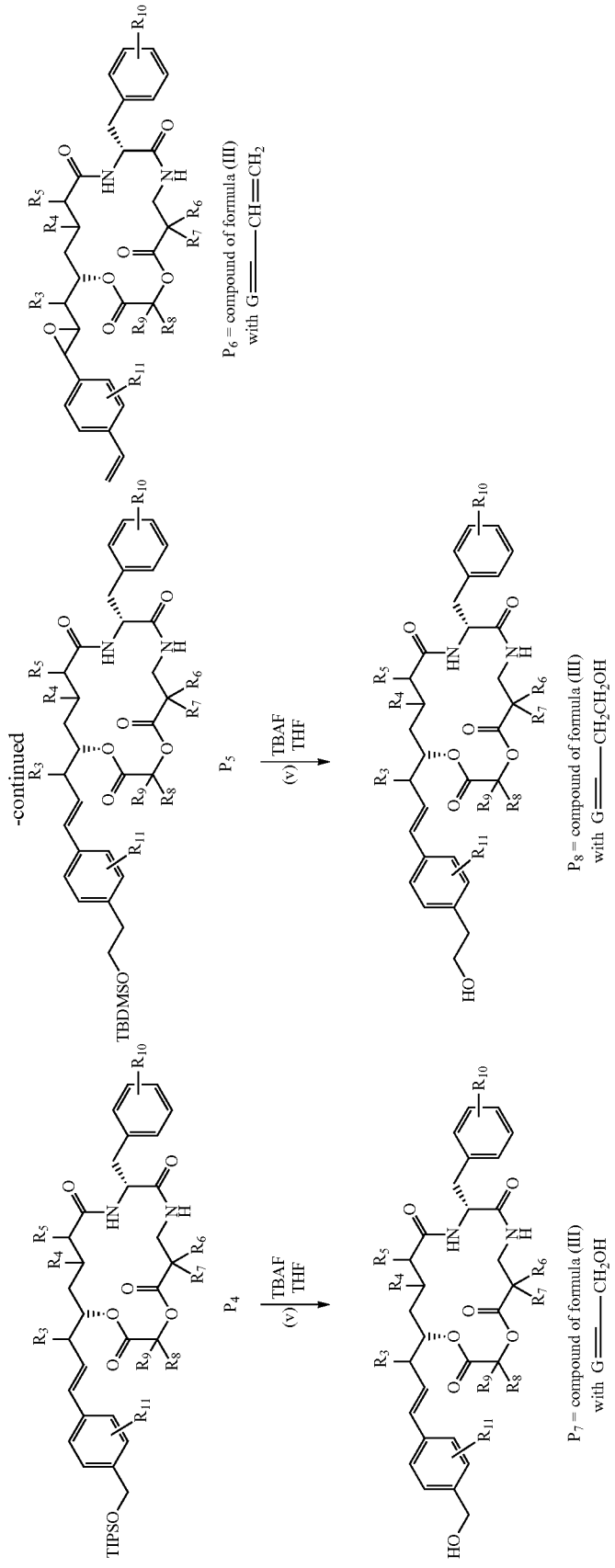

P$_1$ is prepared according to the teaching of patent applications WO 98/08505, WO 00/23429 or WO 00/34252 and also the following publications: Rej R., et al., *J. Org. Chem.* 1996, 61, 6289-6295; Salamonczyk G. M., et al., *J. Org. Chem.* 1996, 61, 6893-6900 or J. Med. Chem. 1999, 42 (14), 2588-2603 (incorporated herein by reference). In pages 158-159 of "The isolation, characterization and development of a novel class of potent antimitotic macrocyclic depsipeptides: the cryptophycins", Chap. 9, in "Anticancer agents from natural products", Taylor & Francis, CRC press book, ISBN=0-8493-1863-7 are given in the synthetic schemes for preparing the various cryptophycin fragments (A, B, C and D) and for producing P$_1$. Rej R., et al., *J. Org. Chem.* 1996, 61, 6289-6295 describes in Schemes 1-6 the route of access to one of the cryptophycin derivatives of FIG. 1, but these schemes may apply to the preparation of P$_1$ using suitable starting reagents.

P$_1$ allows the preparation of other cryptophycin derivatives with the aid of the steps detailed hereinbelow:

Step (i):
Opening of the epoxide ring of P$_1$ in acidic medium so as to obtain the diol function. Concentrated perchloric acid may be used, for example;

Step (ii):
Oxidative cleavage of the diol using, for example, sodium periodate;

Step (iii):
Wittig reaction using a suitable phosphonium halide, for example a bromide, and a strong base, for instance BuLi;

Step (iv):
Corey-Chaykovsky epoxidation reaction involving a chiral sulfonium salt, for example a triflate, in the presence of a base, for instance KOH;

Step (v):
Deprotection of the silyl ether using, for example, a tetrabutylammonium fluoride solution.

4-(Triisopropylsiloxymethyl)benzyltriphenylphosphonium bromide is obtained from 1-(bromomethyl)-4-(triisopropylsiloxymethyl)benzene (CAS No. 934667-38-6), the preparation of which starting from 1,4-benzenedimethanol (CAS No. 589-29-7, commercial product) is described by Potter R. G., et al., *Organic Letters* 2007, 9(7), 1187-1190. The compounds for which R$_{11}$ represents a group (C$_1$-C$_4$) alkyl are obtained in a similar manner starting with the corresponding diol, which is either a commercial product or is obtained by Friedel-Crafts C-alkylation starting with 1,4-benzenedimethanol.

Starting with 1-(bromomethyl)-4-(triisopropylsiloxymethyl)benzene (CAS No. 135408-73-0), the preparation of which is described in Scheme 4a of EP 0 496 548 or on page 83 of the article by Nevill C. R. Jr., et al., *Bioorganic & Med. Chem. Lett.* 1991, 1(1), 83-86, the corresponding phosphonium bromide may be obtained. The compounds for which R$_{11}$ represents a group (C$_1$-C$_4$)alkyl are obtained in a similar manner from a compound equivalent to compound 1 described on page 83 of the article by Nevill C. R. Jr., et al., *Bioorganic & Med. Chem. Lett.* 1991, 1(1), 83-86, which is either a commercial product or is obtained by Friedel-Crafts C-alkylation starting with p-tolylacetic acid.

(1R,4R,5R,6R)-4,7,7-Trimethyl-6-(4-vinylbenzyl)-6-thionia-bicyclo[3.2.1]octane trifluoromethanesulfonate used in step (iv) is obtained from (1R,4R,5R)-isothiocineole (see Aggarwal V. et al., *JACS* 2010, 132, 1828-1830), the preparation of which from (R)-limonene (CAS No. 95327-98-3, commercial product) is described in this same reference. Triphenyl(p-vinylbenzyl)phosphonium bromide (CAS No. 118766-51-1) is obtained from the corresponding bromo derivative (see Drefahl G., et al., *Chem. Ber.* 1961, 94(8), 2002-2010), the preparation of which starting with 4-vinylbenzyl alcohol (CAS No. 1074-61-9, commercial product) is described in the article by Shimomura O., et al., *Tetrahedron* 2005, 61, 12160-12167.

Starting with P$_7$ or P$_8$, which are compounds of formula (III) for which G=—(CH$_2$)$_n$OH, other compounds of formula (III) containing other groups G may be obtained.

In the Case where G=—(CH$_2$)$_n$Cl or —(CH$_2$)$_n$N$_3$

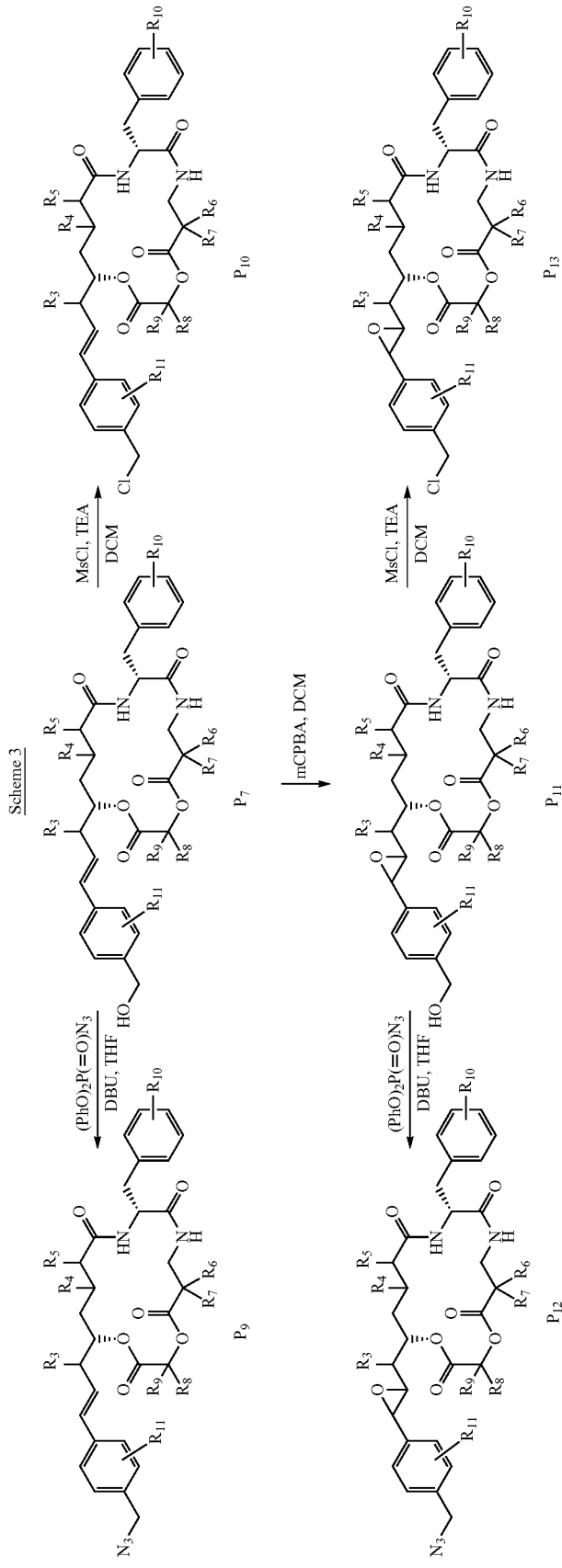
Scheme 3

Starting with the group G=—CH$_2$OH, the groups G=—CH$_2$Cl or —CH$_2$N$_3$ may be obtained:
- the introduction of —Cl may be performed in the presence of CMS: see Ex. 1, compound 2;
- the azidation may be performed in the presence of diphenylphosphorazide (PhO)$_2$P(=O)N$_3$ and a base, for example DBU. Scheme 3 describes these reactions for the case n=1, but it may also apply for n>1.

In the Case where G=—(CH$_2$)$_n$COOH

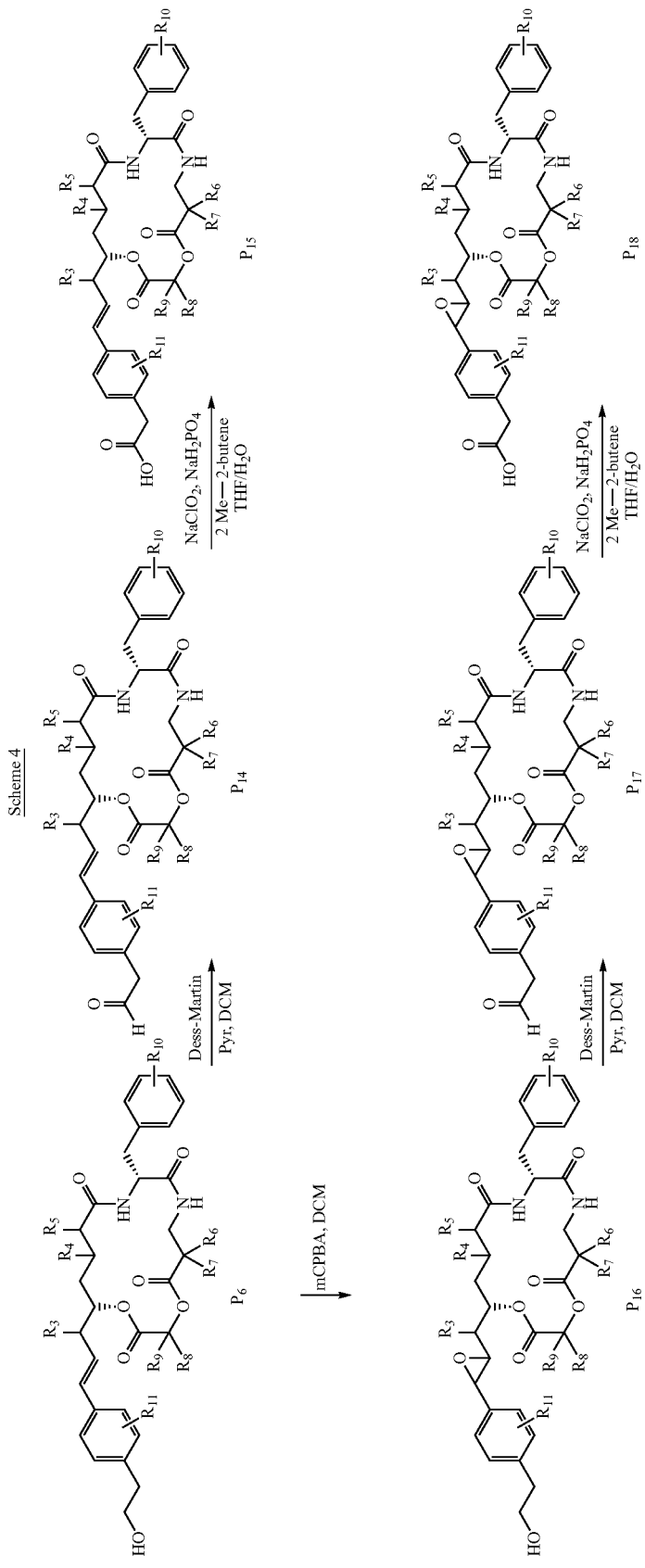

Starting with the group G=—(CH$_2$)$_2$OH, the group G=—CH$_2$COOH may be obtained via an oxidation. Scheme 4 describes a double oxidation: 1$^{st}$ oxidation using the Dess-Martin reagent (see "Encyclopedia of Reagents for Organic Synthesis"; Paquette L. A., Ed.; Wiley: Chichester, UK, 1995, Vol. 7, 4982-4987 or Boeckman R. K. Jr., et al., J. J. "The Dess-Martin Periodinane" *Org. Synth.* 2004, 10, 696-702) followed by a 2$^{nd}$ oxidation of Pinnick type in the presence of 2-methyl-2-butene (Pinnick H. W., *Tetrahedron* 1981, 37, 2091-2096). Scheme 4 describes these reactions for the case of a starting compound for which n=2, but it may also apply for n>2.

In the Case where G=—(CH$_2$)$_n$NH$_2$

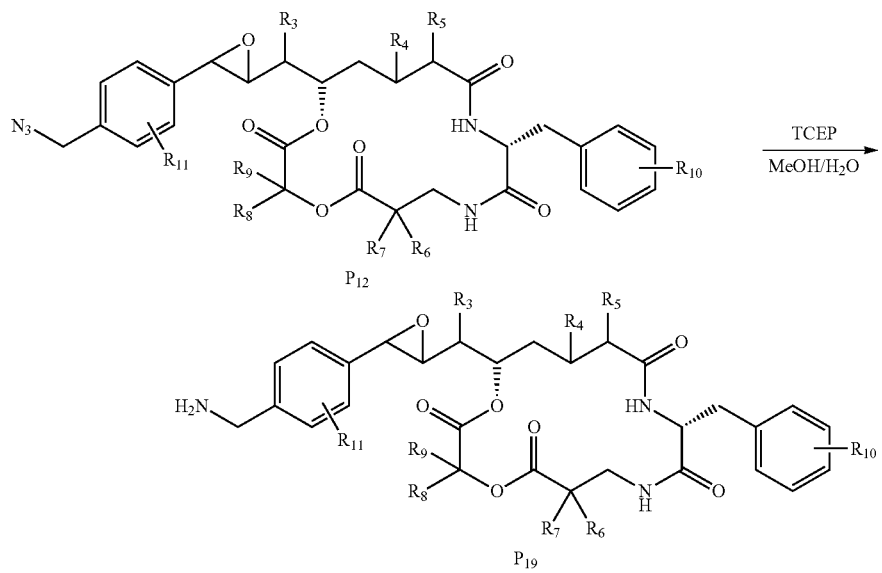

Starting with the group G=—CH$_2$N$_3$, the preparation of which is described in Scheme 3, the group G=—CH$_2$NH$_2$ may be obtained with the aid of a reduction reaction using a phosphine such as TCEP. In this respect, see: Faucher A.-M. et al., *Synthetic Comm.* 2003, 33, 3503-3511:

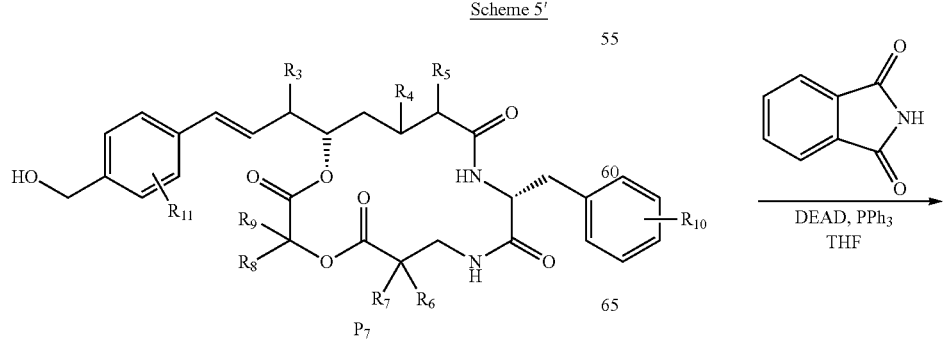

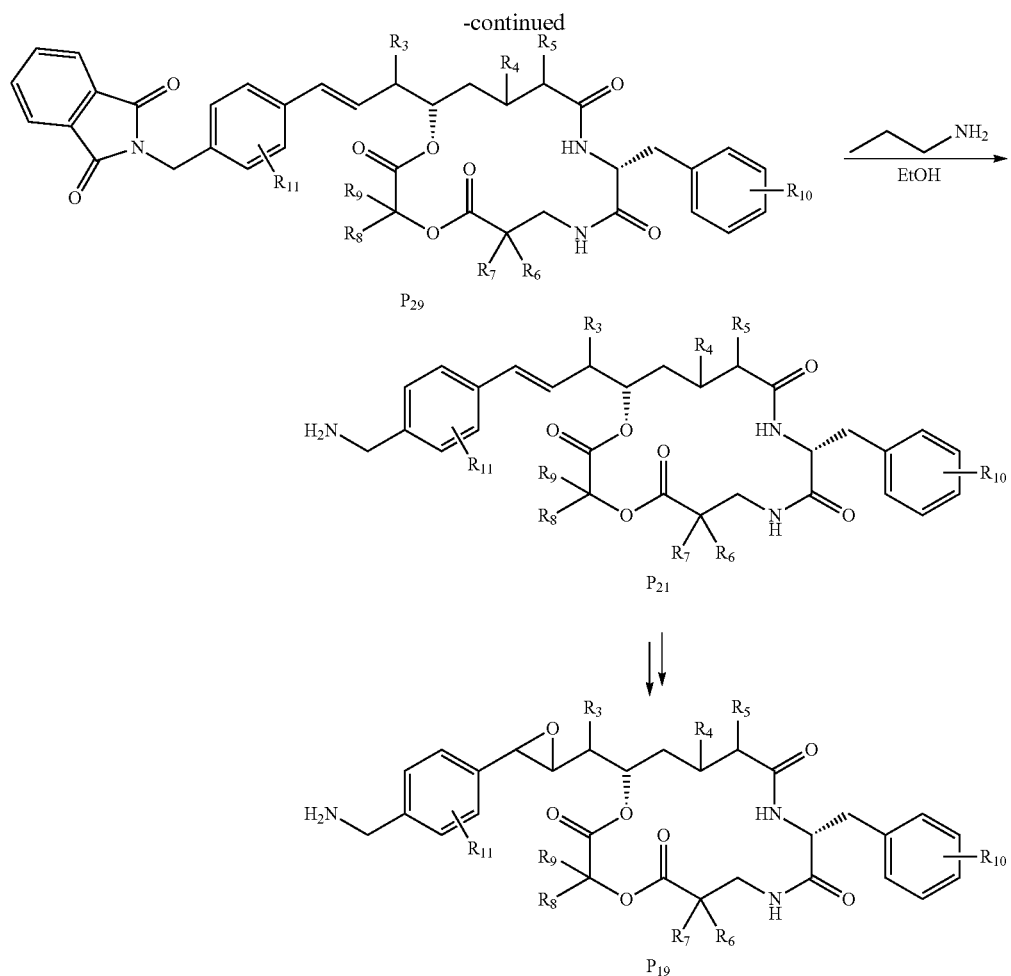

According to one variant, starting with the group G=—CH$_2$OH, the group G=—CH$_2$NH$_2$ may be obtained with the aid of a Mitsunobu reaction using triphenylphosphine and DEAD. In this respect, see: Mitsunobu O., *Synthesis* 1981, 1-28; Hughes D. L., Org. Reactions 1992, 42, 335-656; Hughes D. L., *Org. Prep.* 1996, 28, 127-164. Schemes 5 and 5' describe the case n=1, but they may also apply for n>1.

In the Case where G=—(CH$_2$)$_n$—NR$_{12}$—CH$_2$C≡CH

Starting with the group G=—(CH$_2$)$_n$Cl, the group G=—(CH$_2$)$_n$—NR$_{12}$—CH$_2$—C≡CH may be obtained with the aid of a nucleophilic substitution using the compound of formula NHR$_{12}$—CH$_2$—C≡CH(R$_{12}$=H: propargylamine; R$_{12}$=(C$_1$-C$_6$)alkyl: prepared according to Mock W. L., et al., *J. Org. Chem.* 1989, 54 (22), 5302-8).

In the Case where G=—(CH$_2$)$_n$—SH

Scheme 6

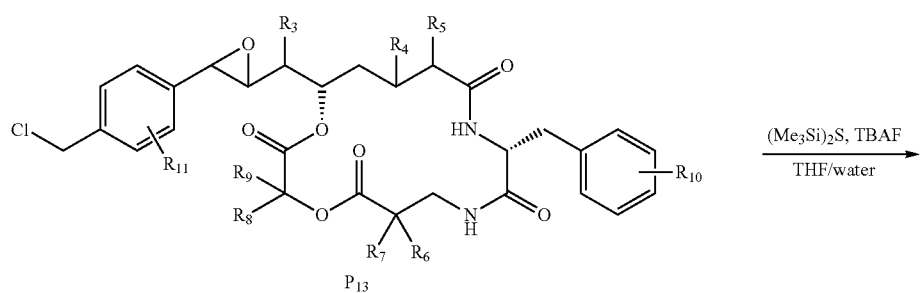

-continued

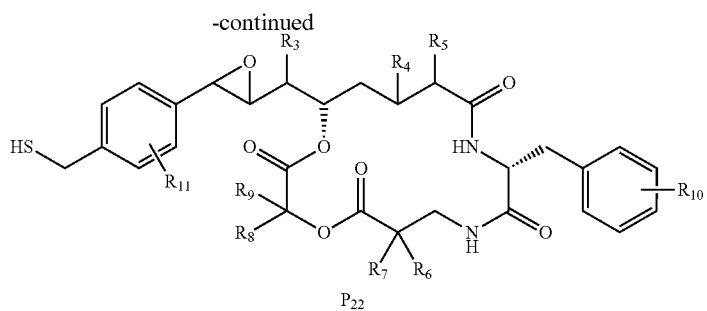

P22

Starting with the group G=—(CH$_2$)$_n$Cl, the group G=—(CH$_2$)$_n$SH may be obtained via a direct functionalization with the aid of tetrabutylammonium trimethylsilylthiolate prepared in situ from tetrabutylammonium fluoride and hexamethyldisilathiane according to Hu J. et al., *J. Org. Chem.* 1999, 64, 4959-4961 (see Ex. 8). Scheme 6 describes this reaction for the case n=1, but it may also apply for n>1. In the course of this reaction, the intermediate dimer having the formula below may be formed:

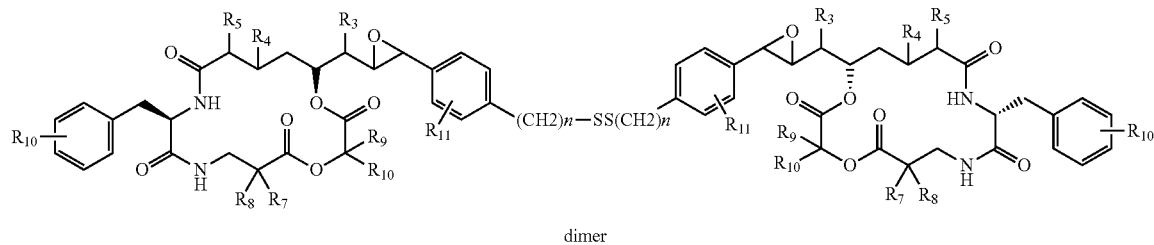

dimer

In the Case where G=-ALK-SH

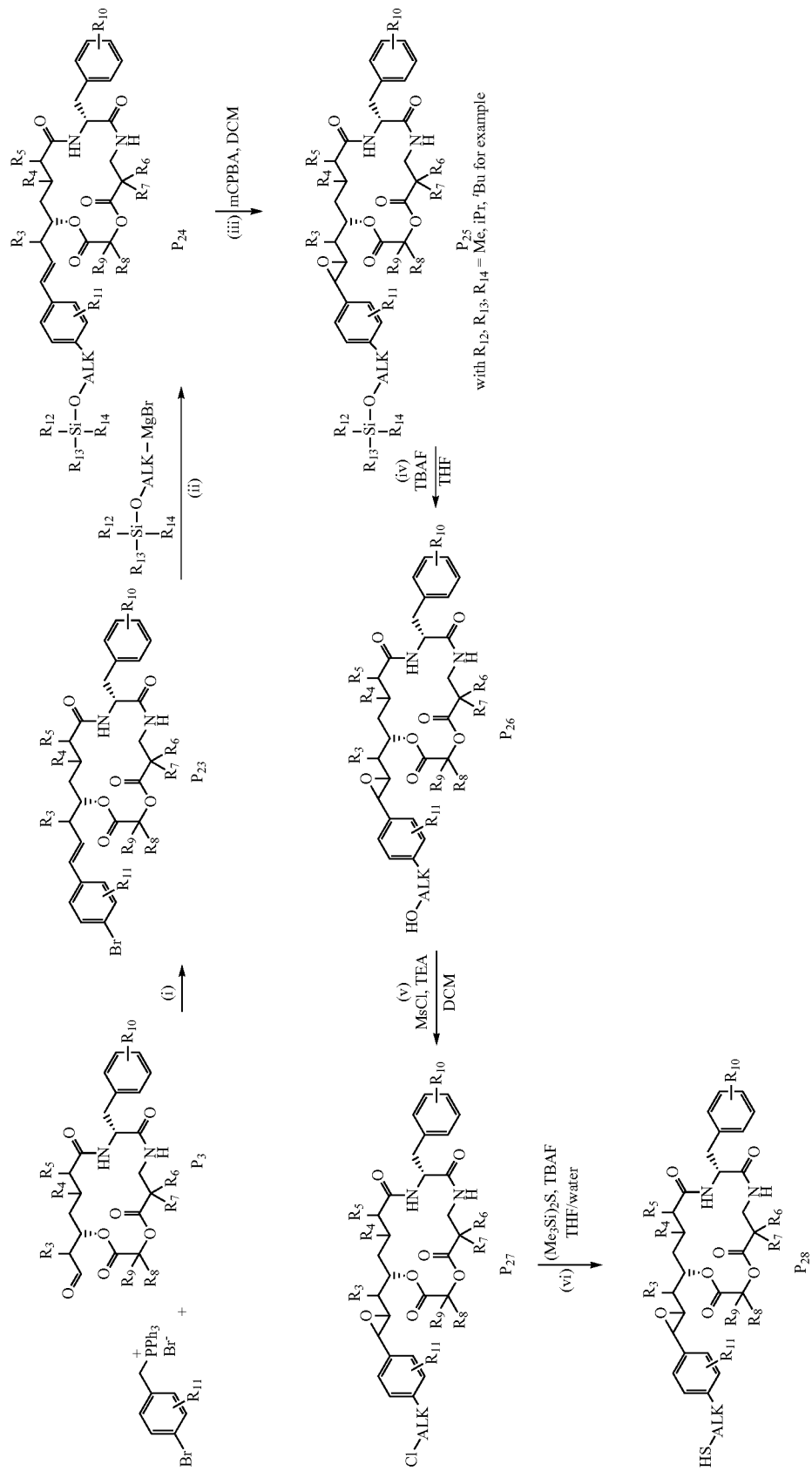

P₃ allows the preparation of other cryptophycin derivatives according to Scheme 7:

Step (i):
Wittig reaction using a suitable phosphonium halide, for example a bromide, and a strong base, for instance BuLi;

Step (ii):
Kumada coupling using a suitable Grignard reagent, for example an alkoxymagnesium bromide protected in silyl ether form, in the presence of a palladium or nickel catalyst (see, for example, *Organic Letters* 2009, 11, 5686-5689 or *Synthesis* 2009, 141, 2408-2412).

Steps (iii) to (v) are described in Scheme 2 and step (vi) is described in Scheme 6.

(4-Bromobenzyl)triphenylphosphonium bromide is a commercial product (CAS No. 51044-13-4). The alkoxymagnesium bromides protected in silyl ether form may be prepared from the corresponding bromo alcohols by protection of the alcohol function with the appropriate chlorosilane, followed by formation of the organomagnesium reagent in the presence of magnesium in an anhydrous polar aprotic solvent, for instance THF (see, for example, *Organic Letters* 2005, 7, 183-186). The linear or branched bromo alcohols containing 1 to 6 carbon atoms are commercially available, for instance 3-bromo-1-propanol (CAS No. 627-18-9) or 1-bromo-2-propanol (CAS No. 19686-73-8) or may be prepared from the corresponding bromo esters or bromo ketones according to methods described in the literature. The chlorosilane may be, for example, tert-butyldimethylchlorosilane (CAS No. 18162-48-6) or triisopropylchlorosilane (CAS No. 13154-24-0).

In the Case where G=—(CH₁)ₙ-maleimido may be obtained via a Mitsunobu reaction in the presence of triphenylphosphine and DEAD according to Matuszak N. et al., *J. Med. Chem.* 2009, 52, 7410-7420. Scheme 8 describes this reaction for the case n=1, but it may also apply for n>1.

Schemes 1-8

Above are given for a linker in the para position, but may identically apply for the ortho or meta positions. Similarly, they are given for a cryptophycin derivative, but may also apply to the preparation of other derivatives of formula (II), especially D₁-D₈.

More particularly, in the case of C-52, the following compounds may be used, the preparations of which are described in Al-awar R. S., et al., *J. Med. Chem.* 2003, 46, 2985-3007 or in WO 98/08505:

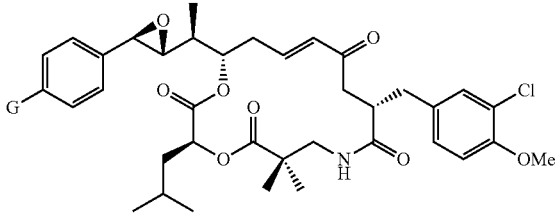

G=—CH₂OH: compound 31b of Scheme 5
G=—CH₂CH₂OH: compound 49 of Scheme 9
G=—CH₂COOH: compound 51 of Scheme 9 or Ex. 81 of WO 98/08505
G=—C(=O)H: Ex. 80 of WO 98/08505

Moreover, starting with compound 31b for which G=—CH₂OH, it is possible to obtain the compounds for which G=—CH₂Cl or —CH₂N₃:

Scheme 8

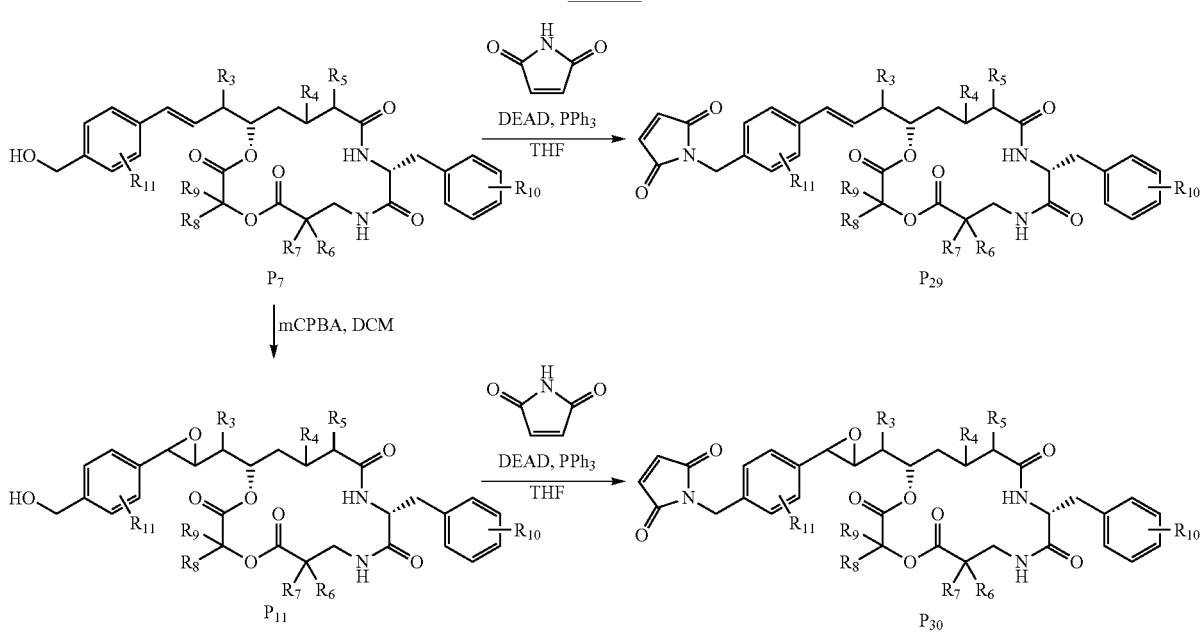

In addition to Scheme 1' which describes a method for preparing cryptophycin derivatives comprising a maleimido unit, starting with the group G=—CH₂OH, the group G=

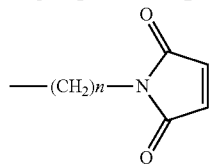

G=—CH₂Cl: see Example 1, compound 2;

G=—CH₂N₃: the conversion of —CH₂OH into —CH₂N₃ may be performed in a polar aprotic solvent in the presence of dipherlylphosphorazide and a base such as DBU, see Example 19, compound 60;

G=—CH₂-maleimido: the conversion of —CH₂OH into —CH₂-maleimido may be performed in a polar aprotic solvent in the presence of maleimide, triphenylphosphine and DEAD.

The teaching of *J. Med. Chem.* 2003, 46, 2985-3007 may apply to other cryptophycin derivatives comprising other substituents $R_6$-$R_9$.

Preparation of the Linker Precursors LP

LP may be one of the following:

$LP_1$

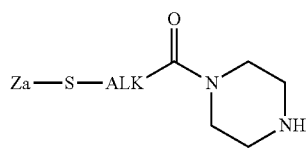

prepared according to the scheme below:

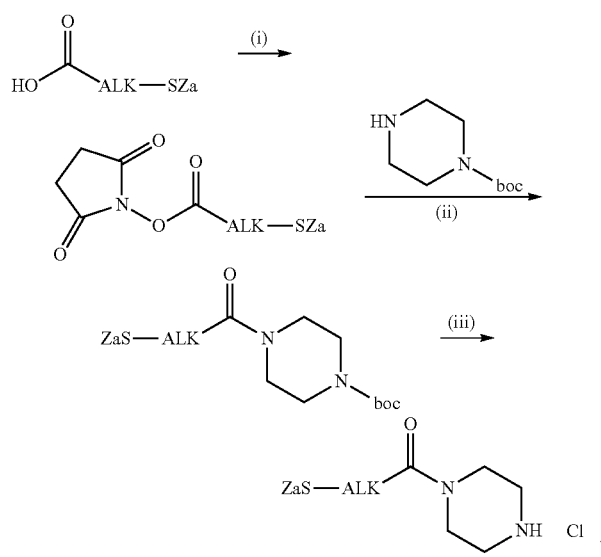

Step (i):

Activation of the acid using NHS; the activation is performed at RT in the presence of a coupling agent, for instance 1-(3-dimethylaminopropyl)-3-ethylcarbodiimide hydrochloride dissolved in an anhydrous aprotic solvent such as DCM. The procedure may be based on the conditions of Example 1, compound 4.

Step (ii):

Amidation with piperidine N-Boc; the peptide coupling is performed in a polar aprotic solvent at RT in the presence of a base, which may be a tertiary amine, for instance TEA or DIPEA. The solvent may be DMF. The procedure may be based on the conditions of Example 1, compound 5.

Step (iii):

Deprotection of the amine using an acid solution, for example hydrochloric acid (for example as a solution in dioxane). The procedure may be based on the conditions of Example 1, compound 6.

The starting acid, for example 4-methyl-4-(methyldithio)pentanoic acid, may be commercially available or prepared from a halocarboxylic acid by successive treatments with potassium thioacetate and a derivative of methanethiosulfonate type. See also U.S. Pat. No. 2,719,170.

$LP_2$

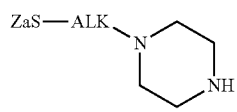

prepared according to the scheme below:

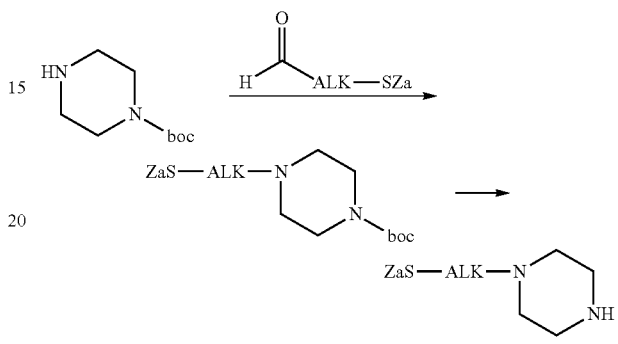

Step (i):

Reductive amination with an aldehyde; the reaction is performed at RT in an anhydrous polar aprotic solvent such as THF in two steps: formation of an intermediate complex in the presence of titanium isopropoxide followed by in situ reduction with a reducing agent, for instance sodium cyanoborohydride. The procedure may be based on the conditions of Example 5, compound 17.

Step (ii):

Deprotection of the amine with an acid solution, for example hydrochloric acid (for example as a solution in dioxane). The procedure may be based on the conditions of Example 5, compound 18.

The starting aldehyde, for example 2-methyl-2-(methyldithio)propanal, may be commercially available or prepared by oxidation of an alcohol bearing a disulfide unit obtained from a suitably protected halogenated alcohol (for example in silyl ether form) by successive treatments with potassium thioacetate and a derivative of methanethiosulfonate type.

$LP_3$ ZaS-ALK-$NHR_{12}$ prepared according to the schemes below:

In the Case where $R_{12}$=H

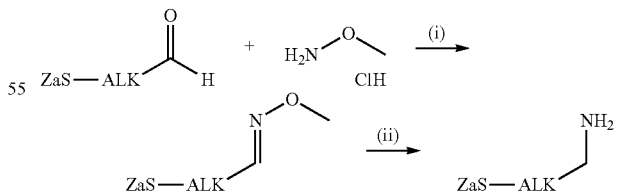

Step (i):

Formation of an oxime; the aldehyde described previously is dissolved in a polar protic solvent such as ethanol and then treated with O-methylhydroxylamine hydrochloride at reflux in the presence of a base such as sodium hydroxide. The procedure may be based on the conditions of Example 3, compound 11.

Step (ii):

Reduction of the oxime; the oxime is reduced via a treatment at reflux with a solution of borane-dimethyl sulfide in an anhydrous polar aprotic solvent such as THF. The procedure may be based on the conditions of Example 3, compound 12.

In the Case where $R_{12} \neq H$

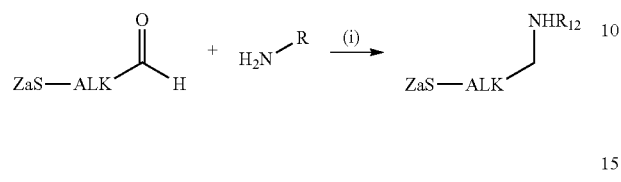

Step (i):

Reductive amination with an aldehyde; the reaction is performed at RT in an anhydrous polar aprotic solvent such as THF in the presence of a reducing agent, for instance sodium triacetoxyborohydride.

LP$_4$

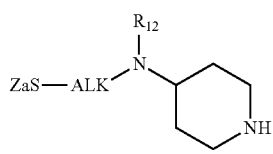

prepared according to the scheme below:

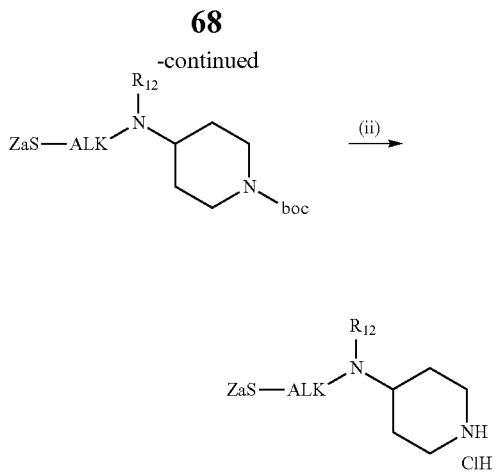

This linker is prepared in a similar manner to that presented for LP$_2$.

Step (i):

Reductive amination with an aldehyde; the reaction is performed at RT in an anhydrous polar aprotic solvent such as THF, in two steps: formation of an intermediate complex in the presence of titanium isopropoxide, followed by in situ reduction with a reducing agent such as sodium cyanoborohydride. The procedure may be based on the conditions of Example 5, compound 17.

Step (ii):

Deprotection of the amine with an acid solution, for example hydrochloric acid (for example in solution in dioxane). The procedure may be based on the conditions of Example 5, compound 18.

LP$_5$

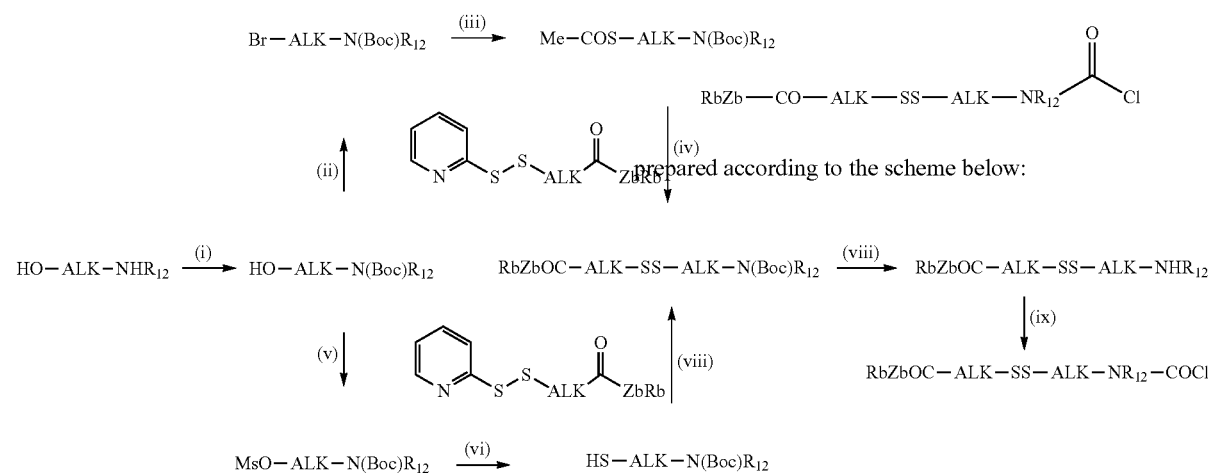

prepared according to the scheme below:

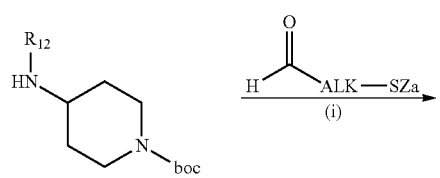

Step (i):

Protection of the amine; the reaction is performed at RT in a polar aprotic solvent such as DCM by treating the amine with di-tert-butyl dicarbonate in the presence of a base, for instance TEA.

Step (ii):

Conversion of the alcohol to a bromide; the reaction is performed at RT in a polar aprotic solvent such as THF, by treating the alcohol function with CBr$_4$ in the presence of a phosphine, for example triphenylphosphine; see in this respect Appel R. *Angew. Chem. Int. Ed. Engl.* 1975, 14, 801-811 or Desmaris N., et al., *Tetrahedron Letters* 2003, 44(41), 7589-7591.

Step (iii):

Substitution of the bromide with thioacetate; the reaction is performed at RT in an anhydrous polar aprotic solvent such as DMF, using potassium thioacetate as nucleophile.

Step (iv):

Formation of the disulfide bond; the reaction is performed in an anhydrous polar protic solvent such as methanol in the presence of a base, for instance sodium methoxide and a reagent comprising a pyridyl disulfide unit.

According to one variant:

Step (v):

Activation of the alcohol in mesylate form; the reaction is performed in an anhydrous polar aprotic solvent such as DCM by treatment with mesyl chloride in the presence of a base, for instance TEA.

Step (vi):

Formation of the free thiol; the reaction is performed in a refluxing polar protic solvent such as an ethanol/water mixture, in two successive steps: displacement of the mesylate with thiourea, followed by in situ hydrolysis of the isothiouronium salt by adding a base such as NaOH.

Step (vii):

Activation of the thiol in the form of pyridyl disulfide; the reaction is performed at RT in a polar protic solvent such as ethanol, by treatment with a reagent comprising a pyridyl disulfide unit in the presence of an acid such as acetic acid.

Step (viii):

Deprotection of the amine with an acid solution, for example hydrochloric acid (for example in solution in dioxane).

Step (ix):

Activation of the amine in the form of carbamoyl chloride; the reaction is performed in an anhydrous polar aprotic solvent such as DCM, by treatment with diphosgene in the presence of a base such as TEA.

$LP_6$ RbZb-OC-ALK-$(OCH_2CH_2)_i$—OH prepared according to the scheme below:

In the Case where ALK=$CH_2CH_2$

Route A:

Route B:

Step (i):

Deprotection with a solution of hydrochloric acid (for example solution in dioxane) or of trifluoroacetic acid.

Step (ii):

Protection of the carboxylic acid in allylic ester form; the reaction is performed at RT in a polar aprotic solvent such as DMF in the presence of allyl bromide and of a base such as potassium carbonate.

Step (iii):

Elongation of the PEG chain; the reaction is performed in an anhydrous polar aprotic solvent such as THF, by treatment of an unsaturated acid protected in ester form with the alkoxide generated by the action of sodium in catalytic amount.

In the Case where ALK≠$CH_2CH_2$

Step (iv):

Elongation of the PEG chain; the reaction is performed in an anhydrous polar aprotic solvent such as THF or DMF by treatment of a halogenated ester with the alkoxide of a PEG diol monoprotected in tetrahydropyran (THP) ether form. The preparation of this type of monoprotected PEG diol is well described in the literature: see, for example, Richard A. et al. *Chem. Eur. J.* 2005, 11, 7315-7321 or Sakellariou E. G., et al. *Tetrahedron* 2003, 59, 9083-9090. The PEG alcohols comprising an acid function protected in tert-butyl ester form are commercially available (for instance tert-butyl 12-hydroxy-4,7,10-trioxadodecanoate) or prepared from tert-butyl acrylate and a PEG diol. The starting PEG diols are commercially available for i=3 to 12.

$LP_7$ RbZbOC-ALK-$(OCH_2CH_2)_i$—$NHR_{12}$ prepared according to the schemes below:

In the Case where ALK=$CH_2CH_2$

In the Case where $R_{12}$=H

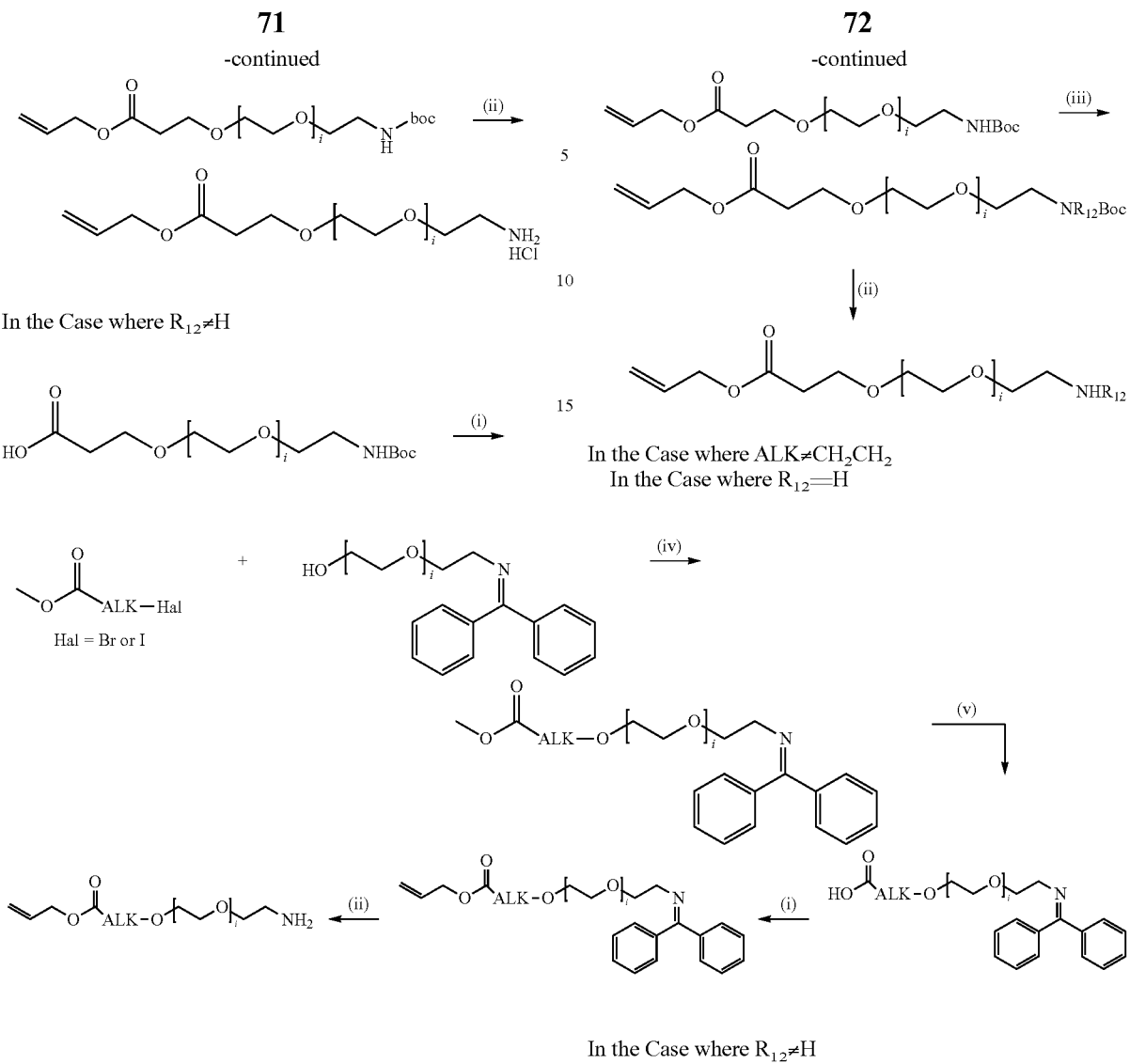

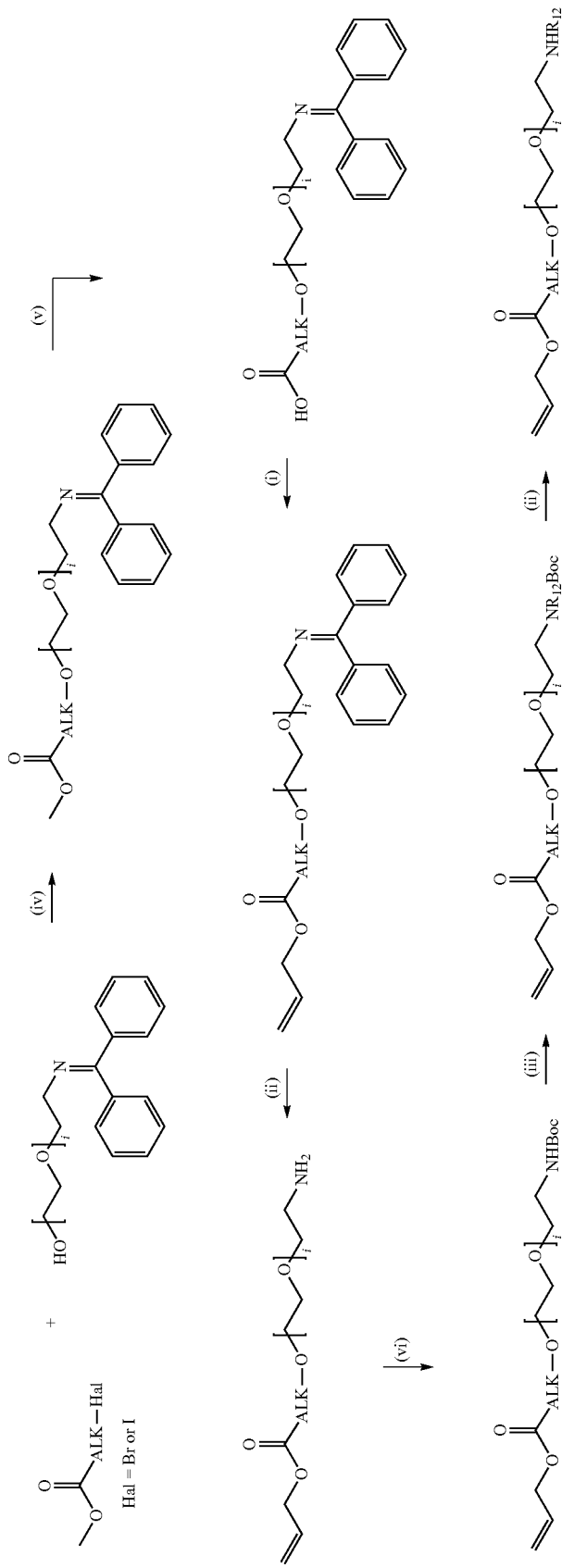

Step (i):
Protection of the carboxylic acid in allylic ester form; the reaction is performed at RT in a polar aprotic solvent such as DCM in the presence of allyl alcohol, a coupling agent such as EDCl and a base such as DMAP. The procedure may be based on the conditions of Example 14, compound 42.

Step (ii):
Deprotection using a solution of hydrochloric acid (for example solution in dioxane) or of trifluoroacetic acid. The procedure may be based on the conditions of Example 14, compound 43.

Step (iii):
Alkylation of the nitrogen atom; the reaction is performed in an anhydrous polar aprotic solvent such as THF by treatment with a base such as NaH in the presence of a reagent bearing a nucleofugal group such as an alkyl halide. The procedure may be based on the conditions of Example 15, compound 46.

Step (iv):
Elongation of the PEG chain; the reaction is performed in an anhydrous polar aprotic solvent such as THF or DMF by treatment of a halogenated ester with the alkoxide of a benzophenone-imine-PEG-alcohol generated via the action of NaH or potassium naphthalenide as described in WO 2007/127 440;

Step (v):
Saponification of the ester; the reaction is performed by reacting the ester with lithium hydroxide in the presence of water.

Step (vi):
Protection of the amine; the reaction is performed at RT in a polar aprotic solvent such as DCM by treating the amine with di-tert-butyl dicarbonate in the presence of a base, for instance TEA.

The amino-PEG-acids are commercially available for i=3, 5, 6, 10 or may be prepared from tert-butyl acrylate and the corresponding amino-PEG-alcohol.

The amino-PEG-alcohols are commercially available, for example for i=3, 4, 7, 8 or may be prepared from the PEG diols, which are commercially available for i=3 to 12, according to the procedure described in U.S. Pat. No. 7,230,101. The protection of the amine function with benzophenone may be performed by azeotropic dehydration in the presence of a Lewis acid such as BF$_3$ etherate.

LP$_8$

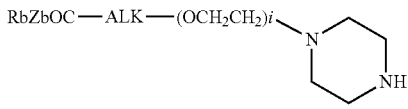

prepared according to the schemes below:

In the Case where ALK=CH$_2$CH$_2$

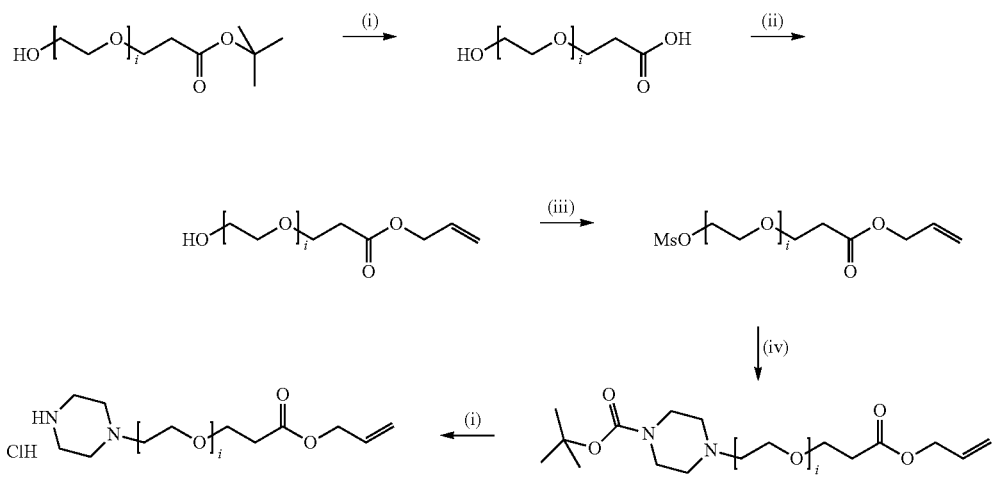

Step (i):
Deprotection of the starting compound using a solution of hydrochloric acid (for example solution in dioxane) or of trifluoroacetic acid. The procedure may be based on the conditions of Example 16, compound 50.

Step (ii):
Protection of the carboxylic acid function in allylic ester form; the reaction is performed at RT in a polar aprotic solvent such as DMF in the presence of allyl bromide and a base such as potassium carbonate. The procedure may be based on the conditions of Example 16, compound 51.

Step (iii):
Activation of the alcohol in mesylate form; the reaction is performed in an anhydrous polar aprotic solvent such as DCM by treatment with mesyl chloride in the presence of a base such as TEA.

Step (iv):
Reaction between the mesylate function and the amine function of the compound

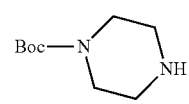

(alkylation); the reaction is performed at RT in an anhydrous polar aprotic solvent such as DCM in the presence of a base such as TEA. The procedure may be based on the conditions of Example 16, compound 52.

In the Case where ALK≠CH$_2$CH$_2$

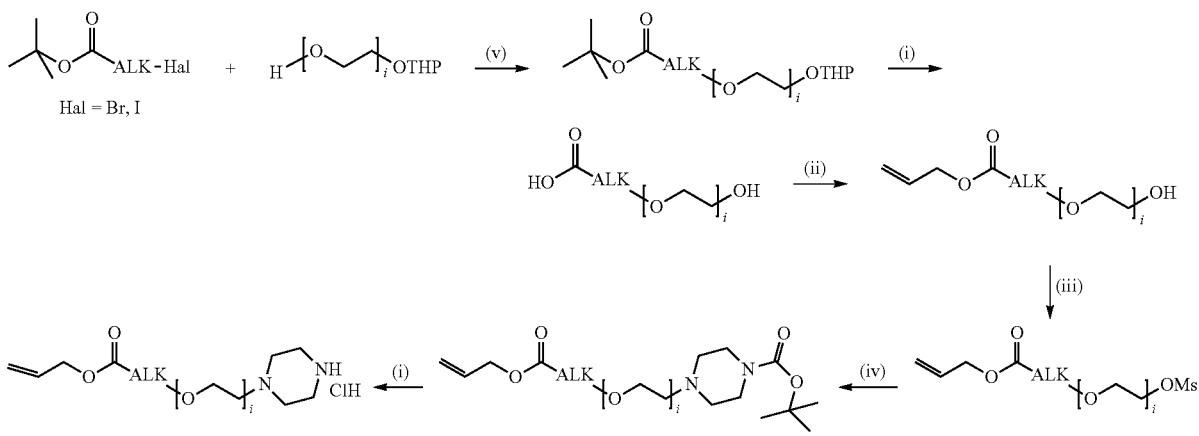

Step (v):

Elongation of the PEG chain; the reaction is performed in an anhydrous polar aprotic solvent such as THF or DMF by treatment of a halogenated ester with the alkoxide of a PEG diol monoprotected in tetrahydropyran (THP) ether form. The preparation of this type of monoprotected PEG diol is well described in the literature: see, for example, Richard A. et al. *Chem. Eur. J.* 2005, 11, 7315-7321 or Sakellariou E. G., et al. *Tetrahedron* 2003, 59, 9083-9090. The PEG alcohols comprising an acid function protected in tert-butyl ester form are commercially available (for instance tert-butyl 12-hydroxy-4,7,10-trioxadodecanoate) or prepared from tert-butyl acrylate and a PEG diol. The starting PEG diols are commercially available for i=3 to 12.

LP$_9$

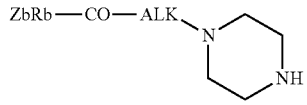

prepared according to the scheme below:

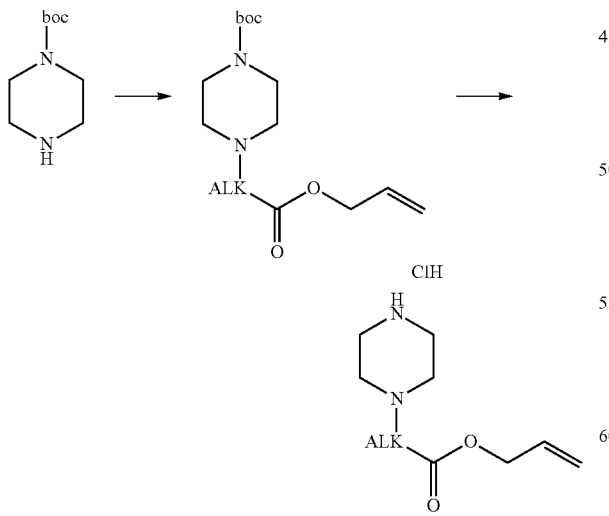

Step (i):

Alkylation of the amine; the reaction is performed in an anhydrous polar aprotic solvent such as acetonitrile with an allyl haloalkylcarboxylate, for instance allyl bromoacetate, in the presence of a base, for instance TEA. The procedure may be based on the conditions of Example 13, compound 38.

Step (ii):

Deprotection of the amine using an acid solution, for example hydrochloric acid (for example in solution in dioxane). The procedure may be based on the conditions of Example 13, compound 39.

The allyl haloalkylcarboxylate may be obtained from allyl alcohol and the corresponding haloacyl halide and is commercially available for ALK=—(CH$_2$)$_{1-6}$— (for instance bromoacetyl bromide or 4-butanoyl chloride).

LP$_{10}$

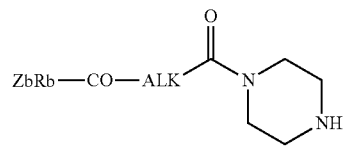

prepared according to the schemes below:

In the Case where ALK=CH$_2$CH$_2$

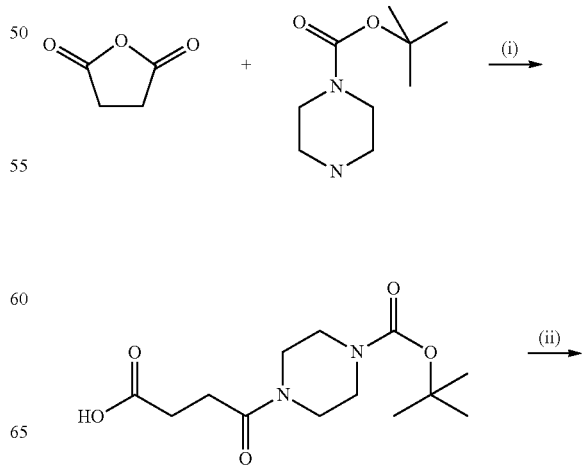

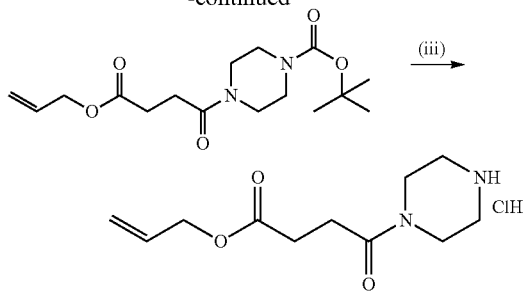

In the Case where ALK≠CH₂CH₂

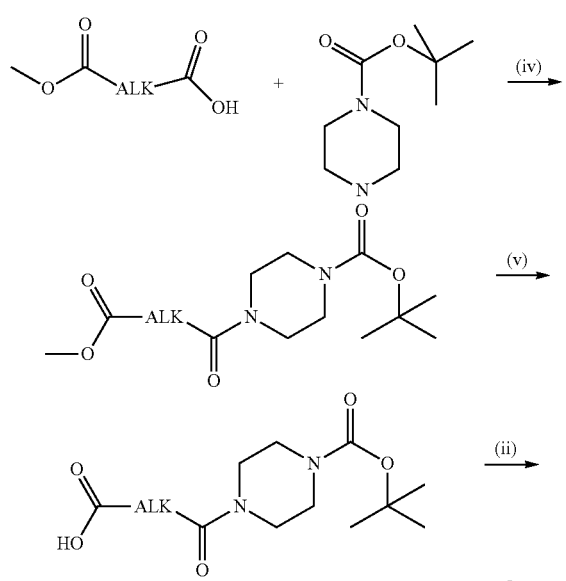

Step (i):
Opening of the cyclic anhydride; the reaction is performed at RT in an anhydrous polar aprotic solvent such as DCM in the presence of a base such as TEA.

Step (ii):
Protection of the carboxylic acid in allylic ester form; the reaction is performed at RT in a polar aprotic solvent such as DCM in the presence of allyl alcohol, a coupling agent such as EDCl and a base such as DMAP.

Step (iii):
Deprotection using a solution of hydrochloric acid (for example solution in dioxane).

Step (iv):
Peptide coupling; the reaction between the carboxylic acid and the amine is performed at RT in a polar aprotic solvent such as DCM in the presence of a coupling agent such as the DIC/HOBt system.

Step (v):
Saponification of the methyl ester; the reaction is performed at RT in a mixture of polar solvents such as a THF/water mixture in the presence of lithium hydroxide.

The diacids monoprotected in methyl ester form are commercially available for ALK=—(CH₂)₁₋₆-(such as the monomethyl ester of 1,6-hexanedioic acid).

$LP_{11}$

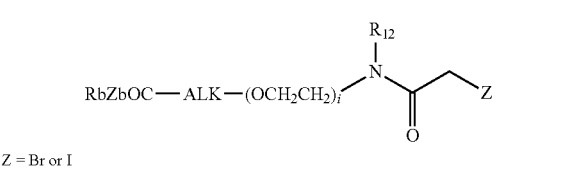

Z = Br or I prepared according to the schemes below:
In the Case where ALK=CH₂CH₂
In the Case where $R_{12}$=H

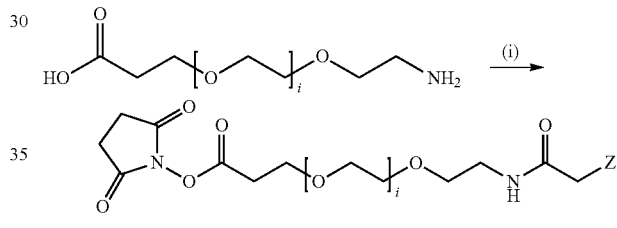

Z = Br or I

Step (i):
Formation of the amide and activation of the acid; the two steps are performed successively in a polar aprotic solvent such as DCM: reaction between the amine function and the N-hydroxysuccinimidyl haloacetate, followed by in situ addition of a coupling agent such as DIC. The procedure may be based on the conditions of Example 17, compound 56.

In the Case where $R_{12}$≠H

-continued

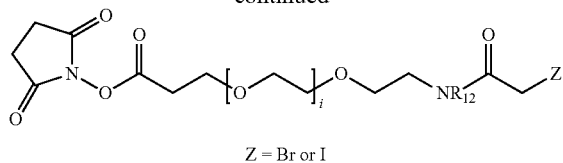

Z = Br or I

Step (ii):
Protections of the carboxylic acid in methyl ester form and of the amine in trifluoroacetamide form; the reaction is performed in two successive steps in a polar aprotic solvent such as DCM: protection of the acid by treatment with trimethylsilyldiazomethane in the presence of methanol, followed by protection of the amine by addition of trifluoroacetic anhydride and of a base such as TEA.

Step (iii):
Alkylation of the amine and saponification of the ester; the reaction is performed in two successive steps in an anhydrous polar aprotic solvent such as THF: alkylation of the amine by treatment with a base such as NaH in the presence of a reagent bearing a nucleofugal group, for instance an alkyl halide $R_{12}Hal$, followed by addition of lithium hydroxide and water.

Step (i):
Following step (iii), the reactions of step (i) for the case where $R_{12}$=H are repeated.

In the Case where ALK≠$CH_2CH_2$

In the Case where $R_{12}$=H

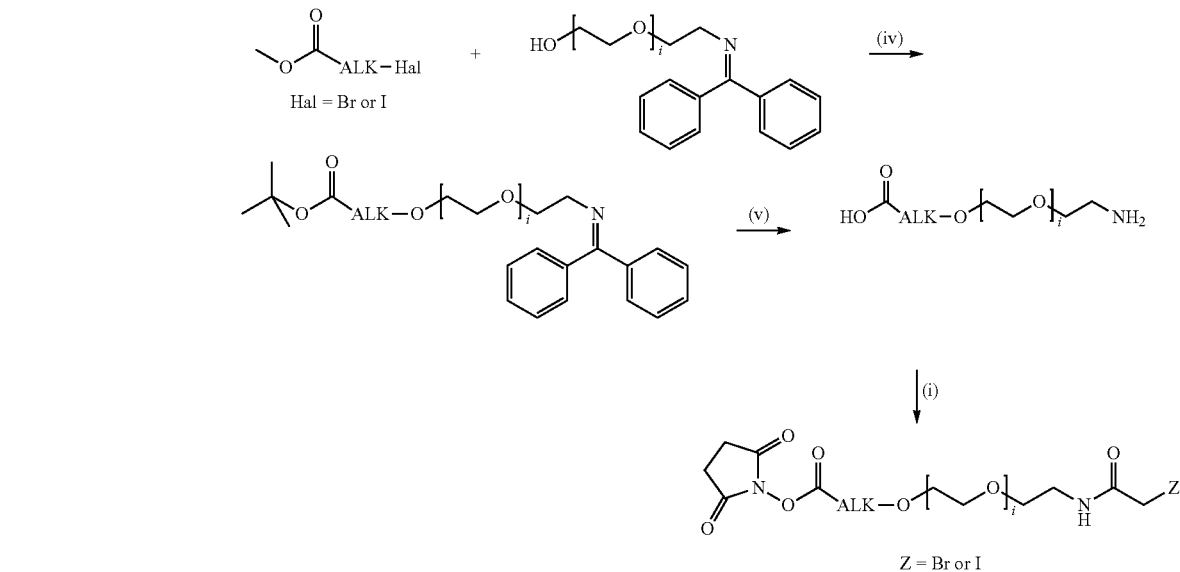

In the Case where $R_{12}$≠H

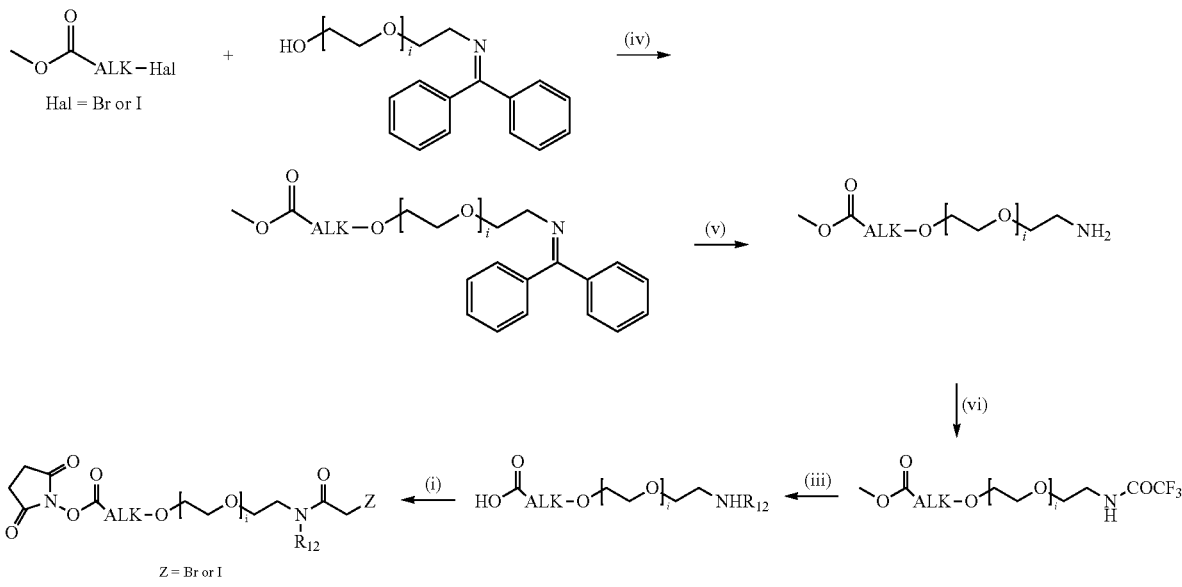

Step (iv):

Elongation of the PEG chain; the reaction is performed in an anhydrous polar aprotic solvent such as THF or DMF by treatment of a halogenated ester with the alkoxide of a benzophenone-imine-PEG-alcohol generated via the action of NaH or potassium naphthalenide (cf. WO 2007/127 440);

Step (v):

Selective cleavage of the imine by hydrogenation in the presence of palladium-on-charcoal (cf. Wessjohann, L. et al., Synthesis 1989, 5, 359-63);

Step (vi):

Protection of the amine by addition of trifluoroacetic anhydride and of a base such as TEA.

The amino-PEG-acids are commercially available for i=3, 5, 6, 10 or may be prepared from tert-butyl acrylate and the corresponding amino-PEG-alcohol.

The amino-PEG-alcohols are commercially available, for example for i=3, 4, 7, 8 or may be prepared from the PEG diols, which are commercially available for i=3 to 12, according to the procedure described in U.S. Pat. No. 7,230,101. The protection of the amine function with benzophenone may be performed by azeotropic dehydration in the presence of a Lewis acid such as $BF_3$ etherate.

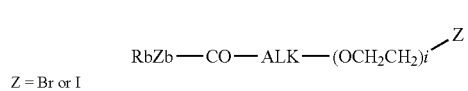

Z = Br or I

LP$_{12}$
prepared according to the schemes below:

In the Case where ALK=$CH_2CH_2$

Route A:

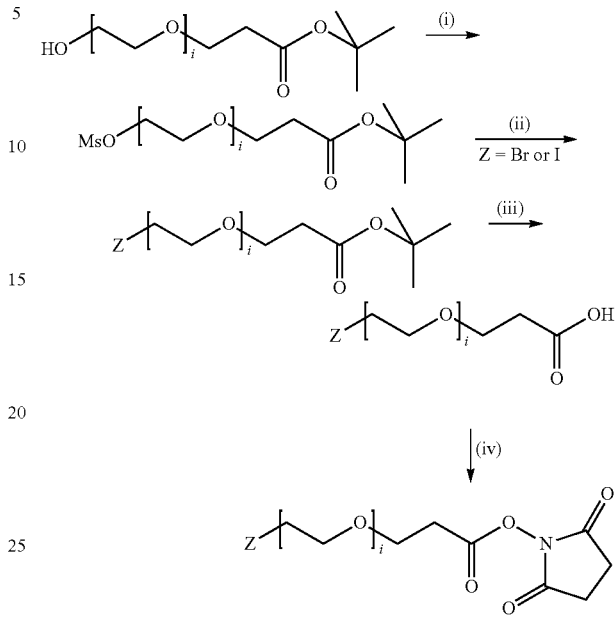

Route B:

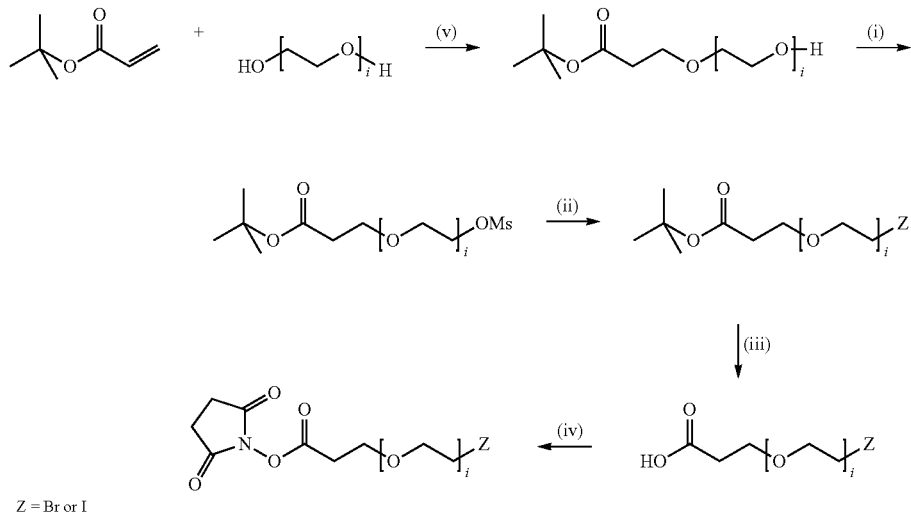

Z = Br or I

In the Case where ALK≠$CH_2CH_2$

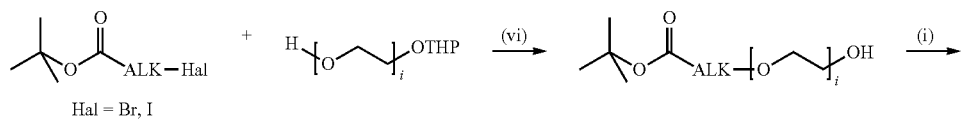

Hal = Br, I

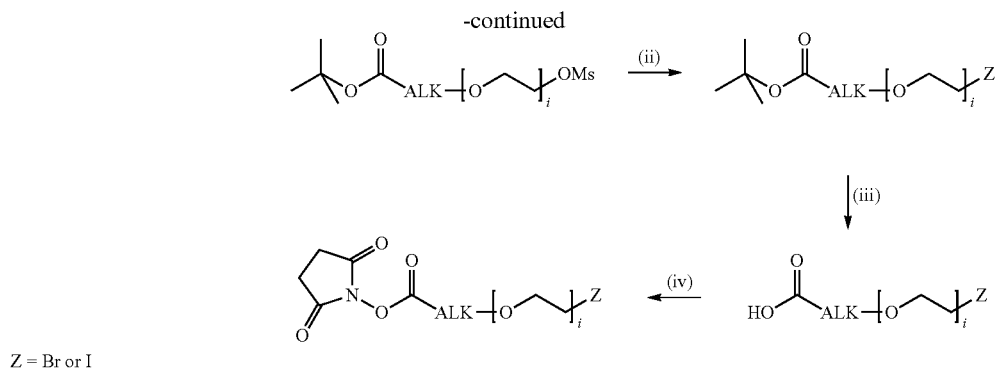

Z = Br or I

Step (i):
Activation of the alcohol in mesylate form; the reaction is performed in an anhydrous polar aprotic solvent such as DCM by treatment with mesyl chloride in the presence of a base such as TEA.

Step (ii):
Mesylate/halogen exchange; the reaction is performed in a refluxing polar aprotic solvent such as acetone, with a sodium halide such as sodium iodide.

Step (iii):
Deprotection using a solution of hydrochloric acid (for example solution in dioxane) or of trifluoroacetic acid.

Step (iv):
Activation of the acid; the reaction is performed at RT in a polar aprotic solvent such as DCM by treatment with NHS in the presence of a coupling agent such as DCC.

Step (v):
Elongation of the PEG chain; the reaction is performed in an anhydrous polar aprotic solvent such as THF by treatment of an unsaturated acid protected in ester form with the alkoxide generated by the action of sodium in catalytic amount.

Step (vi):
Elongation of the PEG chain; the reaction is performed in an anhydrous polar aprotic solvent such as THF or DMF by treatment of a halogenated ester with the alkoxide of PEG diol monoprotected as the tetrahydropyran (THP) ether. The preparation of this type of monoprotected PEG diol is well described in the literature: see, for example, Richard A. et al. *Chem. Eur. J.* 2005, 11, 7315-7321 or Sakellariou E. G., et al. *Tetrahedron* 2003, 59, 9083-9090. The intermediate formed is selectively hydrolysed at pH 5 to the hydroxy ester.

The PEG alcohols comprising an acid function protected in tert-butyl ester form are commercially available (for instance tert-butyl 12-hydroxy-4,7,10-trioxadodecanoate) or prepared from tert-butyl acrylate and a PEG diol. The starting PEG diols are commercially available for i=3 to 12.

$LP_{13}$ RbZb-CO-ALK-$(OCH_2CH_2)i$-SH prepared according to the schemes below:
In the Case where ALK=$CH_2CH_2$
Route A:

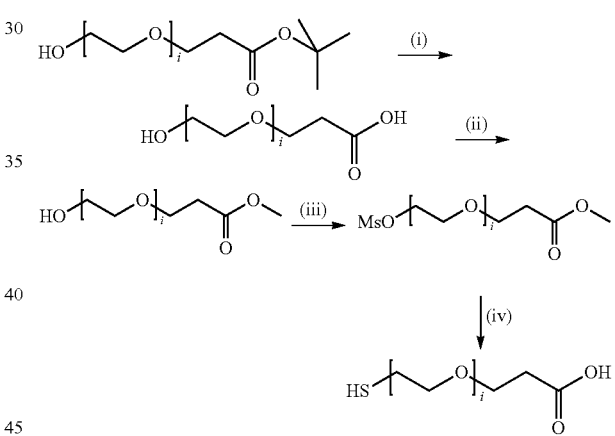

Route B:

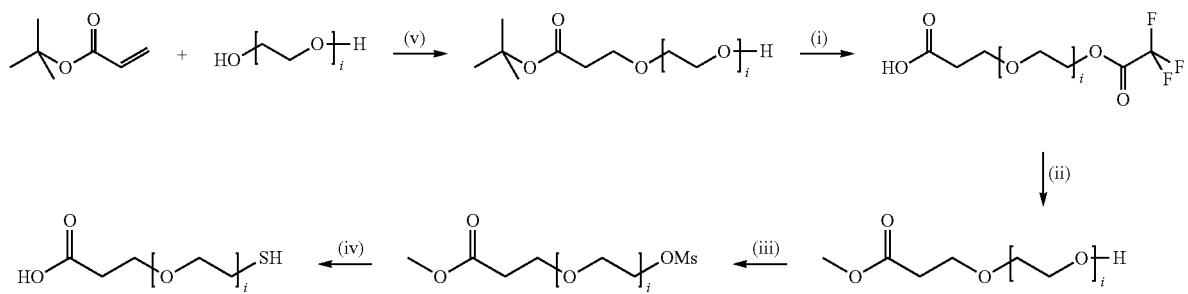

In the Case where ALK≠$CH_2CH_2$

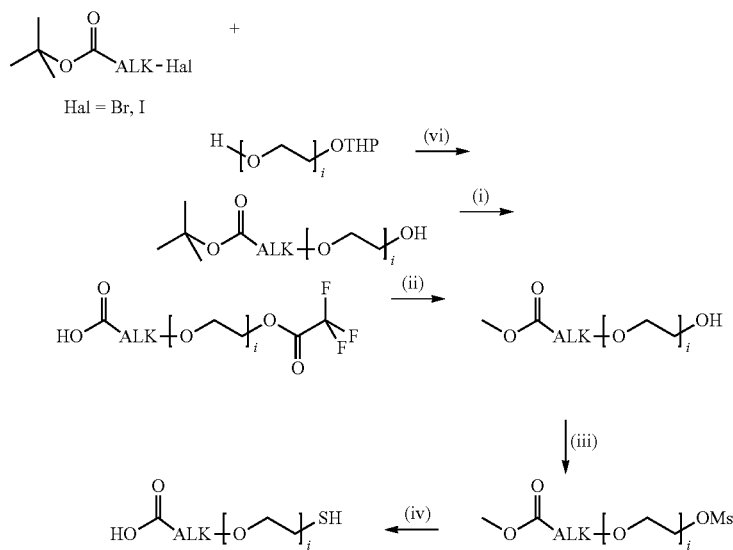

Step (i):
Deprotection using a solution of hydrochloric acid (e.g. solution in dioxane) or of trifluoroacetic acid. In the latter case, trifluoroacetate of the hydroxy function may be formed. It is cleaved during the following step (ii).

Step (ii):
Protection of the carboxylic acid in methyl ester form; the reaction is performed at RT in a polar aprotic solvent such as methanol, by treatment with trimethylsilyldiazomethane.

Step (iii):
Activation of the alcohol in mesylate form; the reaction is performed in an anhydrous polar aprotic solvent such as DCM by treatment with mesyl chloride in the presence of a base such as TEA.

Step (iv):
Formation of the free thiol and saponification of the methyl ester; the reaction is performed in a refluxing polar protic solvent, such as an ethanol/water mixture, in two successive steps: displacement of the mesylate with thiourea, followed by in situ hydrolysis of the isothiouronium salt by addition of a base such as sodium hydroxide.

Step (v):
Elongation of the PEG chain; the reaction is performed in an anhydrous polar aprotic solvent such as THF by treatment of an unsaturated acid protected in ester form with the alkoxide generated by the action of sodium in catalytic amount.

Step (vi):
Elongation of the PEG chain; the reaction is performed in an anhydrous polar aprotic solvent such as THF or DMF by treatment of a halogenated ester with the alkoxide of the PEG diol monoprotected as the tetrahydropyran (THP) ether. The preparation of this type of monoprotected PEG diol is well known in the literature: see, for example, Richard A. et al. *Chem. Eur. J.* 2005, 11, 7315-7321 or Sakellariou E. G., et al. *Tetrahedron* 2003, 59, 9083-9090. The linker with n=8 (3-[2-mercaptoethoxyhepta(ethyleneoxy)]propionic acid) is commercially available. The PEG alcohols comprising an acid function protected in tert-butyl ester form are commercially available (for instance tert-butyl 12-hydroxy-4,7,10-trioxa-dodecanoate) or prepared from tert-butyl acrylate and a PEG diol. The starting PEG diols are commercially available for $i=3$ to 12.

$LP_{14}$

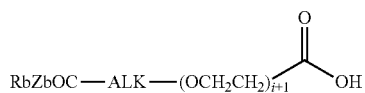

prepared according to the scheme below:
In the Case where ALK=$CH_2CH_2$

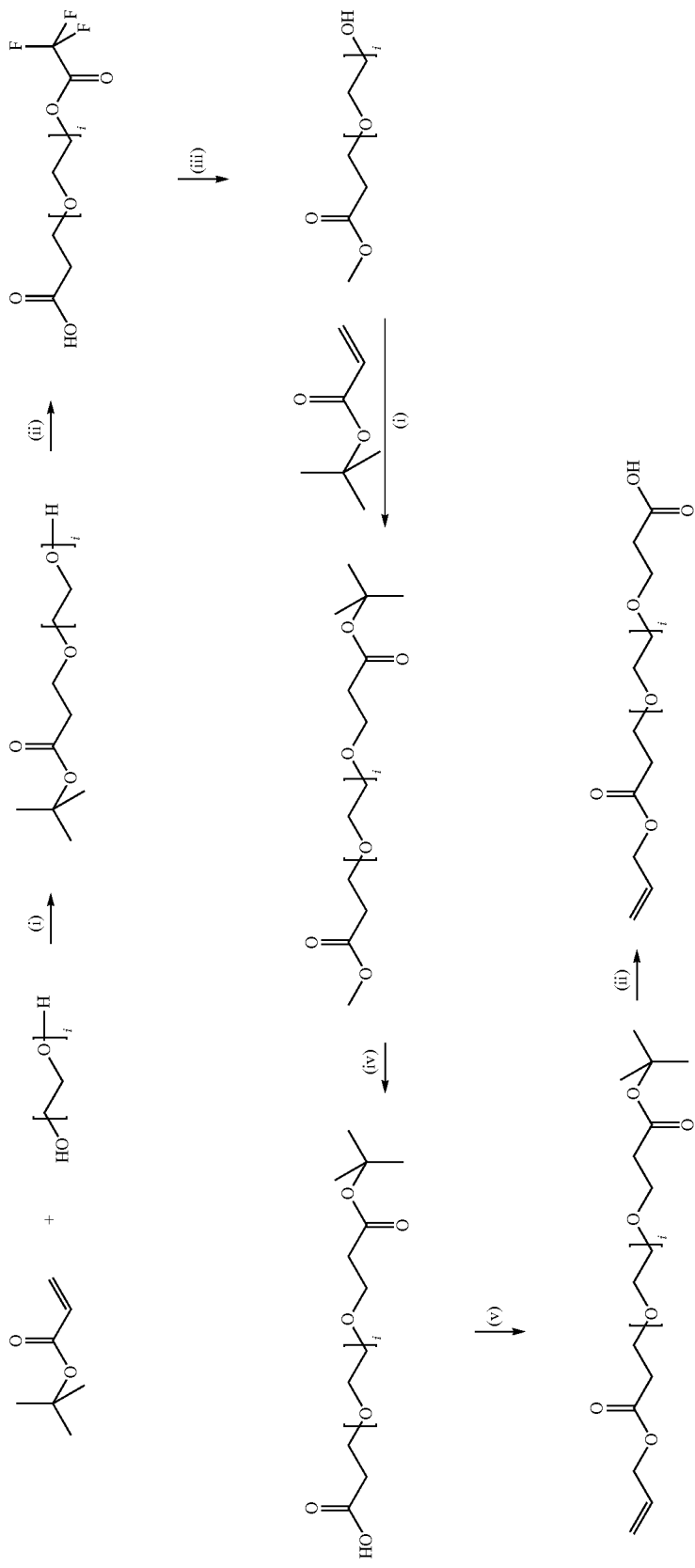

In the Case where ALK≠CH$_2$CH$_2$

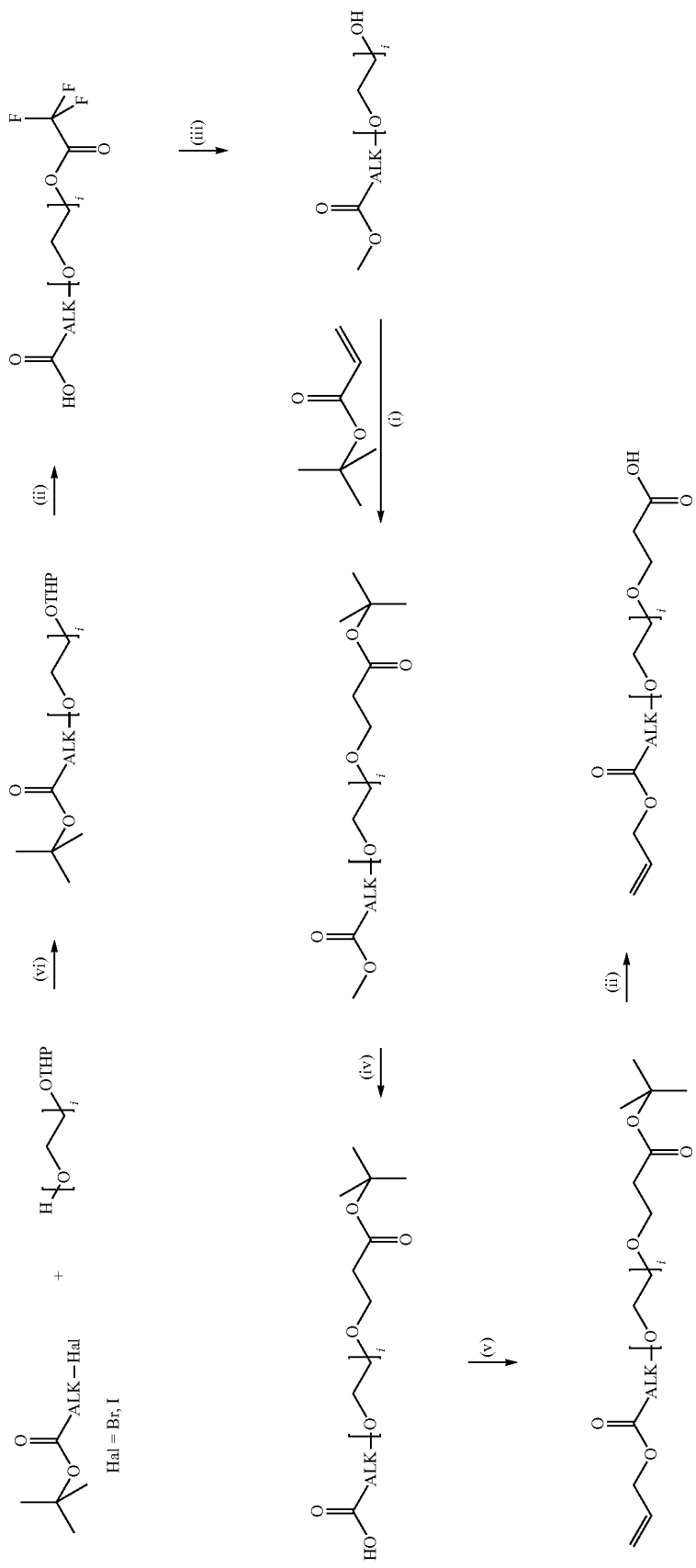

Step (i):
Elongation of the PEG chain; the reaction is performed in an anhydrous polar aprotic solvent, such as THF, by treatment of an unsaturated acid protected in ester form with the alkoxide generated by the action of sodium in catalytic amount.

Step (ii):
Deprotection using a solution of hydrochloric acid (for example solution in dioxane) or of trifluoroacetic acid. In the latter case, trifluoroacetate of the alcohol function optionally present on the structure may be formed. This trifluoroacetate is cleaved during the following step (iii).

Step (iii):
Protection of the carboxylic acid in methyl ester form; the reaction is performed at RT in a polar aprotic solvent such as methanol, by treatment with trimethylsilyldiazomethane.

Step (iv):
Saponification of the methyl ester; the reaction is performed at RT in a mixture of polar solvents such as a THF/water mixture in the presence of lithium hydroxide.

Step (v):
Protection of the carboxylic acid in allyl ester form; the reaction is performed at RT in a polar aprotic solvent such as DCM in the presence of allyl alcohol, a coupling agent such as EDCl and a base such as DMAP.

Step (vi):
Elongation of the PEG chain; the reaction is performed in an anhydrous polar aprotic solvent such as THF or DMF by treatment of a halogenated ester with the alkoxide of the PEG diol monoprotected as the tetrahydropyran (THP) ether. The preparation of this type of monoprotected PEG diol is well described in the literature: see, for example, Richard A. et al. *Chem. Eur. J.* 2005, 11, 7315-7321 or Sakellariou E. G., et al. *Tetrahedron* 2003, 59, 9083-9090.

The starting PEG diols are commercially available for i=3 to 12.

LP$_{15}$

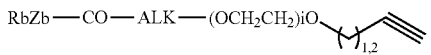

prepared according to the schemes below:

In the Case where ALK=CH$_2$CH$_2$

Route A:

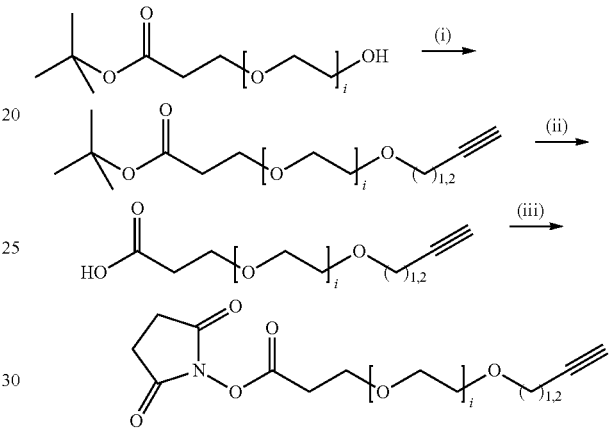

Route B:

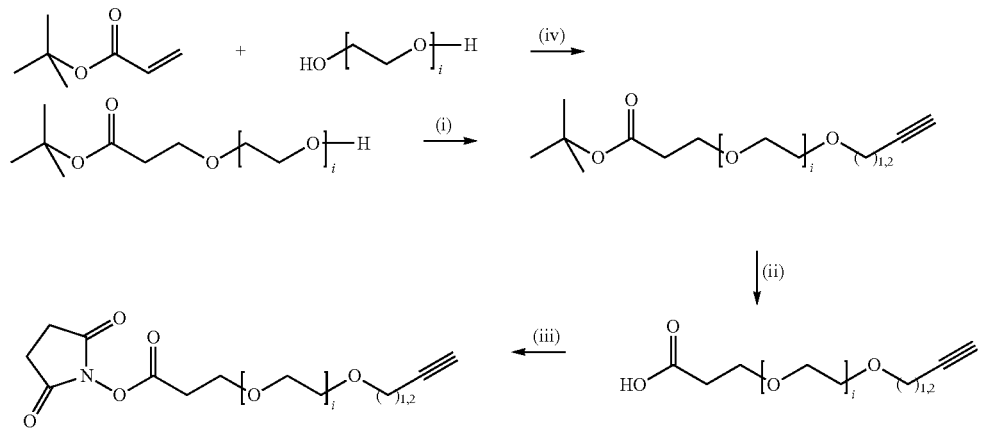

In the Case where ALK≠CH$_2$CH$_2$

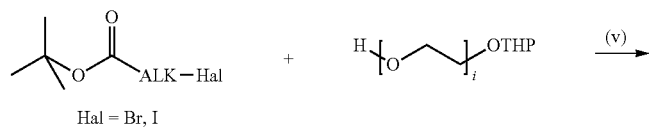

Hal = Br, I

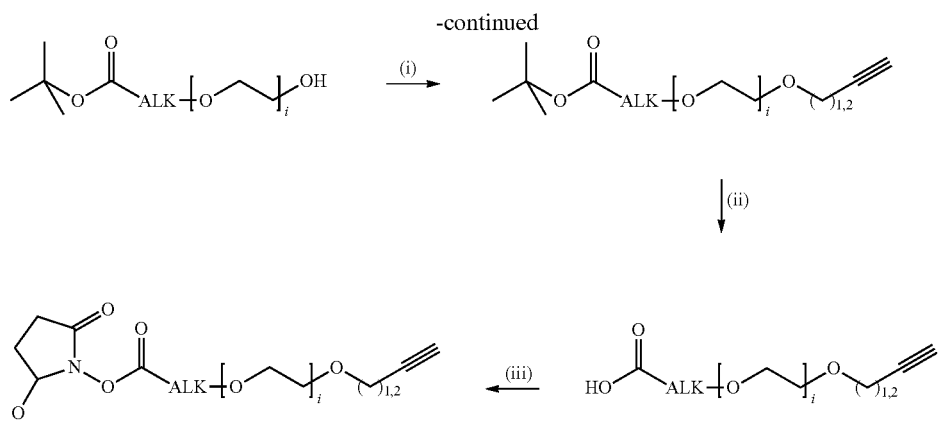

Step (i):

Nucleophilic substitution; the reaction is performed in an anhydrous polar aprotic solvent such as THF, in the presence of a base such as NaH and of an alkynyl halide such as propargyl bromide or 4-bromo-1-butyne. The procedure may be based on the conditions of Example 20, compound 63.

Step (ii):

Deprotection using a solution of hydrochloric acid (for example solution in dioxane) or of trifluoroacetic acid. The procedure may be based on the conditions of Example 20, compound 65.

Step (iii):

Activation of the carboxylic acid in NHS ester form; the reaction is performed at RT in a polar aprotic solvent such as DCM by treatment with NHS in the presence of a coupling agent such as supported DCC.

Step (iv):

Elongation of the PEG chain; the reaction is performed in an anhydrous polar aprotic solvent such as THF by treatment of an unsaturated acid protected in ester form with the alkoxide generated by the action of sodium in catalytic amount. The procedure may be based on the conditions of Example 20, compound 64.

Step (v):

Elongation of the PEG chain; the reaction is performed in an anhydrous polar aprotic solvent such as THF or DMF by treatment of a halogenated ester with the alkoxide of the PEG diol monoprotected as the tetrahydropyran (THP) ether. The preparation of this type of monoprotected PEG diol is well described in the literature: see, for example, Richard A. et al. *Chem. Eur. J.* 2005, 11, 7315-7321 or Sakellariou E. G., et al. *Tetrahedron* 2003, 59, 9083-9090.

The PEG alcohols comprising an acid function protected in tert-butyl ester form are commercially available (for instance tert-butyl 12-hydroxy-4,7,10-trioxadodecanoate) or prepared from tert-butyl acrylate and a PEG diol. The starting PEG diols are commercially available for i=3 to 12.

$LP_{16}$

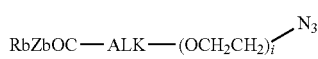

prepared according to the schemes below:

In the Case where $ALK = CH_2CH_2$

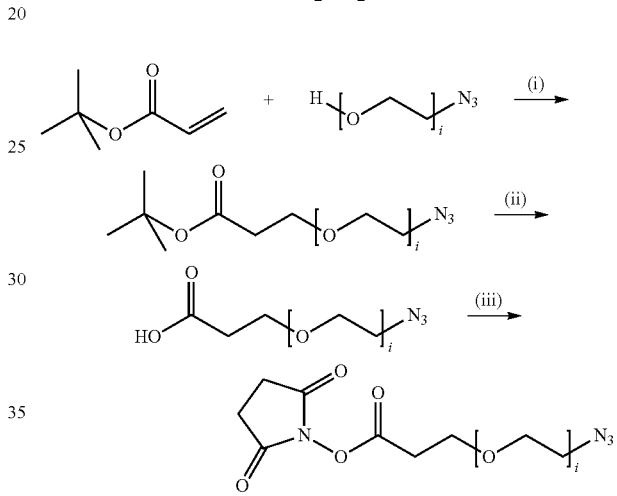

In the Case where $ALK \neq CH_2CH_2$

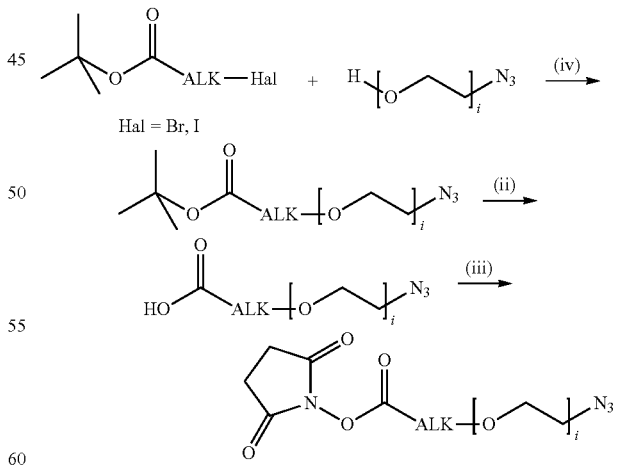

Step (i):

Elongation of the PEG chain; the reaction is performed in an anhydrous polar aprotic solvent such as THF by treatment of an unsaturated acid protected in ester form with the alkoxide generated by the action of sodium in catalytic amount.

Step (ii):

Deprotection using a solution of hydrochloric acid (for example solution in dioxane) or of trifluoroacetic acid.

Step (iii):

Activation of the carboxylic acid in NHS ester form; the reaction is performed at RT in a polar aprotic solvent such as DCM by treatment with NHS in the presence of a coupling agent such as supported DCC.

Step (iv):

Elongation of the hydroxyazido PEG chain; the reaction is performed in an anhydrous polar aprotic solvent such as THF or DMF by treatment of a halogenated ester with the alkoxide of hydroxyazido PEG.

The azido PEG alcohols are commercially available or may be prepared from the corresponding PEG alcohols that are commercially available for i=3 to 12.

$LP_{17}$

RbZb—CO—ALK≡ prepared according to the scheme below:

Step (i):

Activation of the carboxylic acid in NHS ester form; the reaction is performed at RT in a polar aprotic solvent such as DCM by treatment with NHS in the presence of a coupling agent such as supported DCC.

The acids bearing an acetylenic group are commercially available for ALK=—$(CH_2)_m$— with m=1 to 10 (for instance 3-butynoic acid).

$LP_{18}$

RbZb—CO—ALK—$N_3$ prepared according to the scheme below:

Hal = Cl, Br, I

Step (i):

Nucleophilic substitution of the halide by the azide; the reaction is performed in a polar aprotic solvent such as acetone, in the presence of sodium azide.

Step (ii):

Saponification of the methyl ester; the reaction is performed at RT in a mixture of polar solvents such as a THF/water mixture in the presence of lithium hydroxide.

Step (iii):

Activation of the carboxylic acid in NHS ester form; the reaction is performed at RT in a polar aprotic solvent such as DCM by treatment with NHS in the presence of a coupling agent such as supported DCC.

The methyl esters bearing a haloalkyl unit are commercially available for ALK=—$(CH_2)_m$— with m=1 to 6 (for instance methyl bromoacetate).

$LP_{19}$

RbZb—CO—ALK—$(OCH_2CH_2)iO$— prepared according to the schemes below:

In the Case where ALK=$CH_2CH_2$

Route A:

Route B:

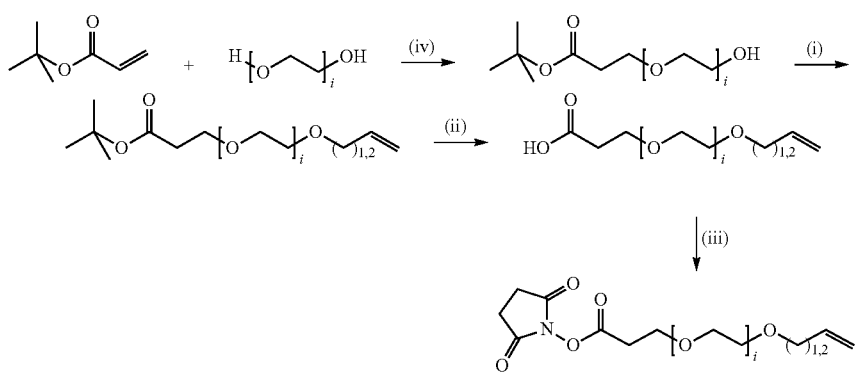

In the Case where ALK≠CH$_2$CH$_2$

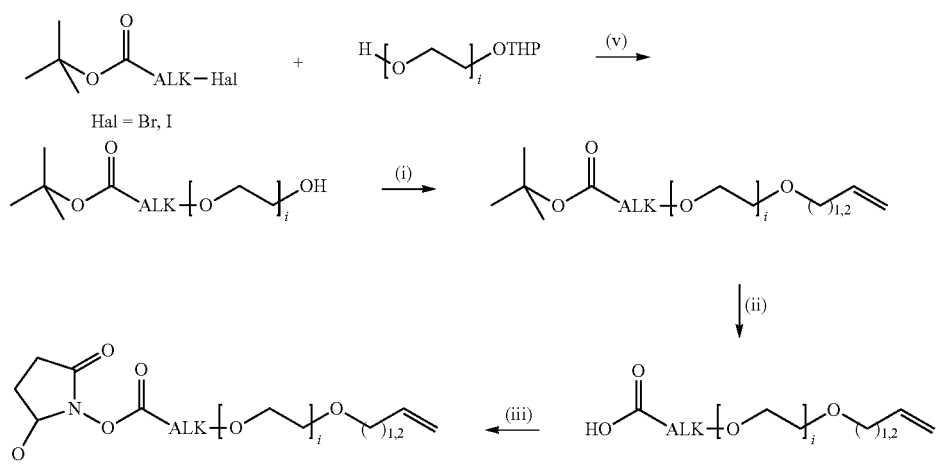

Step (i):
Nucleophilic substitution; the reaction is performed in an anhydrous polar aprotic solvent such as THF in the presence of a base such as NaH and of an alkenyl halide such as allyl bromide or 4-bromo-1-butene.

Step (ii):
Deprotection using a solution of hydrochloric acid (for example solution in dioxane) or of trifluoroacetic acid.

Step (iii):
Activation of the carboxylic acid in NHS ester form; the reaction is performed at RT in a polar aprotic solvent such as DCM by treatment with NHS in the presence of a coupling agent such as supported DCC.

Step (iv):
Elongation of the PEG chain; the reaction is performed in an anhydrous polar aprotic solvent such as THF by treatment of an unsaturated acid protected in ester form with the alkoxide generated by the action of sodium in catalytic amount.

Step (v):
Elongation of the PEG chain; the reaction is performed in an anhydrous polar aprotic solvent such as THF or DMF by treatment of a halogenated ester with the alkoxide of the PEG diol monoprotected as the tetrahydropyran (THP) ether. The preparation of this type of monoprotected PEG, diol is well described in the literature: see, for example, Richard A. et al. Chem. Eur. J. 2005, 11, 7315-7321 or Sakellariou E. G., et al. Tetrahedron 2003, 59, 9083-9090. The PEG alcohols comprising an acid function protected in tert-butyl ester form are commercially available (for instance tert-butyl 12-hydroxy-4,7,10-trioxadodecanoate) or prepared from tert-butyl acrylate and a PEG diol. The starting PEG diols are commercially available for i=3 to 12.

LP$_{20}$

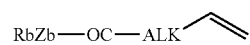

prepared according to the scheme below:

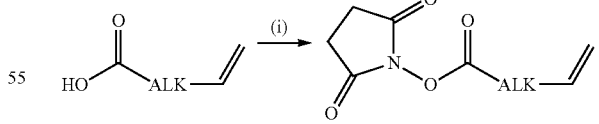

Step (i):
Activation of the carboxylic acid in NHS ester form; the reaction is performed at RT in a polar aprotic solvent such as DCM by treatment with NHS in the presence of a coupling agent such as supported DCC.

The acids bearing an ethylenic group are commercially available for ALK=—(CH$_2$)$_m$— with m=1 to 10 (for instance 3-butenoic acid).

LP$_{21}$  ZaS-ALK-CH$_2$—NR$_{12}$—(CH$_2$CH$_2$O)$_i$—CH$_2$CH$_2$—NHR'$_{12}$ prepared according to the schemes below:

In the Case where $R_{12}$ and $R'_{12}=H$
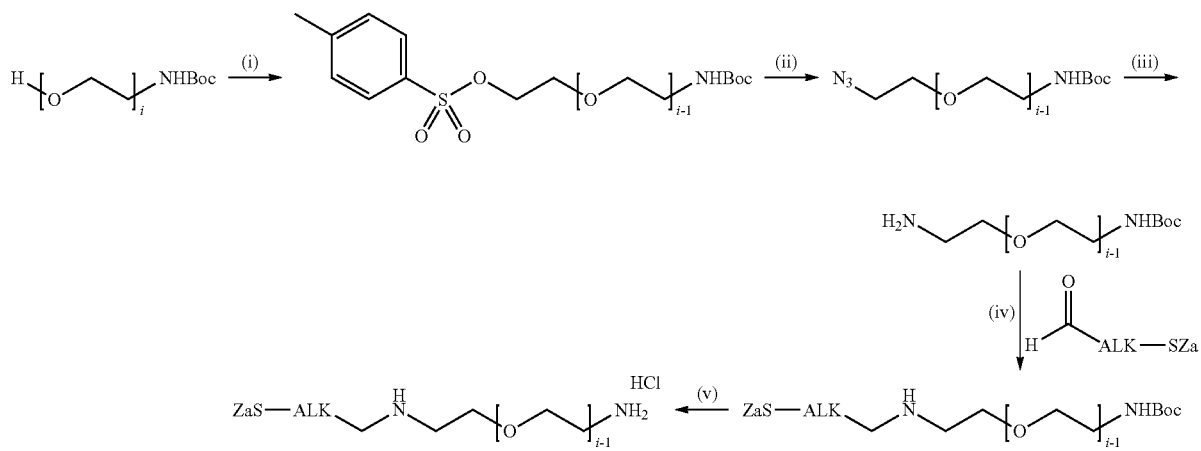
In the Case where $R_{12} \neq H$ and $R'_{12}=H$
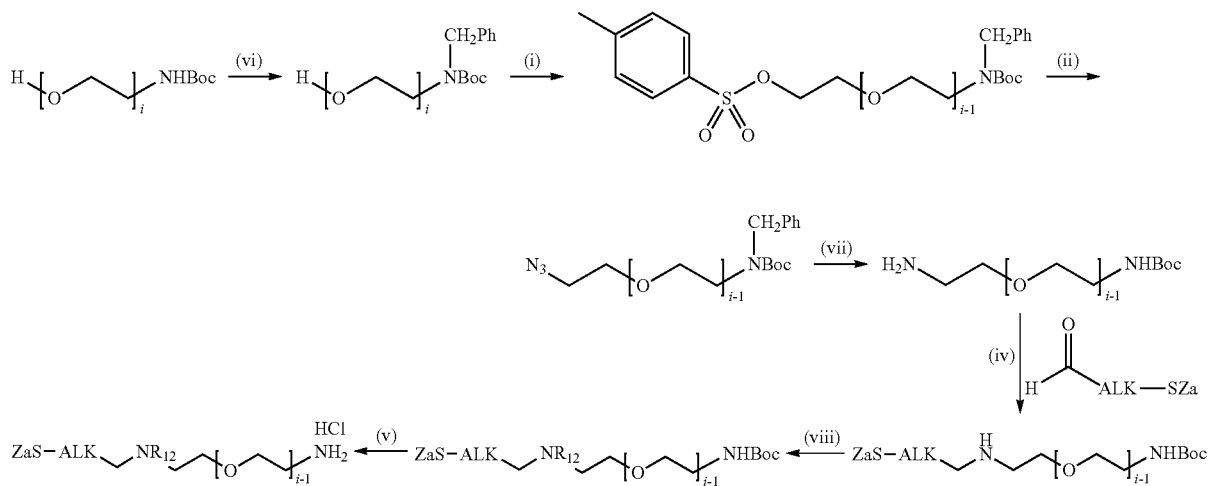
In the Case where $R_{12}=H$ and $R'_{12} \neq H$
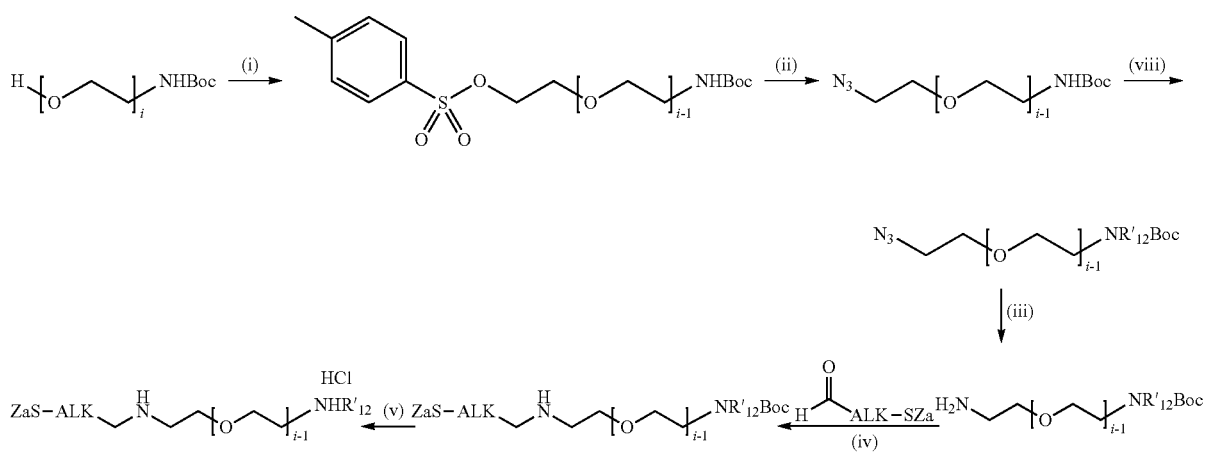

In the Case where $R_{12}$ and $R'_{12} \neq H$

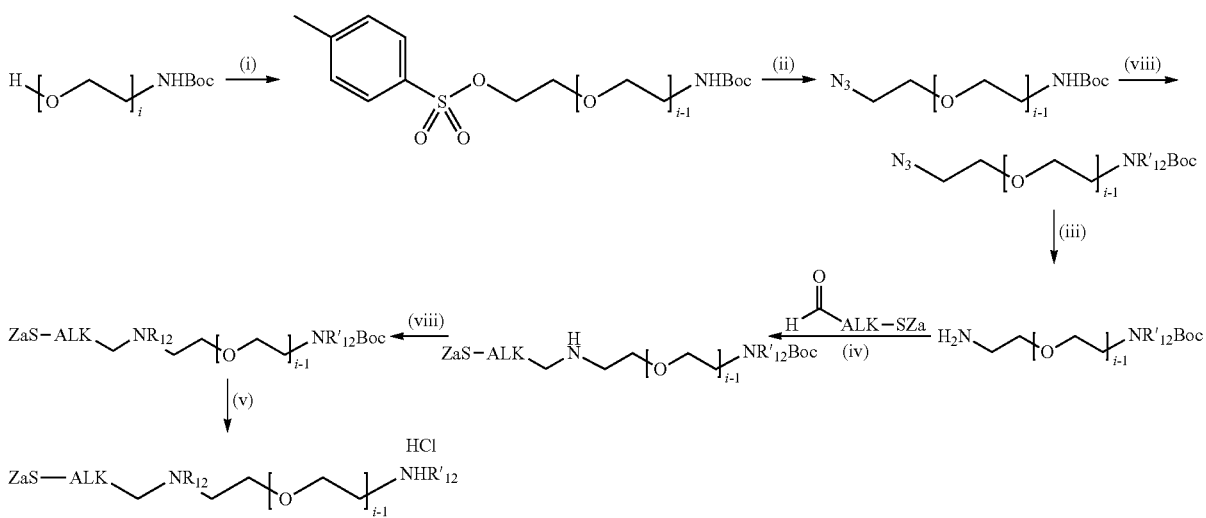

Step (i):
Activation of the alcohol in tosylate form; the reaction is performed in a polar aprotic solvent such as DCM by treatment with tosyl chloride in the presence of silver oxide and potassium iodide. The procedure may be based on the conditions of Example 6, compound 23.

Step (ii):
Nucleophilic substitution of the tosylate; the reaction is performed in a polar aprotic solvent such as acetonitrile by treatment with sodium azide. The procedure may be based on the conditions of Example 6, compound 24.

Step (iii):
Reduction of the azide; the reaction is performed in a polar solvent such as a THF/water mixture in the presence of triphenylphosphine. The procedure may be based on the conditions of Example 6, compound 26.

Step (iv):
Reductive amination with an aldehyde; the reaction is performed at RT in an anhydrous polar aprotic solvent such as DCM in the presence of a reducing agent such as sodium triacetoxyborohydride and, if necessary, acetic acid as catalyst. The procedure may be based on the conditions of Example 6, compound 27.

Step (v):
Deprotection using a solution of hydrochloric acid (for example solution in dioxane) or of trifluoroacetic acid. The procedure may be based on the conditions of Example 6, compound 29.

Step (vi):
Protection of the NHBoc function; the reaction is performed in a polar aprotic solvent such as THF or DMF by treatment with 1 equivalent of base such as sodium hydride, followed by a benzyl halide such as benzyl chloride.

Step (vii):
Cleavage of the benzyl group and reduction of the azido function; the reaction is performed in a protic solvent such as methanol with hydrogen in the presence of a catalyst such as palladium hydroxide.

Step (viii):
Alkylation of the amine; the reaction is performed in an anhydrous polar aprotic solvent such as THF by treatment with a base such as sodium hydride in the presence of a reagent bearing a nucleofugal group such as an alkyl halide. The procedure may be based on the conditions of Example 6, compound 25.

The amino-PEG-alcohols optionally protected with a Boc group on the amine function are commercially available (for instance N-Boc-aminoethoxyethoxyethanol or 1-amino-3,6,9-trioxaundecanyl-11-ol) or may be prepared from PEG diols, which are commercially available for i=3 to 12, according to the procedure described in U.S. Pat. No. 7,230,101. The aldehyde ZaSS-ALK-CHO, for example 2-methyl-2-(methyldithio)propanal, is commercially available or may be prepared by oxidation of an alcohol bearing a disulfide unit obtained from a suitably protected halogenated alcohol (for example in silyl ether form) by successive treatments with potassium thioacetate and a derivative of methanethiosulfonate type.

$LP_{22}$

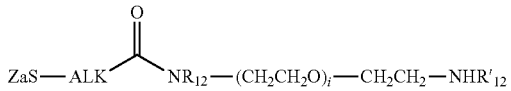

prepared according to the schemes below:
In the Case where $R_{12}$ and $R'_{12} = H$

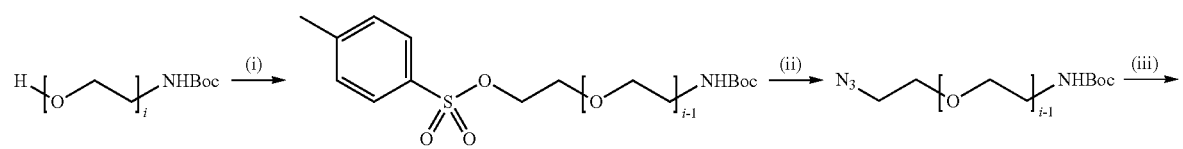

-continued
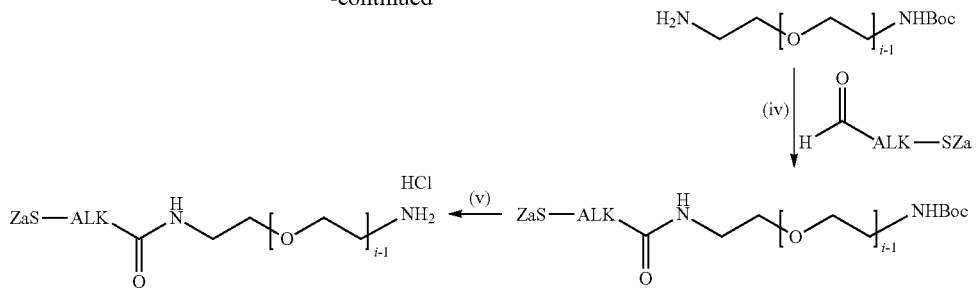
In the Case where $R_{12} \neq H$ and $R'_{12} = H$
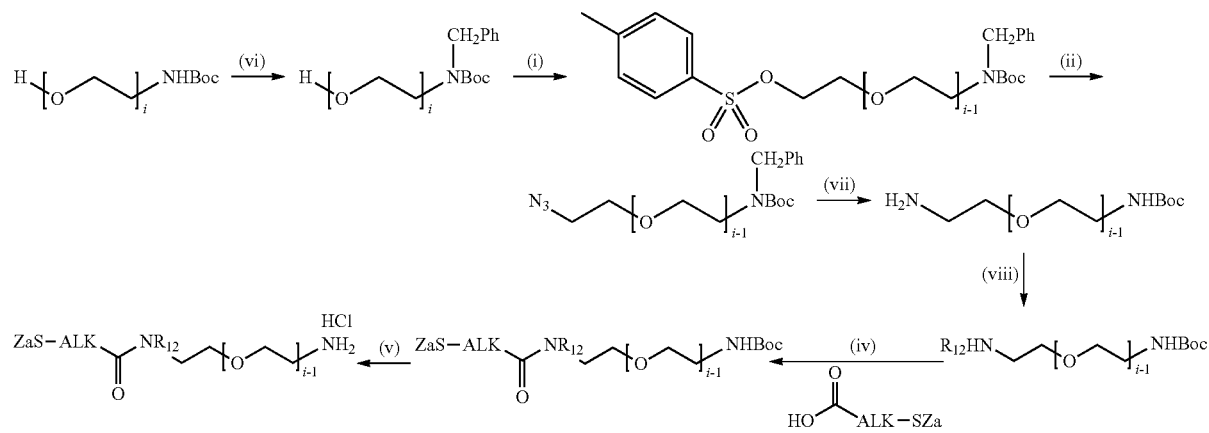
In the Case where $R_{12} = H$ and $R'_{12} \neq H$
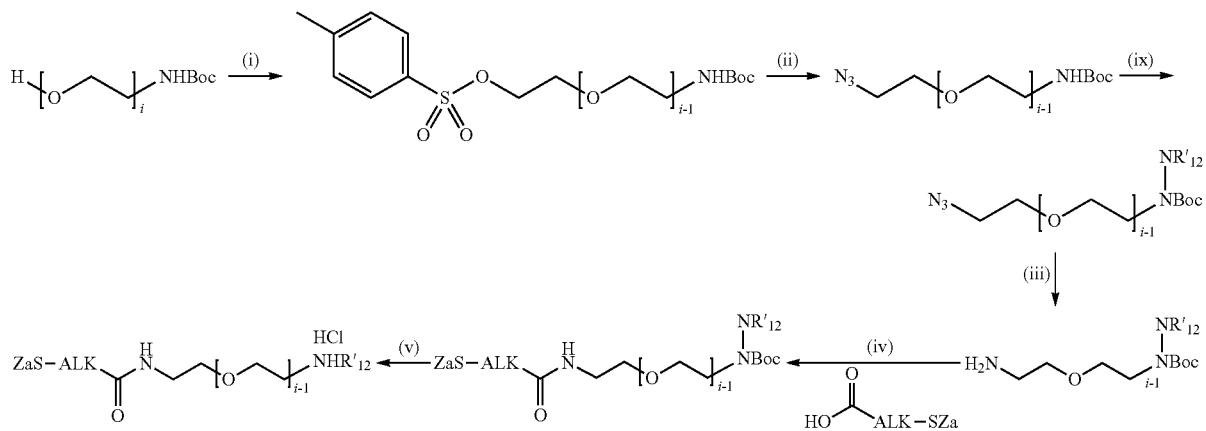
In the Case where $R_{12}$ and $R'_{12} \neq H$
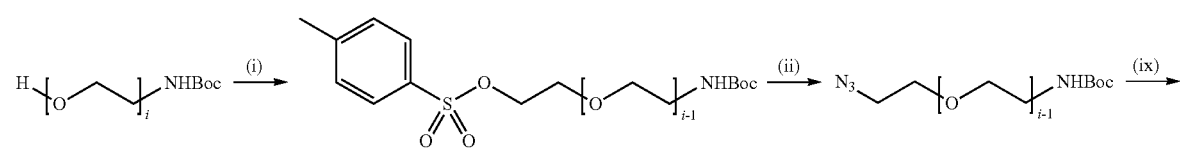

-continued

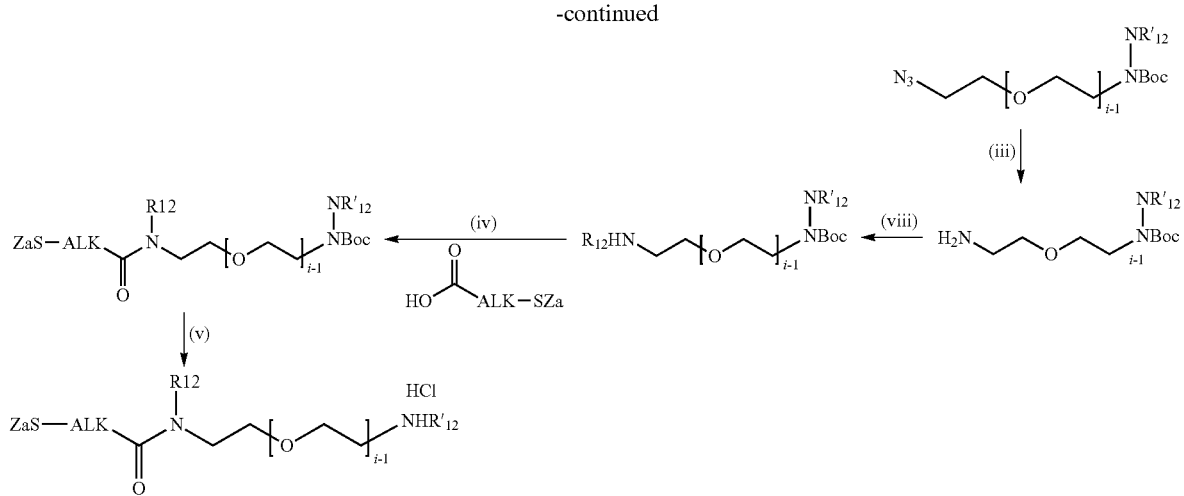

Step (i):
Activation of the alcohol in tosylate form; the reaction is performed in a polar aprotic solvent such as DCM by treatment with tosyl chloride in the presence of silver oxide and potassium iodide. The process may be based on the conditions of Example 6, compound 23.

Step (ii):
Nucleophilic substitution of the tosylate; the reaction is performed in a polar aprotic solvent such as acetonitrile by treatment with sodium azide. The process may be based on the conditions of Example 6, compound 24.

Step (iii):
Reduction of the azide; the reaction is performed in a polar solvent such as a THF/water mixture in the presence of triphenylphosphine. The procedure may be based on the conditions of Example 6, compound 26.

Step (iv):
Peptide coupling; the reaction is performed in a polar aprotic solvent such as dimethylformamide in the presence of coupling agents such as the N,N'-diisopropylcarbodiimide/1-hydroxybenzotriazole system and of a base such as TEA.

Step (v):
Deprotection using a solution of hydrochloric acid (for example solution in dioxane) or of trifluoroacetic acid. The procedure may be based on the conditions of Example 7, compound 32.

Step (vi):
Protection of the function NHBoc; the reaction is performed in a polar aprotic solvent such as THF or DMF by treatment with 1 equivalent of base such as sodium hydride, followed by a benzyl halide such as benzyl chloride.

Step (vii):
Cleavage of the benzyl group and reduction of the azido function; the reaction is performed in a protic solvent such as methanol, with hydrogen in the presence of a catalyst such as palladium hydroxide.

Step (viii):
Alkylation of the amine by reductive amination with an aldehyde; the reaction is performed at RT in an anhydrous polar aprotic solvent such as DCM in the presence of a reducing agent such as sodium triacetoxyborohydride and, if necessary, acetic acid as catalyst.

Step (ix):
Alkylation of the NHBoc group; the reaction is performed in an anhydrous polar aprotic solvent such as THF by treatment with a base such as sodium hydride in the presence of a reagent bearing a nucleofugal group such as an alkyl halide. The procedure may be based on the conditions of Example 6, compound 25.

The amino-PEG-alcohols protected or otherwise with a Boc group on the amine function are commercially available (for instance N-Boc-aminoethoxyethoxyethanol or 1-amino-3,6,9-trioxaundecanyl-11-ol) or may be prepared from the PEG diols, which are commercially available for i=3 to 12, according to the procedure described in U.S. Pat. No. 7,230,101. The carboxylic acid ZaS-ALK-CO$_2$H, for example 4-methyl-4-(methyldithio)pentanoic acid, may be commercially available or prepared from a halogenated carboxylic acid via successive treatments with potassium thioacetate and a derivative of methanethiosulfonate type.

LP$_{23}$  ZaS-(CH$_2$CH$_2$O)$_i$—CH$_2$CH$_2$—NHR$_{12}$  prepared according to the schemes below:

In the Case where R$_{12}$=H

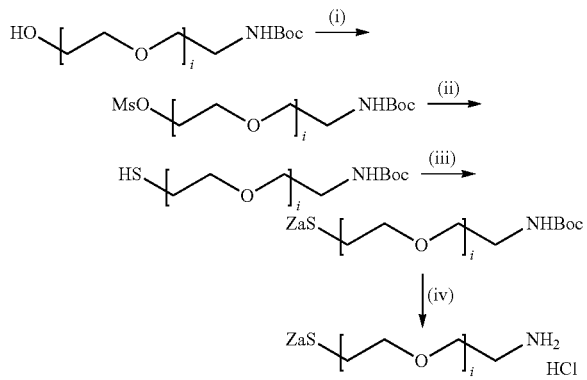

In the Case where R$_{12}$≠H

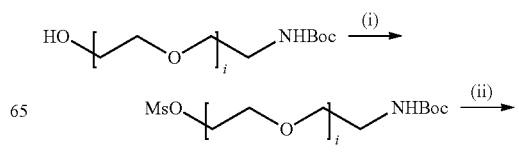

-continued

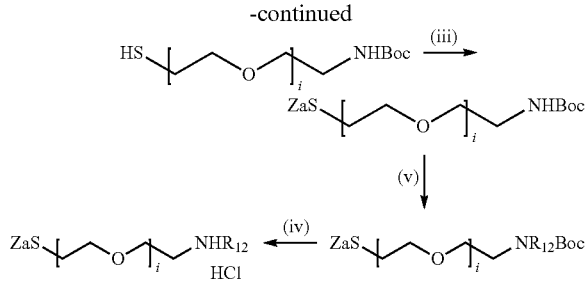

Step (i):
Activation of the alcohol in mesylate form; the reaction is performed in an anhydrous polar aprotic solvent such as DCM by treatment with mesyl chloride in the presence of a base such as TEA.

Step (ii):
Formation of the free thiol; the reaction is performed in a refluxing polar protic solvent such as an ethanol/water mixture in two successive steps: displacement of the mesylate with thiourea, followed by in situ hydrolysis of the isothiouronium salt by addition of a base such as sodium hydroxide.

Step (iii):
Protection of the thiol; the reaction is performed in a mixture of polar solvents such as an ethanol/water mixture with a reagent comprising a methanethiosulfonate function, for instance methyl methanethiosulfonate, in the presence of a base such as sodium carbonate.

Step (iv):
Deprotection using a solution of hydrochloric acid (for example a solution in dioxane) or of trifluoroacetic acid.

Step (v):
Alkylation of the amine; the reaction is performed in an anhydrous polar aprotic solvent such as THF by treatment with a base such as sodium hydride in the presence of a reagent bearing a nucleofugal group, such as an alkyl halide.

The amino-PEG-alcohols protected or not protected with a Boc group on the amine function are commercially available (for instance N-Boc-aminoethoxyethoxyethanol or 1-amino-3,6,9-trioxaundecanyl-11-ol) or may be prepared from PEG diols, which are commercially available for i=3 to 12, according to the procedure described in U.S. Pat. No. 7,230,101.

$LP_{24}$

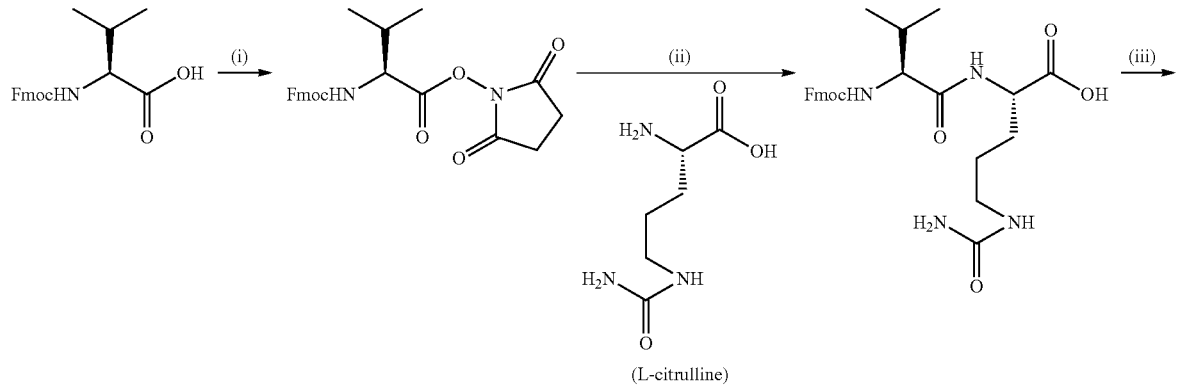

prepared according to the scheme below:

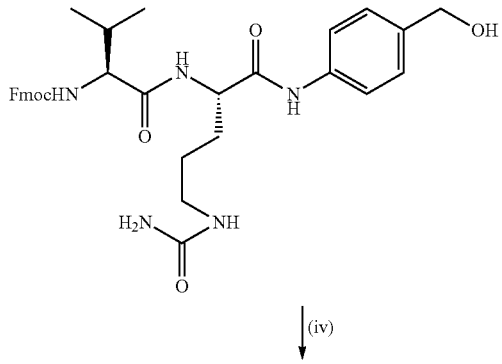

113 114

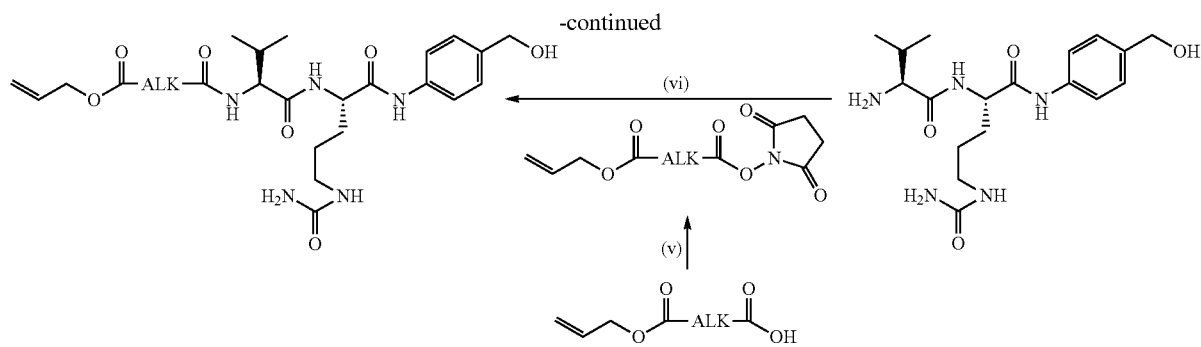

Step (i):
Activation of the Fmoc-L-valine in the form of the NHS ester; the reaction is performed in an anhydrous polar aprotic solvent such as THF by treatment with NHS in the presence of a coupling agent such as DCC.

Step (ii):
Peptide coupling between Fmoc-L-valine-NHS and L-citrulline; the reaction is performed in a polar solvent such as a dimethoxyethane/THF/water mixture in the presence of a base such as sodium bicarbonate.

Step (iii):
Peptide coupling with 4-aminobenzyl alcohol; the reaction is performed in a polar solvent such as a DCM/methanol mixture in the presence of a coupling agent such as EEDQ.

Step (iv):
Deprotection of the amine Fmoc; the reaction is performed in a polar solvent such as a DCM/methanol mixture in the presence of a base such as diethylamine.

Step (v):
Activation of the carboxylic acid in NHS ester form; the reaction is performed in a polar aprotic solvent such as DCM by treatment with NHS in the presence of a coupling agent such as EDCl hydrochloride.

Step (vi):
Peptide coupling between the dipeptide and the NHS ester; the reaction is performed at RT in a polar aprotic solvent such as a DCM/acetonitrile mixture.

The diacids monoprotected in allylic ester form are commercially available for n=2 (monoallyl succinate) or may be prepared by transesterification of the methyl or t-butyl monoesters, which are commercially available for n=2 to 6.

LP$_{25}$

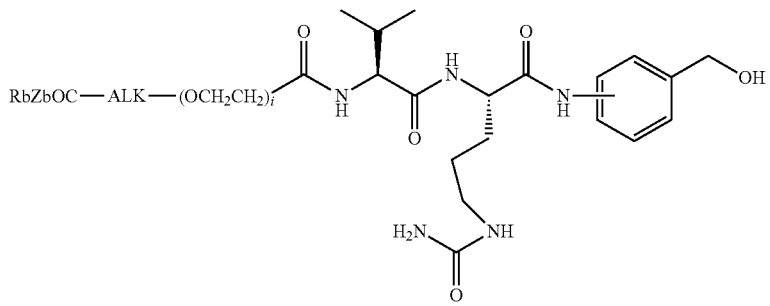

prepared according to the scheme below:

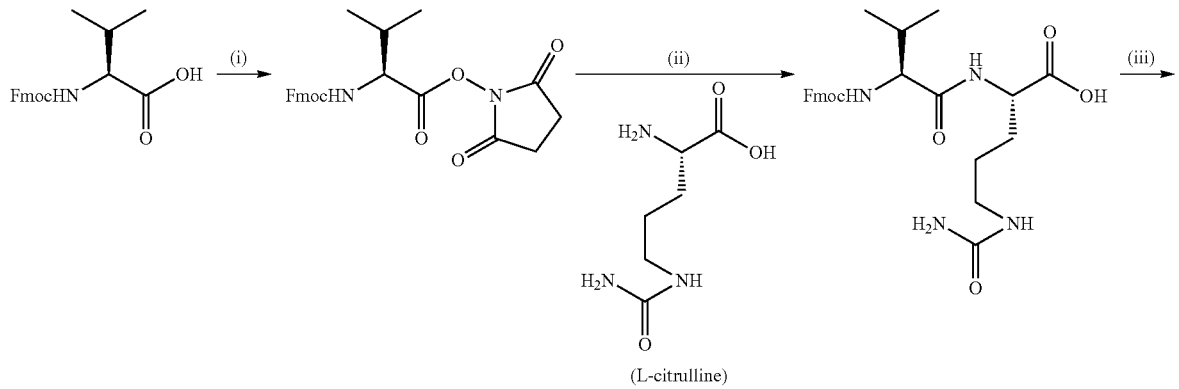

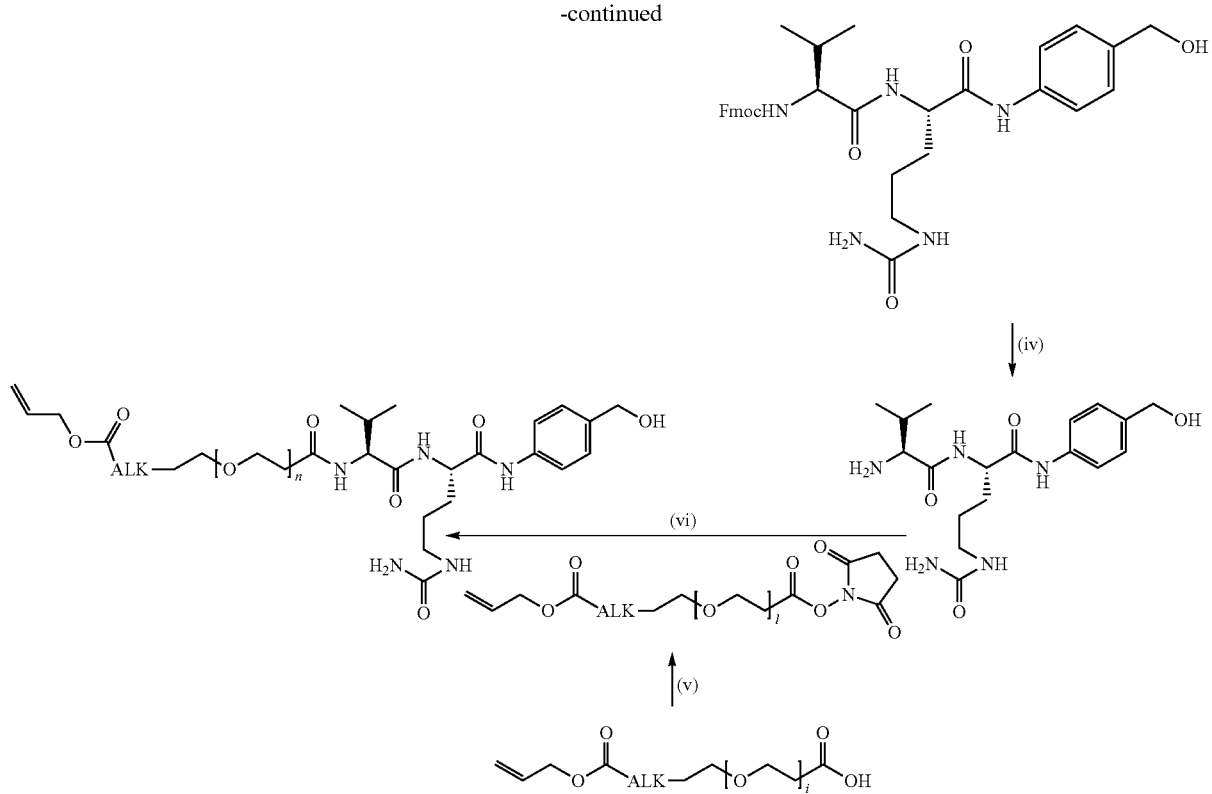

Step (i):
Activation of Fmoc-L-valine in NHS ester form; the reaction is performed in an anhydrous polar aprotic solvent such as THF by treatment with NHS in the presence of a coupling agent such as DCC.

Step (ii):
Peptide coupling between Fmoc-L-valine-NHS and L-citrulline; the reaction is performed in a polar solvent such as a DME/THF/water mixture in the presence of a base such as sodium bicarbonate.

Step (iii):
Peptide coupling with 4-aminobenzyl alcohol; the reaction is performed in a polar solvent such as a DCM/methanol mixture in the presence of a coupling agent such as EEDQ.

Step (iv):
Deprotection of the amine Fmoc; the reaction is performed in a polar solvent such as a DCM/methanol mixture in the presence of a base such as diethylamine.

Step (v):
Activation of the carboxylic acid in NHS ester form; the reaction is performed at RT in a polar aprotic solvent such as DCM by treatment with NHS in the presence of a coupling agent such as supported DCC.

Step (vi):
Peptide coupling between the dipeptide and the NHS ester; the reaction is performed at RT in a polar aprotic solvent such as a DCM/acetonitrile mixture. The PEG diacids monoprotected in allylic form are prepared according to the description of the preparation of the linker $L_{14}$.

$LP_{26}$

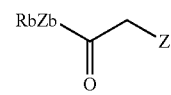

Z = Br or I:

2,5-Dioxopyrrolidin-1-yl bromoacetate and iodoacetate are commercial products, whose CAS numbers are, respectively, 42014-51-7 and 39028-27-8.

TABLE II

| | Linker precursors | | | | Linker family derived from the Cryptophycin derivatives of formula (II)[2,5] | |
|---|---|---|---|---|---|---|
| LP | examples of LP | G | Reaction(s)[1] | L | precursor LP | |
| LP$_1$ | (piperazine amide with S-S-C(CH$_3$)$_2$-CH$_2$-S-CH$_3$) | —(CH$_2$)$_n$Cl | Nucleophilic substitution [for $Z_a$ = H, additional reduction step] | L$_1$ | ZaS—ALK—C(O)—N(piperazine)N—(CH$_2$)$_n$— | |
| LP$_2$ | (piperazine-CH$_2$-C(CH$_3$)$_2$-S-S-CH$_3$) | —(CH$_2$)$_n$ | | L$_2$ | ZaS—ALK—N(piperazine)N—(CH$_2$)$_n$— | |
| LP$_3$ | (NHR$_{12}$-C(CH$_3$)$_2$-S-S-CH$_3$), R$_{12}$ = H or R$_{12}$ = Me | —(CH$_2$)$_n$Cl | | L$_3$ | ZaS—ALK—N(R$_{12}$)—(CH$_2$)$_n$— | |
| LP$_4$ | (piperidine-NH with R$_{12}$-N-CH$_2$-C(CH$_3$)$_2$-S-S-CH$_3$), R$_{12}$ = H or R$_{12}$ = Me | —(CH$_2$)$_n$Cl | | L$_4$ | ZaS—ALK—N(R$_{12}$)(piperidine)N—(CH$_2$)$_n$— | |
| LP$_5$ | (NHS ester-O-C(O)-CH$_2$CH$_2$CH$_2$-S-S-CH$_2$-C(CH$_3$)$_2$-CH$_2$-N(CH$_3$)-C(O)Cl) | —(CH$_2$)$_n$OH | Acylation | L$_5$ | RbZb—CO—ALK—SS—ALK—N(R$_{12}$)—C(O)—O—(CH$_2$)$_n$— | |

TABLE II-continued

| | | | | |
|---|---|---|---|---|
| LP$_6$ |  | —(CH$_2$)$_n$OH | activation, coupling, [optional conversion of a Z$_b$R$_b$ into another Z$_b$R$_b$, for example for | L$_{6a}$ RbZb—CO—ALK—(OCH$_2$CH$_2$)i |
| | | —(CH$_2$)$_n$NH$_2$ | <br>Z$_b$R$_b$ = deprotection, activation with NHS] | L$_{6b}$ RbZb—CO—ALK—(OCH$_2$CH$_2$)i |
| | | —(CH$_2$)$_n$CO$_2$H | Esterification, [optional conversion of a Z$_b$R$_b$ into another Z$_b$R$_b$, for example for<br><br>Z$_b$R$_b$ = deprotection, activation with NHS] | L$_{6c}$ RbZb—CO—ALK—(OCH$_2$CH$_2$)i |
| LP$_7$ | 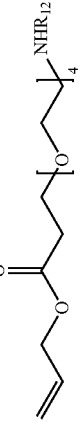
R$_{12}$ = H or Me | —(CH$_2$)$_n$Cl | nucleophilic substitution, [optionally conversion of a Z$_b$R$_b$ into another Z$_b$R$_b$, for example for<br><br>Z$_b$R$_b$ = deprotection, activation with NHS] | L$_{7a}$ RbZb—CO—ALK—(OCH$_2$CH$_2$)i |

TABLE II-continued

| | | | |
|---|---|---|---|
| —(CH₂)ₙOH | activation, coupling, [optionally conversion of a $Z_bR_b$ into another $Z_bR_b$, for example for $Z_bR_b$ = deprotection, activation with NHS] | $L_{7b}$ | RbZb—CO—ALK—(OCH₂CH₂)i—N(R₁₂)—C(O)O—(CH₂)ₙ—⁂ |
| —(CH₂)ₙCO₂H | amidation, [optionally conversion of a $Z_bR_b$ into another $Z_bR_b$, for example for $Z_bR_b$ = deprotection, activation with NHS] | $L_{7c}$ | RbZb—CO—ALK—(OCH₂CH₂)i—C(O)—N(R₁₂)—(CH₂)ₙ—⁂ |
| —(CH₂)ₙCl | nucleophilic substitution, [optionally conversion of a $Z_bR_b$ into another $Z_bR_b$, for example for $Z_bR_b$ = deprotection, activation with NHS] | $L_8$ | RbZb—CO—ALK—(OCH₂CH₂)i—N(piperazine)N—(CH₂)ₙ—⁂ |
| —(CH₂)ₙCl | | $L_9$ | RbZb—CO—ALK—N(piperazine)N—(CH₂)ₙ—⁂ |

LP₈

LP₉

TABLE II-continued

| | | | | |
|---|---|---|---|---|
| LP$_{10}$ | (piperazine-CO-CH$_2$CH$_2$-CO-O-CH$_2$-CH=CH$_2$) | —(CH$_2$)$_n$Cl | Z$_b$R$_b$ = deprotection, activation with NHS | L$_{10}$ RbZb—CO—ALK—(piperazine)—(CH$_2$)$_n$ |
| LP$_{11}$ | (BrCH$_2$-CO-NH-(CH$_2$CH$_2$O)$_3$-CH$_2$CH$_2$-CO-O-NHS) | HS—(CH$_2$)$_n$ ring | nucleophilic substitution | L$_{11}$ RbZb—CO—ALK—(OCH$_2$CH$_2$)i—S—CH$_2$—CO—N(R$_{12}$)—(CH$_2$)$_n$ |
| LP$_{12}$ | (Br-(CH$_2$CH$_2$O)$_5$-CH$_2$CH$_2$-CO-O-NHS) | HS—(CH$_2$)$_n$ ring | nucleophilic substitution | L$_{12}$ RbZb—CO—ALK—(OCH$_2$CH$_2$)i—S—ring—(CH$_2$)$_n$ |
| LP$_{13}$ | (HS-(CH$_2$CH$_2$O)$_2$-CH$_2$CH$_2$-COOH) | —(CH$_2$)$_n$Cl | nucleophilic substitution | L$_{13}$ RbZb—CO—ALK—(OCH$_2$CH$_2$)i—S—(CH$_2$)$_n$ |
| LP$_{14}$ | (HOOC-CH$_2$CH$_2$-(OCH$_2$CH$_2$)$_3$-O-CO-CH$_2$CH$_2$-CH=CH$_2$) | —(CH$_2$)$_n$NH$_2$ | amidation, deprotection, activation | L$_{14a}$ RbZb—CO—ALK—(OCH$_2$CH$_2$)i—CO—N(R$_{12}$)—(CH$_2$)$_n$ |
| | | —(CH$_2$)$_n$OH | esterification, deprotection, activation | L$_{14b}$ RbZb—CO—ALK—(OCH$_2$CH$_2$)i—CO—O—(CH$_2$)$_n$ |
| LP$_{15}$ | (alkyne-(OCH$_2$CH$_2$)$_3$ NHS ester) | —(CH$_2$)$_n$N$_3$ | cycloaddition | L$_{15}$ RbZb—CO—ALK—(OCH$_2$CH$_2$)i—O—(triazole)—(CH$_2$)$_n$ |

TABLE II-continued

| | | | |
|---|---|---|---|
| LP$_{22}$ | MeSS-C(CH$_3$)$_2$-CH$_2$CH$_2$-C(O)-NH-[CH$_2$CH$_2$O]$_i$-NHR'$_{12}$  <br> i = 3  <br> R'$_{12}$ = H or Me | —(CH$_2$)$_n$Cl | L$_{22}$: ZaS—ALK—C(O)—N(R$_{12}$)—CH$_2$CH$_2$—[O]—(CH$_2$)$_3$—N(R'$_{12}$)—(CH$_2$)$_n$—⌇ |
| LP$_{23}$ | MeSS—(CH$_2$CH$_2$O)$_3$—CH$_2$CH$_2$—NHR$_{12}$  <br> R$_{12}$ = H or Me | —(CH$_2$)$_n$Cl | L$_{23}$: ZaS—(CH$_2$CH$_2$O)i—CH$_2$CH$_2$—N(R'$_{12}$)—(CH$_2$)$_n$—⌇ |
| LP$_{24}$ | HOCH$_2$-C$_6$H$_4$-NH-C(O)-CH(NHC(O)-CH(iPr)-NH-C(O)-(CH$_2$)$_3$-C(O)-O-CH$_2$CH=CH$_2$)-(CH$_2$)$_4$-NH-C(O)-NH$_2$ | —(CH$_2$)$_n$NH$_2$  <br> activation, coupling, deprotection, activation | L$_{24}$: RbZb—CO—ALK—C(O)—NH—CH(iPr)—C(O)—NH—CH((CH$_2$)$_3$NHC(O)NH$_2$)—C(O)—NH—C$_6$H$_4$—CH$_2$—O—C(O)—NH—(CH$_2$)$_n$—⌇ |

TABLE II-continued

| | Linker Precursors | | |
|---|---|---|---|
| LP$_{25}$ | (structure) | L$_{25}$ | activation, coupling, deprotection, activation |
| LP$_{26}$ | (structure), Z = I, Br | L$_{26}$ | nucleophilic substitution |

Cryptophycin derivatives of formula (II)[2,5]

with L =

LP examples of LP

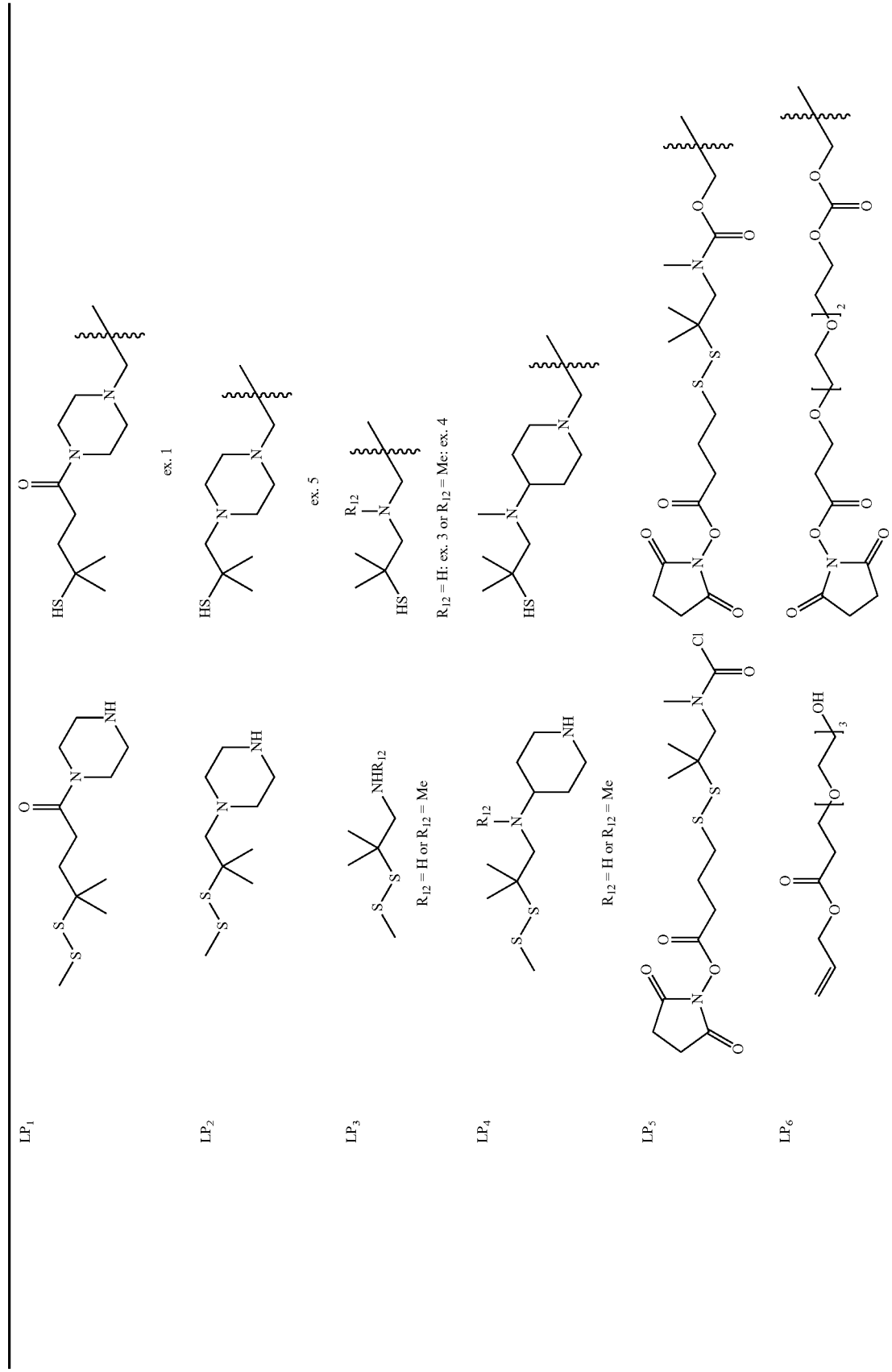

TABLE II-continued
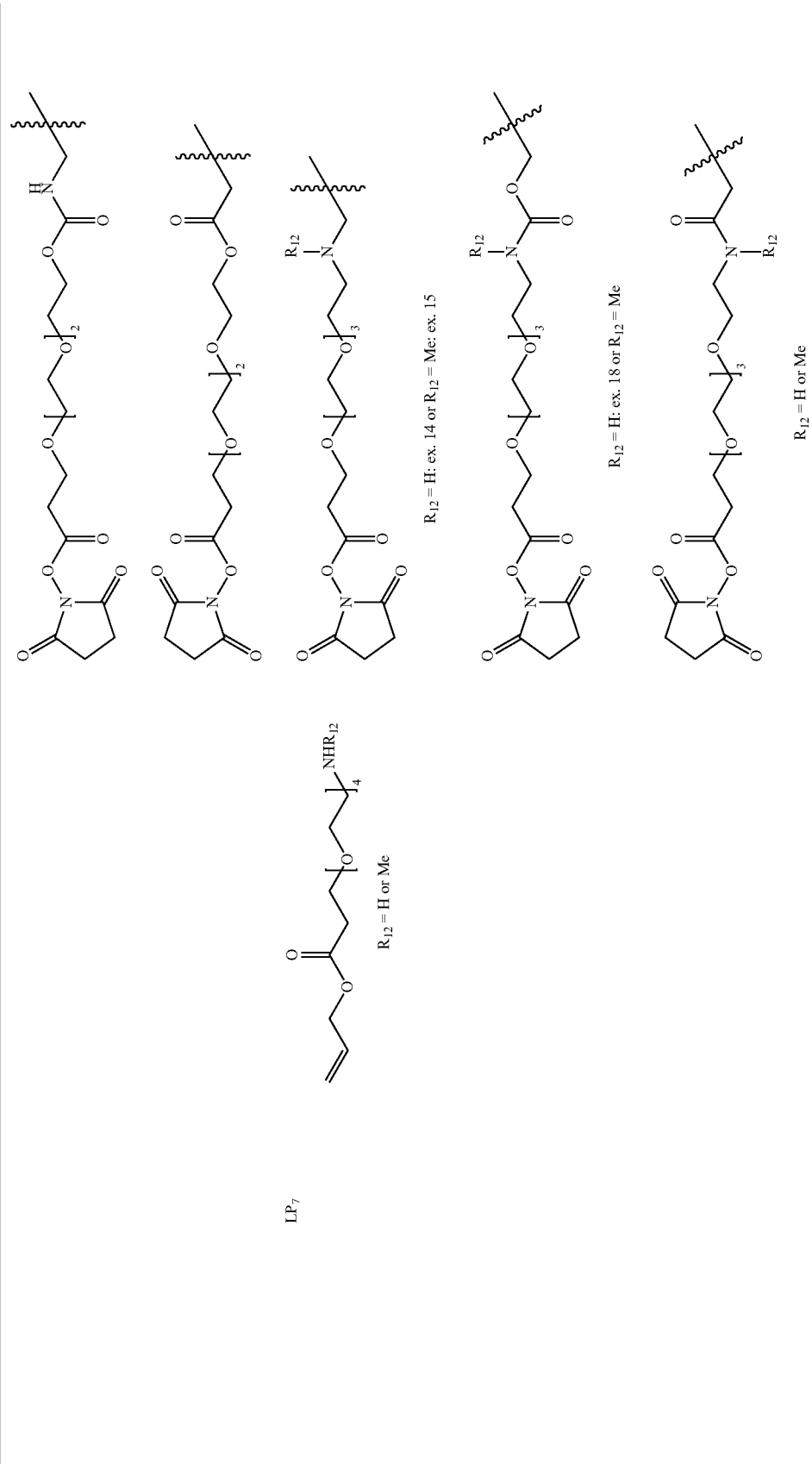
LP7

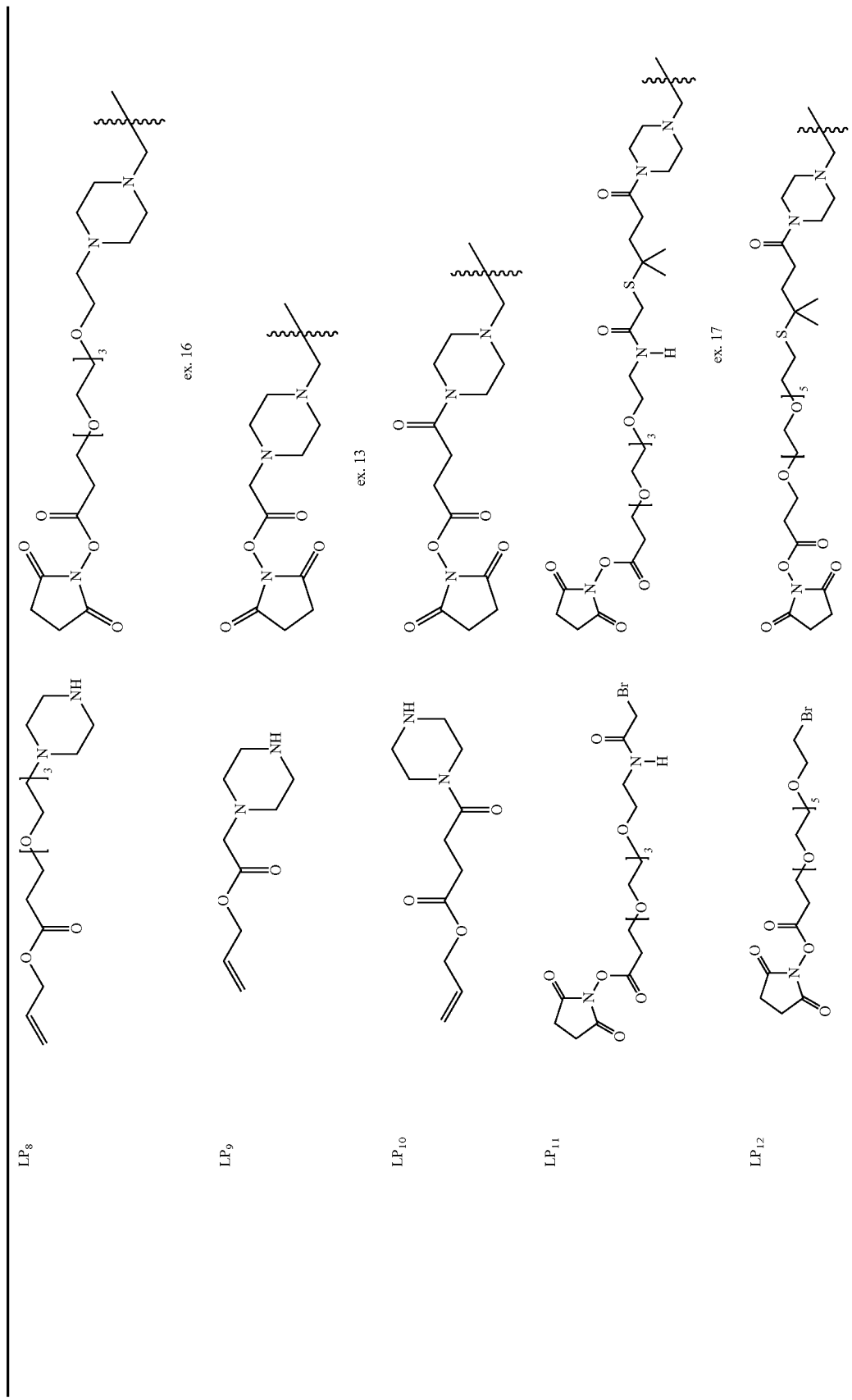

TABLE II-continued

| | | |
|---|---|---|
| LP₁₃ | | |
| LP₁₄ | | |
| LP₁₅ | | Ex. 20 |
| LP₁₆ | | |

TABLE II-continued

TABLE II-continued

| | |
|---|---|
| LP23 | MeSS—(CH$_2$CH$_2$O)$_3$—CH$_2$CH$_2$—NHR$_{12}$<br>R$_{12}$ = H or Me |
| LP24 | |
| LP25 | |

TABLE II-continued

LP$_{26}$

Z = I, Br

[1] for further details, see also the "examples of reactions" section above.
[2] the examples are given for a particular cryptophycin derivative, but may apply to any cryptophycin derivative of formula (II), especially D$_1$-D$_8$.
[3]  corresponds to a cleavable disulfide linker structure chosen from linkers L$_1$ to L$_4$ or L$_{21}$ to L$_{23}$.
[4] R$_{12}$ and R'$_{12}$: H or group (C$_1$-C$_6$)alkyl, for example methyl; n: integer ranging from 1 to 6; i: integer ranging from 1 to 20, more particularly from 1 to 10, more particularly from 1 to 8, or from 1 to 6, and even more particularly from 2 to 5. i may take each of the values of these ranges, and may especially be 2, 3, 4 or 5.
[5] in Table II, L is given here in the para position, but it is possible to obtain compounds in a similar manner with L in an ortho or meta position.

Process for Preparing the Conjugate

The conjugate is obtained via the process that consists in:
(i) placing in contact and leaving to react an optionally buffered aqueous solution of the binding agent and a solution of the cryptophycin derivative of formula (II);
(ii) and then in optionally separating the conjugate formed in step (i) from the cryptophycin derivative and/or from the unreacted binding agent and/or from any aggregates formed.

More particularly, in step (ii) the conjugate from step (i) is separated only from the unreacted cryptophycin derivative and from any aggregates formed, and any unreacted binding agent is left in the solution.

The function of the placing in contact is to react the chemical groups RCG1 and RCG2 in order to ensure attachment of the cryptophycin derivative to the binding agent by formation of a covalent bond; preferably when RCG1 represents —$SZ_a$: the binding agent is modified with a modifying agent so as to introduce onto the binding agent suitable groups RCG2, especially those described in the $2^{nd}$ column of the Table I:
  disulfide chemical groups in the case where RCG1 represents —SH;
  thiol chemical groups in the case where RCG1 represents —$SZ_a$ with $Z_a \neq H$;
  maleimido or iodoacetamido chemical groups in the case where RCG1 represents —SH;
In the case of an antibody (MAb), the formulae of the conjugates are found in the $4^{th}$ column of Table I;
when RCG1 represents —C(=O)—$Z_bR_b$: the reaction preferably takes place on the amino functions of the binding agent, especially the c-amino groups borne by the side chains of the lysine (Lys) residues of an antibody. In the case of an antibody (MAb), a conjugate of the following formula is obtained in this case: MAb-[NH—C(=O)-L*-Crypto]$_d$ with L*=fragment of a linker L comprising RCG1=—C(=O)—$Z_bR_b$ and such that L=-L*C(=O)—$Z_bR_b$;
in the presence of a cryptophycin derivative of formula (III) with G=—$(CH_2)_nY$, the binding agent comprises groups —SH when Y=—Cl, groups —C≡CH when Y=—$N_3$ or carboxylic acid groups when Y=—OH or —$NH_2$;
in the presence of a cryptophycin derivative comprising a reactive chemical group RCG1 of maleimido or haloacetamido type, the binding agent comprises thiol chemical groups.

The term "aggregates" means associations that may form between two or more binding agents, the binding agents possibly having been modified by conjugation. Aggregates are liable to form under the influence of a wide variety of parameters such as a high concentration of binding agent in the solution, the pH of the solution, high shear forces, the number of grafted dimers and their hydrophobic nature, the temperature (see the references cited in the introduction of *J. Membrane Sci.* 2008, 318, 311-316), the influence of some of them not, however, having been clearly elucidated. In the case of proteins or antibodies, reference may be made to *AAPS Journal*, "Protein Aggregation and Bioprocessing" 2006, 8(3), E572-E579. The aggregate content may be determined via known techniques such as SEC (see in this respect *Analytical Biochemistry* 1993, 212 (2), 469-480).

The aqueous solution of the binding agent may be buffered, for example with buffers such as potassium phosphate or N-2-hydroxyethylpiperazine-N'-2-ethanesulfonic acid (HEPES buffer) or a mixture of buffers such as buffer A described later. The buffer depends on the nature of the binding agent. The cryptophycin derivative is dissolved in a polar organic solvent, for example DMSO or DMA.

The reaction takes place at a temperature generally of between 20 and 40° C. The reaction time may vary between 1 and 24 hours. The reaction between the antibody and the cryptophycin derivative may be monitored by SEC with a refractometric and/or ultraviolet detector in order to determine its degree of progress. If the degree of substitution is insufficient, the reaction can be left for longer and/or cryptophycin derivative can be added. Reference may be made to the general method given in the examples section for further details regarding particular conditions. Particular embodiments are described in Examples 9, 10, 11, 25, 26 and 27.

A person skilled in the art has at his disposal various chromatographic techniques for the separation of step (ii): the conjugate may be purified, for example, by steric exclusion chromatography (SEC), by adsorption chromatography (for instance ion exchange, IEC), by hydrophobic interaction chromatography (HIC), by affinity chromatography, by chromatography on mixed supports such as ceramic hydroxyapatite, or by HPLC. Purification by dialysis or diafiltration may also be used.

After step (i) or (ii), the solution of the conjugate may undergo an ultrafiltration and/or diafiltration step (iii). After these steps, the conjugate in aqueous solution is thus obtained.

Antibody

The antibody (see in this respect, Janeway et al. "Immunobiology", $5^{th}$ edition, 2001, Garland Publishing, New York) may be chosen from those described especially in WO 04/043 344, WO 08/010,101, WO 08/047,242, WO 05/009 369 (anti CA6) or WO 2010/014 812. The antibody may optionally be modified with a modifying agent so as to promote the attachment of the cryptophycin derivative (see above). The antibody may especially be monoclonal, polyclonal or multispecific. It may also be an antibody fragment. It may also be a murine, human, humanized or chimeric antibody.

Conjugate

A conjugate generally comprises from about 1 to 10 cryptophycin derivatives covalently attached to the binding agent (this is the degree of grafting or "drug-to-antibody ratio" or "DAR"). This number varies as a function of the nature of the binding agent and of the cryptophycin derivative, and also of the operating conditions used in the conjugation process (for example the number of equivalents of cryptophycin derivative relative to the binding agent, the reaction time, the nature of the solvent and of any cosolvent). Placing of the binding agent and the cryptophycin derivative in contact leads to a mixture comprising several conjugates that are individually distinguished from each other by different DARs; optionally the unreacted binding agent; optionally aggregates. The DAR that is determined on the final solution thus corresponds to an average DAR.

In the case where the binding agent is an antibody, UV spectroscopy may be a method used for determining the DAR. This method is based on that presented in Antony S. Dimitrov (ed), LLC, 2009, "Therapeutic Antibodies and Protocols", vol. 525, 445, Springer Science. It consists in measuring the absorbance of a solution of conjugate after the separation step (ii) at two wavelengths noted λ1 and λ2. The following molar extinction coefficients of the naked antibody and of the cryptophycin derivative measured prior to conjugation are used.

The absorbances of the conjugate solution at λ1 and λ2 ($A_{\lambda,1}$) and ($A_{\lambda,2}$) are measured either on the corresponding peak of the SEC spectrum (this allows calculation of a "DAR (SEC)") or by using a standard UV spectrophotometer (this allows calculation of a "DAR(UV)"). The absorbances may be expressed in the form:

$$A_{\lambda 1} = (c_D \times \epsilon_{D\lambda 1}) + (c_A \times \epsilon_{A\lambda 1})$$

$$A_{\lambda 2} = (c_D \times \epsilon_{D\lambda 2}) + (c_A \times \epsilon_{A\lambda 2})$$

for which equations:
- $c_D$, and $c_A$ denote, respectively, the concentrations in the solution of the part of the conjugate relative to the cryptophycin derivative and the part of the conjugate relative to the antibody;
- $\epsilon_{D\lambda 1}$ and $\epsilon_{D\lambda 2}$ denote, respectively, the molar absorption coefficients for the cryptophycin derivative before conjugation at the two wavelengths λ1 and λ2, these coefficients measured on the compounds of formula (II) of the type $SZ_a$ with $Z_a$=—SMe or of the type —C(=O)—$Z_bR_b$ with $Z_bR_b$=OMe or OCH$_2$—CH=CH$_2$;
- $\epsilon_{A\lambda 1}$ and $\epsilon_{A\lambda 2}$ denote, respectively, the molar absorption coefficients of the naked antibody at the wavelengths λ1 and λ2.

The term "naked antibody" means the antibody to which no cryptophycin derivative is attached, i.e. the antibody before the conjugation step.

Resolution of these two equations leads to:

$$c_D = [(\epsilon_{A\lambda 1} \times A_{\lambda 2}) - (\epsilon_{A\lambda 2} \times A_{\lambda 1})]/[(\epsilon_{D\lambda 2} \times \epsilon_{A\lambda 1}) - (\epsilon_{A\lambda 2} \times \epsilon_{D\lambda 1})]$$

$$c_A = [A_{\lambda 1} - (c_D \times \epsilon_{D\lambda 1})]/\epsilon_{A\lambda 1}$$

The average DAR thus corresponds to $c_D/c_A$. In the case of cryptophycin derivatives, the wavelength λ1=280 nm may be considered, and, depending on the nature of the cryptophycin derivative, λ2 is chosen in the specific wavelength range 246 nm-252 nm. The DAR(UV) is preferably greater than 0.5, more particularly between 1 and 10 and even more particularly between 2 and 7.

The conjugate may be used as an anticancer agent. Owing to the presence of the binding agent, the conjugate is made highly selective towards tumour cells rather than healthy cells. This makes it possible to direct the cryptophycin derivative in an environment similar thereto or directly therein; (in this respect, see the following publications that describe the use of monoclonal antibody conjugates in cancer treatment: "Antibody-drug conjugates for cancer therapy" Carter P. J., et al., *Cancer J.* 2008, 14, 154-169; "Targeted cancer therapy: conferring specificity to cytotoxic drugs" Chari R., *Acc. Chem. Res.* 2008, 41, 98-107). It is possible to treat solid or liquid cancers. The conjugate may be used alone or in combination with at least one other anticancer agent.

The conjugate is formulated in the form of a buffered aqueous solution at a concentration generally of between 1 and 10 mg/ml. This solution may be injected in perfusion form per se or may be rediluted to form a perfusion solution.

EXAMPLES

Analytical Methods Used

High-Pressure Liquid Chromatography-Mass Spectrometry (LCMS)

Method A1

The analysis is performed on a Waters ZQ machine and an XBridge $C_{18}$ 2.5 μm (3×50 mm) column at 70° C. with a flow rate of 0.9 ml/min, an elution gradient (7 min) of (A) water/0.1% formic acid and of (B) acetonitrile/0.1% formic acid (gradient: from 5% to 100% B' over 5.3 minutes; 5.5 minutes: 100% B; 6.3 minutes: 5% B) and an electrospray ionization in positive and/or negative mode.

Method A2

The analysis is performed on a Waters HPLC-SQD machine and an Acquity BEH $C_{18}$ 1.7 μm (2.1×50 mm) column at 50° C. with a flow rate of 1 ml/min, an elution gradient (2 minutes) of (A) water/0.1% formic acid and of (B) acetonitrile/0.1% formic acid (gradient: from 5% to 50% B over 0.8 minute; 1.2 minutes: 100% B; 1.85 minutes: 100% B; 1.95 minutes: 5% B) and electrospray ionization in positive and/or negative mode.

Method A3

The analysis is performed on a Waters HPLC-SQD machine and an Acquity BEH $C_{18}$ 1.7 μm (2.1×50 mm) column at 70° C. with a flow rate of 1 ml/min, an elution gradient (2 minutes) of (A) water/0.1% formic acid and of (B) acetonitrile/0.1% formic acid (gradient: from 5% to 50% B over 1 minute; 1.3 minutes: 100% B; 1.45 minutes: 100% B; 1.75 minutes: 5% B) and electrospray ionization in positive and/or negative mode.

Method A4

The analysis is performed on a Waters ZQ machine and a Phenomenex Kinetex $C_{18}$ 100A 2.6 μm (3×50 mm) column at 45° C. with a flow rate of 1 ml/minute, an elution gradient (6 minutes) of (A) water/0.1% formic acid and of (B) acetonitrile/0.1% formic acid (gradient: 6% B: 0.8 minute; from 6% to 100% B over 4.1 minutes; 4.8 minutes: 100% B; 5.0-6.0 minutes: 6% B) and electrospray ionization in positive and/or negative mode.

Method A5

The analysis is performed on a Waters ZQ machine and a Phenomenex Kinetex $C_{18}$ 2.6 μm (3×1000 mm) column at 50° C. with a flow rate of 0.8 ml/minute, an elution gradient (8 minutes) of (A) water/0.1% formic acid and of (B) acetonitrile/0.1% formic acid (gradient: 4% B: 0.15 minute; from 4% to 100% B over 6.85 minutes; 7.1 minutes: 100% B; 7.4-8.2 minutes: 4% B) and electrospray ionization in positive and/or negative mode.

Mass Spectrometry (MS)

The spectra were acquired by direct introduction onto a Waters GCT of machine (direct introduction without LC).

Steric Exclusion Chromatography-High Resolution Mass Spectrometry (SEC-HRMS)

The analysis may necessitate a prior step of deglycosylation of the conjugate. This is performed by adding to the conjugate solution 2% by volume of a solution of enzyme PNGase F (prepared by making up to 100 ml a flask of 100 units of lyophilizate of N-glycanase enzyme with MilliQ water). The solution is homogenized by vortex and incubated at 37° C. for 19 hours. The deglycosylated sample is ready to be analyzed by SEC-HRMS. The chromatographic analysis is performed on an Agilent HP1100 machine and a Waters Biosuite 250 HR SEC 4 μm (4.6×300 mm) column at 30° C. with a flow rate of 0.4 ml/minute and an isocratic elution of (A) 25 mM ammonium formate pH=7/(B) acetonitrile 70/30 for 15 minutes. The mass spectrometry is performed on a Waters QTOF II machine with electrospray ionization in positive mode. The mass spectra are deconvoluted with the Waters MaxEnt1 software.

Steric Exclusion Chromatography (SEC HPLC)

The analysis is performed on a Merck Lachrom Elite HPLC machine with an L2455 DAD spectrophotometric detector and a Tosoh Bioscience TSKgel G3000 SWXL 5 μm (7.8×300 mm) column with a flow rate of 0.5 ml/minute and an isocratic elution of 30 minutes with a pH 7 buffer containing 0.2 M of KCl, 0.052 M of $KH_2PO_4$, 0.107 M of $K_2HPO_4$ and 20% by volume of isopropanol.

¹H Nuclear Magnetic Resonance (NMR)

The ¹H NMR spectra were acquired on a Bruker Avance spectrometer, either of model DRX-300, DRX-400, DRX-500 or DMX-600. The chemical shifts are given in ppm.

General Method Used for Preparing the Conjugates in the Case of the Cryptophycin Derivatives Comprising a Linker L Ending with —$SZ_a$ Method in Two Successive Steps 1$^{st}$ Step The antibody is first modified with an activated NHS ester, so as to introduce onto its surface pyridyldisulfide groups. A solution of antibody hu2H11 in an aqueous pH 6.5 buffer containing 0.05 M of potassium phosphate and 0.05 M of NaCl (referred to as buffer A) is treated with 5 to 10 eq. of the NHS activated ester dissolved in DMA such that the final antibody concentration is between 5 and 10 mg/ml and the percentage of DMA in the aqueous buffer is 5%. The reaction is continued for 2 hours at RT. The mixture is deposited onto a filtration column on gel (Sephadex™ G25 matrix, GE Healthcare) pre-equilibrated in an aqueous pH 8 buffer containing 0.05 M of HEPES, 0.05 M of NaCl and 2 mM of EDTA. The modified antibody is eluted with the pH 8 HEPES buffer, collected and then assayed by UV spectrometry so as to determine the antibody concentration of the sample and the number of pyridyldisulfide groups. A specimen of the modified antibody is treated with dithiothreitol so as to reduce the disulfide bond, and the pyridine-2-thione released is assayed by spectrometry (extinction coefficients: $\epsilon_{343\,nm}$: 8080 $M^{-1}cm^{-1}$, $\epsilon_{280\,nm}$: 5100 $M^{-1}\,cm^{-1}$ for pyridine-2-thione, and $\epsilon_{280\,nm}$: 208380 $M^{-1}\,cm^{-1}$ for the antibody). On average, from 3 to 6 pyridyldisulfide groups are grafted per antibody molecule.

2$^{nd}$ Step

The modified antibody solution from the 1$^{st}$ step is diluted in the aqueous pH 8 buffer described above and then treated with a solution of the cryptophycin derivative (5 eq.) such that the final antibody concentration is 3 mg/ml and the percentage of DMA in the aqueous buffer is 20%; the number of equivalents of cryptophycin derivative is expressed relative to the number of pyridyldisulfide molecules introduced during the first step. The reaction is continued overnight at 30° C. or with stirring at about 2000 rpm. The mixture is analyzed by SEC HPLC so as to determine the degree of grafting of the cryptophycin derivative onto the antibody. If the degree of substitution is insufficient, the mixture is treated with an additional 1 to 5 eq. of cryptophycin derivative in DMA for 3 hours at 30° C. or with stirring at about 2000 rpm. The mixture is filtered through a Millex®-SV 5 µm filter (PVDF membrane, Durapore, Millipore) and then purified by gel filtration using a Superdex 200 pg matrix (HiLoad 16/60 desalting column, GE Healthcare) pre-equilibrated with an aqueous pH 6.5 buffer containing 0.01 M of phosphate, 0.14 M of NaCl and 10% to 20% of NMP. The fractions containing the conjugated antibody in monomer form are collected, pooled and concentrated on Amicon Ultra-15 (Ultracel 10 k or 50 k membrane, Millipore) to a concentration of between 2 and 5 mg/ml. A change of buffer is finally performed so as to remove the organic solvent from the conjugate storage buffer. The conjugate is deposited on a gel filtration column composed of a Sephadex™ G25 matrix (Nap-5, -10, PD-10, Hiprep 26/10 desalting columns, GE Healthcare) pre-equilibrated with an aqueous buffer whose composition and pH are suited to each conjugate. The final conjugate is assayed by UV spectrometry using the extinction coefficients determined for the antibody and the corresponding cryptophycin derivative so as to measure the antibody concentration and the average cytotoxic number per antibody. The degree of substitution may also be calculated from the deconvolution of the SEC-HRMS spectrum of the conjugate.

"One-Pot" Two-Step Method

The antibody is first modified by an activated NHS ester, so as to introduce onto its surface pyridyldisulfide groups. A solution of antibody hu2H11 in an aqueous pH 6.5 buffer containing 0.05 M of potassium phosphate and 0.05 M of NaCl is diluted with the pH 6.5 phosphate buffer and an aqueous 1N solution of HEPES such that the final proportion of initial pH 6.5 phosphate buffer and of HEPES is 96/4, in order to obtain a pH≈7.5-8. This antibody solution is treated with 5 to 10 eq. of the NHS activated ester dissolved in DMA such that the final antibody concentration is between 5 and 10 mg/ml and the percentage of DMA in the aqueous buffer is 5%. The reaction is continued for 2 hours at RT. The antibody solution thus modified is directly diluted with a 96/4 mixture of pH 6.5 phosphate buffer and of HEPES and then treated with a solution of the cryptophycin derivative (4 eq.) in DMA such that the final antibody concentration is 3 mg/ml and the percentage of DMA in the aqueous buffer is 20%; the number of equivalents of cryptophycin derivative is expressed relative to the number of equivalents of NHS activated ester introduced during the first step. The reaction is continued overnight at 30° C. or with stirring at about 2000 rpm. The mixture is analyzed by SEC HPLC so as to determine the degree of grafting of the cryptophycin derivative onto the antibody. If the degree of substitution is insufficient, the mixture is treated with a further 1 to 5 eq. of cryptophycin derivative in DMA for 3 hours at 30° C. or with stirring at about 2000 rpm. The mixture is filtered through a Millex®-SV 5 µm filter (PVDF membrane, Durapore, Millipore) and then purified by gel filtration using a Superdex 200 pg matrix (HiLoad 16/60 desalting column, GE Healthcare) pre-equilibrated in an aqueous pH 6.5 buffer containing 0.01 M of phosphate, 0.14 M of NaCl and 10% to 20% of NMP. The fractions containing the conjugated antibody in monomer form are collected, pooled and concentrated on Amicon Ultra-15 (Ultracel 10 k or 50 k membrane, Millipore) to a concentration of between 2 and 5 mg/ml. A change of buffer is finally performed so as to remove the organic solvent from the conjugate storage buffer. The conjugate is deposited on a gel filtration column composed of a Sephadex™ G25 matrix (Nap-5, -10, PD-10, Hiprep 26/10 desalting columns, GE Healthcare) pre-equilibrated with an aqueous buffer whose composition and pH are suited to each conjugate. The final conjugate is assayed by UV spectrometry using the extinction coefficients determined for the antibody and the corresponding cryptophycin derivative so as to measure the antibody concentration and the average cytotoxic number per antibody. The degree of substitution may also be calculated from the deconvolution of the SEC-HRMS spectrum of the conjugate.

General Method Used for Preparing the Conjugates in the Case of Cryptophycin Derivatives Comprising a Linker Ending with —C=(=O)$Z_b R_b$ A solution of antibody hu2H11 in an aqueous pH 8 buffer containing 0.05 M of HEPES, 0.05 M of NaCl and 2 mM of EDTA or composed of a 96/4 mixture of an aqueous pH 6.5 buffer containing 0.05 M of potassium phosphate and 0.05 M of NaCl/1N HEPES is treated with an excess of a solution in DMA on the cryptophycin derivative such that the final antibody concentration is 3 mg/ml and the percentage of DMA in the aqueous buffer is 20%. The reaction is continued for 3 hours at 30° C. or with stirring at about 2000 rpm. The mixture is analyzed by SEC HPLC so as to determine the degree of grafting of cytotoxic agent on the population of monomer antibodies. If the degree of substitution is insufficient, the mixture is treated with a further 1 to 5 eq. of cryptophycin derivative in DMA for 3 hours at 30° C. or with stirring at about 2000 rpm. The mixture is filtered through a Millex®-SV 5 µm filter (PVDF membrane, Durapore, Millipore) and then purified by gel filtration using a Superdex 200 pg matrix (HiLoad 16/60 desalting column, GE Healthcare) pre-equilibrated in an aqueous pH 6.5 buffer containing 0.01 M of phosphate, 0.14 M of NaCl and 10% to 20% of NMP. The fractions containing the conjugated antibody in monomer form are collected, pooled and concentrated on Amicon Ultra-15 (Ultracel 10 k or 50 k membrane, Millipore) to a concentration of between 2 and 5 mg/ml. A change of buffer is finally performed so as to remove the organic solvent from the conjugate storage buffer. The conjugate is deposited on a gel filtration column composed of a Sephadex™ G25 matrix (Nap-5, -10, PD-10 columns or Hiprep 26/10 desalting column, GE Healthcare) pre-equilibrated with an aqueous buffer whose composition and pH are suited to each conjugate. The final conjugate is assayed by UV spectrometry using the extinction coefficients determined for the antibody and the corresponding cryptophycin derivative, so as to measure the antibody concentration and the degree of grafting. The degree of substitution may also be calculated from the deconvolution of the SEC-HRMS spectrum of the conjugate.

The methods described for the case of the antibody hu2H11 may also be similarly applied to other antibodies, and also to other binding agents.

Example 1

(E)-(3S,10R,16S)-10-(3-Chloro-4-methoxybenzyl)-3-isobutyl-16-[(S)-1-((2R,3R)-3-{4-[4-(4-mercapto-4-methylpentanoyl)piperazin-1-ylmethyl]phenyl}oxiranyl)ethyl]-6,6-dimethyl-1,4-dioxa-8,11-diazacyclohexadec-13-ene-2,5,9,12-tetraone

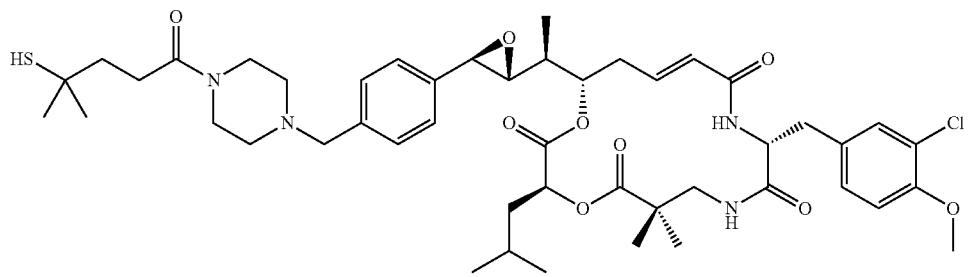

Compound 2

(E)-(3S,10R,16S)-10-(3-Chloro-4-methoxybenzyl)-16-{(S)-1-[(R)-3-(4-chloro-methylphenyl)oxiranyl]ethyl}-3-isobutyl-6,6-dimethyl-1,4-dioxa-8,11-diazacyclohexadec-13-ene-2,5,9,12-tetraone

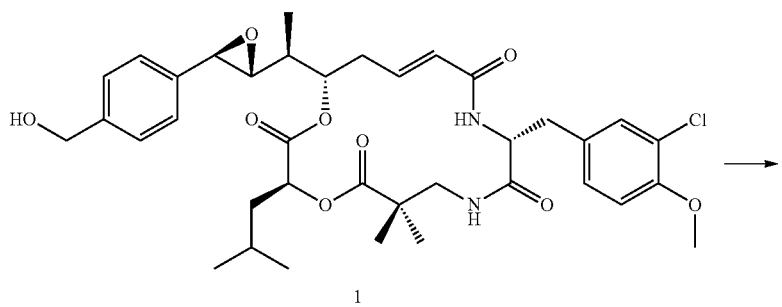

1

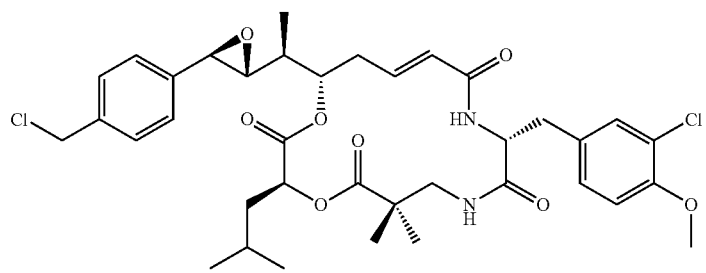

2

Compound 1 (30 mg; 42.9 µmol, prepared according to Al-awar R. S., et al., *J. Med. Chem.* 2003, 46, 2985-3007) is dissolved in anhydrous DMF (2 ml) and the mixture is cooled to 0° C., followed by addition of TEA (107 µmol) and then CMS (64.6 µmol). After 15 minutes, the bath is removed and stirring is continued for 12 hours at RT. The mixture is diluted by adding EtOAc (2 ml) and the organic phase is washed with water (2×1 ml), with saturated aqueous NaHCO$_3$ solution (1 ml) and with saturated aqueous NaCl solution (1 ml). The organic phase is dried over MgSO$_4$ and, after filtering and evaporating off the solvents under reduced pressure, product 2 is obtained in the form of a colourless oil that crystallizes (25 mg; 81%). $^1$H NMR (500 MHz, DMSO-d$_6$): 0.77-0.83 (m, 6H); 1.02 (s, 3H); 1.04-1.07 (m, 3H); 1.14 (s, 3H); 1.29-1.36 (m, 1H); 1.54-1.63 (m, 2H); 1.80-1.87 (m, 1H); 2.24-2.33 (m, 1H); 2.63-2.73 (m, 2H); 2.96-3.06 (m, 3H); 3.28-3.32 (m, 1H); 3.83 (s, 3H); 3.93 (d, J=1.6 Hz, 1H); 4.27 (ddd, J=11.3, 8.0, 3.6 Hz, 1H); 4.78 (s, 2H); 4.93 (dd, J=9.6, 3.6 Hz, 1H); 5.13 (dd, J=10.8, 5.1 Hz, 1H); 5.81 (d, J=14.8 Hz, 1H); 6.49 (ddd, J=15.0, 11.2, 3.7 Hz, 1H); 7.07 (d, J=8.5 Hz, 1H); 7.18 (dd, J=8.5, 1.9 Hz, 1H); 7.23 (d, J=9.6 Hz, 1H); 7.29 (d, J=1.9 Hz, 1H); 7.34 (d, J=8.2 Hz, 2H); 7.47 (d, J=8.2 Hz, 2H); 8.35 (d, J=8.2 Hz, 1H). LCMS (A1): ES m/z=713 [M+H]$^+$; m/z=715 [M−H]$^-$; t$_R$=5.17 min.

Compound 4

2,5-Dioxopyrrolidin-1-yl 4-methyl-4-methyldisulfanylpentanoate

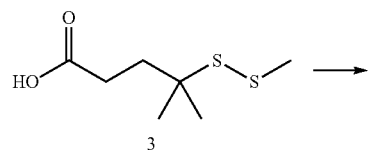

To a solution, purged with argon, of compound 3 (3.05 g, 15.7 mmol, prepared according to WO 2007/085 930) in DCM (30 ml) are successively added NHS (17.3 mmol) and EDCl chloride (17.3 mmol). The mixture is stirred for 3 hours at RT and then washed with pH 6 phosphate buffer (2×30 ml) and then with saturated NaCl solution (30 ml), dried over MgSO$_4$ and concentrated to dryness. The amber-coloured oil obtained, which crystallizes, is washed with a 75/25 heptane/EtOAc mixture and filtered through a sinter funnel to give compound 4 in the form of a white solid (2.08 g, 45%). The filtrate is concentrated to dryness and the crude product obtained is purified by chromatography on silica gel, eluting with a heptane/EtOAc mixture from 50/50 to 0/100. The fractions containing the expected product are concentrated to dryness and taken up in isopropyl ether (5 ml); the precipitate is filtered through a sinter funnel to give the expected compound 4 (1 g, 22%). $^1$H NMR (400 MHz, DMSO-d6): 1.29 (s, 6H); 1.92 to 1.98 (m, 2H); 2.41 (s, 3H); 2.72 to 2.78 (m, 2H); 2.81 (s, 4H). LCMS (A4): EI, m/z=291 [M+H]$^+$.

Compound 5 tert-Butyl 4-(4-methyl-4-methyldisulfanylpentanoyl)piperazine-1-carboxylate

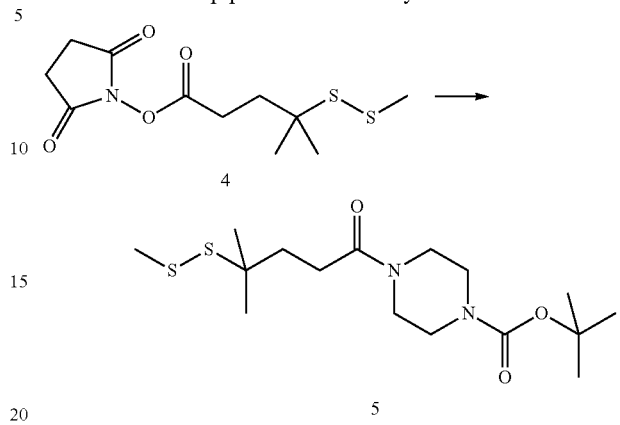

Compound 4 (200 mg, 686 µmol), 1-Boc-piperazine (686 µmol), TEA (755 µmol) and DMF (1.6 ml) are placed in a Wheatton tube. The mixture is stirred at RT overnight and then diluted with EtOAc (5 ml), washed with water (2×5 ml) dried over MgSO$_4$ and concentrated to dryness. The crude product is taken up in isopropyl ether (3 ml); the precipitate is filtered through a sinter funnel to give compound 5 (213 g, 86%). $^1$H NMR (400 MHz, DMSO-d$_6$): 1.27 (s, 6H); 1.41 (s, 9H); 1.73 to 1.87 (m, 2H); 2.34 to 2.41 (m, 2H); 2.40 (s, 3H); 3.23 to 3.36 (partially masked m, 4H); 3.39 to 3.45 (m, 4H). LCMS (A2): ES m/z=363 [M+H]$^+$; m/z=307 [M+H—C$_4$H$_8$]$^-$; t$_R$=1.08 min.

Compound 6

4-Methyl-4-methyldisulfanyl-1-piperazin-1-ylpentan-1-one hydrochloride

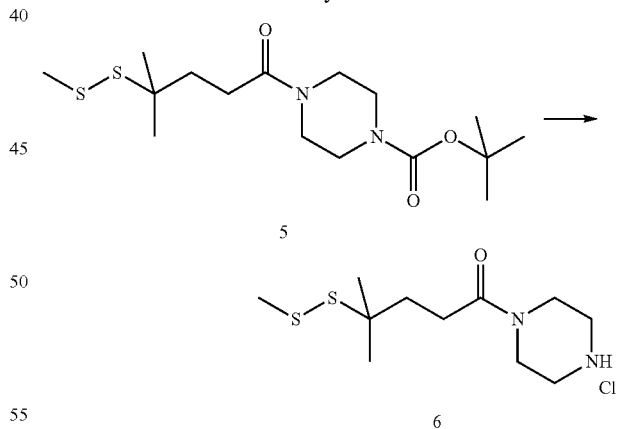

To a solution of compound 5 (213 mg, 588 µmol) in dioxane (4.4 ml) is added a 4M solution of HCl in dioxane (4.4 ml). Stirring is continued for 4 hours at RT. The mixture is filtered through a sinter funnel and the solid obtained is rinsed with dioxane (2 ml) and then with isopropyl ether (2 ml) to give compound 6 (132 mg, 75%) in the form of a cream-coloured solid. $^1$H NMR (500 MHz, DMSO-d$_6$): 1.27 (s, 6H); 1.73 to 1.85 (m, 2H); 2.37 to 2.45 (m, 2H); 2.40 (s, 3H); 2.98 to 3.15 (m, 4H); 3.62 to 3.73 (m, 4H); 9.39 (broad m, 2H). LCMS (A1): ES m/z=263 [M+H]$^+$; t$_R$=2.40 min.

Compound 7

(E)-(3S,10R,16S)-10-(3-Chloro-4-methoxybenzyl)-3-isobutyl-6,6-dimethyl-16-[(S)-1-((2R,3R)-3-{4-[4-(4-methyl-4-methyldisulfanylpentanoyl)piperazin-1-ylmethyl]phenyl}oxiranyl)-ethyl]-1,4-dioxa-8,11-diazacyclohexadec-13-ene-2,5,9,12-tetraone

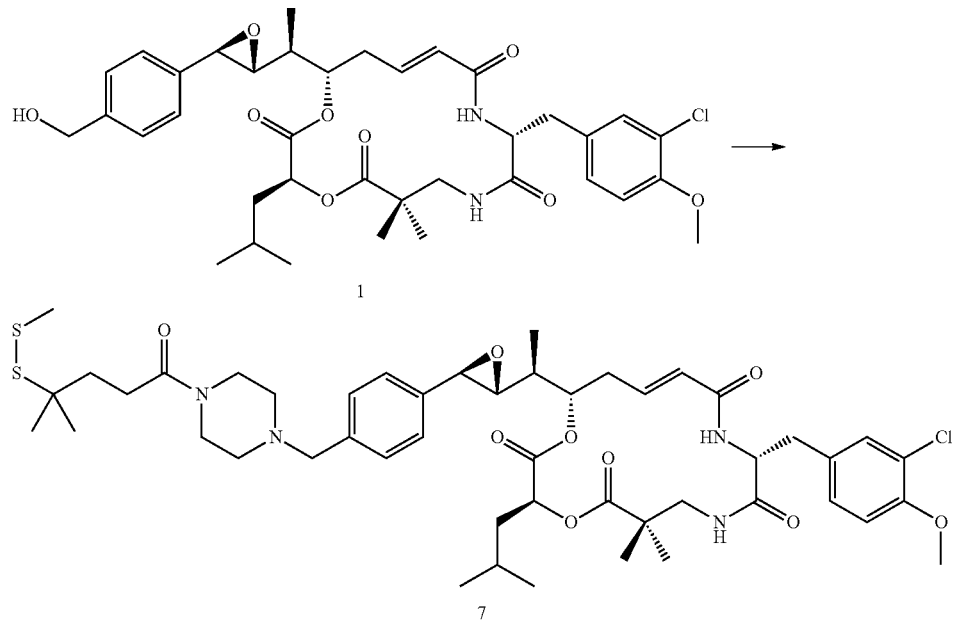

Compound 1 (20.3 mg; 29.0 μmol) is dissolved in anhydrous DMF (0.77 ml) and TEA (72.6 μmol), and then CMS (43.6 μmol) is added. After 12 hours at RT, the product 2 formed is not isolated, and TEA (58.0 μmol) and then 4-methyl-4-methyldisulfanyl-1-piperazin-1-ylpentan-1-one hydrochloride 6 (34.8 μmol) are added. The mixture is stirred for a further 72 hours at RT and then diluted with EtOAc (10 ml). The organic phase is washed with water (2×2 ml), with saturated aqueous NaHCO$_3$ solution (2 ml) and with saturated aqueous NaCl solution (2 ml). After drying over MgSO$_4$ and filtering, the solvents are evaporated off under reduced pressure. The crude reaction product is purified by chromatography on silica gel, eluting with a 99/1 to 98/2 DCM/methanol mixture. A white solid, 7, is obtained (5.7 mg; 21%). TLC (DCM 90/MeOH 10): Rf=0.6; $^1$H NMR (400 MHz, DMSO-d$_6$): 0.75-0.81 (m, 6H); 1.01 (s, 3H); 1.05 (d, J=6.8 Hz, 3H); 1.12 (s, 3H); 1.26 (s, 6H); 1.28-1.33 (m, 1H); 1.52-1.61 (m, 2H); 1.76-1.83 (m, 2H); 2.27-2.38 (m, 4H); 2.39 (s, 3H); 2.64-2.74 (m, 2H); 2.95-3.05 (m, 2H); 3.24-3.34 (m, 6H); 3.44 (br. s., 4H); 3.49 (s, 2H); 3.81 (s, 3H); 3.88 (d, J=1.7 Hz, 1H); 4.22-4.29 (m, 1H); 4.92 (dd, J=9.9, 3.5 Hz, 1H); 5.08-5.15 (m, 1H); 5.81 (d, J=14.2 Hz, 1H); 6.48 (ddd, J=15.2, 11.3, 3.5 Hz, 1H); 7.05 (d, J=8.6 Hz, 1H); 7.17 (dd, J=8.4, 2.3 Hz, 1H); 7.22 (d, J=9.3 Hz, 1H); 7.25-7.34 (m, 5H); 8.34 (d, J=8.1 Hz, 1H); LCMS (A1): ES m/z=943 [M+H]$^+$; m/z=941 [M−H]$^−$; t$_R$=4.03 min.

Example 1

(E)-(3S,10R,16S)-10-(3-Chloro-4-methoxybenzyl)-3-isobutyl-6,6-dimethyl-16-[(S)-1-((2R,3R)-3-{4-[4-(4-mercapto-4-methylpentanoyl)piperazin-1-ylmethyl]phenyl}oxiranyl)ethyl]-1,4-dioxa-8,11-diazacyclohexadec-13-ene-2,5,9,12-tetraone

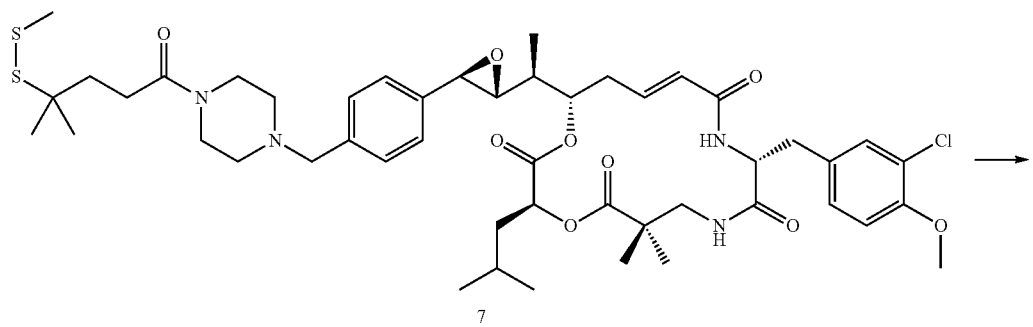

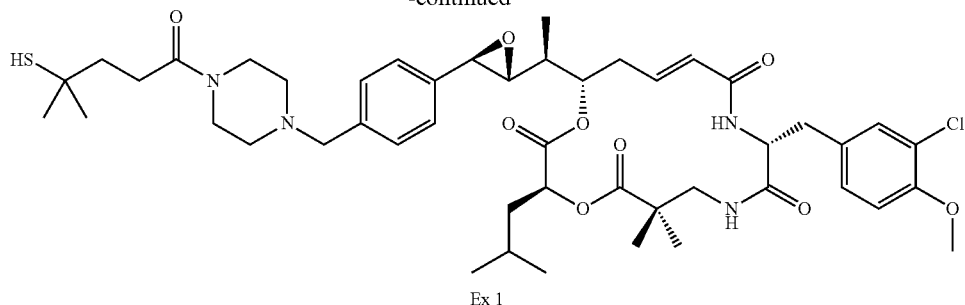

Ex 1

Product 7 (9.6 mg; 10.2 µmol) is dissolved in a mixture of ethanol (1.2 ml)/water (1 ml) and the mixture becomes cloudy. TCEP (25.4 µmol) is then added and the mixture is stirred for 5 hours at RT. The mixture is diluted by adding EtOAc and the organic phase is washed with a 1/1 mixture in water and saturated aqueous NH$_4$Cl solution (1 ml). After drying the organic phase over MgSO$_4$, filtering and evaporating off the solvents under reduced pressure, the final product, Ex. 1, is obtained in the form of a white solid (6.5 mg; 71%). TLC (DCM 90/MeOH 10): Rf=0.56; $^1$H NMR (500 MHz, DMSO-d$_6$): 0.76-0.81 (m, 6H); 1.01 (s, 3H); 1.06 (d, J=6.8 Hz, 3H); 1.13 (s, 3H); 1.24 (s, 6H); 1.27-1.31 (m, 1H); 1.56-1.64 (m, 2H); 1.73-1.85 (m, 3H); 2.26-2.33 (m, 3H); 2.36-2.45 (m, 4H); 2.63-2.75 (m, 2H); 2.95-3.06 (m, 3H); 3.34-3.36 (m, 1H); 3.42-3.51 (m, 6H); 3.82 (s, 3H); 3.89 (s, 1H); 4.22-4.29 (m, 1H); 4.92 (dd, J=9.8, 3.4 Hz, 1H); 5.12 (dd, J=10.8, 4.9 Hz, 1H); 5.81 (d, J=15.2 Hz, 1H); 6.48 (ddd, J=15.0, 11.4, 3.4 Hz, 1H); 7.06 (d, J=8.3 Hz, 1H); 7.18 (dd, J=8.3, 1.5 Hz, 1H); 7.24 (d, J=9.8 Hz, 1H); 7.26-7.36 (m, 5H); 8.37 (d, J=7.8 Hz, 1H); LCMS (A2): ES m/z=897 [M+H]$^+$; m/z=895 [M–H]$^-$; t$_R$=0.97 min.

Example 2

(E)-(3S,6R,10R,16S)-10-(3-Chloro-4-methoxybenzyl)-3-isobutyl-16-[(S)-1-((2R,3R)-3-{4-[4-(4-mercapto-4-methylpentanoyl)piperazin-1-ylmethyl]phenyl}oxiranyl)-ethyl]-6-methyl-1,4-dioxa-8,11-diazacyclohexadec-13-ene-2,5,9,12-tetraone

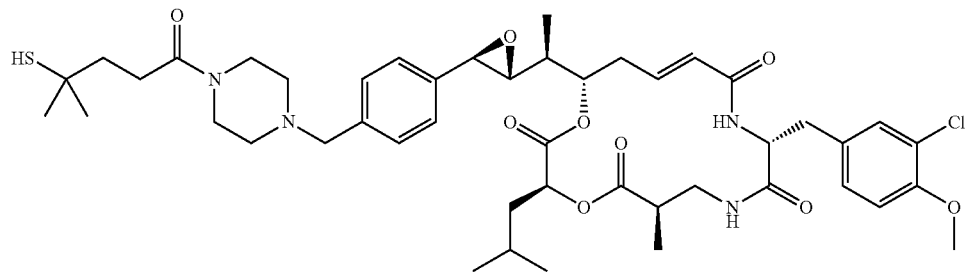 [SMILES: COc1ccc(C[C@H]2NC(=O)/C=C/C[C@@H]([C@H](C)[C@H]3O[C@@H]3c3ccc(CN4CCN(C(=O)CCC(C)(C)S)CC4)cc3)OC(=O)[C@H](CC(C)C)OC(=O)[C@H](C)CNC2=O)cc1Cl]

Compound 9

(E)-(3S,6R,10R,16S)-10-(3-Chloro-4-methoxybenzyl)-16-{(S)-1-[(R)-3-(4-chloro-methylphenyl)oxiranyl]ethyl}-3-isobutyl-6-methyl-1,4-dioxa-8,11-diazacyclohexadec-13-ene-2,5,9,12-tetraone

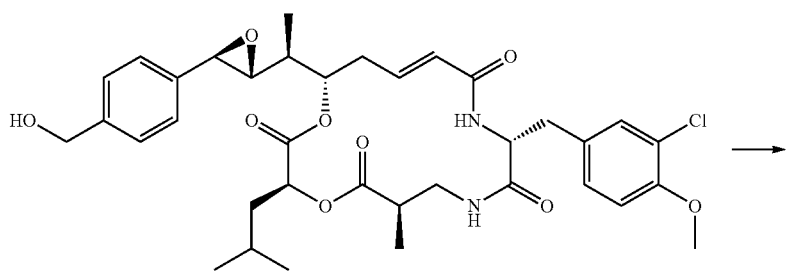

8

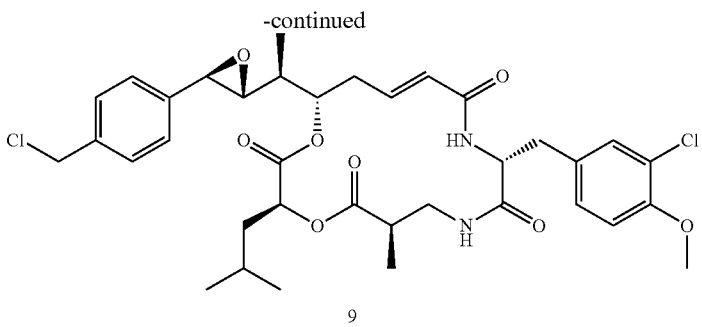

9

Compound 8 (49 mg; 71.4 μmol, which may be prepared according to Al-awar R. S., et al., *J. Med. Chem.* 2003, 46, 2985-3007) is dissolved in anhydrous DCM (5 ml) and the mixture is cooled to 0° C., followed by addition of DIPEA (428 μmol) and then CMS (214 μmol). The mixture is allowed to return to RT and stirring is continued for 40 hours at RT. The mixture is hydrolyzed with 5 ml of water and the aqueous phase is extracted with DCM (3×5 ml). The organic phases are combined, washed with saturated aqueous $NaHCO_3$ solution (10 ml) and with saturated aqueous NaCl solution (10 ml) and dried over $MgSO_4$. After filtering and evaporating off the solvents under reduced pressure, the crude product is purified by chromatography on silica gel, eluting with a 100/0 to 90/10 DCM/MeOH mixture. Compound 9 is obtained in the form of a white solid (37 mg; 79%). $^1$H NMR (500 MHz, DMSO-$d_6$): 0.78 (d, J=6.6 Hz, 3H); 0.80 (d, J=6.6 Hz, 3H); 1.01 (d, J=6.9 Hz, 3H); 1.05 (d, J=6.9 Hz, 3H); 1.30 (m, 1H); 1.54 (m, 1H); 1.60 (m, 1H); 1.82 (m, 1H); 2.27 (m, 1H); 2.60 to 2.78 (m, 3H); 2.97 to 3.05 (m, 2H); 3.15 (m, 1H); 3.41 (m, 1H); 3.81 (s, 3H); 3.92 (d, J=1.6 Hz, 1H); 4.26 (ddd, J=3.8 and 8.2 and 11.5 Hz, 1H); 4.77 (s, 2H); 4.88 (dd, J=3.8 and 9.6 Hz, 1H); 5.12 (ddd, J=1.5 and 5.3 and 11.2 Hz, 1H); 5.80 (dd, J=1.5 and 15.0 Hz, 1H); 6.47 (ddd, J=3.7 and 11.2 and 15.0 Hz, 1H); 7.05 (d, J=8.5 Hz, 1H); 7.17 (dd, J=2.2 and 8.5 Hz, 1H); 7.23 (dd, J=2.7 and 9.1 Hz, 1H); 7.29 (d, J=2.2 Hz, 1H); 7.32 (d, J=8.2 Hz, 2H); 7.45 (d, J=8.2 Hz, 2H); 8.34 (d, J=8.2 Hz, 1H). LCMS (A2): ES m/z=703 $[M+H]^+$; m/z=701 $[M-H]^-$; m/z=747 $[M-H+HCO_2H]^-$ base peak; $t_R$=1.17 min.

Compound 10

(E)-(3S,6R,10R,16S)-10-(3-Chloro-4-methoxybenzyl)-3-isobutyl-6-methyl-16-[(S)-1-((2R,3R)-3-{4-[4-(4-methyl-4-methyldisulfanylpentanoyl)piperazin-1-ylmethyl]phenyl}oxiranyl)-ethyl]-1,4-dioxa-8,11-diazacyclohexadec-13-ene-2,5,9,12-tetraone

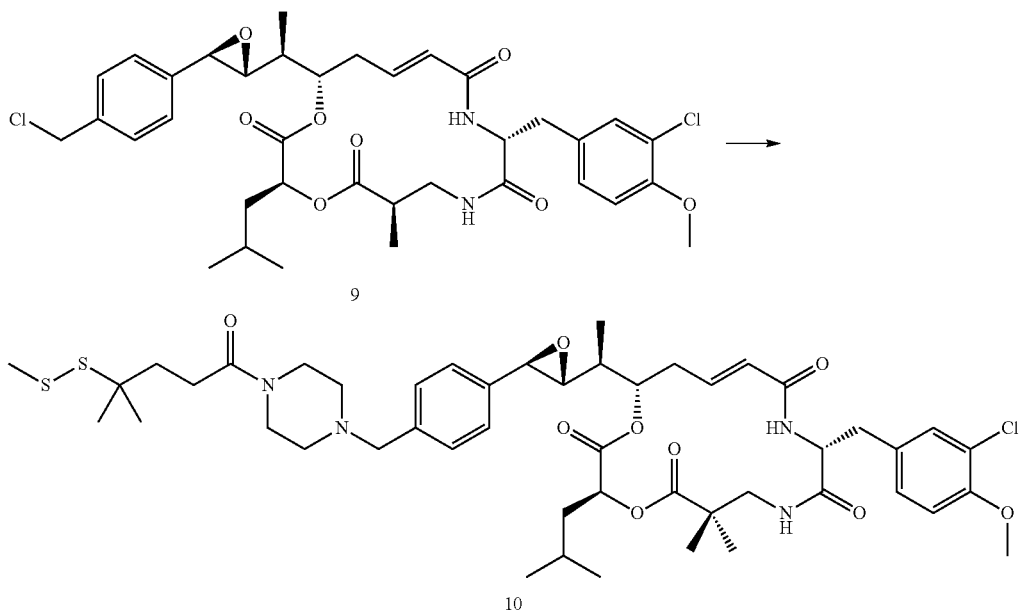

Compound 9 (36.6 mg; 52 μmol) is dissolved in anhydrous acetonitrile (3 ml), followed by successive addition of DIPEA (260 μmol) and Compound 6 (156 μmol). The reaction medium is stirred for 20 hours at RT and then hydrolyzed by addition of 4 ml of water. The aqueous phase is extracted with EtOAc (3×4 ml) and the organic phases are combined, washed with saturated aqueous $NaHCO_3$ solution (5 ml) and with saturated aqueous NaCl solution (5 ml). After drying over $MgSO_4$ and filtering, the solvents are evaporated off under reduced pressure. The crude reaction product is purified by chromatography on silica gel, eluting with a 100/0 to 95/5 DCM/methanol mixture. Compound 10 is obtained in the form of a white solid (39 mg; 80%). $^1$H NMR (500 MHz, DMSO-$d_6$): 0.78 (d, J=6.6 Hz, 3H); 0.80 (d, J=6.6 Hz, 3H); 1.01 (d, J=6.9 Hz, 3H); 1.05 (d, J=6.9 Hz, 3H); 1.26 (s, 6H); 1.30 (m, 1H); 1.53 (m, 1H); 1.60 (m, 1H); 1.75 to 1.84 (m, 3H); 2.26 to 2.37 (m, 7H); 2.39 (s, 3H); 2.61 to 2.77 (m, 3H); 2.96 to 3.05 (m, 2H); 3.15 (m, 1H); 3.38 (partially masked m, 1H); 3.44 (m, 4H); 3.48 (s, 2H); 3.81 (s, 3H); 3.88 (d, J=1.6 Hz, 1H); 4.27 (ddd, J=4.0 and 8.1 and 11.5 Hz, 1H); 4.88 (dd, J=3.8 and 9.6 Hz, 1H); 5.12 (ddd, J=1.6 and 5.3 and 11.5 Hz, 1H); 5.80 (dd, J=1.6 and 15.1 Hz, 1H); 6.47 (ddd, J=3.6 and 11.5 and 15.1 Hz, 1H); 7.05 (d, J=8.5 Hz, 1H); 7.17 (dd, J=2.2 and 8.5 Hz, 1H); 7.23 (dd, J=2.6 and 9.2 Hz, 1H); 7.27 (d, J=8.4 Hz, 2H); 7.29 (d, J=2.2 Hz, 1H); 7.32 (d, J=8.4 Hz, 2H); 8.35 (d, J=8.1 Hz, 1H). LCMS (A2): ES m/z=929 [M+H]$^+$; m/z=927 [M−H]$^−$; m/z=973 [M−H+HCO$_2$H]$^−$ base peak; $t_R$=0.99 min.

Example 2

(E)-(3S,6R,10R,16S)-10-(3-Chloro-4-methoxybenzyl)-3-isobutyl-6-methyl-16-[(S)-1-((2R,3R)-3-{4-[4-(4-mercapto-4-methylpentanoyl)piperazin-1-ylmethyl]phenyl}oxiranyl)ethyl]-1,4-dioxa-8,11-diazacyclohexadec-13-ene-2,5,9,12-tetraone

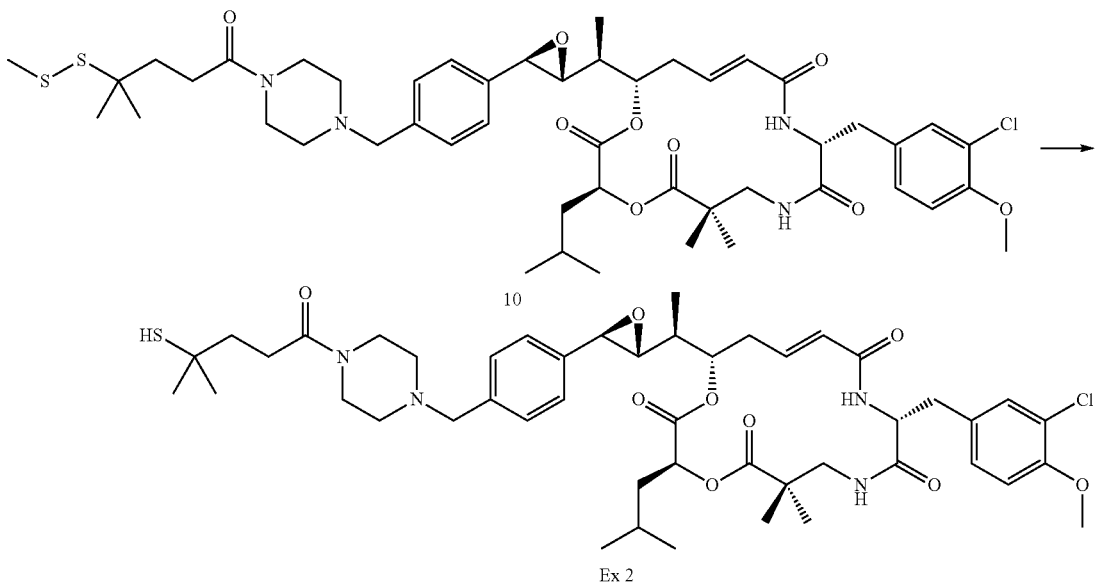

Ex 2

Product 10 (34 mg; 36.6 μmol) is dissolved in a mixture of ethanol (4.3 ml)/water (3.6 ml) and the mixture turns cloudy. TCEP (146 μmol) is then added, the mixture becomes colourless, and is stirred for 2 hours at RT. The mixture is diluted by adding EtOAc (20 ml) and the organic phase is washed with a 1/1 mixture of water and saturated aqueous NH$_4$Cl solution (20 ml). The aqueous phase is extracted with 2×20 ml of EtOAc and the organic phases are combined and washed with saturated NaCl solution (20 ml). After drying over MgSO$_4$, filtering and evaporating off the solvents under reduced pressure, the crude product is purified by chromatography on silica gel, eluting with a 98/2 to 90/10 DCM/MeOH mixture. The compound Ex. 2 is obtained in the form of a white solid (28.2 mg; 87%). $^1$H NMR (500 MHz, DMSO-$d_6$): 0.77 (d, J=6.6 Hz, 3H); 0.79 (d, J=6.6 Hz, 3H); 1.01 (d, J=6.9 Hz, 3H); 1.04 (d, J=6.9 Hz, 3H); 1.27 (m, 1H); 1.31 (s, 6H); 1.53 (m, 1H); 1.59 (m, 1H); 1.77 (m, 2H); 1.82 (m, 1H); 2.24 to 2.32 (m, 3H); 2.34 to 2.44 (m, 4H); 2.62 to 2.76 (m, 4H); 2.98 to 3.04 (m, 2H); 3.15 (m, 1H); 3.41 (m, 1H); 3.46 (m, 4H); 3.48 (s, 2H); 3.81 (s, 3H); 3.88 (d, J=2.0 Hz, 1H); 4.26 (ddd, J=3.4 and 8.3 and 11.5 Hz, 1H); 4.88 (dd, J=3.7 and 10.0 Hz, 1H); 5.12 (ddd, J=2.0 and 5.3 and 11.1 Hz, 1H); 5.80 (dd, J=2.0 and 15.0 Hz, 1H); 6.47 (ddd, J=3.7 and 11.1 and 15.0 Hz, 1H); 7.05 (d, J=8.3 Hz, 1H); 7.17 (dd, J=2.0 and 8.3 Hz, 1H); 7.23 (dd, J=2.9 and 9.3 Hz, 1H); 7.27 (d, J=8.5 Hz, 2H); 7.29 (d, J=2.0 Hz, 1H); 7.32 (d, J=8.5 Hz, 2H); 8.35 (d, J=8.3 Hz, 1H). LCMS (A2): ES m/z=883 [M+H]$^+$; m/z=881 [M−H]$^−$; $t_R$=0.92 min.

Example 3

(E)-(3S,10R,16S)-10-(3-Chloro-4-methoxybenzyl)-3-isobutyl-16-[(S)-1-42R,3R)-3-{4-[(2-mercapto-2-methylpropylamino)methyl]phenyl}oxiranyl)ethyl]-6,6-dimethyl-1,4-dioxa-8,11-diazacyclohexadec-13-ene-2,5,9,12-tetraone

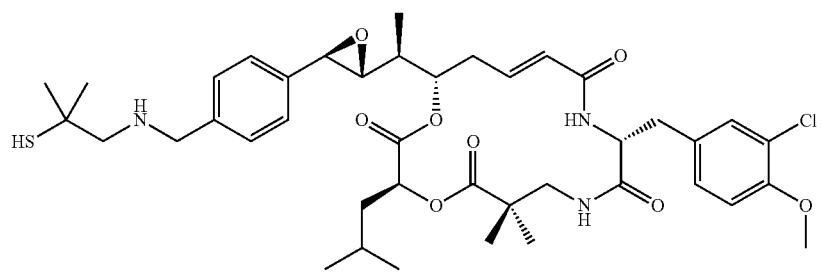

Compound 11

2-Methyl-2-methyldisulfanylpropionaldehyde O-methyloxime

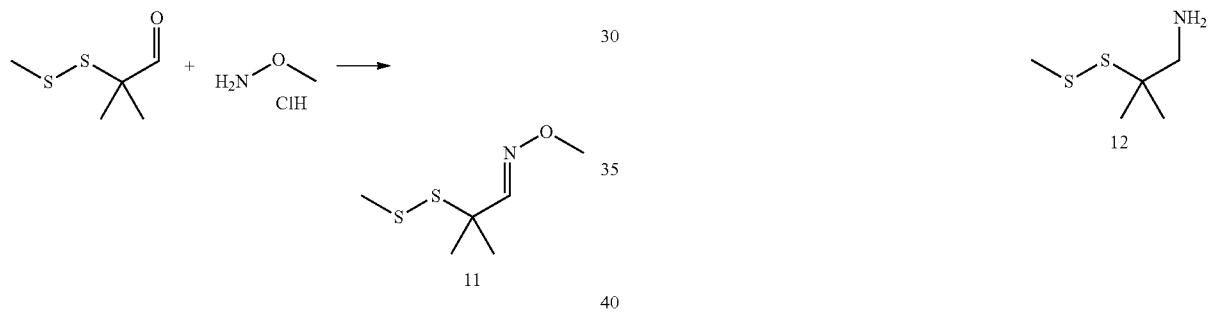

5 g (33.3 mmol) of 2-(methyldithio)isobutyraldehyde are dissolved in 50 ml of ethanol, under an inert atmosphere. A suspension of 5.56 g (66.54 mmol) of O-methylhydroxylamine chloride in 50 ml of ethanol and then 6.65 ml (66.54 mmol) of NaOH are successively added. The cloudy white mixture is refluxed overnight. After cooling to RT, the mixture is poured into 500 ml of water. The aqueous phase is extracted with EtOAc (3×175 ml), and the combined organic phases are washed with saturated NaCl solution (200 ml) and dried over $MgSO_4$. After filtering and concentrating under reduced pressure, compound 11 is obtained in the form of a colourless oil (5.89 g, 32.9 mmol).

Compound 12

2-Methyl-2-methyldisulfanylpropylamine

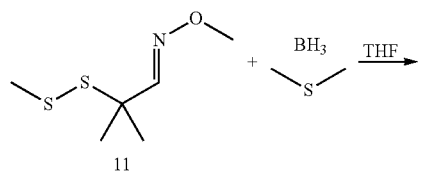

1.78 g (9.9 mmol) of oxime ether 11, 19 ml of anhydrous THF and 99.5 ml of a 2M solution of borane-methyl sulfide in THF are successively introduced, at RT, into a round-bottomed flask purged with argon. The mixture is refluxed for 16 hours. The reaction is then stopped and the mixture is allowed to cool to RT, followed by cautious dropwise addition of 100 ml of MeOH at 0° C. while the foam forms, and then at RT. The mixture is evaporated under reduced pressure to give about 2.8 g of a yellow oil, which is taken up in 30 ml of a 5 to 6N solution of HCl in isopropanol. The mixture is refluxed for 1 hour and then left at RT overnight. After evaporating under reduced pressure, the residue obtained is taken up in 80 ml of 1N HCl and then extracted with diethyl ether (3×20 ml). The aqueous phase is treated with aqueous 30% ammonia until a pH of 12.5-13 is obtained, i.e. 12 ml (pale purple aqueous phase) and then extracted again with 3×20 ml of ether. The organic phases are combined, dried over $MgSO_4$, filtered and evaporated to dryness under reduced pressure to give 760 mg of crude product. This residue is finally purified by chromatography on silica gel, eluting with a 100/0 to 90/10 DCM/methanol mixture. Compound 12 is obtained in the form of a pale yellow oil (301 mg, 20%). LCMS (A2): ES m/z=152 [M+H]$^+$; $t_R$=0.27 min.

Compound 13

(E)-(3S,10R,16S)-10-(3-Chloro-4-methoxybenzyl)-
3-isobutyl-16-[(S)-1-((2R,3R)-3-{4-[(2-methyl-2-
methyldisulfanylpropylamino)methyl]
phenyl}oxiranyl)ethyl]-6,6-dimethyl-1,4-dioxa-8,11-
diazacyclohexadec-13-ene-2,5,9,12-tetraone

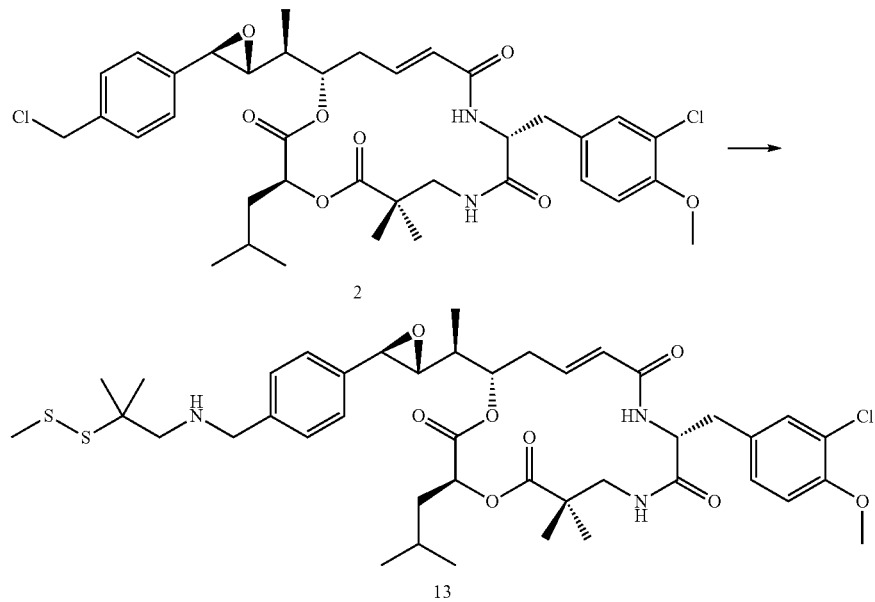

To a solution, purged with argon, of 25 mg (35 μmol) of compound 2 in 3.1 ml of anhydrous DMF are successively added, at RT, 9.8 μl (70 μmol) of TEA and 6.3 mg (42 μmol) of compound 12. Stirring is continued at 40° C. After reaction for 72 hours, some starting compound 2 remains, so a further 9.8 μl (70 μmol) of TEA and 6.3 mg (42 μmol) of the amine 12 are added. After a further 72 hours at 40° C., some compound 2 still remains: 6.3 mg (42 μmol) of the amine 12 are added and stirring is continued at 40° C. One day later, the reaction is complete. The mixture is diluted in 10 ml of EtOAc, washed with 2×10 ml of water, with 10 ml of saturated $NaHCO_3$ solution and 10 ml of saturated NaCl solution. After drying the organic phase over $MgSO_4$, it is filtered and then evaporated under reduced pressure to give 30 mg of crude product. This residue is purified by chromatography on silica gel, eluting with a 98/2 to 93/7 DCM/methanol mixture. Compound 13 is obtained in the form of a white powder (23.3 mg, 81%). TLC (DCM 90/MeOH 10): Rf=0.55; $^1$H NMR (500 MHz, DMSO-$d_6$): 0.76 to 0.81 (m, 6H); 1.02 (s, 3H); 1.07 (d, J=6.9 Hz, 3H); 1.13 (s, 3H); 1.27 to 1.33 (m, 7H); 1.52 to 1.63 (m, 2H); 1.82 (sxt, J=6.8 Hz, 1H); 2.06 (broad s, 1H); 2.25 to 2.34 (m, 1H); 2.37 (s, 3H); 2.57 (s, 2H); 2.66 to 2.76 (m, 2H); 2.97 to 3.06 (m, 3H); 3.33 to 3.38 (m, 1H); 3.75 (s, 2H); 3.83 (s, 3H); 3.88 (d, J=1.6 Hz, 1H); 4.27 (ddd, J=3.7 and 8.0 and 11.4 Hz, 1H); 4.93 (dd, J=3.7 and 9.7 Hz, 1H); 5.12 (dd, J=5.8 and 11.3 Hz, 1H); 5.82 (dd, J=1.5 and 15.2 Hz, 1H); 6.49 (ddd, J=3.8 and 11.3 and 15.2 Hz, 1H); 7.07 (d, J=8.5 Hz, 1H); 7.18 (dd, J=1.9 and 8.5 Hz, 1H); 7.23 (dd, J=2.6 and 9.5 Hz, 1H); 7.26 (d, J=8.2 Hz, 2H); 7.30 (d, J=1.9 Hz, 1H); 7.35 (d, J=8.2 Hz, 2H); 8.35 (d, J=8.0 Hz, 1H). LCMS (A2): ES m/z=832 [M+H]$^+$; m/z=830 [M−H]$^−$; $t_R$=0.96 min.

Example 3

(E)-(3S,10R,16S)-10-(3-Chloro-4-methoxybenzyl)-
3-isobutyl-16-[(S)-1-((2R,3R)-3-(4-[(2-mercapto-2-
methylpropylamino)methyl]phenyl}oxiranyl)ethyl]-
6,6-dimethyl-1,4-dioxa-8,11-diazacyclohexadec-13-
ene-2,5,9,12-tetraone

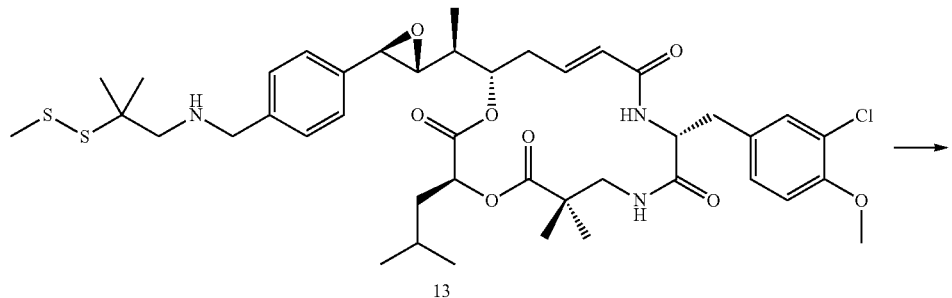

-continued

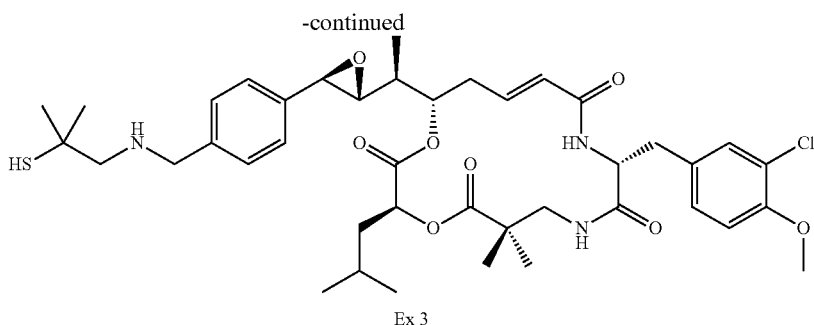

Ex 3

Product 13 (10.6 mg; 12.8 µmol) is dissolved in a mixture of ethanol (1.5 ml)/water (1.26 ml). TCEP (9.1 mg, 31.9 µmol) is then added and the mixture is stirred for 2 hours 30 minutes at RT. The mixture is diluted in 15 ml of EtOAc and the organic phase is washed with a 1/1 mixture of water and saturated aqueous NH$_4$Cl solution (5 ml). After drying the organic phase over MgSO$_4$, filtering and evaporating off the solvents under reduced pressure, the crude product obtained is finally purified by chromatography on silica gel, eluting with a 98/2 to 92/8 DCM/methanol mixture. The compound Ex. 3 is obtained in the form of a white solid (6.4 mg; 63%). TLC (DCM 90/MeOH 10): Rf=0.47; $^1$H NMR (500 MHz, DMSO-d$_6$): 0.80 to 0.86 (m, 6H); 1.06 (s, 3H); 1.11 (d, J=6.9 Hz, 3H); 1.18 (s, 3H); 1.31 to 1.38 (m, 7H); 1.57 to 1.67 (m, 2H); 1.87 (sxt, J=6.8 Hz, 1H); 2.29 to 2.38 (m, 1H); 2.56 (s, 2H); 2.70 to 2.80 (m, 2H); 3.00 to 3.11 (m, 3H); 3.39 to 3.43 (m, 1H); 3.82 (s, 2H); 3.87 (s, 3H); 3.92 (d, J=1.9 Hz, 1H); 4.31 (ddd, J=3.6 and 8.0 and 11.5 Hz, 1H); 4.97 (dd, J=3.7 and 9.7 Hz, 1H); 5.17 (dd, J=5.8 and 11.3 Hz, 1H); 5.86 (dd, J=1.4 and 15.1 Hz, 1H); 6.54 (ddd, J=3.8 and 11.3 and 15.1 Hz, 1H); 7.11 (d, J=8.7 Hz, 1H); 7.23 (dd, J=1.9 and 8.7 Hz, 1H); 7.27 (dd, J=2.7 and 9.6 Hz, 1H); 7.31 (d, J=8.0 Hz, 2H); 7.34 (d, J=1.9 Hz, 1H); 7.42 (d, J=8.0 Hz, 2H); 8.40 (d, J=8.0 Hz, 1H). LCMS (A2): ES m/z=786 [M+H]$^+$; m/z=784 [M-H]$^-$; t$_R$=0.92 min.

Example 4

(E)-(3S,10R,16S)-10-(3-Chloro-4-methoxybenzyl)-3-isobutyl-16-[(S)-1-((2R,3R)-3-{4-[({2-mercapto-2-methylpropyl}methylamino)methyl]phenyl}oxiranyl)ethyl]-6,6-dimethyl-1,4-dioxa-8,11-diazacyclohexadec-13-ene-2,5,9,12-tetraone

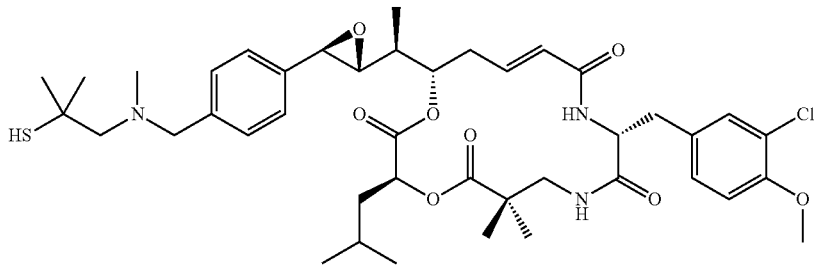

Compound 14

Methyl[2-methyl-2-methyldisulfanylprop-(E)-ylidene]amine

14

1 g (6.66 mmol) of 2-(methyldithio)isobutyraldehyde are dissolved in 10 ml of anhydrous THF, under an inert atmosphere. A 2M solution of methylamine in THF (33.3 ml, 66.6 mmol) is added and the mixture is then stirred for 5 hours at RT. It is diluted in 50 ml of EtOAc, washed with water (30 ml) and with saturated NaCl solution (30 ml) and dried over MgSO$_4$. After filtering and concentrating under reduced pressure, compound 14 is obtained in the form of a pale yellow oil (1.01 g, 93%). $^1$H NMR (400 MHz, chloroform-d): 1.46 (s, 6H); 2.36 (s, 3H); 3.32 (s, 3H); 7.52 (s, 1H).

Compound 15

2-Methyl-2-methyldisulfanylpropylamine

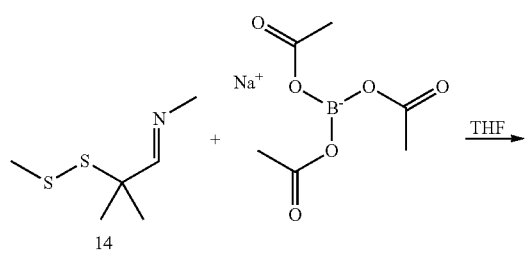

A solution of compound 14 (1.01 g, 6.185 mmol) in 30 ml of THF is purged with argon and cooled to 0° C., followed by addition, at 0° C., of 1.44 g (6.80 mmol) of sodium triacetoxyborohydride. Stirring is continued for 15 hours at RT: some starting imine remains; 1.44 g (6.80 mmol) of sodium triacetoxyborohydride and 354 µl (6.185 mmol) of acetic acid are added at 0° C. and stirring is then continued for 3 hours at RT. The mixture is diluted in 50 ml of EtOAc and washed with water (50 ml). The pH of the aqueous phase is adjusted to about 12 by adding 14 ml of aqueous 1N sodium hydroxide solution, and it is then extracted with diethyl ether (3×50 ml). The organic phases are combined, washed with saturated NaCl solution (50 ml) and dried over MgSO$_4$. After filtering and concentrating under reduced pressure, compound 15 is obtained in the form of a colourless oil (695 mg, 68%). $^1$H NMR (400 MHz, DMSO-d$_6$): 1.25 (s, 6H); 1.47 (broad m, 1H); 2.31 (s, 3H); 2.38 (s, 3H); 2.53 (m, 2H). LCMS (A2): ES m/z=166 [M+H]$^+$; t$_R$=0.28 min.

Compound 16

(E)-(3S,10R,16S)-10-(3-Chloro-4-methoxybenzyl)-3-isobutyl-16-{(S)-1-[(2R,3R)-3-(4-{[(2-methyl-2-methyldisulfanylpropyl)methylamino]methyl}phenyl)oxiranyl]ethyl]-6,6-dimethyl-1,4-dioxa-8,11-diazacyclohexadec-13-ene-2,5,9,12-tetraone

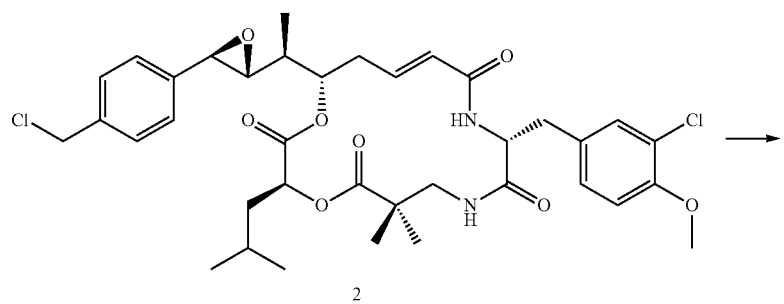

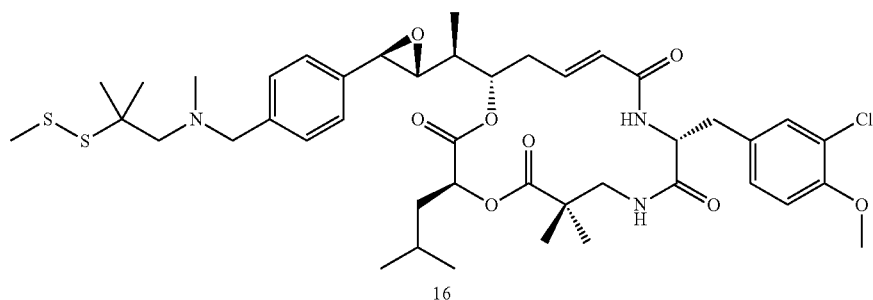

Compound 16 may be obtained by nucleophilic substitution of the chloro group of the derivative 2 with the amine 15 by applying the method described for the preparation of compound 30.

Example 4

(E)-(3S,10R,16S)-10-(3-Chloro-4-methoxybenzyl)-3-isobutyl-16-{(S)-1-[(2R,3R)-3-(4-{[(2-mercapto-2-methylpropyl)methylamino]methyl}phenyl)oxiranyl)ethyl]-6,6-dimethyl-1,4-dioxa-8,11-diazacyclohexadec-13-ene-2,5,9,12-tetraone

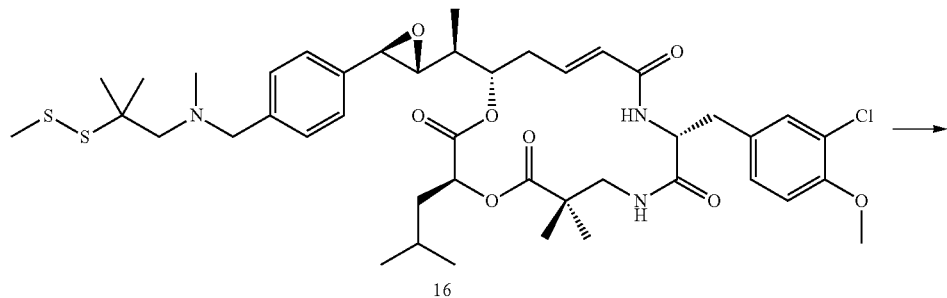

16

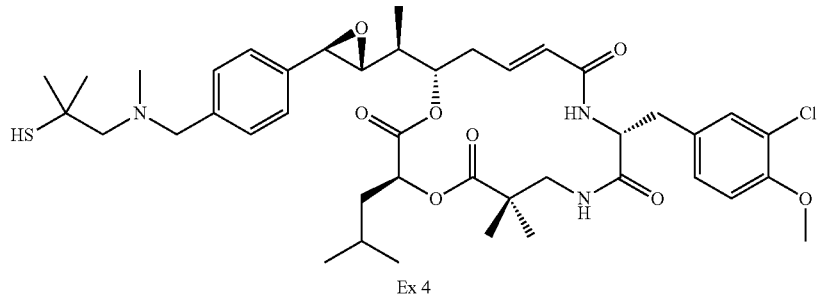

Ex 4

Example 4 may be obtained by applying the method described for the preparation of Example 6 to compound 16.

Example 5

(E)-(3S,10R,16S)-10-(3-Chloro-4-methoxybenzyl)-3-isobutyl-16-[(S)-1-((2R,3R)-3-{4-[4-(2-mercapto-2-methylpropyl)piperazin-1-ylmethyl]phenyl}oxiranyl)ethyl]-6,6-dimethyl-1,4-dioxa-8,11-diazacyclohexadec-13-ene-2,5,9,12-tetraone

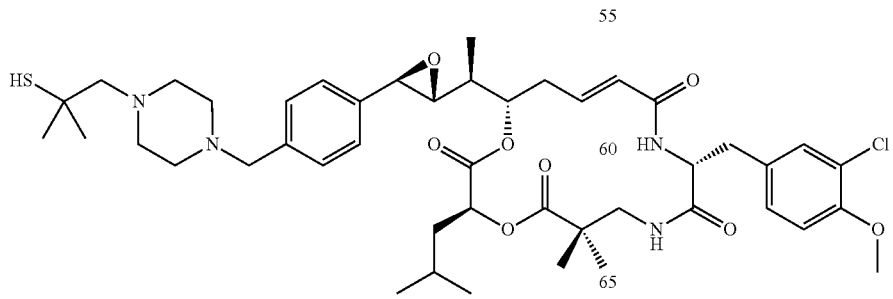

Compound 17 tert-Butyl 4-(2-methyl-2-methyldisulfanylpropyl)piperazine-1-carboxylate

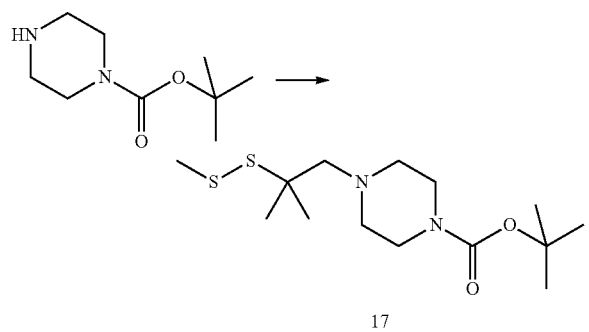

To a solution, purged with argon, of 1-Boc-piperazine (1.0 g, 5.37 mmol) in anhydrous THF (20 ml) are added 2-(methyldithio)isobutyraldehyde (5.37 mmol) and titanium(IV) isopropoxide (6.71 mmol). The mixture is stirred for 20 minutes at RT, and a further addition of 2-(methyldithio)-isobutyraldehyde (5.37 mmol) and of titanium(IV) isopropoxide (6.71 mmol) is performed. Stirring is continued for 2 hours, and then 12 ml of ethanol are added and stirring is continued for 5 minutes. Sodium cyanoborohydride (5.37 mmol) is added and the mixture is stirred for 1 hour, followed by addition of a further 5.37 mmol of sodium cyanoborohydride. Stirring is continued for 1 hour. The mixture is concentrated to dryness and then taken up in EtOAc. Water is added, causing the formation of a precipitate, which is filtered off on a sinter funnel and rinsed with EtOAc and water. The solid obtained is dissolved in aqueous 1N HCl solution (50 ml) and the medium is neutralized with aqueous 5N NaOH solution and then extracted with DCM. The organic phases are combined, washed with saturated NaCl solution, dried over MgSO$_4$, filtered and concentrated under reduced pressure. The crude product is purified by chromatography on silica gel, eluting with a 100/0 to 97/3 DCM/methanol mixture. Compound 17 is obtained in the form of a pale yellow oil (650 mg; 40%). $^1$H NMR (400 MHz, DMSO-d$_6$): 1.26 (s, 6H); 1.39 (s, 9H); 2.39 (s, 3H); 2.42 (s, 2H); 2.44 to 2.48 (m, 4H); 3.27 (partially masked m, 4H). LCMS (A1): ES m/z=321 [M+H]$^+$; m/z=265 base peak; t$_R$=3.02 min.

Compound 18

1-(2-Methyl-2-methyldisulfanylpropyl)piperazine hydrochloride

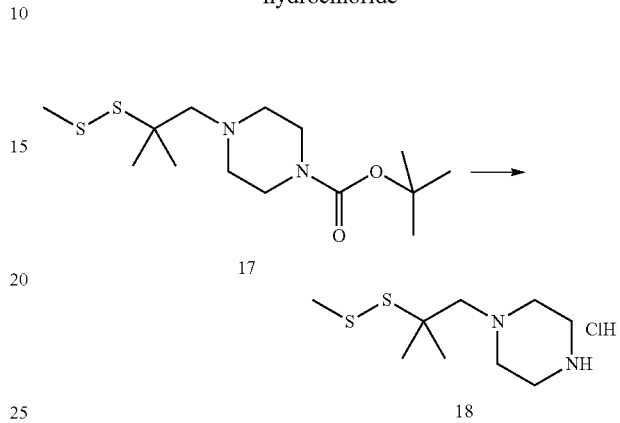

To a solution of compound 17 (322 mg, 1.01 mmol) in dioxane (13 ml) is added a 4M solution of HCl in dioxane (5 ml). Stirring is continued for 16 hours at RT. The mixture is filtered through a sinter funnel and the solid obtained is rinsed with dioxane to give compound 18 (231 mg, 90%) in the form of a white powder. $^1$H NMR (400 MHz, DMSO-d$_6$): 1.31 (broad s, 6H); 2.42 (s, 3H); 2.59 to 3.38 (very broad m, 10H); 8.78 (broad m, 2H). LCMS (A2): ES m/z=221 [M+H]$^+$; t$_R$=0.46 min.

Compound 19

(E)-(3S,10R,16S)-10-(3-Chloro-4-methoxybenzyl)-3-isobutyl-6,6-dimethyl-16-[(S)-1-((2R,3R)-3-{4-[4-(2-methyl-2-methyldisulfanylpropyl)piperazin-1-ylmethyl]phenyl}oxiranyl)ethyl]-1,4-dioxa-8,11-diazacyclohexadec-13-ene-2,5,9,12-tetraone

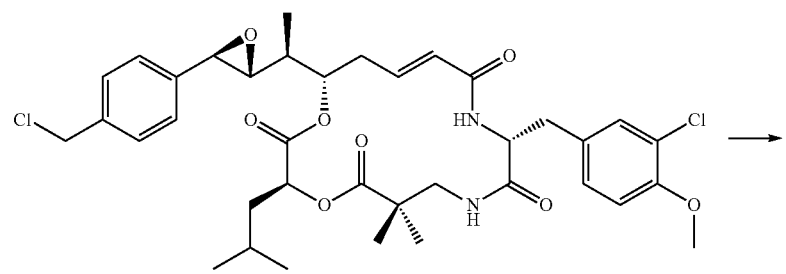

-continued

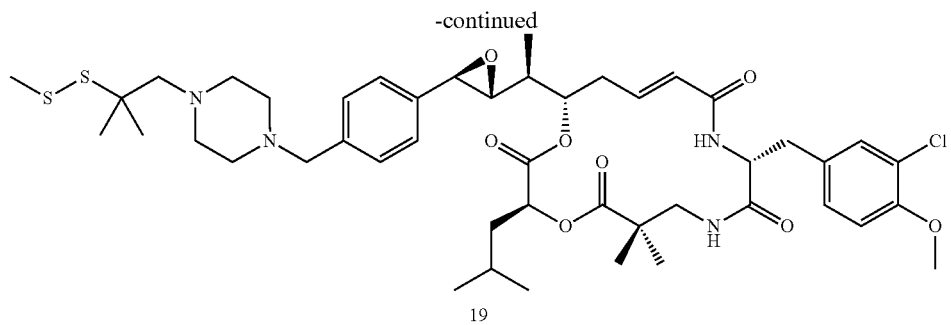

19

To a solution, purged with argon, of compound 2 (15.02 mg, 20.93 μmol) in anhydrous DMF (0.9 ml) is added a solution of compound 18 (25.12 μmol) and TEA (52.3 μmol) in DMF (1 ml). The mixture is stirred at 40° C. under argon. After 24 hours, 25.12 μmol of compound 18 and 31.4 μmol of TEA are added. After a further 24 hours at 40° C., the reaction is complete. The mixture is diluted with EtOAc (6 ml) and washed with water (2×6 ml), with saturated NaHCO$_3$ solution (6 ml) and with saturated NaCl solution (6 ml). After drying the organic phase over MgSO$_4$, it is filtered and then evaporated under reduced pressure to give 46 mg of crude product. The residue is purified by chromatography on silica gel, eluting with a 100/0 to 95/5 DCM/methanol mixture. Compound 19 is obtained in the form of a white powder (5.2 mg, 28%). $^1$H NMR (500 MHz, DMSO-d$_6$): 0.76 (d, J=6.4 Hz, 3H); 0.78 (d, J=6.4 Hz, 3H); 1.01 (s, 3H); 1.06 (d, J=6.8 Hz, 3H); 1.13 (s, 3H); 1.25 (s, 6H); 1.27 to 1.33 (m, 1H); 1.51 to 1.63 (m, 2H); 1.76 to 1.85 (m, 1H); 2.23 to 2.32 (m, 1H); 2.37 (m, 4H); 2.39 (s, 3H); 2.41 (s, 2H); 2.53 to 2.56 (m, 4H); 2.63 to 2.76 (m, 2H); 2.94 to 3.06 (m, 3H); 3.34 (partially masked m, 1H); 3.40 to 3.48 (m, 2H); 3.82 (s, 3H); 3.87 (d, J=2.0 Hz, 1H); 4.26 (ddd, J=3.8 and 7.8 and 11.3 Hz, 1H); 4.92 (dd, J=3.8 and 9.8 Hz, 1H); 5.07 to 5.14 (m, 1H); 5.81 (d, J=15.2 Hz, 1H); 6.48 (ddd, J=3.8 and 11.3 and 15.2 Hz, 1H); 7.06 (d, J=8.5 Hz, 1H); 7.18 (dd, J=2.2 and 8.5 Hz, 1H); 7.21 to 7.32 (m, 6H); 8.35 (d, J=8.3 Hz, 1H). LCMS (A1): ES m/z=901 [M+H]$^+$; m/z=451 base peak; t$_R$=4.33 min.

Example 5

(E)-(3S,10R,16S)-10-(3-Chloro-4-methoxybenzyl)-3-isobutyl-16-[(S)-1-((2R,3R)-3-(4-[4-(2-mercapto-2-methylpropyl)piperazin-1-ylmethyl]phenyl}oxiranyl)ethyl]-6,6-dimethyl-1,4-dioxa-8,11-diazacyclohexadec-13-ene-2,5,9,12-tetraone

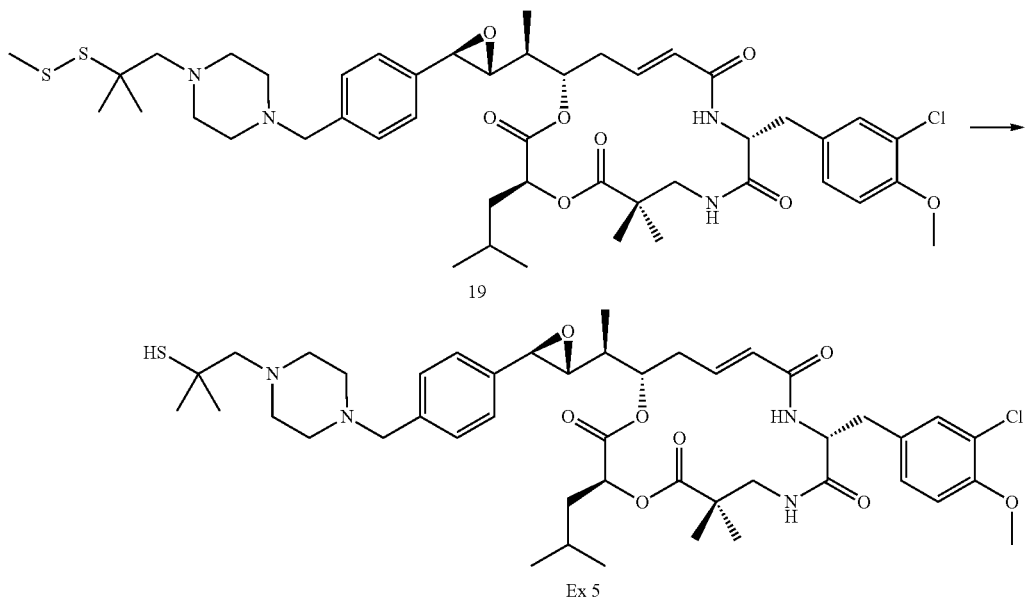

Product 19 (5.7 mg; 6.3 μmol) is dissolved in a mixture of ethanol (0.8 ml)/water (0.5 ml). TCEP (4.54 mg, 15.83 μmol) is then added and the mixture is stirred for 1 hour at RT. The mixture is diluted in 7 ml of EtOAc and the organic phase is washed with a 1/1 mixture of water and saturated aqueous NH$_4$Cl solution (7 ml). After drying the organic phase over MgSO$_4$, filtering and evaporating off the solvents under reduced pressure, the crude product obtained is purified by chromatography on silica gel, eluting with a 99/1 to 95/5 DCM/methanol mixture. The compound Ex. 5 is obtained in the form of a white solid (2.95 mg; 55%). $^1$H NMR (500 MHz, DMSO-d$_6$): 0.77 (d, J=6.3 Hz, 3H); 0.78 (d, J=6.3 Hz, 3H); 1.02 (s, 3H); 1.06 (d, J=6.9 Hz, 3H); 1.13 (s, 3H); 1.27 (s, 6H); 1.29 to 1.34 (m, 1H); 1.52 to 1.63 (m, 2H); 1.82 (m, 1H); 2.29 (m, 1H); 2.37 (s, 2H); 2.39 to 2.41 (m, 4H); 2.57 to 2.62 (m, 4H); 2.65 to 2.76 (m, 2H); 2.96 to 3.06 (m, 3H); 3.34 (partially masked m, 1H); 3.46 (s, 2H); 3.83 (s, 3H); 3.88 (d, J=2.2 Hz, 1H); 4.27 (ddd, J=3.7 and 8.0 and 11.5 Hz, 1H); 4.93 (dd, J=3.7 and 9.7 Hz, 1H); 5.12 (m, 1H); 5.82 (d, J=15.2 Hz, 1H); 6.49 (ddd, J=3.7 and 11.5 and 15.2 Hz, 1H); 7.07 (d, J=8.5 Hz, 1H); 7.18 (dd, J=2.2 and 8.5 Hz, 1H); 7.21 to 7.33 (m, 6H);

Example 6

(E)-(3S,10R,16S)-10-(3-Chloro-4-methoxybenzyl)-3-isobutyl-16-[(S)-1-((2R,3R)-3-{4-[4-({2-[2-(2-{2-methyl[2-mercapto-2-methylpropyl]aminoethoxy}ethoxy]ethoxy]ethyl}-methylamino)methyl]phenyl}oxiranyl)ethyl]-6,6-dimethyl-1,4-dioxa-8,11-diazacyclohexadec-13-ene-2,5,9,12-tetraone

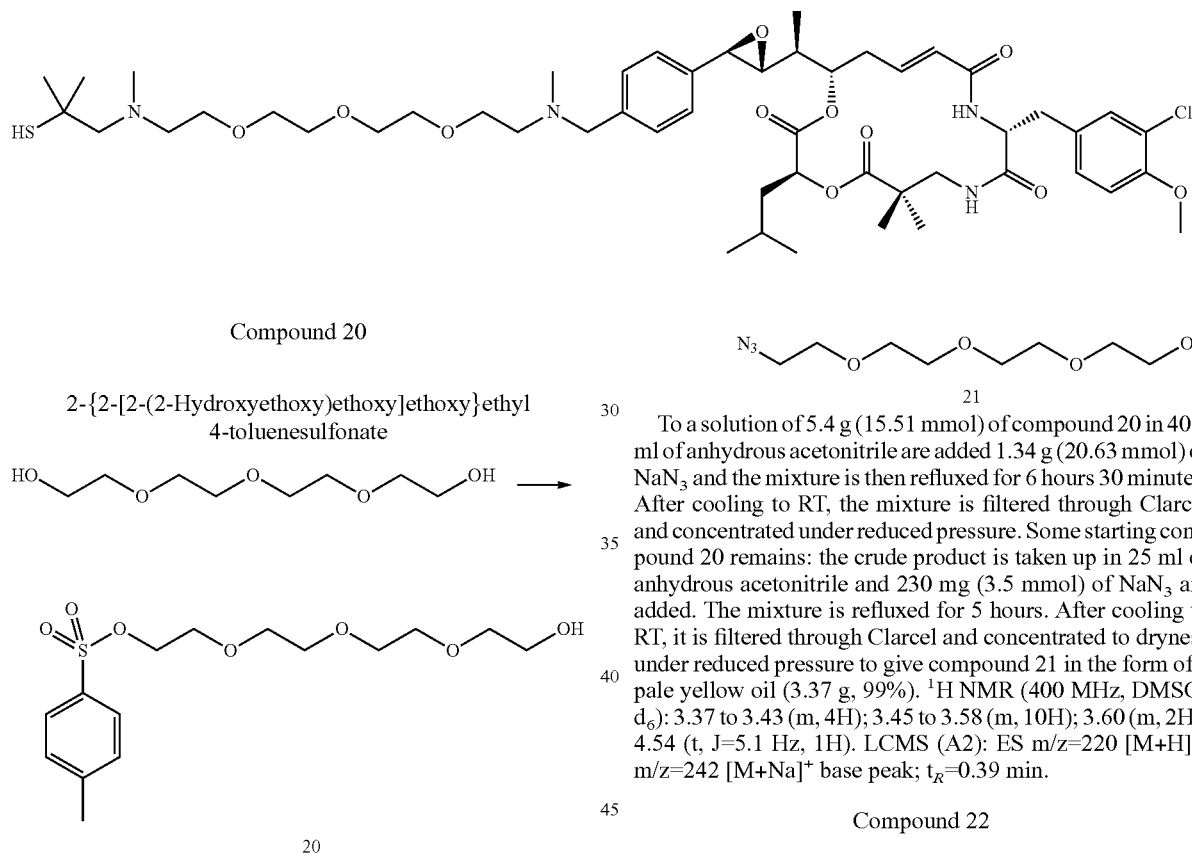

Compound 20

2-{2-[2-(2-Hydroxyethoxy)ethoxy]ethoxy}ethyl 4-toluenesulfonate

To a solution, purged under argon and cooled to 0° C., of 5 g (25.74 mmol) of tetraethylene glycol in 68.7 ml of DCM are successively added portionwise, so as to maintain suitable stirring, 8.95 g (38.61 mmol) of silver oxide and 5.40 g (28.31 mmol) of tosyl chloride. 855 mg (5.15 mmol) of KI are added portionwise so as to maintain the temperature of the mixture below 5° C. Stirring is continued for 1 hour while keeping the temperature below 5° C. After warming to RT, the mixture is filtered through Clarcel, the residue is rinsed with DCM and the filtrate is then concentrated to dryness under reduced pressure. The crude product is purified by chromatography on silica gel, using a 99/1 to 95/5 DCM/methanol mixture as eluent. Compound 20 is obtained in the form of a colourless oil (5.4 g, 60%). $^1$H NMR (400 MHz, DMSO-d$_6$): 2.43 (s, 3H); 3.40 (m, 2H); 3.44 to 3.52 (m, 10H); 3.58 (m, 2H); 4.11 (m, 2H); 4.53 (t, J=5.4 Hz, 1H); 7.48 (d, J=8.3 Hz, 2H); 7.78 (d, J=8.3 Hz, 2H). LCMS (A2): ES m/z=349 [M+H]$^+$; m/z=371 [M+Na]$^+$; t$_R$=0.69 min.

Compound 21

1-Azido-3,6-9-trioxaundecan-11-ol

To a solution of 5.4 g (15.51 mmol) of compound 20 in 40.6 ml of anhydrous acetonitrile are added 1.34 g (20.63 mmol) of NaN$_3$ and the mixture is then refluxed for 6 hours 30 minutes. After cooling to RT, the mixture is filtered through Clarcel and concentrated under reduced pressure. Some starting compound 20 remains: the crude product is taken up in 25 ml of anhydrous acetonitrile and 230 mg (3.5 mmol) of NaN$_3$ are added. The mixture is refluxed for 5 hours. After cooling to RT, it is filtered through Clarcel and concentrated to dryness under reduced pressure to give compound 21 in the form of a pale yellow oil (3.37 g, 99%). $^1$H NMR (400 MHz, DMSO-d$_6$): 3.37 to 3.43 (m, 4H); 3.45 to 3.58 (m, 10H); 3.60 (m, 2H); 4.54 (t, J=5.1 Hz, 1H). LCMS (A2): ES m/z=220 [M+H]$^+$; m/z=242 [M+Na]$^+$ base peak; t$_R$=0.39 min.

Compound 22

N-Boc-aminoethoxyethoxyethoxyethanol

To a solution, rendered inert under argon, of 320 mg of 10% palladium-on-charcoal in 5 ml of EtOAc is added a solution of 3.25 g (14.8 mmol) of compound 21, 6.46 g (29.6 mmol) of tert-butyl dicarbonate and 4.13 ml (29.6 mmol) of TEA in 45 ml of EtOAc. The reaction is performed for 17 hours at 30° C. under a hydrogen pressure of 2 bar. After cooling to RT and atmospheric pressure, the mixture is filtered through Clarcel and concentrated under reduced pressure. The crude product 8.36 (d, J=8.0 Hz, 1H). LCMS (A1): ES m/z=855 [M+H]$^+$; m/z=428 [M+2H]$^{2+}$ base peak; t$_R$=4.13 min.

is purified by chromatography on silica gel, using a 98/2 to 90/10 DCM/methanol mixture as eluent. Compound 22 is obtained in the form of a colourless oil (2.92 g, 67%). $^1$H NMR (400 MHz, DMSO-$d_6$): 1.37 (s, 9H); 3.06 (q, J=6.1 Hz, 2H); 3.37 (t, J=6.1 Hz, 2H); 3.42 (m, 2H); 3.46 to 3.53 (m, 10H); 4.54 (broad t, J=5.1 Hz, 1H); 6.71 (broad t, J=6.1 Hz, 1H). LCMS (A1): ES m/z=316 [M+Na]$^+$; m/z=194 base peak; $t_R$=2.81 min.

LCMS (A2): ES m/z=448 [M+H]$^+$; m/z=470 [M+Na]$^+$; m/z=348 base peak; m/z=492 [M−H+HCO$_2$H]$^-$; $t_R$=1.00 min.

Compound 24 tert-Butyl (2-{2-[2-(2-azidoethoxy)ethoxy]ethoxy}ethyl)carbamate

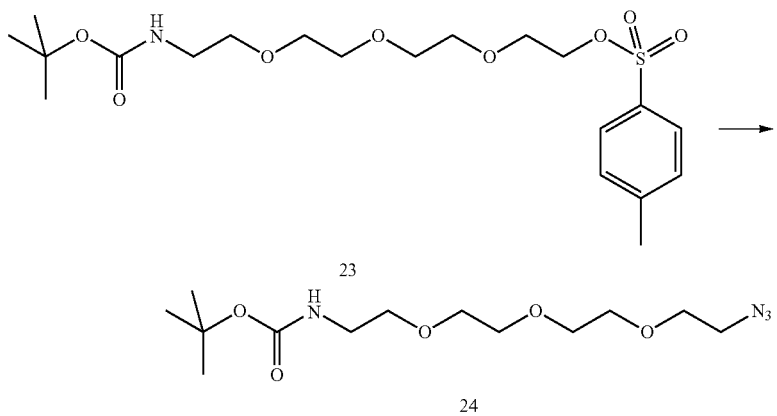

24

To a solution of 4.38 g (9.79 mmol) of compound 23 in 25 ml of acetonitrile are added 846 mg (13.02 mmol) of sodium azide and the mixture is then refluxed for 6 hours. A large proportion of starting compound remains: after cooling to RT, 1.7 g (26.13 mmol) are added to the mixture. Stirring is continued at reflux for 24 hours. After cooling to RT, the mixture is filtered through Clarcel and concentrated under reduced pressure. The crude product is purified by chromatography on silica gel, using a 98/2 to 90/10 DCM/methanol mixture as eluent. Compound 24 is obtained in the form of a pale yellow oil (2.16 g, 69%). $^1$H NMR (400 MHz, DMSO-$d_6$): 1.37 (s, 9H); 3.06 (q, J=6.1 Hz, 2H); 3.34 to 3.43 (m, 4H); 3.46 to 3.58 (m, 8H); 3.60 (m, 2H); 6.70 (broad t, J=6.1 Hz, 1H). LCMS (A2): ES m/z=341 [M+Na]$^+$; $t_R$=0.81 min.

Compound 23

2-{2-[2-(2-tert-Butoxycarbonylaminoethoxy)ethoxy]ethoxy}ethyl 4-toluenesulfonate

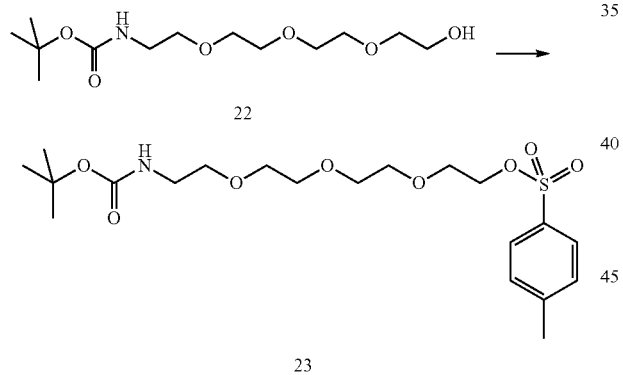

To a solution, purged with argon, of 3.06 g (10.42 mmol) of compound 22 in 20 ml of DCM are added 2.53 ml (31.26 mmol) of pyridine. The mixture is cooled to 0° C., followed by dropwise addition of a solution of 2.98 g (15.63 mmol) of tosyl chloride in 10 ml of DCM. Stirring is continued for 15 hours at RT. The mixture is diluted in 20 ml of DCM, washed with saturated NaHCO$_3$ solution (30 ml), with water (2×30 ml) and with saturated NaCl solution (30 ml) and dried over MgSO$_4$. After filtering and concentrating under reduced pressure, the crude product is purified by chromatography on silica gel, using a 100/0 to 90/10 DCM/methanol mixture as eluent. Compound 23 is obtained in the form of a pale yellow oil (4.38 g, 94%). $^1$H NMR (400 MHz, DMSO-$d_6$): 1.37 (s, 9H); 2.42 (s, 3H); 3.05 (q, J=6.1 Hz, 2H); 3.36 (t, J=6.1 Hz, 2H); 3.46 (m, 8H); 3.58 (m, 2H); 4.10 (m, 2H); 6.71 (broad t, J=6.1 Hz, 1H); 7.48 (d, J=7.8 Hz, 2H); 7.78 (d, J=7.8 Hz, 2H).

Compound 25 tert-Butyl (2-{2-[2-(2-azidoethoxy)ethoxy]ethoxy}ethyl)methylcarbamate

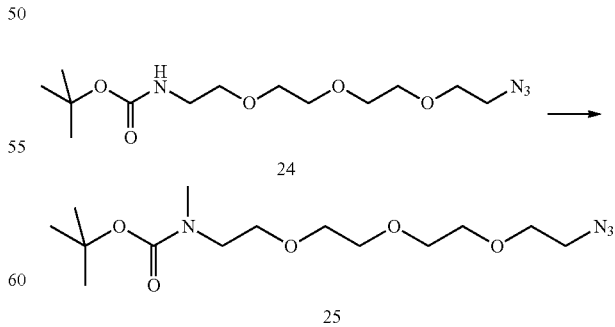

To a solution, purged with argon and cooled to 0° C., of 2.06 g (6.47 mmol) of compound 24 in 25 ml of anhydrous THF are successively added, at 0° C., 854 mg (21.35 mmol) of 60% NaH as a dispersion in mineral oil (portionwise) and 886 µl (14.23 mmol) of methyl iodide. Stirring is continued for 1 hour at 0° C. and then for 16 hours at RT. The mixture is filtered through Clarcel, washed with THF and concentrated under reduced pressure. The crude product is purified by chromatography on silica gel, using a 99/1 to 90/10 DCM/methanol mixture as eluent. Compound 25 is obtained in the form of a colourless oil (1.67 g, 78%). $^1$H NMR (400 MHz, DMSO-d$_6$): 1.39 (s, 9H); 2.80 (broad s, 3H); 3.29 (partially masked t, J=5.6 Hz, 2H); 3.38 (m, 2H); 3.46 to 3.56 (m, 10H); 3.60 (t, J=5.4 Hz, 2H).

Compound 26 tert-Butyl (2-{2-[2-(2-aminoethoxy)ethoxy]ethoxy}ethyl)methylcarbamate

To a solution, purged with argon, of 1.66 g (4.99 mmol) of compound 25 in 20 ml of THF are successively added 1.31 g (4.994 mmol) of triphenylphosphine and 108 µl (5.99 mmol) of water. Stirring is continued for 25 hours 30 minutes and the mixture is then concentrated to dryness and purified by SPE filtration on an SCX cartridge (Varian) conditioned and washed with methanol and then eluted with a 0.5 N solution of aqueous ammonia in methanol. Compound 26 is obtained in the form of a colourless oil (1.23 g, 80%). $^1$H NMR (400 MHz, DMSO-d$_6$): 1.39 (s, 9H); 2.65 (t, J=5.9 Hz, 2H); 2.80 (broad s, 3H); 3.29 (t, J=5.9 Hz, 2H); 3.36 (t, J=5.7 Hz, 2H); 3.45 to 3.56 (m, 10H). LCMS (A2): ES m/z=307 [M+H]$^+$; t$_R$=0.49 min.

Compound 27 tert-Butyl methyl[2-(2-{2-[2-(2-methyl-2-methyldisulfanylpropylamino)ethoxy]-ethoxy}ethoxy)ethyl]carbamate

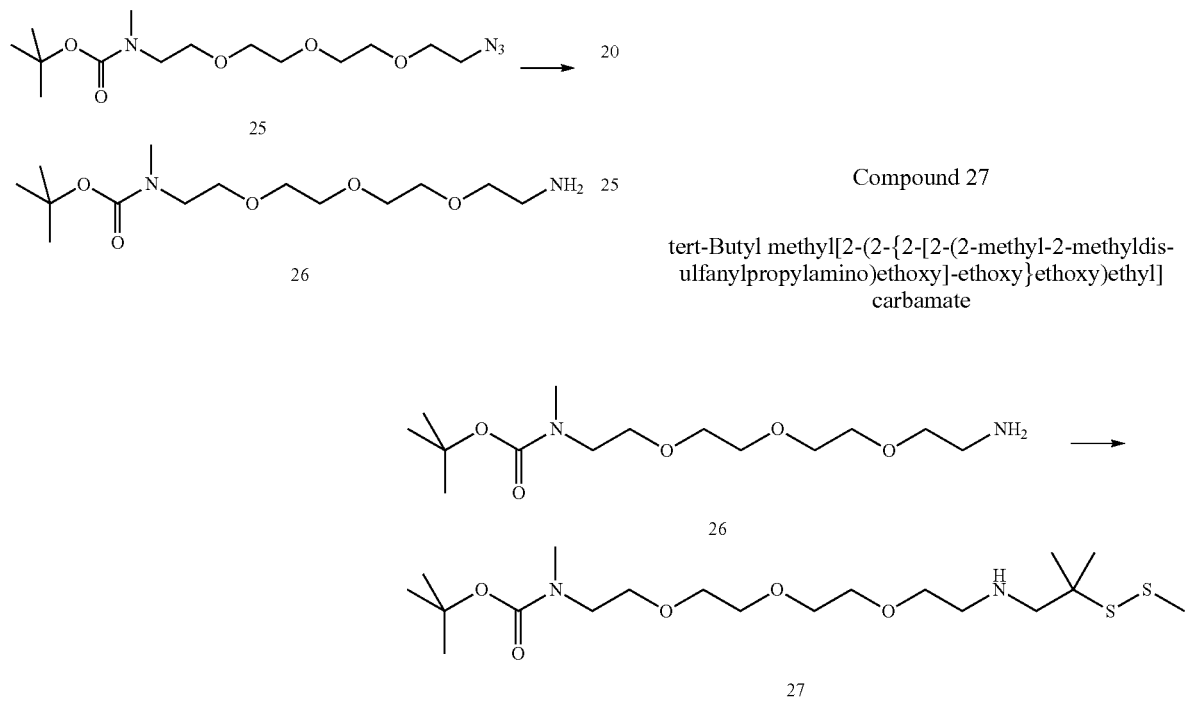

To a solution, purged with argon, of 131 mg (426 µmol) of compound 26 in 3 ml of DCM are successively added 64 mg (426 µmol) of 2-methyldithioisobutyraldehyde, 126 mg (596 µmol) of sodium triacetoxyborohydride and 24.4 µl (426 µmol) of acetic acid. Stirring is continued for 6 hours at RT under argon, the reaction is quenched by addition of 1 ml of aqueous 1N sodium hydroxide solution and then the mixture is extracted with 10 ml of diethyl ether. After concentrating under reduced pressure, the crude product is purified by chromatography on silica gel, using a 90/10 DCM/isopropanol mixture as eluent, which does not make it possible to separate out the expected product from the residual starting amine. The product obtained is again purified by RP18 reverse-phase chromatography using a 95/5 to 5/95 water/acetonitrile mixture as eluent. Compound 27 is obtained in the form of a colourless oil (67 mg, 36%). $^1$H NMR (400 MHz, DMSO-d$_6$): 1.25 (s, 6H); 1.39 (s, 9H); 1.58 (broad m, 1H); 2.38 (s, 3H); 2.59 (s, 2H); 2.68 (t, J=5.6 Hz, 2H); 2.80 (broad s, 3H); 3.46 (t, J=5.6 Hz, 2H); 3.48 to 3.54 (m, 12H). LCMS (A1): ES m/z=441 [M+H]$^+$; t$_R$=3.29 min.

Compound 28 tert-Butyl methyl{2-[2-(2-{2-[methyl(2-methyl-2-methyldisulfanylpropyl)amino]-ethoxy}ethoxy)ethoxy]ethyl}carbamate

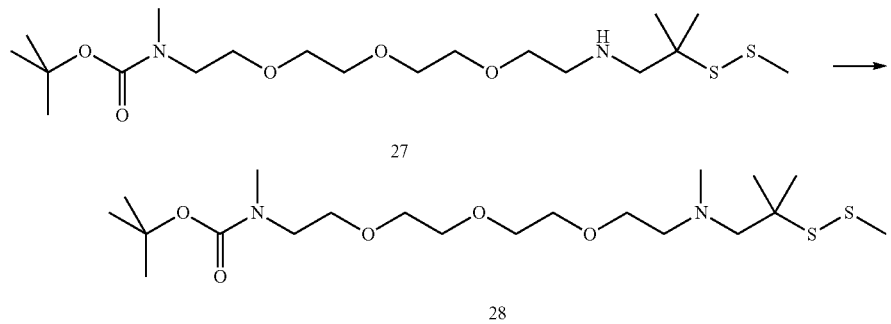

To a solution, purged with argon and cooled to 0° C., of 65 mg (148 µmol) of compound 27 in 1 ml of DCM are successively added 19.5 mg (487 µmol) of NaH as a 60% dispersion in a mineral oil and 20 µl (325 µmol) of methyl iodide. Stirring is continued for 45 minutes at 0° C. and then for 72 hours at RT. The mixture is filtered through Clarcel and then concentrated under reduced pressure. The crude product is purified by chromatography on silica gel, using a 99/1 to 90/10 DCM/methanol mixture as eluent. Compound 28 is obtained in the form of a colourless oil (43 mg, 64%). $^1$H NMR (400 MHz, DMSO-$d_6$): 1.25 (s, 6H); 1.39 (s, 9H); 2.32 (s, 3H); 2.39 (s, 3H); 2.54 (m, 2H); 2.61 (t, J=6.1 Hz, 2H); 2.80 (broad s, 3H); 3.42 to 3.54 (m, 14H). LCMS (A2): ES m/z=455 [M+H]$^+$; $t_R$=0.77 min.

Compound 29

Methyl(2-{2-[2-(2-methylaminoethoxy)ethoxy]ethoxy}ethyl)(2-methyl-2-methyl-disulfanylpropyl)amine

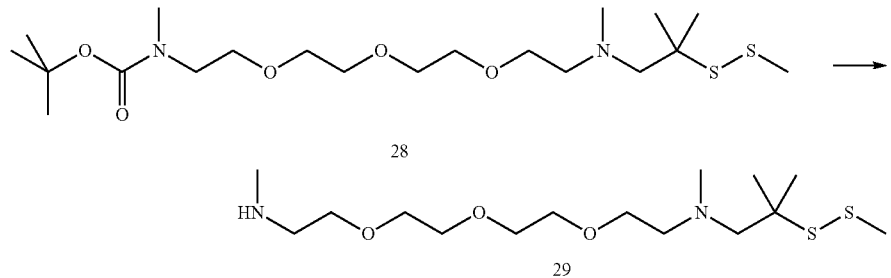

To a solution of 43 mg (95 µmol) of compound 28 in 1.5 ml of DCM are added 351 µl of TFA. Stirring is continued for 5 hours at RT and the mixture is then concentrated to dryness. The crude product is purified by SPE filtration on an SCX cartridge (Varian) conditioned and washed with methanol, and then eluted with a 0.5 N solution of aqueous ammonia in methanol. Compound 29 is obtained in the form of a colourless oil (25 mg, 75%). $^1$H NMR (400 MHz, DMSO-$d_6$): 1.25 (s, 6H); 1.75 (broad m, 1H); 2.27 (s, 3H); 2.32 (s, 3H); 2.39 (s, 3H); 2.53 (m, 2H); 2.57 to 2.64 (m, 4H); 3.44 (t, J=5.7 Hz, 2H); 3.46 to 3.55 (m, 10H). LCMS (A2): ES m/z=355 [M+H]$^+$; $t_R$=0.30 min.

Compound 30

(E)-(3S,10R,16S)-10-(3-Chloro-4-methoxybenzyl)-3-isobutyl-16-[(S)-1-((2R,3R)-3-{4-[4-({2-[2-(2-{2-methyl-2-methyl-2-methyldisulfanylpropyl]aminoethoxy}ethoxy)ethoxy]-ethyl}methylamino)methyl]phenyl}oxiranyl)ethyl]-6,6-dimethyl-1,4-dioxa-8,11-diazacyclohexadec-13-ene-2,5,9,12-tetraone

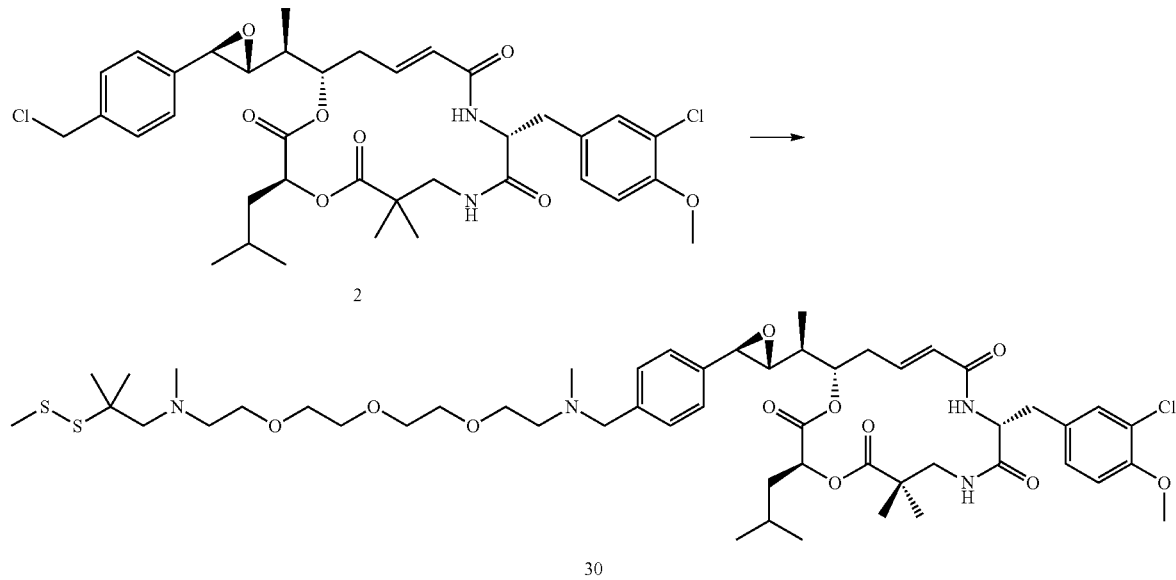

To a solution, purged with argon, of 15.3 mg (21.3 μmol) of compound 2 in 1 ml of anhydrous acetonitrile are successively added 18.6 μl (106.6 μmol) of DIPEA and a solution of 22.7 mg (64 μmol) of compound 29 in 1 ml of anhydrous acetonitrile. Stirring is continued for 24 hours under argon at 40° C. After cooling to RT, the mixture is diluted with 7 ml of EtOAc, washed with water (2×3 ml), with saturated NaHCO$_3$ solution (3 ml) and with saturated NaCl solution (3 ml) and dried over MgSO$_4$. After filtering and concentrating under reduced pressure, the crude product is purified by chromatography on silica gel, using a 90/10 DCM/methanol mixture as eluent. Compound 30 is obtained in the form of a colourless solid (14.6 mg, 66%). $^1$H NMR (500 MHz, DMSO-d$_6$): 0.76 (d, J=6.1 Hz, 3H); 0.76 (d, J=6.1 Hz, 3H); 1.00 (s, 3H); 1.04 (d, J=6.8 Hz, 3H); 1.12 (s, 3H); 1.24 (s, 6H); 1.29 (m, 1H); 1.50 to 1.62 (m, 2H); 1.81 (m, 1H); 2.15 (s, 3H); 2.27 (m, 1H); 2.31 (s, 3H); 2.38 (s, 3H); 2.45 to 2.54 (partially masked m, 4H); 2.60 (t, J=6.1 Hz, 2H); 2.63 to 2.75 (m, 2H); 2.92 to 3.06 (m, 3H); 3.25 to 3.35 (partially masked m, 1H); 3.44 to 3.54 (m, 14H); 3.81 (s, 3H); 3.87 (d, J=2.0 Hz, 1H); 4.25 (ddd, J=3.9 and 8.3 and 11.7 Hz, 1H); 4.91 (dd, J=3.4 and 9.8 Hz, 1H); 5.11 (ddd, J=1.5 and 5.7 and 11.5 Hz, 1H); 5.80 (dd, J=1.5 and 15.5 Hz, 1H); 6.47 (ddd, J=3.5 and 11.5 and 15.5 Hz, 1H); 7.05 (d, J=8.8 Hz, 1H); 7.17 (dd, J=2.0 and 8.8 Hz, 1H); 7.20 to 7.26 (m, 3H); 7.27 to 7.33 (m, 3H); 8.35 (d, J=8.3 Hz, 1H). LCMS (A2): ES m/z=1035 [M+H]$^+$; m/z=518 [M+2H]$^{2+}$ base peak; $t_R$=0.86 min.

Example 6

(E)(3S,10R,16S)-10-(3-Chloro-4-methoxybenzyl)-3-isobutyl-16-[(S)-1-((2R,3R)-3-(4-[4-({2-[2-(2-{2-methyl[2-mercapto-2-methylpropyl]aminoethoxy}ethoxy)ethoxy]ethyl}methylamino)-methyl]phenyl}oxiranyl)ethyl]-6,6-dimethyl-1,4-dioxa-8,11-diazacyclohexadec-13-ene-2,5,9,12-tetraone

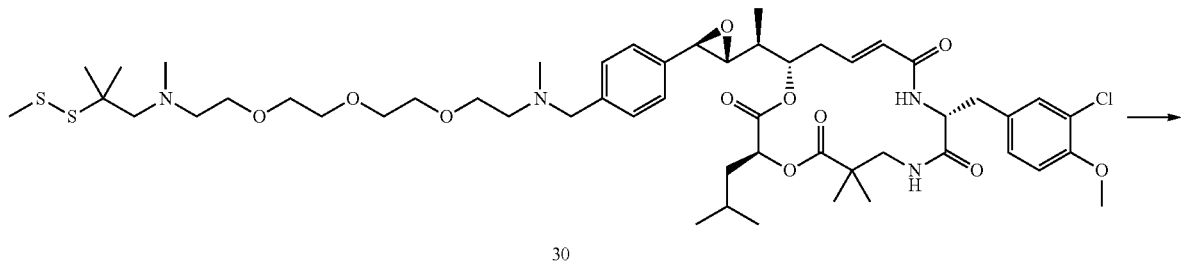

-continued

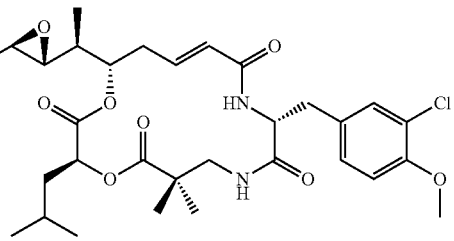

Ex6

To a solution of 10.9 mg (10.5 μmol) of compound 30 in 1.24 ml of ethanol is added a solution of 12.06 mg (42.1 μmol) of TCEP in 1.04 ml of water. Stirring is continued for 4 hours at RT. The mixture is diluted with 6 ml of EtOAc, washed with a 1/1 mixture of water/NH$_4$Cl$_{sat}$ (6 ml) and with saturated NaCl solution (6 ml), and dried over MgSO$_4$. After filtering and concentrating under reduced pressure, the crude product is purified by chromatography on silica gel, using a 99/1 to 90/10 DCM/methanol mixture. Compound Ex. 6 is obtained in the form of a white solid (7.36 mg, 71%). $^1$H NMR (500 MHz, DMSO-d$_6$): 0.76 (d, J=5.9 Hz, 3H); 0.78 (d, J=5.9 Hz, 3H); 1.00 (s, 3H); 1.04 (d, J=6.8 Hz, 3H); 1.12 (s, 3H); 1.25 (s, 6H); 1.28 (m, 1H); 1.51 to 1.62 (m, 2H); 1.80 (m, 1H); 2.15 (s, 3H); 2.27 (m, 1H); 2.34 (s, 3H); 2.44 (s, 2H); 2.51 (t, J=6.4 Hz, 2H); 2.60 (s, 1H); 2.63 (t, J=6.4 Hz, 2H); 2.66 to 2.74 (m, 2H); 2.93 to 3.04 (m, 3H); 3.25 to 3.37 (partially masked m, 1H); 3.45 to 3.55 (m, 14H); 3.81 (s, 3H); 3.87 (d, J=1.5 Hz, 1H); 4.25 (ddd, J=3.7 and 8.0 and 11.5 Hz, 1H); 4.91 (dd, J=3.4 and 9.8 Hz, 1H); 5.11 (ddd, J=1.5 and 5.6 and 11.5 Hz, 1H); 5.80 (dd, J=1.5 and 15.2 Hz, 1H); 6.47 (ddd, J=3.9 and 11.5 and 15.2 Hz, 1H); 7.05 (d, J=8.8 Hz, 1H); 7.17 (dd, J=2.2 and 8.8 Hz, 1H); 7.20 to 7.26 (m, 3H); 7.27 to 7.32 (m, 3H); 8.35 (d, J=8.0 Hz, 1H), LCMS (A1): ES m/z=989 [M+H]$^+$; m/z=495 [M+2H]$^{2+}$ base peak; t$_R$=3.24 min.

Example 7

(E)-(3S,10R,16S)-10-(3-Chloro-4-methoxybenzyl)-3-isobutyl-16-[(S)-1-((2R,3R)-3-{4-(4-({2-[2-(2-{4-methyl-4-methyldisulfanylpentanoylaminoethoxy}ethoxy)-ethoxy]ethyl}methylamino)methyl]phenyl}oxiranyl)ethyl]-6,6-dimethyl-1,4-dioxa-8,11-diazacyclohexadec-13-ene-2,5,9,12-tetraone

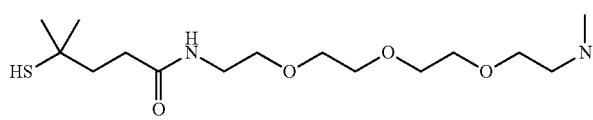

Compound 31 tert-Butyl methyl[2-(2-(2-[2-(4-methyl-4-methyldis-ulfanylpentanoylamino)ethoxy]-ethoxy}ethoxy)ethyl]carbamate

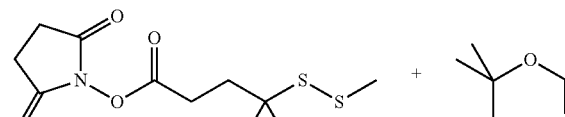

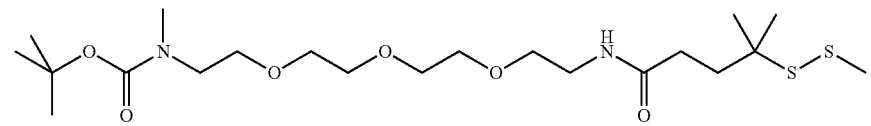

31

270 mg (649 µmol) of compound 4, 199 mg (649 µmol) of compound 26 are dissolved in 1.5 ml of DMF, and 100 µl (714 µmol) of TEA are then added to the mixture. Stirring is continued for 16 hours at RT. The mixture is diluted with 10 ml of EtOAc, washed with water (2×5 ml) and with saturated NaCl solution (5 ml) and dried over $MgSO_4$. After filtering and concentrating under reduced pressure, the crude product is purified by chromatography on silica gel, using a 98/2 to 90/10 DCM/methanol mixture as eluent. Compound 31 is obtained in the form of a colourless oil (251 mg, 80%). $^1H$ NMR (400 MHz, DMSO-$d_6$): 1.24 (s, 6H); 1.39 (s, 9H); 1.79 (m, 2H); 2.16 (m, 2H); 2.40 (s, 3H); 2.80 (broad s, 3H); 3.18 (q, J=5.9 Hz, 2H); 3.39 (t, J=5.9 Hz, 2H); 3.45 to 3.54 (m, 12H); 7.88 (broad t, J=5.9 Hz, 1H). LCMS (A2): ES m/z=483 $[M+H]^+$; m/z=505 $[M+Na]^+$; m/z=527 $[M-H+HCO_2H]^-$; $t_R$=1.04 min.

Compound 32
N-(2-{2-[2-(2-Methylaminoethoxy)ethoxy]ethoxy}ethyl)-4-methyl-4-methyl-disulfanylpentamide

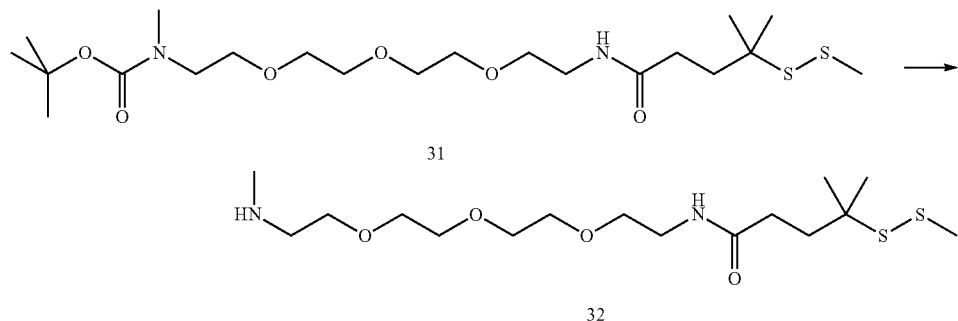

To a solution of 251 mg (520 µmol) of compound 31 in 8 ml of DCM are added 1.93 ml (26 mmol) of TFA. Stirring is continued for 3 hours at RT and the mixture is then concentrated to dryness. The crude product is dissolved in a minimum amount of DCM and then entrained several times with toluene. The crude product is purified by SPE filtration on an SCX cartridge (Varian) conditioned and washed with methanol and then eluted with a 0.5 N solution of aqueous ammonia in methanol. Compound 32 is obtained in the form of a colourless oil (159 mg, 80%). $^1H$ NMR (400 MHz, DMSO-$d_6$): 1.24 (s, 6H); 1.79 (m, 2H); 2.15 (m, 2H); 2.27 (s, 3H); 2.40 (s, 3H); 2.58 (t, J=5.7 Hz, 2H); 3.18 (q, J=5.7 Hz, 2H); 3.39 (t, J=5.7 Hz, 2H); 3.44 (t, J=5.7 Hz, 2H); 3.47 to 3.54 (m, 8H); 7.89 (broad t, J=5.7 Hz, 1H), LCMS (A1): ES m/z=383 $[M+H]^+$; $t_R$=2.68 min.

Example 7
(E)-(3S,10R,16S)-10-(3-Chloro-4-methoxybenzyl)-3-isobutyl-16-[(S)-1-((2R,3R)-3-(4-[4-({2-[2-(2-{4-methyl-4-methyldisulfanylpentanoylaminoethoxy}ethoxy)ethoxy]ethyl}methyl-amino)methyl]phenyl}oxiranyl)ethyl]-6,6-dimethyl-1,4-dioxa-8,11-diazacyclohexadec-13-ene-2,5,9,12-tetraone

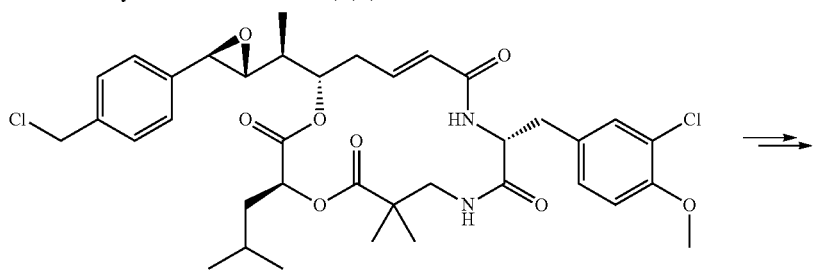

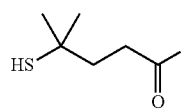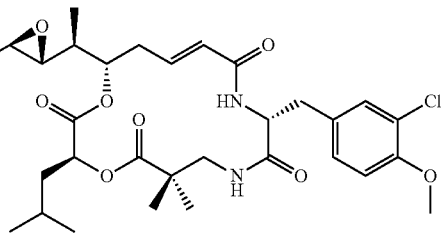

Ex7

Example 7 may be obtained by nucleophilic substitution of the chloro group of derivative 2 with the amine 32 by applying the method described for the preparation of compound 30, followed by reduction of the disulfide by applying the method described for the preparation of Example 6.

Example 8

(E)-(3S,10R,16S)-10-(3-Chloro-4-methoxybenzyl)-3-isobutyl-16-{(S)-1-[(2R,3R)-3-(4-mercaptomethylphenyl)oxiranyl]ethyl}-6,6-dimethyl-1,4-dioxa-8,11-diazacyclohexadec-13-ene-2,5,9,12-tetraone

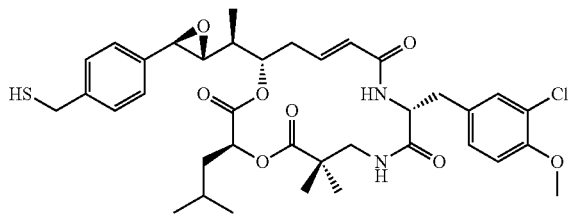

Compound 33
Dimer of Example 8

Compound 2 (24.5 mg; 34.1 µmol) is dissolved in anhydrous THF (2.5 ml) and the mixture is cooled to −10° C., followed by addition of hexamethyldisilathiane (44.3 µmol) and then a 1M solution of tetrabutylammonium fluoride in THF (40.9 µmol). The mixture is cooled to room temperature and stirring is continued for 1 hour 30 minutes. The mixture is diluted by adding EtOAc (5 ml) and the organic phase is washed with saturated aqueous NH$_4$Cl solution (5 ml). The aqueous phase is extracted with EtOAc (2×5 ml). The organic phases are combined and washed with saturated aqueous NaCl solution (5 ml). After drying over MgSO$_4$ and filtering, the solvents are evaporated off under reduced pressure. The crude reaction product is purified by chromatography on silica gel, eluting with a 100/0 to 97/3 DCM/methanol mixture as eluent. A white solid, compound 33, is obtained (19 mg; 78%). $^1$H NMR (400 MHz, DMSO-d$_6$): 0.78 (m, 12H); 1.00 (s, 6H); 1.04 (d, J=6.8 Hz, 6H); 1.11 (s, 6H); 1.30 (m, 2H); 1.49-1.63 (m, 4H); 1.82 (m, 2H); 2.26 (m, 2H); 2.63-2.72 (m, 4H); 2.93-3.05 (m, 6H); 3.25-3.37 (partially masked m, 2H); 3.81 (s, 6H); 3.82 (s, 4H); 3.89 (d, J=2.0 Hz, 2H); 4.25 (ddd, J=3.7, 8.0 and 11.5 Hz, 2H); 4.91 (dd, J=3.7, 9.6 Hz, 2H); 5.10 (ddd, J=1.3, 5.3 and 10.8 Hz, 2H); 5.79 (dd, J=1.3,

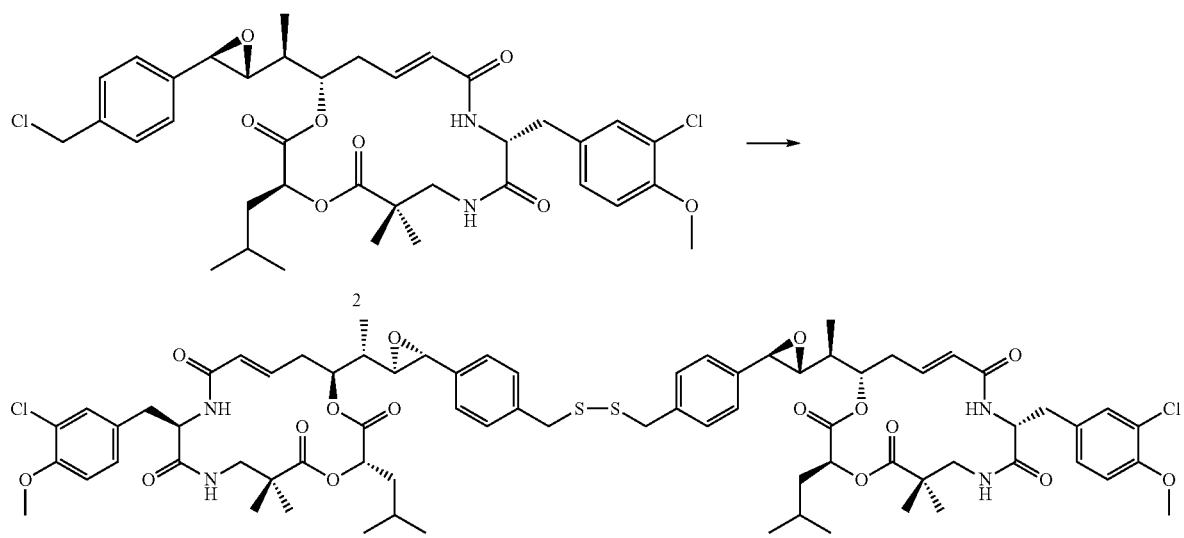

2

15.3 Hz, 2H); 6.47 (ddd, J=3.7, 10.8 and 15.3 Hz, 2H); 7.05 (d, J=8.6 Hz, 2H); 7.17 (dd, J=2.0, 8.6 Hz, 2H); 7.22 (dd, J=2.5, 9.3 Hz, 2H); 7.26-7.32 (m, 10H); 8.34 (d, J=8.0 Hz, 2H), LCMS (A2): ES m/z=1427 [M+H]$^+$; $t_R$=1.31 min.

Example 8

(E)-(3S,10R,16S)-10-(3-Chloro-4-methoxybenzyl)-3-isobutyl-16-{(S)-1-[(2R,3R)-3-(4-mercaptomethylphenyl)oxiranyl]ethyl}-6,6-dimethyl-1,4-dioxa-8,11-diazacyclohexadec-13-ene-2,5,9,12-tetraone 2.93-3.06 (m, 3H); 3.34 (partially masked m, 1H); 3.73 (broad d, J=6.5 Hz, 2H); 3.81 (s., 3H); 3.87 (d, J=1.6 Hz, 1H); 4.25 (ddd, J=3.7, 8.0 and 11.4 Hz, 1H); 4.91 (dd, J=3.6, 9.6 Hz, 1H); 5.11 (ddd, J=1.3, 5.3 and 11.4 Hz, 1H); 5.79 (dd, J=1.3, 15.2 Hz, 1H); 6.47 (ddd, J=3.4, 11.3 and 15.2 Hz, 1H); 7.05 (d, J=8.5 Hz, 1H); 7.17 (dd, J=1.9, 8.5 Hz, 1H); 7.22 (dd, J=2.3, 9.5 Hz, 1H); 7.25 (d, J=8.3 Hz, 2H); 7.28 (d, J=1.9 Hz, 2H); 7.35 (d, J=8.3 Hz, 2H); 8.34 (d, J=8.0 Hz, 2H). LCMS (A2): ES m/z=715 [M+H]$^+$; m/z=713 [M−H]$^-$; $t_R$=1.18 min.

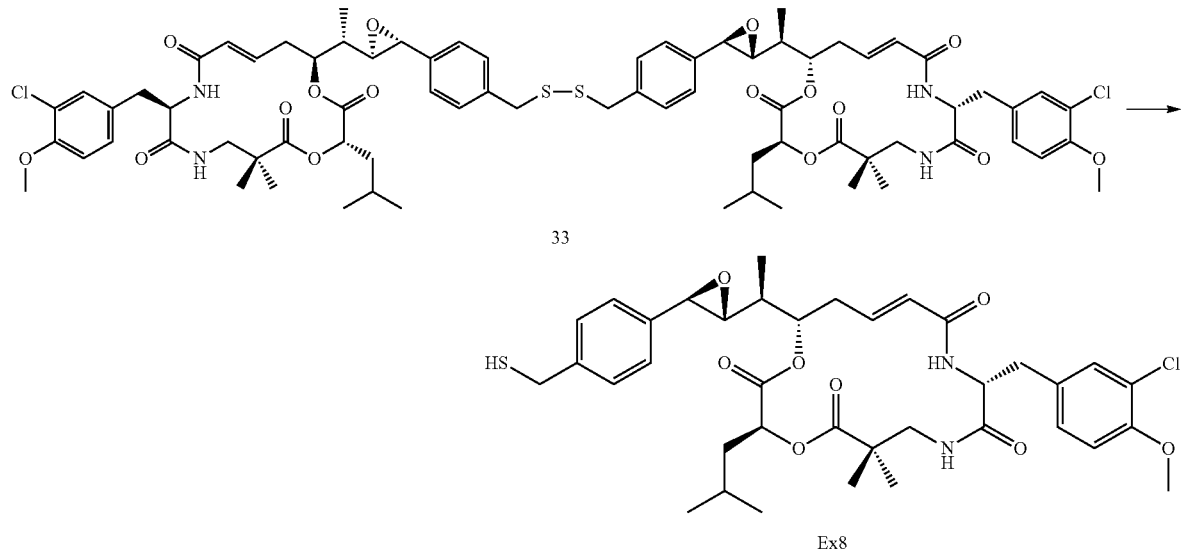

Compound 33 (11 mg; 7.7 μmol) is dissolved in methanol (8.8 ml). TCEP (76.7 μmol) dissolved in 2.2 ml of water is then added and the mixture is stirred for 2 hours at RT. The mixture is diluted in 20 ml of EtOAc and the organic phase is washed with a 1/1 mixture of water and of saturated aqueous NH$_4$Cl solution (20 ml). The aqueous phase is extracted with EtOAc (2×15 ml). The organic phases are combined, washed with saturated aqueous NaCl solution (15 ml). After drying over MgSO$_4$ and filtering, the solvents are evaporated off under reduced pressure. The crude reaction product is purified by chromatography on silica gel, eluting with a 100/0 to 95/5 DCM/methanol mixture. A white solid, Ex. 8, is obtained (4.7 mg; 31%). $^1$H NMR (400 MHz, DMSO-d$_6$): 0.79 (d, J=6.4 Hz, 6H); 1.00 (s, 3H); 1.05 (d, J=6.9 Hz, 3H); 1.12 (s, 3H); 1.30 (m, 1H); 1.50-1.63 (m, 2H); 1.80 (m, 1H); 2.27 (m, 1H); 2.62-2.75 (m, 2H); 2.84 (broad t, J=6.5 Hz, 1H);

Example 9 hu2H11-SPDB-Ex1

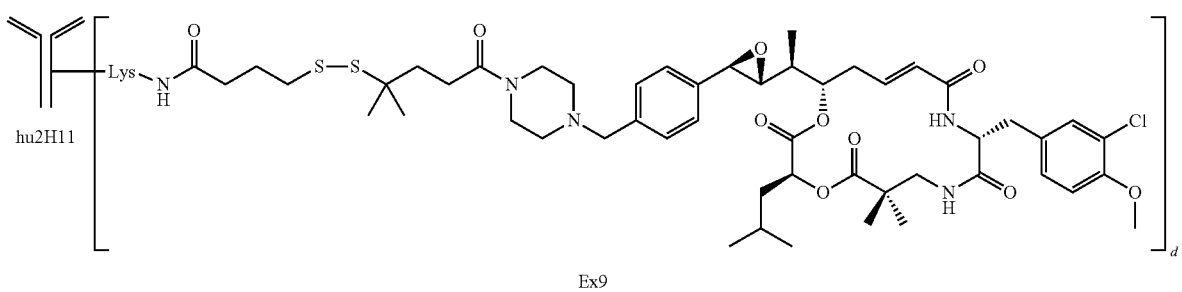

According to the general two-step method, 10.4 mg (0.071 μmol, 1.174 ml) of naked antibody hu2H11 with an initial concentration of 8.86 mg/ml are treated with 7 eq. of the N-hydroxy-succinimidyl ester of 4-(2-pyridyldithio)butanoic acid (0.16 mg, 0.496 μmol) dissolved in 34.2 μl of DMA such that the final antibody concentration is 8 mg/ml in the mixture. After purification, 2.2 ml of modified antibody hu2H11 at a concentration of 4.28 mg/ml (9.42 mg, 91%) are Obtained with, on average, 4.68 pyridyldisulfide molecules per antibody. 1.68 ml (7.2 mg, 0.049 µmol) of modified antibody hu2H11 are treated with 1.03 mg of (E)-(3S,10R,16S)-10-(3-chloro-4-methoxy-benzyl)-3-isobutyl-16-[(S)-1-((2R,3R)-3-{4-[4-(4-mercapto-4-methylpentanoyl)piperazin-1-ylmethyl]phenyl}oxiranyl)ethyl]-6,6-dimethyl-1,4-dioxa-8,11-diazacyclohexadec-13-ene-2,5,9,12-tetraone (compound Ex. 1, 1.148 µmol) dissolved in 101.2 µl of DMA. After purification on Superdex in the presence of 10% NMP and concentration on Amicon Ultra-15, the final change of buffer is performed in an aqueous pH 6.5 buffer containing 0.01 M of phosphate and 0.14 M of NaCl. 1.5 ml of conjugate Ex. 9 are thus obtained at a concentration of 1.1 mg/ml with, on average, 3 cryptophycin derivatives per antibody (HRMS) and a monomer purity of 99.9%.

Example 10 hu2H11-SPDB-Ex2

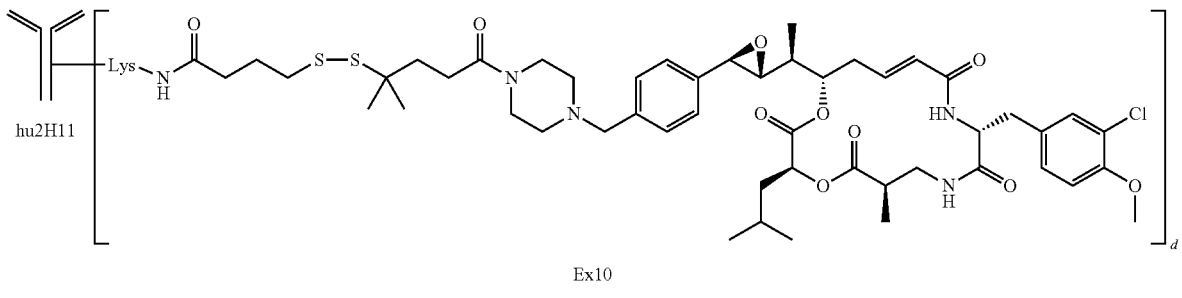

Ex10

According to the one-step general method, 13.5 mg (0.092 µmol, 1.318 ml) of naked antibody hu2H11 at an initial concentration of 10.24 mg/ml are treated with 6 eq. of the N-hydroxy-succinimidyl ester of 4-(2-pyridyldithio)butanoic acid (0.18 mg, 0.551 µmol) dissolved in 38.4 µl of DMA such that the final antibody concentration is 9 mg/ml in the mixture. After stirring for 2 hours at about 2000 rpm at RT, 1.333 ml (12.0 mg, 0.081 µmol) of the mixture of modified antibody hu2H11, 1.760 ml of pH 7.5-8 buffer, 543 µl of DMA and then 1.73 mg of (E)-(3S,6R,10R,16S)-10-(3-chloro-4-methoxy-benzyl)-3-isobutyl-16-[(S)-1-((2R,3R)-3-{-4-[4-(4-mercapto-4-methyl-pentanoyl)piperazin-1-ylmethyl]phenyl}oxiranyl)ethyl]-6-methyl-1,4-dioxa-8,11-diazacyclohexa-dec-13-ene-2,5,9,12-tetraone (compound Ex. 2, 1.958 µmol) dissolved in 182 µl of DMA are successively added. After purification on Superdex in the presence of 20% of NMP and concentration on Amicon Ultra-15, the final buffer change is performed in an aqueous pH 6.5 buffer containing 0.01 M of histidine, 10% of sucrose (w/v) and 5% of NMP (v/v). 1.5 ml of conjugate Ex. 10 are thus obtained at a concentration of 2.83 mg/ml with, on average, 3.7 cryptophycin derivatives per antibody and a monomeric purity of 98.8%.

Example 11 hu2H11-SPDB-Ex5

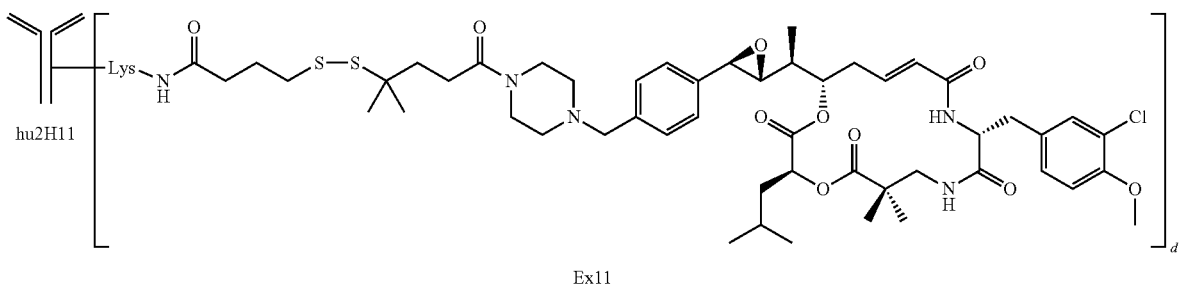

Ex11

According to the one-step general method, 9.45 mg (0.064 μmol, 0.923 ml) of naked antibody hu2H11 at an initial concentration of 10.24 mg/ml are treated with 6 eq. of the N-hydroxy-succinimidyl ester of 4-(2-pyridyldithio)butanoic acid (0.13 mg, 0.398 μmol) dissolved in 26.88 μl of DMA, such that the final antibody concentration is 9 mg/ml in the mixture. After stirring for 2 hours at about 2000 rpm at RT, 1.0 ml (9.0 mg, 0.061 μmol) of the reaction medium of modified antibody hu2H11, 1.45 ml of pH≈7.5-8 buffer, 265 μl of DMA and then 1.26 mg of (E)(3S,10R,16S)-10-(3-chloro-4-methoxybenzyl)-3-isobutyl-16-[(S)-1-((2R,3R)-3-{4-[4-(2-mercapto-2-methylpropyl)piperazin-1-ylmethyl]phenyl}oxiranyl)ethyl]-6,6-dimethyl-1,4-dioxa-8,11-diazacyclohexadec-13-ene-2,5,9,12-tetraone (compound Ex. 5, 1.472 μmol) dissolved in 285 μl of DMA are successively added. After purification on Superdex in the presence of 20% of NMP and concentration on Amicon Ultra-15, the final buffer change is formed in an aqueous pH 6.5 buffer containing 0.01 M of histidine, 10% of sucrose (w/v) and 5% of NMP (v/v). 2.5 ml of conjugate Ex. 12 are thus obtained at a concentration of 1.70 mg/ml with, on average, 3.7/3.1 cryptophycin derivatives (UV/HRMS) per antibody and a monomer purity of 98.0%.

Example 12 hu2H11-SPDB-Ex6

Ex12

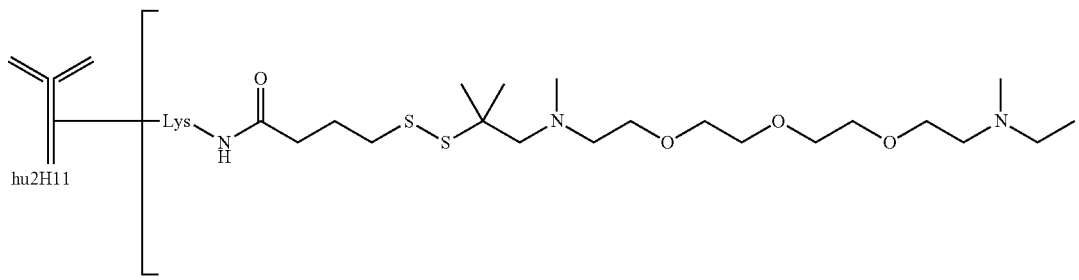

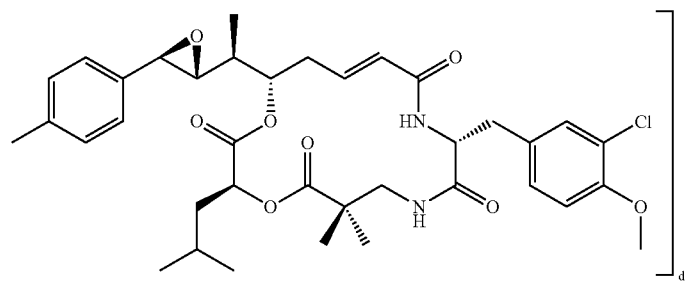

According to the one-step general method, 10.31 mg (0.070 μmol, 1.006 ml) of naked antibody hu2H11 at an initial concentration of 10.24 mg/ml are treated with 6 eq. of the N-hydroxy-succinimidyl ester of 4-(2-pyridyldithio)butanoic acid (0.14 mg, 0.429 μmol) dissolved in 29.32 μl of DMA, such that the final antibody concentration is 9 mg/ml in the mixture. After stirring for 2 hours at about 2000 rpm at RT, 1.595 ml of pH≈7.5-8 buffer, 291 μl of DMA and then 1.60 mg of (E)-(3S,10R,16S)-10-(3-chloro-4-methoxybenzyl)-3-isobutyl-16-[(S)-1-((2R,3R)-3-{4-[4-({2-[2-(2-{2-methyl[2-mercapto-2-methylpropyl]aminoethoxy}ethoxy)ethoxy]ethyl}methylamino)methyl]-phenyl}oxiranyl)ethyl]-6,6-dimethyl-1,4-dioxa-8,11-diazacyclohexadec-13-ene-2,5,9,12-tetraone (compound Ex. 6, 1.617 μmol) dissolved in 314 μl of DMA are successively added to 1.1 ml (9.9 mg, 0.067 μmol) of the mixture of modified antibody hu2H11. After purification on Superdex in the presence of 20% of NMP and concentrating on Amicon Ultra-15, the final buffer change is performed in an aqueous pH 6.5 buffer containing 0.01 M of histidine, 10% of sucrose (w/v) and 5% of NMP (v/v). 3 ml of conjugate Ex. 12 at a concentration of 1.97 mg/ml are thus obtained with, on average, 3.4 cryptophycin derivatives per antibody (HRMS) and a monomer purity of 99.8%.

Example 13

2,5-Dioxopyrrolidin-1-yl (4-{-4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexa-dec-13-en-16-yl}ethyl)oxiranyl]benzyl}piperazin-1-yl)acetate

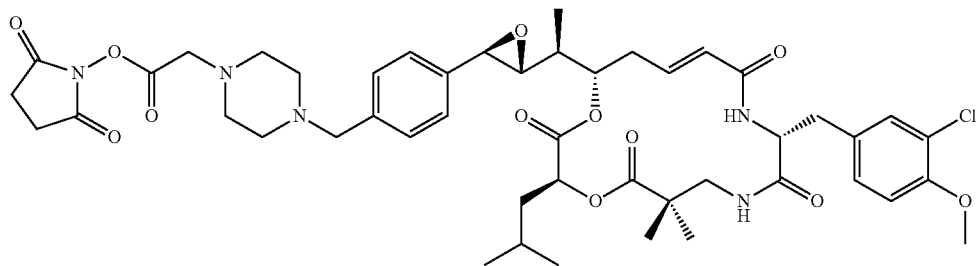

Compound 34 tert-Butyl 4-methoxycarbonylmethylpiperazine-1-carboxylate

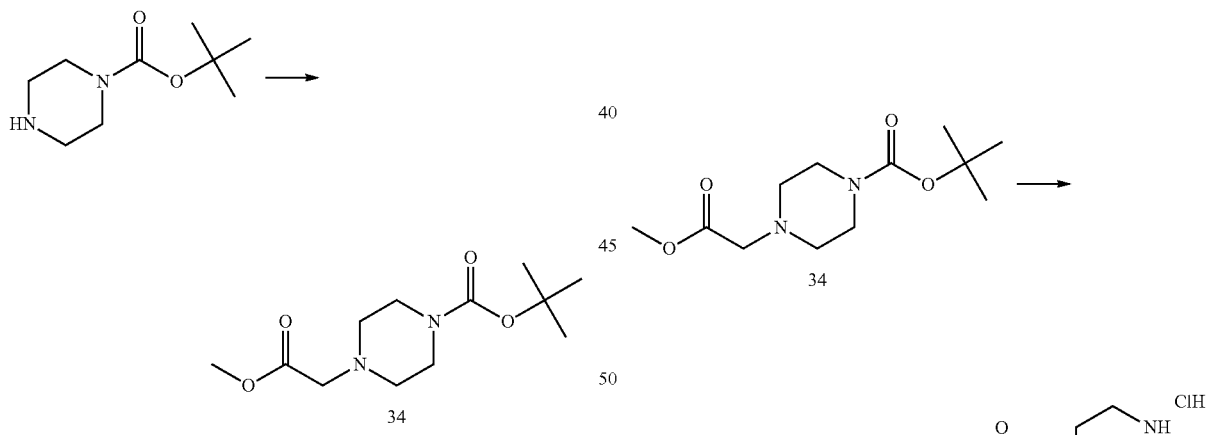

200 mg (1.07 mmol) of tert-butyl piperazine-1-carboxylate are dissolved in anhydrous acetonitrile (10 ml). TEA (1.07 mmol) and then methyl bromoacetate (1.61 mmol) are then added. The white suspension is stirred for 48 hours at RT, followed by addition of saturated aqueous NaHCO$_3$ solution (10 ml). The aqueous phase is extracted with DCM (3×10 ml) and the organic phases are combined, washed with saturated aqueous NaCl solution and dried over MgSO$_4$. After filtering and evaporating off the solvents under reduced pressure, the crude product is obtained. This crude product is purified by chromatography on silica gel, eluting with a 98/2 DCM/methanol mixture. The expected product 34, a colourless oil, is thus obtained (174.8 mg; 63%). TLC (DCM 90/MeOH 10): Rf=0.66; $^1$H NMR (300 MHz, DMSO-d$_6$): 1.39 (s, 9H); 2.40 to 2.48 (m, 4H); 3.25 (s, 2H); 3.28 to 3.33 (partially masked m, 4H); 3.61 (s, 3H).

Compound 35

Methyl piperazin-1-ylacetate hydrochloride

Compound 34 (174 mg; 0.67 mmol) is dissolved in anhydrous dioxane (5 ml) and a 4 M solution of HCl in dioxane (0.02 mmol) is added. The mixture is stirred for 5 hours at RT and the suspension is then filtered on a sinter funnel. The solid thus obtained is washed with dioxane (2 ml) and then with isopropyl ether (2 ml), and then dried under vacuum. A beige-coloured solid, 35, is obtained (131 mg; 100%). $^1$H NMR (300 MHz, DMSO-d$_6$): 2.88 to 2.97 (m, 4H); 3.09 to 3.19 (m, 4H); 3.53 to 3.59 (m, 2H); 3.65 (s, 3H); 8.65 to 9.22 (broad m, 2H).

Compound 36

Methyl (4-{4-[(2R,3R)-3-((S)-1-{(E)-(3S,10R,16S)-10-[3-Chloro-4-methoxy-benzyl]-3-isobutyl-6,6-dimethyl-2,5,9,12-tetraoxo-1,4-dioxa-8,11-diazacyclohexadec-13-en-16-yl}ethyl)oxiranyl]benzyl}piperazin-1-yl)acetate

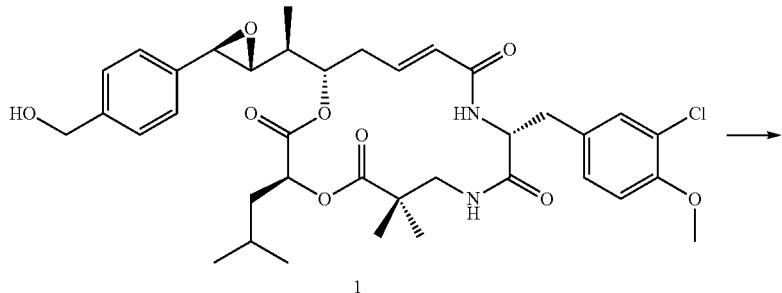

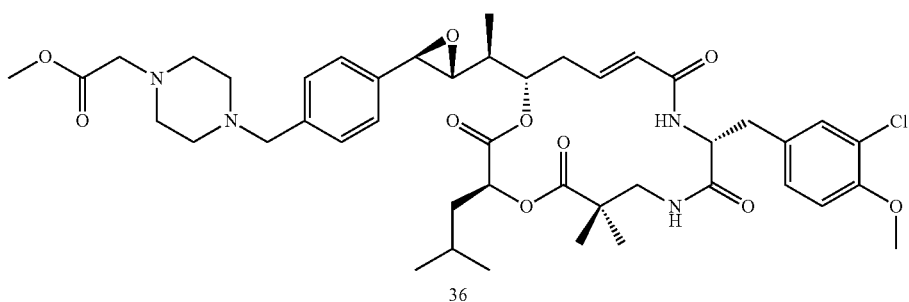

The derivative 1 (20 mg; 28.6 µmol) is dissolved in anhydrous DCM (1 ml), and TEA (71.5 µmol) and then CMS (45.8 µmol) are added. After 12 hours at RT, the product 2 formed is not isolated. TEA (85.7 µmol) and then methyl piperazin-1-ylacetate hydrochloride 35 (42.8 µmol) are added. The mixture is stirred for a further 72 hours at RT, followed by addition of anhydrous DMF (1 ml) and NaI (30 µmol). The mixture is stirred for 48 hours at 45° C., followed by dilution with EtOAc (5 ml). The organic phase is washed with water (2×2 ml), with saturated aqueous NaHCO$_3$ solution (2 ml) and with saturated aqueous NaCl solution (2 ml). After drying over MgSO$_4$ and filtering, the solvents are evaporated off under reduced pressure. The crude reaction product is purified by chromatography on silica gel, eluting with a 100/0 to 98/2 DCM/methanol mixture. Compound 36 is obtained in the form of a white solid (8.2 mg; 34%). TLC (DCM 90/MeOH 10): Rf=0.45; $^1$H NMR (400 MHz, DMSO-d$_6$): 0.77 (d, J=6.1 Hz, 3H); 0.78 (d, J=6.1 Hz, 3H); 1.00 (s, 3H); 1.05 (d, J=7.1 Hz, 3H); 1.12 (s, 3H); 1.27 to 1.32 (m, 1H); 1.50 to 1.60 (m, 2H); 1.74 to 1.84 (m, 1H); 2.21 to 2.30 (m, 1H); 2.37 (broad s, 4H); 2.64 to 2.74 (m, 2H); 2.94 to 3.06 (m, 3H); 3.18 to 3.52 (partially masked m, 9H); 3.60 (s, 3H); 3.81 (s, 3H); 3.87 (d, J=2.0 Hz, 1H); 4.20 to 4.31 (m, 1H); 4.91 (dd, J=3.8 and 9.9 Hz, 1H); 5.11 (m, 1H); 5.80 (d, J=15.2 Hz, 1H); 6.48 (ddd, J=3.8 and 11.2 and 15.2 Hz, 1H); 7.05 (d, J=8.3 Hz, 1H); 7.17 (dd, J=2.2 and 8.3 Hz, 1H); 7.20 to 7.33 (m, 6H); 8.34 (d, J=8.1 Hz, 1H). LCMS (A1): ES m/z=839 [M+H]$^+$; m/z=420 [M+2H]$^{2+}$ (base peak); m/z=837 [M−H]$^−$; m/z=883 [M+HCO2H−H]$^−$ (base peak); t$_R$=3.57 min.

Compound 37

Allyl Bromoacetate

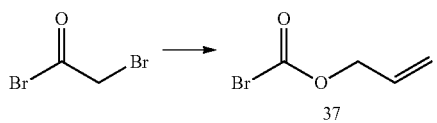

288 mg (4.95 mmol) of allyl alcohol are dissolved in 25 ml of DCM. The solution is cooled to 0° C. and then 760 µl (5.45 mmol) of TEA and 3.03 mg (24.8 µmol) of DMAP are added. The mixture is stirred at 0° C. and 1.0 g (4.95 mmol) of bromoacetyl bromide is then added. The reaction is continued overnight at RT. Water is added to the mixture; the aqueous phase is washed with DCM. The organic fractions are combined, washed with water and with saturated NaCl solution and dried over MgSO$_4$. After filtering and evaporating off the solvents under reduced pressure, product 37 is obtained (747 mg, 84%). $^1$H NMR (400 MHz, DMSO-d$_6$): 4.18 (s, 2H); 4.64

(td, J=1.5 and 5.4 Hz, 2H); 5.25 (qd, J=1.5 and 10.5 Hz, 1H); 5.35 (qd, J=1.5 and 17.2 Hz, 1H); 5.92 (tdd, J=5.4 and 10.5 and 17.2 Hz, 1H).

Compound 38 tert-Butyl 4-allyloxycarbonylmethylpiperazine-1-carboxylate

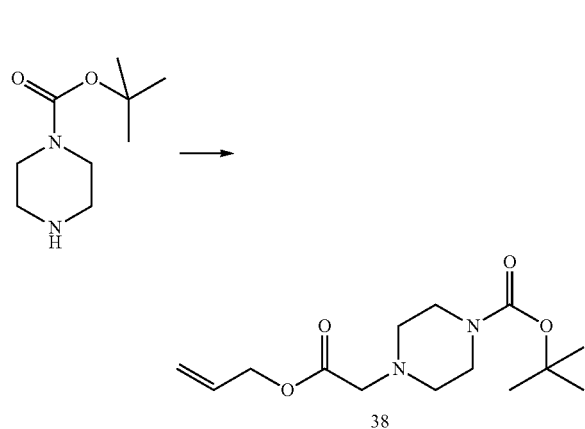

To a solution of 200 mg (1.07 mmol) of 1-Boc-piperazine in 8 ml of acetonitrile are added 150 µl (1.07 mmol) of TEA and 250 mg (1.40 mmol) of allyl bromoacetate 37. The mixture is stirred at RT overnight. The reaction is stopped by adding saturated NaHCO₃ solution. The mixture is extracted with EtOAc (3 times); the organic phases are combined, washed with saturated NaCl solution and dried over MgSO₄. After filtering and evaporating off the solvent under reduced pressure, the crude product is purified by chromatography on silica gel, eluting with a 100/0 to 95/5 DCM/methanol mixture. The expected product 38 is obtained in the form of a yellow oil (314 mg; 100%). $^1$H NMR (400 MHz, DMSO-$d_6$): 1.39 (s, 9H); 2.45 to 2.48 (m, 4H); 3.25 to 3.34 (partially masked m, 6H); 4.57 (td, J=1.5 and 5.6 Hz, 2H); 5.22 (qd, J=1.5 and 10.3 Hz, 1H); 5.30 (qd, J=1.5 and 17.1 Hz, 1H); 5.83 to 5.98 (m, 1H). LCMS (A2):ES m/z=285 [M+H]$^+$; m/z=229 base peak; $t_R$=0.51 min.

Compound 39

Allyl piperazin-1-ylacetate hydrochloride

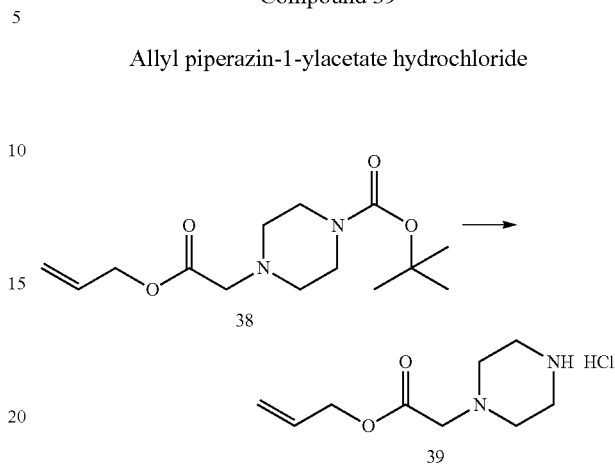

314 mg (1.10 mmol) of compound 38 are dissolved in 12.6 ml of dioxane, followed by addition of 5.5 ml (22.0 mmol) of a 4M solution of HCl in dioxane. Stirring is continued overnight at RT. The mixture is concentrated to dryness to give the expected compound 39 in the form of a yellow oil (260 mg; 100%). $^1$H NMR (400 MHz, DMSO-$d_6$): 2.79 to 2.88 (m, 4H); 3.07 to 3.15 (m, 4H); 3.48 to 3.51 (m, 2H); 4.60 (td, J=1.5 and 5.6 Hz, 2H); 5.23 (qd, J=1.5 and 10.3 Hz, 1H); 5.32 (qd, J=1.5 and 7.4 Hz, 1H); 5.86 to 5.98 (m, 1H); 8.74 (broad s, 2H). LCMS (A2): ES m/z=185 [M+H]$^+$; $t_R$=0.19 min.

Compound 40

Allyl (4-{4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexadec-13-en-16-yl}ethyl)-oxiranyl]benzyl}piperazin-1-yl)acetate

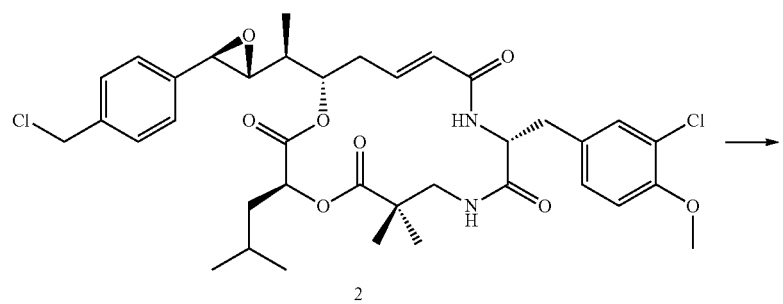

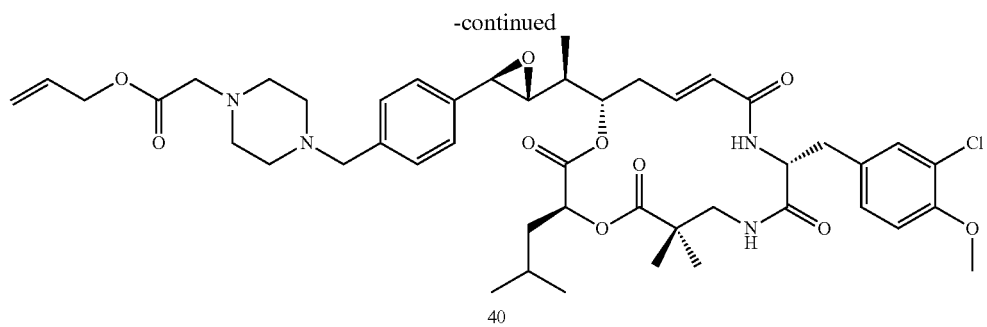

To a solution, purged with argon, of compound 2 (28.3 mg, 39.5 μmol) in anhydrous acetonitrile (2.5 ml) is added a solution of compound 39 (118.5 μmol) and TEA (198 μmol) in anhydrous acetonitrile (1 ml). Stirring is continued for 24 hours at 40° C. The mixture is diluted in EtOAc (10 ml). The organic phase is washed with water (10 ml), with saturated aqueous NaHCO$_3$ solution (10 ml) and saturated aqueous NaCl solution (10 ml). After drying over MgSO$_4$ and filtering, the solvents are evaporated off under reduced pressure. The crude reaction product is purified by chromatography on silica gel, eluting with a 98/2 DCM/methanol mixture. Compound 40 is obtained in the form of a white solid (19.2 mg; 56%). $^1$H NMR (500 MHz, DMSO-d$_6$): 0.75 (d, J=6.3 Hz, 3H); 0.77 (d, J=6.3 Hz, 3H); 1.00 (s, 3H); 1.05 (d, J=6.9 Hz, 3H); 1.12 (s, 3H); 1.25 to 1.33 (m, 1H); 1.50 to 1.61 (m, 2H); 1.74 to 1.84 (m, 1H); 2.27 (dt, J=11.3 and 14.2 Hz, 1H); 2.32 to 2.42 (m, 4H); 2.52 (partially masked m, 4H); 2.64 to 2.74 (m, 2H); 2.94 to 3.05 (m, 3H); 3.25 (s, 2H); 3.32 to 3.35 (partially masked m, 1H); 3.40 to 3.48 (m, 2H); 3.81 (s, 3H); 3.87 (d, J=1.6 Hz, 1H); 4.25 (ddd, J=3.7 and 8.0 and 11.6 Hz, 1H); 4.56 (td, J=1.5 and 5.5 Hz, 2H); 4.91 (dd, J=3.7 and 9.7 Hz, 1H); 5.11 (m, 1H); 5.21 (qd, J=1.5 and 10.5 Hz, 1H); 5.30 (qd, J=1.5 and 17.3 Hz, 1H); 5.80 (d, J=16.2 Hz, 1H); 5.86 to 5.95 (m, 1H); 6.47 (ddd, J=3.8 and 11.2 and 15.2 Hz, 1H); 7.05 (d, J=8.5 Hz, 1H); 7.17 (dd, J=2.2 and 8.5 Hz, 1H); 7.19 to 7.32 (m, 6H); 8.34 (d, J=8.0 Hz, 1H). LCMS (A2): ES m/z=865 [M+H]$^+$; m/z=433.5 [M+2H]$^{2+}$ (base peak); m/z=863 [M−H]$^−$; m/z=909 [M+HCO$_2$H−H]$^−$; t$_R$=0.92 min.

Compound 41

(4-{4-[(2R,3R)-3-((S)-1-{(E)-(3S,10R,16S)-10-[3-Chloro-4-methoxybenzyl]-3-isobutyl-6,6-dimethyl-2,5,9,12-tetraoxo-1,4-dioxa-8,11-diazacyclohexadec-13-en-16-yl}ethyl)-oxiranyl]benzyl}piperazin-1-yl) acetic acid

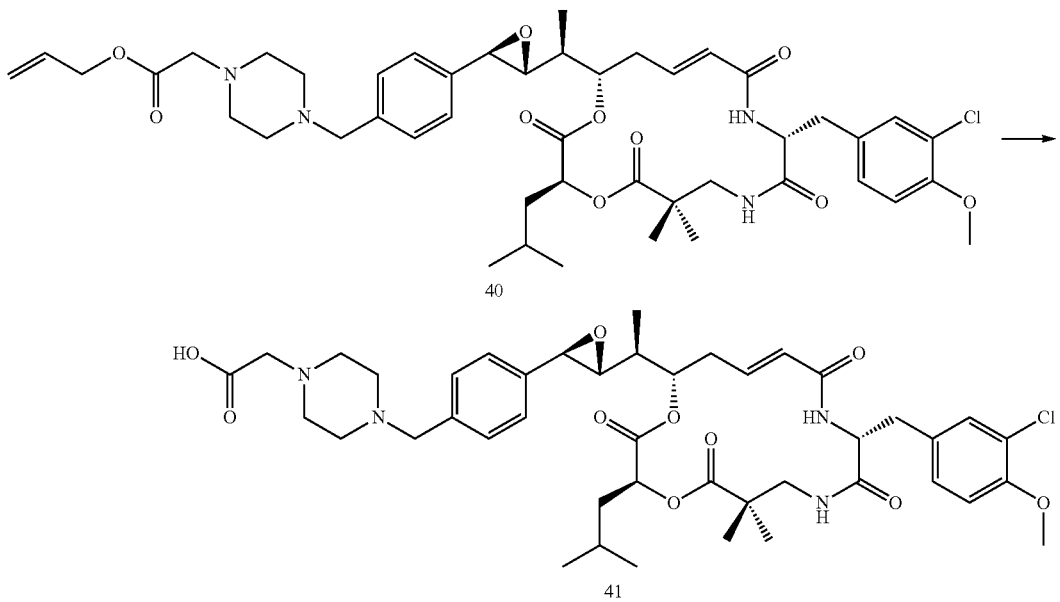

To a solution under argon of compound 40 (12.8 mg, 14.8 μmol) in anhydrous THF are added tetrakis(triphenylphosphine)palladium (1.48 μmol) and morpholine (148 μmol). After reaction for 3 hours, the mixture is concentrated to dryness and taken up in 5 ml of DCM. The organic phase is washed with 1 ml of 0.1N HCl solution in 3 ml of water (pH≈5), dried over MgSO$_4$, filtered and evaporated to give compound 41 (6.7 mg, 55%). $^1$H NMR (500 MHz, DMSO-d$_6$): 0.76 (d, J=6.0 Hz, 3H); 0.78 (d, J=6.0 Hz, 3H); 1.00 (s, 3H); 1.05 (d, J=6.9 Hz, 3H); 1.12 (s, 3H); 1.28 (m, 1H); 1.52 to 1.59 (m, 2H); 1.76 to 1.84 (m, 1H); 2.21 to 2.32 (m, 1H); 2.42 (d, J=6.6 Hz, 4H); 2.58 to 2.76 (m, 6H); 2.97 to 3.09 (m, 3H); 3.14 (broad s, 2H); 3.33 (masked m, 1H); 3.46 (broad s, 2H); 3.81 (s, 3H); 3.87 (d, J=1.8 Hz, 1H); 4.20 to 4.29 (m, 1H); 4.89 to 4.93 (m, 1H); 5.06 to 5.14 (m, 1H); 5.80 (d, J=15.2 Hz, 1H); 6.43 to 6.50 (m, 1H); 7.05 (d, J=8.5 Hz, 1H); 7.17 (dd, J=2.2 and 8.5 Hz, 1H); 7.20 to 7.32 (m, 6H); 8.34 (d, J=8.0 Hz, 1H). LCMS (A2): ES m/z=825 [M+H]$^+$; m/z=413 [M+2H]$^{2+}$ (base peak); m/z=823 [M−H]$^-$; $t_R$=0.86 min.

Example 13

2,5-Dioxopyrrolidin-1-yl (4-{4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexadec-13-en-16-yl}ethyl)oxiranyl]benzyl}piperazin-1-yl)acetate

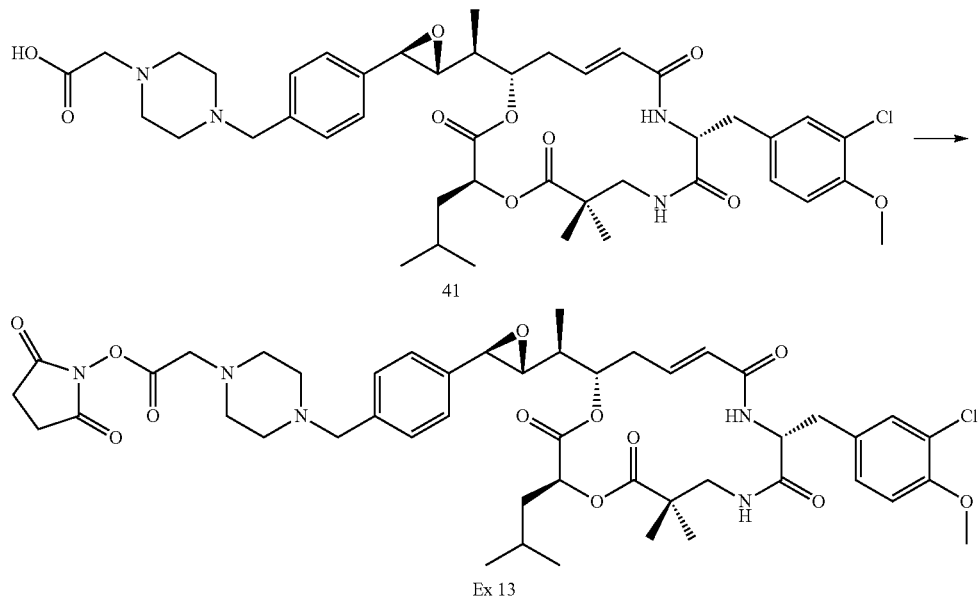

Example 13 may be obtained by activating the acid 41 according to the method described for Example 18.

Example 14

2,5-Dioxopyrrolidin-1-yl (2-{2-[2-(2{-4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diaza-cyclohexadec-13-en-16-yl}ethyl)oxiranyl]benzylamino}ethoxy)ethoxy]ethoxy}ethoxy)-propanoate

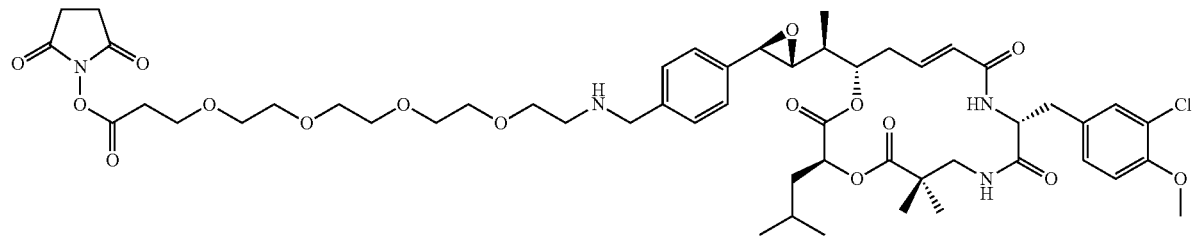

Compound 42

Allyl 3-(2-{2-[2-(2-tert-butoxycarbonylaminoethoxy)ethoxy]ethoxy}ethoxy)-propanoate

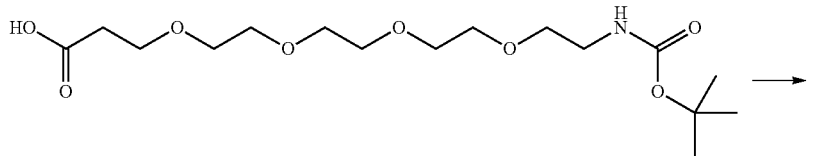

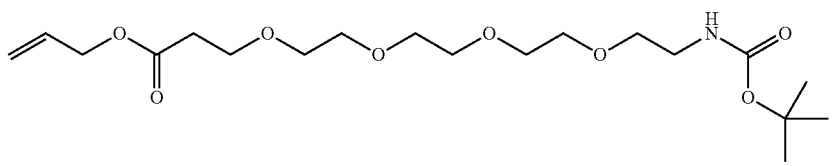

42

To a solution of Boc-15-amino-4,7,10,13-tetraoxapentadecanoic acid (50 mg, 137 µmol) in 1.25 ml of DCM are successively added EDCl hydrochloride (164.2 µmol), DMAP (13.7 µmol) and allyl alcohol (164.2 µmol). The mixture is stirred at RT for 16 hours and then evaporated to dryness. The crude product is purified by chromatography on silica gel, eluting with a 100/0 to 95/5 DCM/methanol mixture. Compound 42 is obtained in the form of a colourless oil (37.5 mg; 67%). $^1$H NMR (400 MHz, DMSO-$d_6$): 1.37 (s, 9H); 2.57 (t, J=6.1 Hz, 2H); 3.06 (q, J=6.1 Hz, 2H); 3.37 (t, J=6.1 Hz, 2H); 3.44 to 3.53 (m, 12H); 3.64 (t, J=6.1 Hz, 2H); 4.55 (td, J=1.6 and 5.4 Hz, 2H); 5.20 (qd, J=1.6 and 10.5 Hz, 1H); 5.30 (qd, J=1.6 and 17.3 Hz, 1H); 5.90 (tdd, J=5.4 and 10.5 and 17.3 Hz, 1H); 6.70 (broad t, J=6.1 Hz, 1H). LCMS (A2) ES m/z=406 [M+H]$^+$; m/z=428 [M+Na]$^+$; m/z=306 base peak; $t_R$=0.91 min.

Compound 43

Allyl 3-(2-{2-[2-(2-aminoethoxy)ethoxy]ethoxy}ethoxy)propanoate hydrochloride

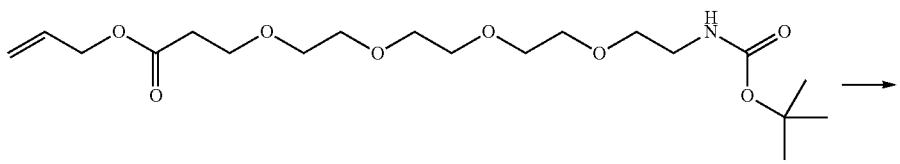

42

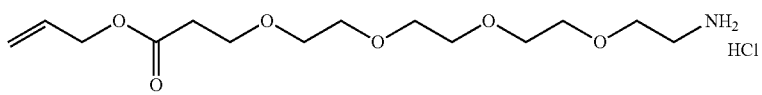

43

To a solution of compound 42 (37.5 mg, 92.5 µmol) in 2 ml of dioxane are added 460 µl (1.85 mmol) of a 4M solution of hydrogen chloride in dioxane. Stirring is continued at RT overnight and the reaction medium is then evaporated to dryness to give compound 43 in the form of a colourless oil (31 mg, quantitative). $^1$H NMR (400 MHz, DMSO-$d_6$): 2.58 (t, J=6.1 Hz, 2H); 2.96 (t, J=5.4 Hz, 2H); 3.48 to 3.53 (m, 8H); 3.55 to 3.58 (m, 4H); 3.60 (t, J=5.4 Hz, 2H); 3.65 (t, J=6.1 Hz, 2H); 4.56 (td, J=1.6 and 5.4 Hz, 2H); 5.21 (qd, J=1.6 and 10.5 Hz, 1H); 5.30 (qd, J=1.6 and 17.3 Hz, 1H); 5.91 (tdd, J=5.4 and 10.5 and 17.3 Hz, 1H); 7.91 (broad m, 3H). LCMS (A2): ES m/z=306 [M+H]$^+$; $t_R$=0.42 min.

Compound 44

Allyl (2-{2-[2-(2-{4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diazacyclohexadec-13-en-16-yl}ethyl)oxiranyl]benzylamino}ethoxy)ethoxy]ethoxy}ethoxy)propanoate

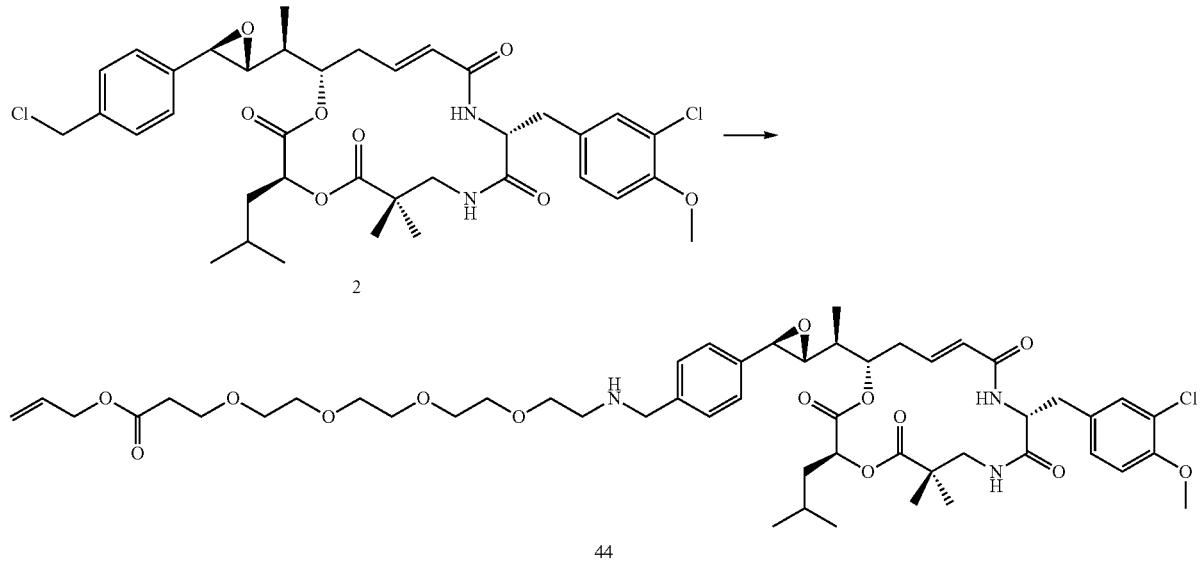

To a solution, purged with argon, of compound 2 (12.7 mg, 17.7 μmol) in 1.48 ml of anhydrous acetonitrile are successively added 22.2 μl of TEA (159 μmol) and 30.2 mg of compound 43 (88.4 μmol). Stirring is continued at 40° C. for 24 hours. Some starting compound 2 remains; 22.2 μl of TEA (159 μmol) and 30.2 mg of compound 43 (88.4 μmol) are added to the mixture and stirring is continued at 40° C. for a further 48 hours. 2 ml of water are added to the mixture, which is then extracted with 2×2 ml of EtOAc. The organic phases are combined, washed with saturated NaHCO$_3$ solution (2 ml) and with saturated sodium chloride solution (2 ml) and dried over MgSO$_4$. After filtering and concentrating under reduced pressure, the crude reaction product is purified by chromatography on silica gel, eluting with a 100/0 to 95/5 DCM/methanol mixture. Compound 44 is obtained in the form of a white solid (4.8 mg; 27%). $^1$H NMR (500 MHz, DMSO-d$_6$): 0.77 (m, 6H); 1.00 (s, 3H); 1.05 (d, J=6.9 Hz, 3H); 1.12 (s, 3H); 1.29 (m, 2H); 1.49 to 1.60 (m, 2H); 1.81 (m, 1H); 2.26 (m, 1H); 2.56 (t, J=6.1 Hz, 2H); 2.61 to 2.73 (m, 4H); 2.93 to 3.04 (m, 3H); 3.28 to 3.38 (partially masked m, 1H); 3.45 to 3.53 (m, 14H); 3.63 (t, J=6.1 Hz, 2H); 3.72 (s, 2H); 3.81 (s, 3H); 3.86 (broad s, 1H); 4.25 (ddd, J=3.4 and 8.2 and 11.4 Hz, 1H); 4.55 (dm, J=5.4 Hz, 2H); 4.90 (dd, J=3.9 and 9.8 Hz, 1H); 5.11 (ddd, J=1.4 and 5.4 and 11.2 Hz, 1H); 5.19 (dm, J=10.8 Hz, 1H); 5.29 (dm, J=17.2 Hz, 1H); 5.79 (dd, J=1.4 and 15.2 Hz, 1H); 5.90 (m, 1H); 6.47 (ddd, J=3.9 and 11.2 and 15.2 Hz, 1H); 7.05 (d, J=8.8 Hz, 1H); 7.17 (dd, J=2.0 and 8.8 Hz, 1H); 7.21 (m, 1H); 7.24 (d, J=8.3 Hz, 2H); 7.28 (d, J=2.0 Hz, 1H); 7.33 (d, J=8.3 Hz, 2H); 8.35 (d, J=8.2 Hz, 1H). LCMS (A2): ES m/z=986 [M+H]$^+$; m/z=493.5 [M+2H]$^{2+}$ base peak; m/z=984 [M−H]$^−$; m/z=1030 [M−H+HCO$_2$H]$^−$ base peak; t$_R$=0.95 min.

Example 14

2,5-Dioxopyrrolidin-1-yl (2-{2-[2-(2-{4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diazacyclo-hexadec-13-en-16-yl}ethyl)oxiranyl]benzylamino}ethoxy)ethoxy]ethoxy}ethoxy)propanoate

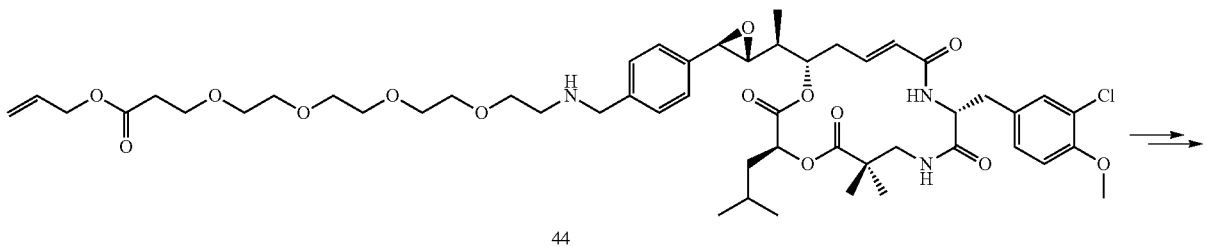

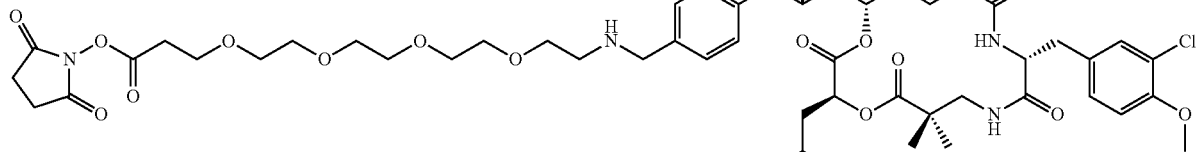

Ex 14

Example 14 may be obtained by deprotecting compound 44 according to the method described for compound 41 and by activating the acid obtained according to the method described for Example 18.

Example 15

2,5-Dioxopyrrolidin-1-yl (2-[2-}2-(2-(4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diaza-cyclohexadec-13-en-16-yl}ethyl)oxiranyl]benzylmethylamino}ethoxy)ethoxy]ethoxy}-ethoxy)propanoate

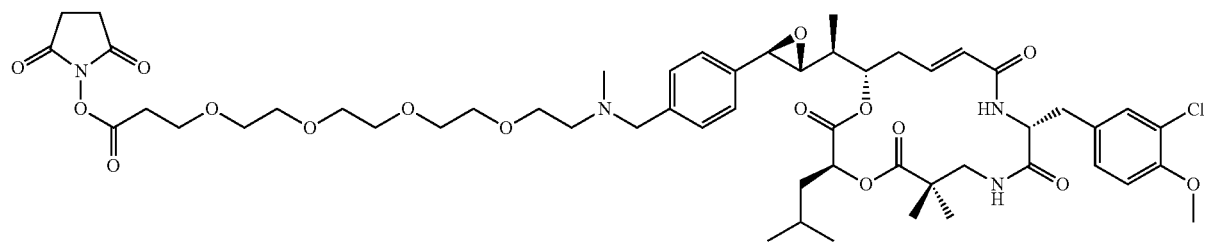

Compound 45

3-[2-(2-{2-[2-(tert-Butoxycarbonylmethylamino)ethoxy]ethoxy}ethoxy)ethoxy]-propanoic acid

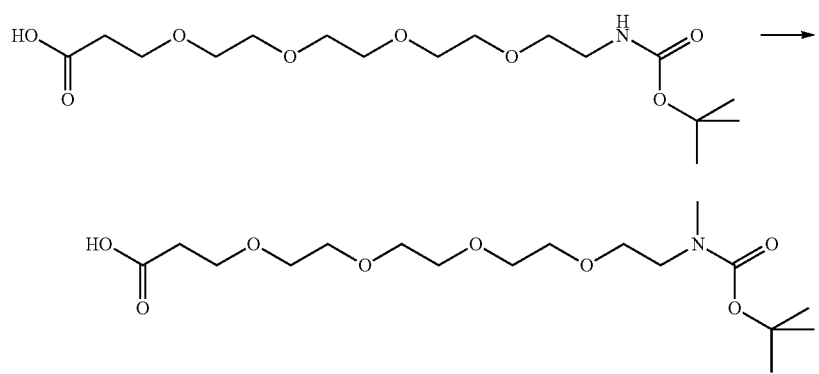

520 mg (1.423 mmol) of Boc-15-amino-4,7,10,13-tetraoxapentadecanoic acid are dissolved in 14 ml of anhydrous THF and the mixture is then cooled to 0° C., followed by addition, by spatula, of 85.4 mg (2.135 mmol) of sodium hydride. Stirring is continued for 10 minutes at 0° C., and then 150.6 µl (2.419 mmol) of methyl iodide are added at 0° C. The temperature is allowed to return to RT and stirring is continued for 2 hours. 8 ml of water are added to the mixture, the pH of which is then acidified by addition of acetic acid to obtain pH≈4. It is extracted with 3×10 ml of EtOAc. The organic phases are combined, washed with 10 ml of saturated NaCl solution and dried over MgSO$_4$. After filtering and concentrating to dryness under reduced pressure, compound 45 is obtained in the form of a colourless oil (414 mg, 77%). $^1$H NMR (400 MHz, DMSO-d$_6$): 1.38 (s, 9H); 2.43 (t, J=6.4 Hz, 2H); 2.80 (broad s, 3H); 3.29 (t, J=5.9 Hz, 2H); 3.45 to 3.52 (m, 14H); 3.60 (t, J=6.4 Hz, 2H); 12.01 (broad m, 1H). LCMS (A2): ES m/z=402 [M+Na]$^+$; m/z=378 [M−H]$^-$; m/z=280 base peak; $t_R$=0.95 min.

Compound 46

Allyl 3-[2-(2-{2-[2-(tert-butoxycarbonylmethylamino)ethoxy]ethoxy}ethoxy)ethoxy]-propanoate

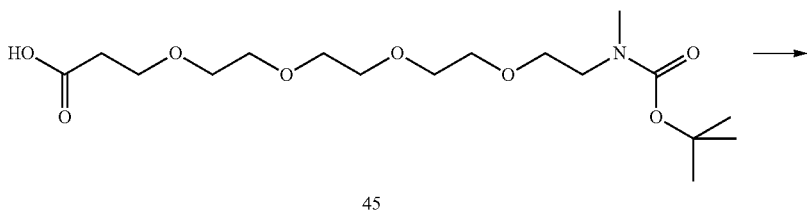

45

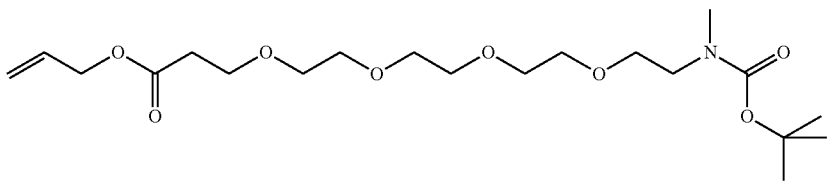

46

To a solution of 540 mg (1.423 mmol) of compound 45 in 15 ml of anhydrous DCM are successively added 327 mg (1.71 mmol) of EDCl, 17.4 mg (142 µmol) of DMAP and 116 µl (1.71 mmol) of allyl alcohol. Stirring is continued for 15 hours at RT and the mixture is then concentrated to dryness. The crude product obtained is purified by chromatography on silica gel, eluting with a 100/0 to 90/10 DCM/methanol mixture. Compound 46 is obtained in the form of a colourless oil (337 mg; 56%). $^1$H NMR (400 MHz, DMSO-d$_6$): 1.38 (s, 9H); 2.57 (t, J=6.1 Hz, 2H); 2.80 (broad s, 3H); 3.22 to 3.33 (partially masked m, 2H); 3.44 to 3.54 (m, 14H); 3.64 (t, J=6.1 Hz, 2H); 4.55 (broad d, J=4.9 Hz, 2H); 5.20 (broad d, J=10.3 Hz, 1H); 5.30 (broad d, J=17.1 Hz, 1H); 5.90 (m, 1H). LCMS (A2): ES m/z=442 [M+Na]$^+$; m/z=320 base peak; $t_R$=0.98 min.

Compound 47

Allyl 3-(2-{2-[2-(2-methylaminoethoxy)ethoxy]ethoxy}ethoxy)propanoate

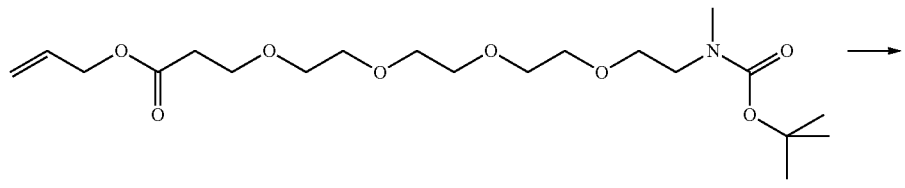

46

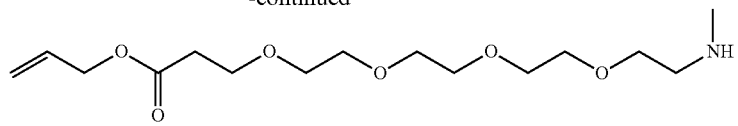

47

To a solution of 337 mg (0.802 mmol) of compound 46 in 20 ml of DCM are added 1.19 ml (16.04 mmol) of TFA. Stirring is continued for 3 hours at RT and the mixture is then concentrated to dryness under reduced pressure. The crude product is purified by SPE filtration on an SCX cartridge (Varian) conditioned and washed with methanol, and then eluted with a 0.5 N solution of aqueous ammonia in methanol. Compound 47 is obtained in the form of a colourless oil (208 mg, 81%). $^1$H NMR (400 MHz, DMSO-$d_6$): 2.27 (s, 3H); 2.54 to 2.61 (m, 4H); 3.44 (t, J=5.6 Hz, 2H); 3.47 to 3.52 (m, 12H); 3.65 (t, J=6.2 Hz, 2H); 4.56 (broad d, J=5.4 Hz, 2H); 5.20 (broad d, J=10.5 Hz, 1H); 5.30 (broad d, J=17.2 Hz, 1H); 5.90 (m, 1H). LCMS (A2): ES m/z=320 [M+H]$^+$; $t_R$=0.42 min.

Compound 48

Allyl (2-{2-[2-(2-{4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diazacyclohexadec-13-en-16-yl}ethyl)oxiranyl]benzylamino}ethoxy)ethoxy]ethoxy}ethoxy)propanoate To a solution, purged with argon, of compound 2 (40 mg, 55.7 μmol) in 5 ml of anhydrous acetonitrile are successively added 48.5 μl of DIPEA (279 μmol) and 53 mg of compound 47 (167 μmol). Stirring is continued at 40° C. for 15 hours; 5 ml of water are added to the mixture, which is then extracted with 4×5 ml of EtOAc. The organic phases are combined, washed with saturated NaHCO$_3$ solution (5 ml) and with saturated NaCl solution (5 ml) and dried over MgSO$_4$. After filtering and concentrating under reduced pressure, the crude reaction product is purified by chromatography on silica gel, eluting with a 100/0 to 90/10 DCM/methanol mixture. Compound 48 is obtained in the form of a colourless solid (45.3 mg; 80%). $^1$H NMR (500 MHz, DMSO-$d_6$): 0.76 (d, J=5.9 Hz, 3H); 0.78 (d, J=5.9 Hz, 3H); 1.00 (s, 3H); 1.04 (d, J=6.8 Hz, 3H); 1.12 (s, 3H); 1.29 (m, 1H); 1.50 to 1.61 (m, 2H); 1.80 (m, 1H); 2.15 (s, 3H); 2.28 (m, 1H); 2.52 (t, J=6.4 Hz, 2H); 2.56 (t, J=6.4 Hz, 2H); 2.63 to 2.73 (m, 2H); 2.94 to 3.06 (m, 3H); 3.25 to 3.35 (partially masked m, 1H); 3.48 (s, 2H); 3.49 to 3.51 (m, 12H); 3.52 (t, J=6.4 Hz, 2H); 3.63 (t, J=6.4 Hz, 2H); 3.81 (s, 3H); 3.87 (d, J=1.5 Hz, 1H); 4.25 (ddd, J=3.4 and 8.3 and 11.5 Hz, 1H); 4.55 (broad d, J=5.0 Hz, 2H); 4.91 (dd, J=3.7 and 9.5 Hz, 1H); 5.11 (ddd, J=1.5 and 5.7 and 11.5 Hz, 1H); 5.19 (dm, J=10.3 Hz, 1H); 5.29 (dm, J=17.6 Hz, 1H); 5.80 (dd, J=1.5 and 15.2 Hz, 1H); 5.90 (m, 1H); 6.47 (ddd, J=3.7 and 11.5 and 15.2 Hz, 1H); 7.05 (d, J=8.5 Hz, 1H); 7.17 (dd, J=2.0 and 8.5 Hz, 1H); 7.22 (dd, J=2.9 and 9.8 Hz, 1H); 7.25 (d, J=8.3 Hz, 2H); 7.28 (d, J=2.0 Hz, 1H); 7.30 (d, J=8.3 Hz, 2H); 8.35 (d, J=8.3 Hz, 1H). LCMS (A2): ES m/z=1000 [M+H]$^+$; m/z=500.5 [M+2H]$^{2+}$; m/z=1044 [M−H+HCO$_2$H]$^-$; $t_R$=1.01 min.

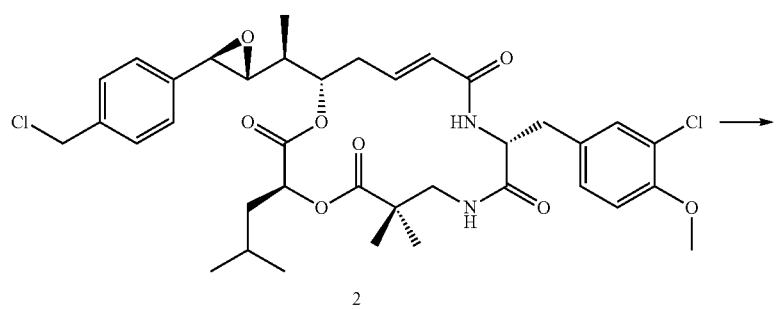

2

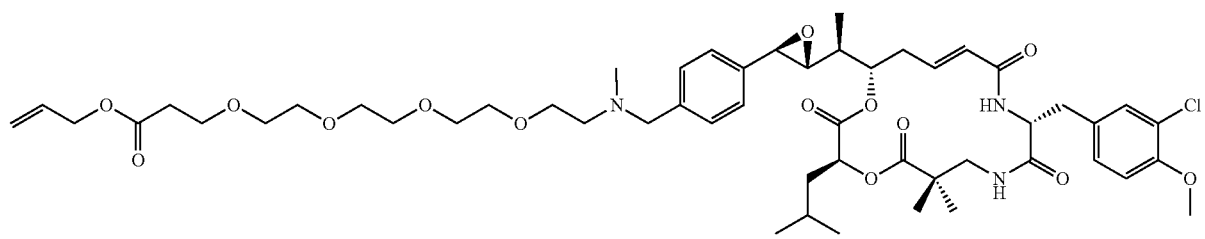

48

Compound 49

(2-{2-[2-(2-{4-[(2R,3R)-3-((S)-1-{(E)-(3S,10R,16S)-10-[3-Chloro-4-methoxy-benzyl]-3-isobutyl-6,6-dimethyl-2,5,9,12-tetraoxo-1,4-dioxa-8,11-diaza-cyclohexadec-13-en-16-yl}ethyl)oxiranyl]benzylamino}ethoxy)ethoxy]ethoxy}ethoxy)propanoic acid methanol mixture. Compound 49 is obtained in the form of a colourless solid (5.4 mg; 30%). $^1$H NMR (500 MHz, DMSO-$d_6$): 0.76 (t, J=5.9 Hz, 3H); 0.78 (t, J=5.9 Hz, 3H); 1.00 (s, 3H); 1.04 (d, J=6.8 Hz, 3H); 1.12 (s, 3H); 1.31 (m, 1H); 1.51 to 1.62 (m, 2H); 1.80 (m, 1H); 2.15 (s, 3H); 2.28 (m, 1H); 2.42 (t, J=6.4 Hz, 2H); 2.52 (t, J=6.4 Hz, 2H); 2.64 to 2.73 (m, 2H); 2.94 to 3.04 (m, 3H); 3.25 to 3.44 (partially masked m, 3H); 3.45 to 3.51 (m, 12H); 3.53 (t, J=6.4 Hz, 2H); 3.59 (t, J=6.4 Hz, 2H); 3.81 (s, 3H); 3.87 (d, J=2.0 Hz, 1H); 4.25 (ddd, J=4.2

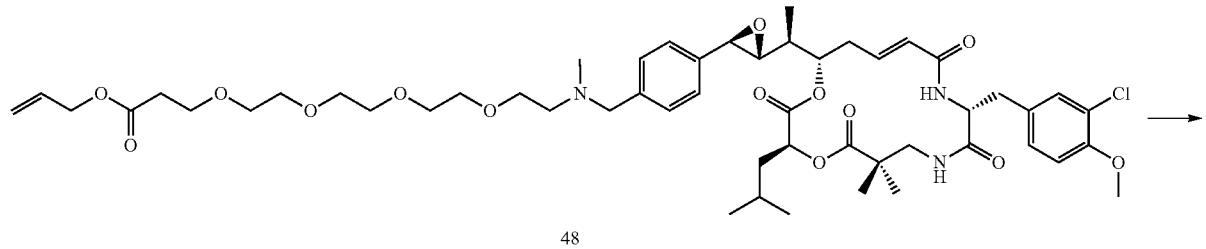

48

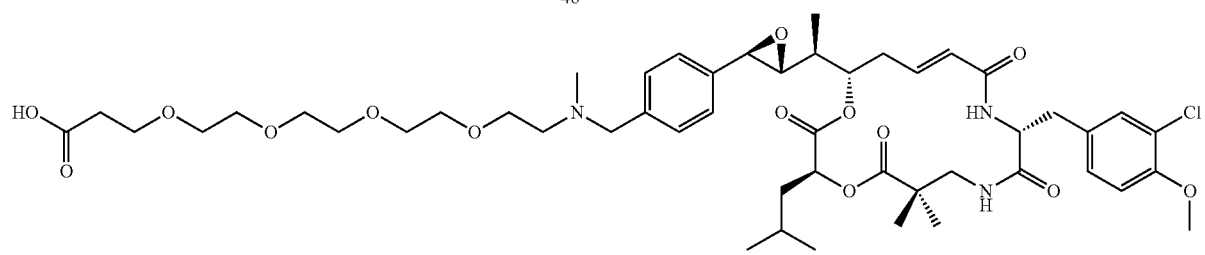

49

19 mg (18.9 μmol) of compound 48 are dissolved in 3.8 ml of anhydrous THF and purged with argon. 6 μl (18.9 μmol) of diethylamine are added to the mixture, which is stirred for 15 minutes at RT, followed by addition of 4.45 mg (19.8 μmol) of palladium(II) acetate and 18.89 mg of supported triphenylphosphine. Stirring is continued for 6 days at RT: some starting material remains, but the reaction no longer proceeds. The mixture is filtered, concentrated to dryness, taken up in 2 ml of anhydrous THF and treated with 10 μl (31.5 μmol) of diethylamine and 10 mg of tetrakis(triphenylphosphine)palladium for 1 hour. The mixture is hydrolyzed with 2 ml of aqueous 2M sodium hydrogensulfate solution and extracted with 3×2 ml of DCM. The organic phases are combined, washed with saturated NaCl solution (2 ml) and dried over MgSO$_4$. After filtering and concentrating under reduced pressure, the crude product is purified by chromatography on diol-grafted silica gel, eluting with a 98/2 to 90/10 DCM/ and 7.8 and 11.5 Hz, 1H); 4.91 (dd, J=3.4 and 9.8 Hz, 1H); 5.11 (dd, J=5.4 and 11.2 Hz, 1H); 5.80 (d, J=15.2 Hz, 1H); 6.47 (ddd, J=3.7 and 11.2 and 15.2 Hz, 1H); 7.05 (d, J=8.3 Hz, 1H); 7.17 (dd, J=2.0 and 8.3 Hz, 1H); 7.21 to 7.27 (m, 3H); 7.28 to 7.32 (m, 3H); 8.38 (broad d, J=7.8 Hz, 1H); 11.22 (very broad m, 1H). LCMS (A2): ES m/z=960 [M+H]$^+$; m/z=480.5 [M+2H]$^{2+}$ base peak; m/z=958 [M−H]$^−$; $t_R$=0.90 min.

Example 15

2,5-Dioxopyrrolidin-1-yl (2-{2-[2-(2-{4-[(2R,3R)-3-((S)-1-{(E)-(3S,10R,16S)-10-[3-chloro-4-methoxy-benzyl]-3-isobutyl-6,6-dimethyl-2,5,9,12-tetraoxo-1,4-dioxa-8,11-diazacyclo-hexadec-13-en-16-yl}ethyl)oxiranyl]benzylamino}ethoxy)ethoxy]ethoxy}ethoxy)propanoate

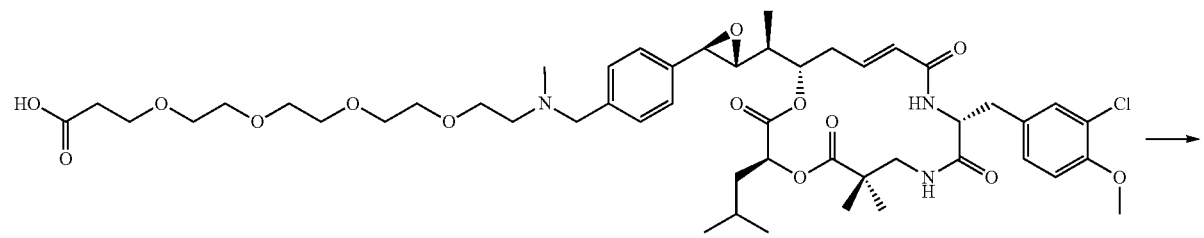

49

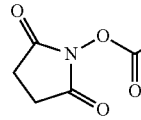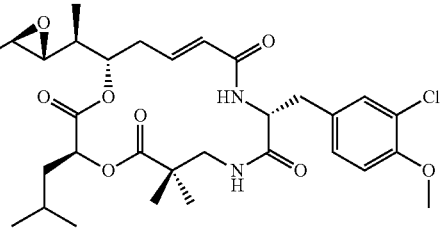

Ex 15

Example 15 may be prepared by activating the acid 49 according to the method described for Example 18.

Example 16

2,5-Dioxopyrrolidin-1-yl (2-{2-[2-(4-{[(2R,3R)-3-[(S)-1-((E)-(3S,10R,16S)-10-{3-chloro-4-methoxy-benzyl}-3-isobutyl-6,6-dimethyl-2,5,9,12-tetraoxo-1,4-dioxa-8,11-diaza-cyclohexadec-13-en-16-yl)ethyl]oxiranyl}benzylpiperazin-1-yl)ethoxy]ethoxy}ethoxy)-propanoate

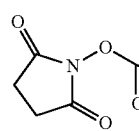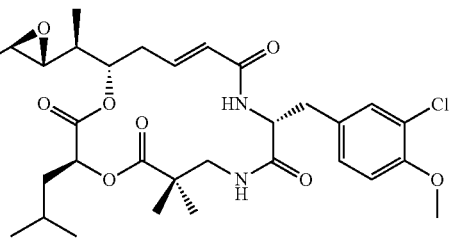

Compound 50

3-{2-[2-(2-Hydroxyethoxy)ethoxy]ethoxy}propanoic acid

Compound 51

Allyl 3-{2-[2-(2-hydroxyethoxy)ethoxy]ethoxy}propanoate

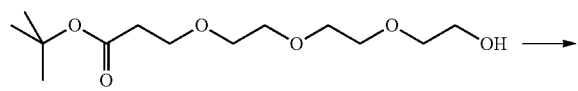

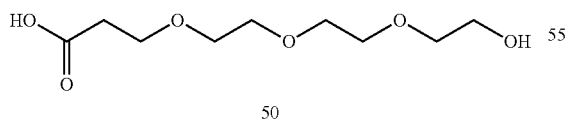

51

To a solution of 300 mg (1.08 mmol) of tert-butyl 12-hydroxy-4,7,10-trioxadodecanoate in 6 ml of DCM are added 1.6 ml (21.56 mmol) of TFA. Stirring is continued at RT for 3 hours. The mixture is concentrated to dryness, taken up in a minimum amount of DCM and entrained several times with toluene to give compound 50 in the form of a pale yellow oil (240 mg, quantitative).

To a solution of 240 mg (1.08 mmol) of compound 50 in 3 ml of DCM are successively added 248 mg (1.29 mmol) of EDCl, 13.2 mg (1.29 mmol) of DMAP and 88 μl (1.29 mmol) of allyl alcohol. Stirring is continued at RT for 15 hours and the mixture is then concentrated to dryness under reduced pressure, and the crude product purified by chromatography on silica gel using as eluent a 98/2 to 90/10 DCM/methanol mixture. Compound 51 is obtained in the form of a colourless oil (144 mg, 51%). $^1$H NMR (400 MHz, DMSO-$d_6$): 2.57 (t, J=6.2 Hz, 2H); 3.41 (m, 2H); 3.46 to 3.52 (m, 10H); 3.65 (t, J=6.2 Hz, 2H); 4.52 (t, J=5.5 Hz, 1H); 4.56 (m, 2H); 5.20 (dm, J=10.5 Hz, 1H); 5.50 (dm, J=17.4 Hz, 1H); 5.90 (m, 1H).

Compound 52 tert-Butyl 4-(2-{2-[2-(2-allyloxycarbonylethoxy)ethoxy]ethoxy}ethyl)piperazine-1-carboxylate

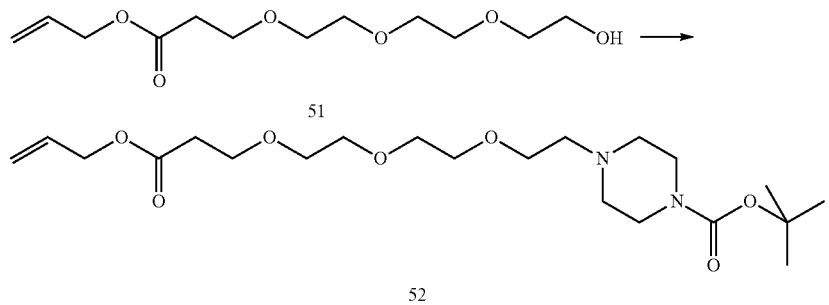

To a solution, cooled to 0° C., of 94 mg (357 μmol) of compound 51 in 3.7 ml of DCM are successively added 125 μl (893 μmol) of TEA and 30.4 μl (393 μmol) of mesyl chloride, and stirring is continued at RT for 1 hour. The mixture is concentrated to dryness under reduced pressure and then taken up in 5 ml of acetonitrile. 249 μl (1.785 mmol) of TEA and 200 mg (1.071 mmol) of Boc-piperazine are added to the solution and the mixture is stirred and heated for 15 hours at 40° C. After cooling to RT, the mixture is concentrated to dryness and purified by chromatography on silica gel, using a 98/2 to 90/10 DCM/methanol mixture as eluent. Compound 52 is obtained in the form of a colourless oil (69 mg, 45%). $^1$H NMR (400 MHz, DMSO-$d_6$): 1.39 (s, 9H); 2.33 (m, 4H); 2.46 (t, J=5.9 Hz, 2H); 2.57 (t, J=6.2 Hz, 2H); 3.28 (partially masked m, 4H); 3.45 to 3.53 (m, 10H); 3.64 (t, J=6.2 Hz, 2H); 4.55 (m, 2H); 5.20 (dm, J=10.5 Hz, 1H); 5.30 (dm, J=17.2 Hz, 1H); 5.90 (m, 1H).

Compound 53

Allyl 3-{2-[2-(2-piperazin-1-ylethoxy)ethoxy]ethoxy}propanoate

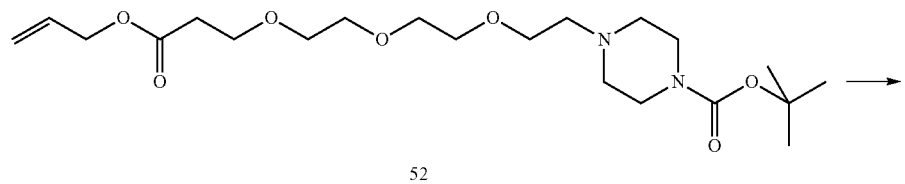

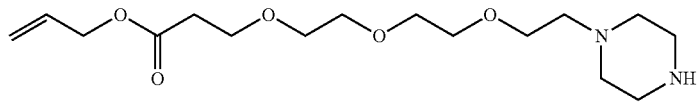

To a solution of 110 mg (256 μmol) of compound 52 in 10 ml of DCM are added 380 μl (5.11 mmol) of TFA. Stirring is continued for 24 hours at RT. The mixture is concentrated to dryness, taken up in a minimum amount of DCM and entrained several times with toluene. The crude product is purified by SPE filtration on an SCX cartridge (Varian) conditioned and washed with methanol and then eluted with a 0.5 N solution of aqueous ammonia in methanol. Compound 53 is obtained in the form of a colourless oil (47 mg, 55%). $^1$H NMR (400 MHz, DMSO-$d_6$): 2.58 (t, J=6.2 Hz, 2H); 3.10 to 3.36 (broad m, 6H); 3.45 to 3.78 (partially masked m, 16H); 4.56 (m, 2H); 5.20 (dm, J=10.5 Hz, 1H); 5.30 (dm, J=17.2 Hz, 1H); 5.90 (m, 1H); 9.00 (broad m, 1H).

Compound 54

Allyl (2-{2-[2-[2-(4-{(2R,3R)-3-[(S)-1-((E)-(3S,10R,16S)-10-{3-chloro-4-methoxy-benzyl}-3-isobutyl-6,6-dimethyl-2,5,9,12-tetraoxo-1,4-dioxa-8,11-diaza-cyclohexadec-13-en-16-yl)ethyl]oxiranyl}benzylpiperazin-1-yl)ethoxy]ethoxy}ethoxy)propanoate

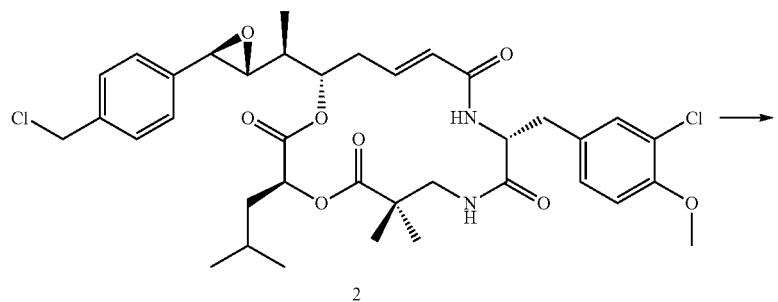

2

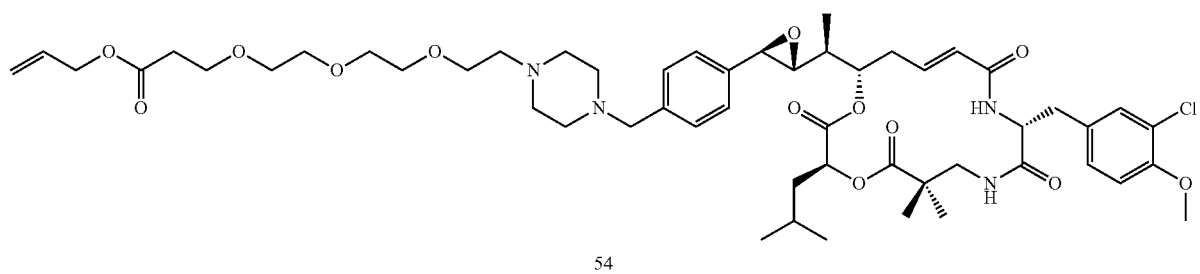

54

Compound 54 may be obtained by nucleophilic substitution of the chloro group of derivative 2 with the amine 53 by applying the method described for the preparation of compound 30.

Compound 55

(2-{2-[2-[2-(4-{(2R,3R)-3-[(S)-1-((E)-(3S,10R,16S)-10-{3-Chloro-4-methoxybenzyl}-3-isobutyl-6,6-dimethyl-2,5,9,12-tetraoxo-1,4-dioxa-8,11-diazacyclohexadec-13-en-16-yl)ethyl]oxiranyl}benzylpiperazin-1-yl)ethoxy]ethoxy}ethoxy)propanoic acid

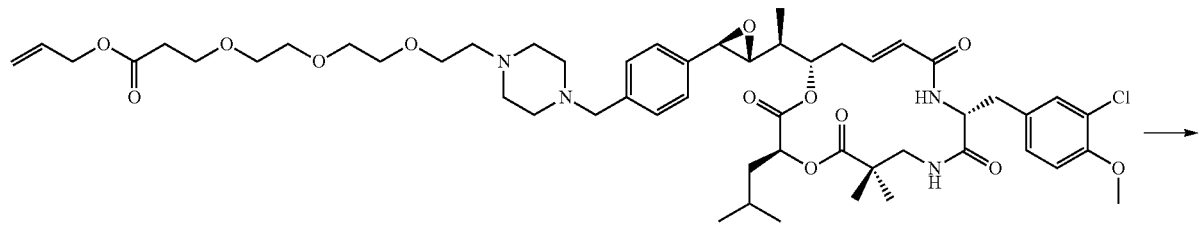

54

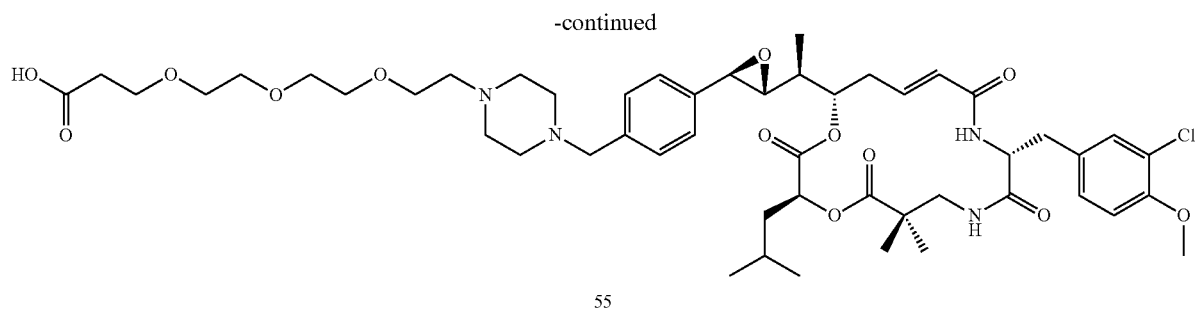
55
Compound 55 may be obtained according to the method described for Compound 41.
Example 16
2,5-Dioxopyrrolidin-1-yl (2-{2-[2-(4-{(2R,3R)-3-[(S)-1-(((E)-(3S,10R,16S)-10-{3-chloro-4-methoxy-benzyl}-3-isobutyl-6,6-dimethyl-2,5,9,12-tetraoxo-1,4-dioxa-8,11-diazacyclo-hexadec-13-en-16-yl)ethyl]oxiranyl}benzylpiperazin-1-yl)ethoxy]ethoxy}ethoxy)propanoate
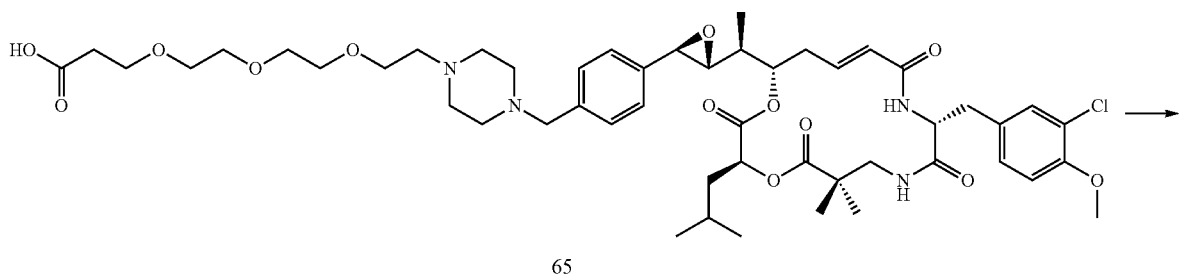
65
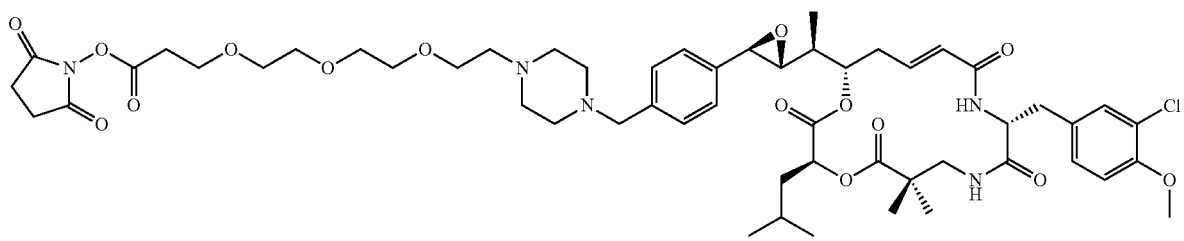
Ex 18
Example 16 may be obtained according to the method described for Example 18.

Example 17

2,5-Dioxopyrrolidin-1-yl 3-(2-{2-[2-(2-{2-[4-(4-{4-[(2R,3R)-3-((S)-1-{(E)-(10R,16S)-10-(3-chloro-4-methoxybenzyl)-3-isobutyl-6,6-dimethyl-2,5,9,12-tetraoxo-1,4-dioxa-8,11-diazacyclohexadec-13-en-16-yl}ethyl)oxiranyl]benzyl}piperazin-1-yl)-1,1-dimethyl-4-oxobutylsulfanyl]acetylamino}ethoxy)ethoxy]ethoxy}ethoxy)propanoate

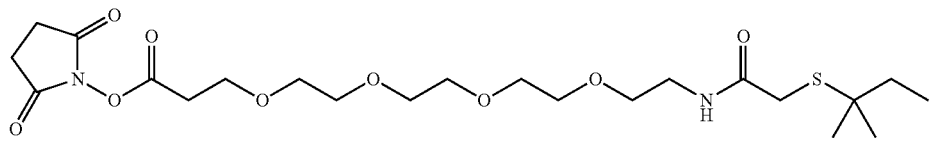

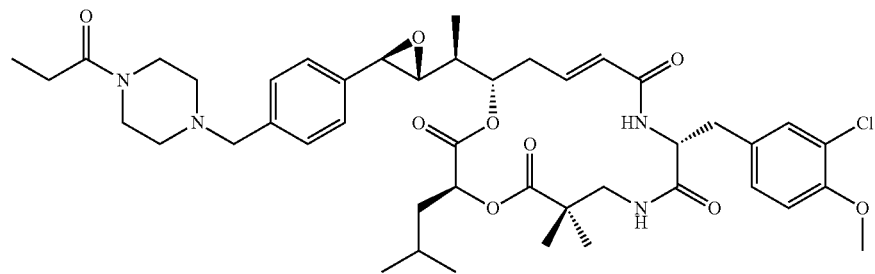

Compound 56

2,5-Dioxopyrrolidin-1-yl 3-(2-{2-[2-(2-{2-bromoacetylamino}ethoxy)ethoxy]ethoxy}-ethoxy)propanoate

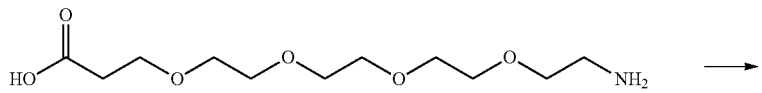

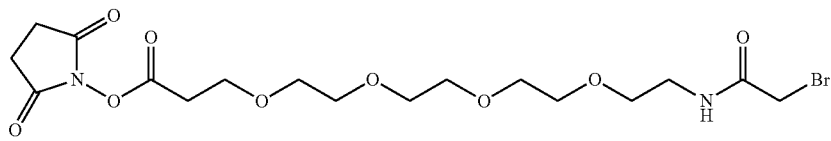

56

To a solution of 3-(2-{2-[2-(2-aminoethoxy)ethoxy]ethoxy}ethoxy)propionic acid (671 mg, 2.53 mmol) in DCM (10 ml) is added a solution of 2,5-dioxopyrrolidin-1-yl bromoacetate (2.53 mmol) in 4.7 ml of DCM. Stirring is continued for 15 minutes at RT and DCC is then added to the mixture. After reaction for 4 hours, the mixture is filtered through a sinter funnel and the filtrate is then evaporated and purified by chromatography on silica gel, eluting with a 99/1 to 94/6 DCM/methanol mixture. The oil obtained (800 mg) is again purified by chromatography on a cyano-grafted silica gel, eluting with a 99/1 DCM/methanol mixture. Compound 56 is obtained in the form of a colourless oil (611 mg, 50%). $^1$H NMR (500 MHz, DMSO-$d_6$): 2.81 (s, 4H); 2.92 (t, J=5.9 Hz, 2H); 3.23 (q, J=5.9 Hz, 2H); 3.43 (t, J=5.9 Hz, 2H); 3.48 to 3.55 (m, 12H); 3.72 (t, J=5.9 Hz, 2H); 3.85 (s, 2H); 8.30 (broad t, J=5.9 Hz, 1H). LCMS (A2): ES m/z=483 [M+H]$^+$; m/z=481 [M−H]$^-$; $t_R$=0.51 min.

Compound 7

(E)-(3S,10R,16S)-10-(3-Chloro-4-methoxybenzyl)-3-isobutyl-6,6-dimethyl-16-[(S)-1-((2R,3R)-3-{4-[4-(4-methyl-4-methyldisulfanylpentanoyl)piperazin-1-ylmethyl]phenyl}oxiranyl)-ethyl]-1,4-dioxa-8,11-diazacyclohexadec-13-ene-2,5,9,12-tetraone

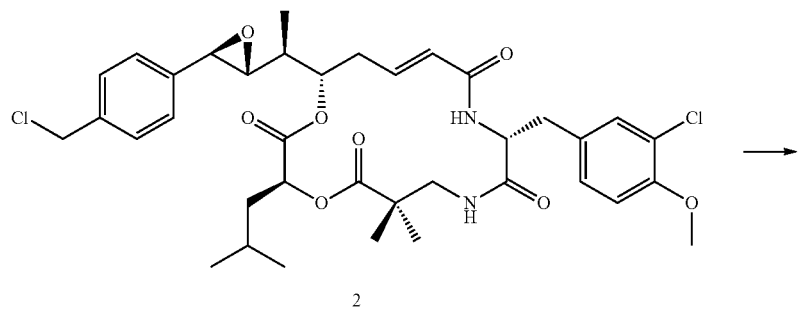

2

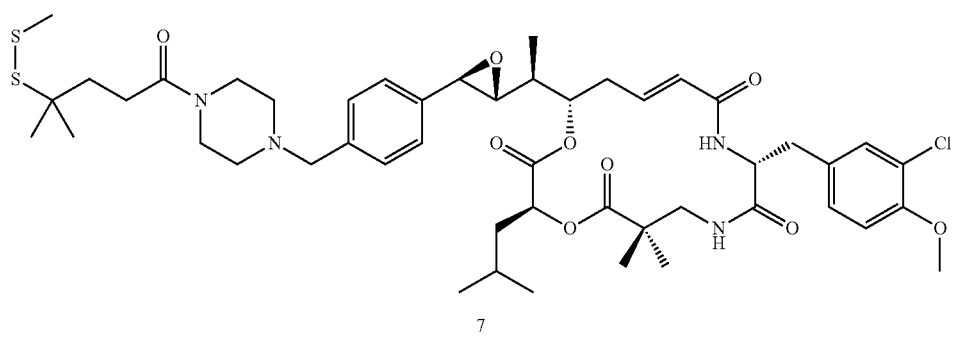

7

To a solution, purged with argon, of compound 2 (19.8 mg, 27.6 µmol) in anhydrous acetonitrile (2.5 ml) are successively added TEA (138 µmol) and 4-methyl-4-methyldisulfanyl-1-piperazin-1-ylpentan-1-one hydrochloride 6 (83 µmol). Stirring is continued at 40° C. for 24 hours and the mixture is then diluted in EtOAc (10 ml). The organic phase is washed with water (2×10 ml), with saturated aqueous $NaHCO_3$ solution (10 ml) and with saturated aqueous NaCl solution (10 ml). After drying over $MgSO_4$ and filtering, the solvents are evaporated off under reduced pressure. The crude reaction product is purified by chromatography on silica gel, eluting with a 99/1 to 90/10 DCM/methanol mixture. A white powder, 7, is obtained (19.4 mg; 75%). TLC (DCM 90/MeOH 10): Rf=0.6; $^1$H NMR (400 MHz, DMSO-$d_6$): 0.75-0.81 (m, 6H); 1.01 (s, 3H); 1.05 (d, J=6.8 Hz, 3H); 1.12 (s, 3H); 1.26 (s, 6H); 1.28-1.33 (m, 1H); 1.52-1.61 (m, 2H); 1.76-1.83 (m, 2H); 2.27-2.38 (m, 4H); 2.39 (s, 3H); 2.64-2.74 (m, 2H); 2.95-3.05 (m, 2H); 3.24-3.34 (m, 6H); 3.44 (br. s., 4H); 3.49 (s, 2H); 3.81 (s, 3H); 3.88 (d, J=1.7 Hz, 1H); 4.22-4.29 (m, 1H); 4.92 (dd, J=9.9, 3.5 Hz, 1H); 5.08-5.15 (m, 1H); 5.81 (d, J=14.2 Hz, 1H); 6.48 (ddd, J=15.2, 11.3, 3.5 Hz, 1H); 7.05 (d, J=8.6 Hz, 1H); 7.17 (dd, J=8.4, 2.3 Hz, 1H); 7.22 (d, J=9.3 Hz, 1H); 7.25-7.34 (m, 5H); 8.34 (d, J=8.1 Hz, 1H). LCMS (A1): ES m/z=943 [M+H]$^+$; m/z=941 [M−H]$^−$; $t_R$=4.03 min.

Note: Compound 7 may also be prepared from G=OMs (see Example 1)

Compound Ex. 1

(E)-(3S,10R,16S)-10-(3-Chloro-4-methoxybenzyl)-3-isobutyl-6,6-dimethyl-16-[(S)-1-((2R,3R)-3-{4-[4-(4-mercapto-4-methylpentanoyl)piperazin-1-ylmethyl]phenyl}oxiranyl)-ethyl]-1,4-dioxa-8,11-diazacyclohexadec-13-ene-2,5,9,12-tetraone

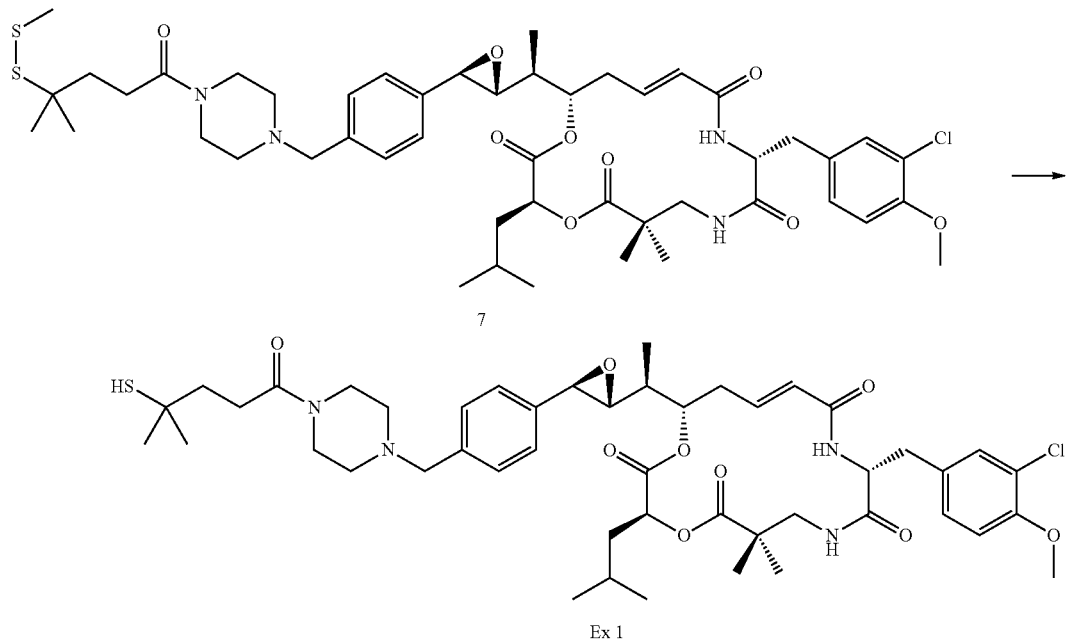

Compound 7 (17.9 mg; 18.97 μmol) is dissolved in a mixture of ethanol (2.2 ml)/water (1.8 ml), and the mixture turns cloudy. TCEP (47.4 μmol) is then added and the mixture is stirred for 3 hours at RT and then diluted by adding EtOAc (20 ml) and the organic phase is washed with a 1/1 mixture of water and saturated aqueous NH$_4$Cl solution (20 ml) and then with 20 ml of saturated NaCl solution. After drying the organic phase over MgSO$_4$, filtering and evaporating off the solvents under reduced pressure, the product Ex. 1 is obtained in the form of a white solid (15.6 mg; 92%). TLC (DCM 90/MeOH 10): Rf=0.56; $^1$H NMR (500 MHz, DMSO-d$_6$): 0.76-0.81 (m, 6H); 1.01 (s, 3H); 1.06 (d, J=6.8 Hz, 3H); 1.13 (s, 3H); 1.24 (s, 6H); 1.27-1.31 (m, 1H); 1.56-1.64 (m, 2H); 1.73-1.85 (m, 3H); 2.26-2.33 (m, 3H); 2.36-2.45 (m, 4H); 2.63-2.75 (m, 2H); 2.95-3.06 (m, 3H); 3.34-3.36 (m, 1H); 3.42-3.51 (m, 6H); 3.82 (s, 3H); 3.89 (s, 1H); 4.22-4.29 (m, 1H); 4.92 (dd, J=9.8, 3.4 Hz, 1H); 5.12 (dd, J=10.8, 4.9 Hz, 1H); 5.81 (d, J=15.2 Hz, 1H); 6.48 (ddd, J=15.0, 11.4, 3.4 Hz, 1H); 7.06 (d, J=8.3 Hz, 1H); 7.18 (dd, J=8.3, 1.5 Hz, 1H); 7.24 (d, J=9.8 Hz, 1H); 7.26-7.36 (m, 5H); 8.37 (d, J=7.8 Hz, 1H). LCMS (A2): ES m/z=897 [M+H]$^+$; m/z=895 [M−H]$^−$; t$_R$=0.97 min.

Example 17

2,5-Dioxopyrrolidin-1-yl 3-(2-{2-[2-(2-{2-[4-(4-{4-[(2R,3R)-3-((S)-1-{(E)-(10R,16S)-10-(3-chloro-4-methoxybenzyl)-3-isobutyl-6,6-dimethyl-2,5,9,12-tetraoxo-1,4-dioxa-8,11-diazacyclo-hexadec-13-en-16-yl}ethyl)oxiranyl]benzyl}piperazin-1-yl)-1,1-dimethyl-4-oxo-butylsulfanyl]-acetylamino}ethoxy)ethoxy]ethoxy}ethoxy)propanoate

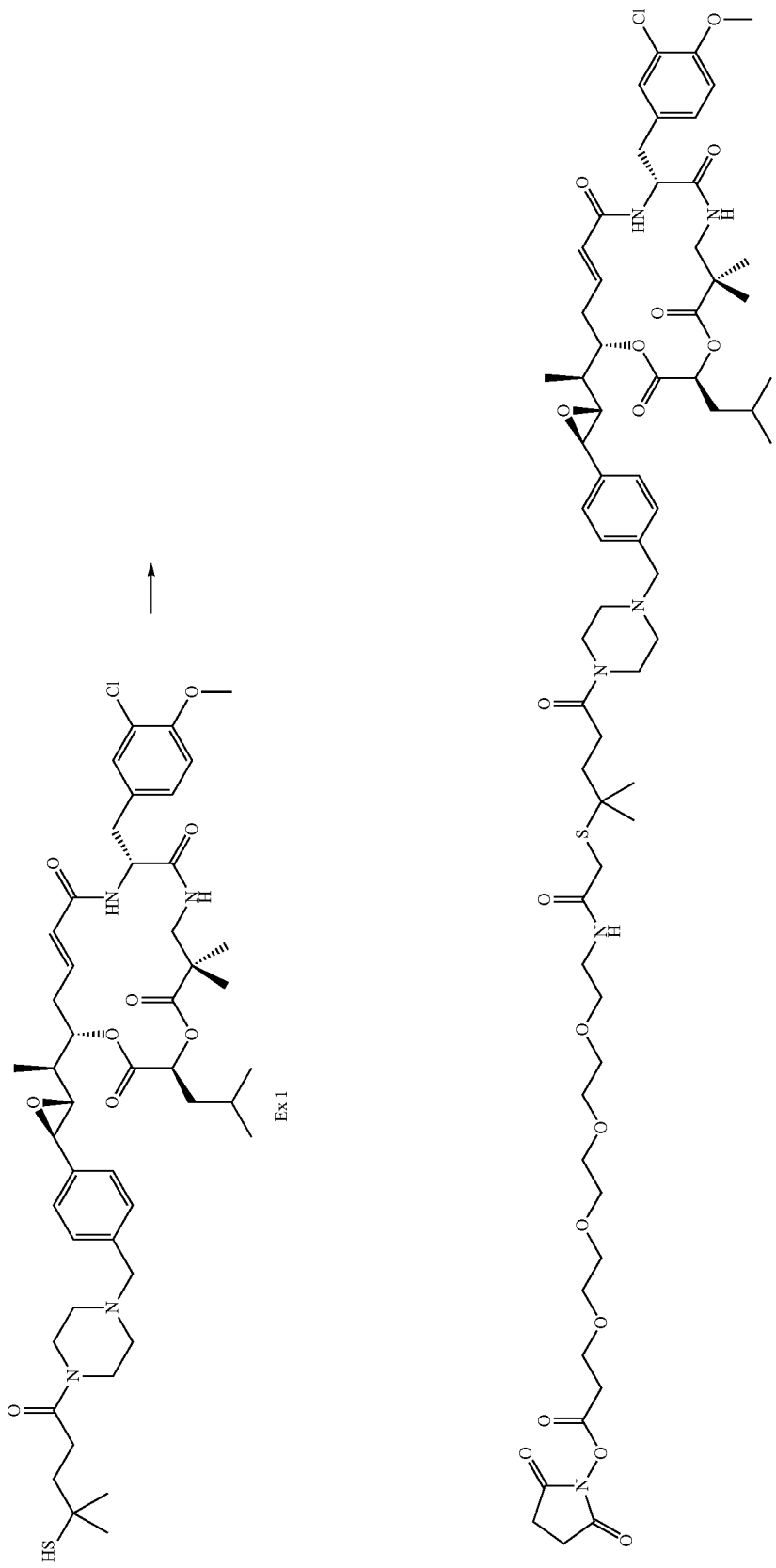

To a solution, purged with argon, of compound Ex. 1 (15.6 mg, 17.8 µmol) in anhydrous acetonitrile (1.0 ml) are successively added DIPEA (19.12 µmol) and compound 56 (19.12 µmol). Stirring is continued at RT for 4 hours, and a further 29.5 µmol of DIPEA are then added, and stirring is continued for 16 hours. The next day, a further 29.5 µmol of compound 56 and of DIPEA are added and the mixture is heated to 50° C. After reaction for a further 24 hours, 22.6 µmol of compound 56 and 29.5 µmol of DIPEA are added and the mixture is heated at 60° C. for a further 24 hours. The heating is then stopped and stirring is continued at RT for 64 hours. The mixture is diluted in 10 ml of EtOAc and the organic phase is washed with 2×10 ml of water and then with 10 ml of saturated NaCl solution. After drying the organic phase over MgSO$_4$, filtering and evaporating off the solvents under reduced pressure, the crude product is purified by chromatography on silica gel, eluting with a 99/1 to 90/10 DCM/methanol mixture. The product Ex. 17 is obtained in the form of a colourless solid (9.2 mg; 41%). $^1$H NMR (500 MHz, DMSO-d$_6$): 0.77 to 0.82 (m, 6H): 1.02 (s, 3H): 1.06 (d, J=6.9 Hz, 3H): 1.13 (s, 3H): 1.23 (s, 6H): 1.26 to 1.35 (m, 1H): 1.52 to 1.64 (m, 2H): 1.68 to 1.77 (m, 2H): 1.78 to 1.86 (m, 1H): 2.26 to 2.33 (m, 3H): 2.35 to 2.41 (m, 4H): 2.68 to 2.76 (m, 2H): 2.82 (s, 4H): 2.93 (t, J=6.0 Hz, 2H): 2.96 to 3.07 (m, 4H): 3.13 (s, 2H): 3.20 (q, J=5.8 Hz, 2H): 3.33 (m, 1H): 3.38 to 3.57 (m, 18H): 3.73 (t, J=5.8 Hz, 2H): 3.83 (s, 3H): 3.89 (s, 2H): 4.27 (m, 1H): 4.93 (dd, J=3.8 and 10.0 Hz, 1H): 5.13 (m, 1H): 5.82 (d, J=15.4 Hz, 1H): 6.49 (ddd, J=3.8 and 11.1 and 15.4 Hz, 1H): 7.07 (d, J=8.8 Hz, 1H): 7.15 to 7.37 (m, 7H): 8.01 (t, J=5.8 Hz, 1H): 8.35 (d, J=8.0 Hz, 1H). LCMS (A2): ES m/z=1299 [M+H]$^+$: m/z=650 [M+2H]$^{2+}$: m/z=1297 [M−H]$^−$; t$_R$=0.92 min.

Example 18

2,5-Dioxopyrrolidin-1-yl 3-(2-{2-[2-(2-{4-[(2S,3S)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diaza-cyclohexadec-13-en-16-yl}ethyl)oxiranyl]benzyloxycarbonylamino}ethoxy)ethoxy]ethoxy}-ethoxy)propanoate

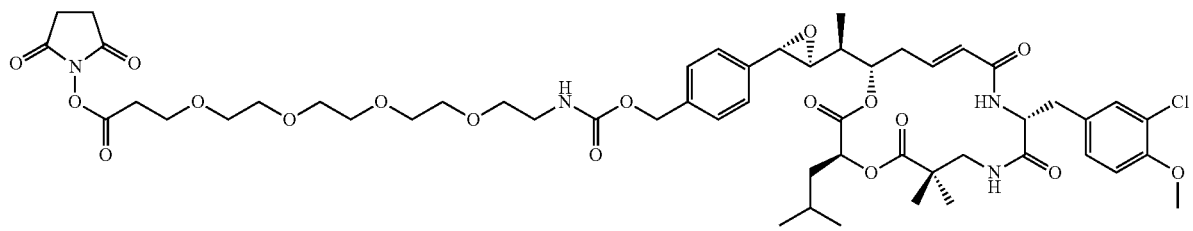

Compound 58

4-Nitrophenyl 4-((2S,3S)-3-{(S)-1-[(E)-(3S,10R,16S)-10-(3-Chloro-4-methoxybenzyl)-3-isobutyl-6,6-dimethyl-2,5,9,12-tetraoxo-1,4-dioxa-8,11-diaza-cyclohexadec-13-en-16-yl]ethyl}oxiranyl)benzyl carbonate

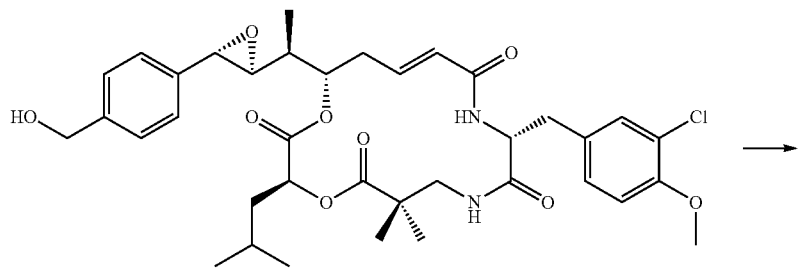

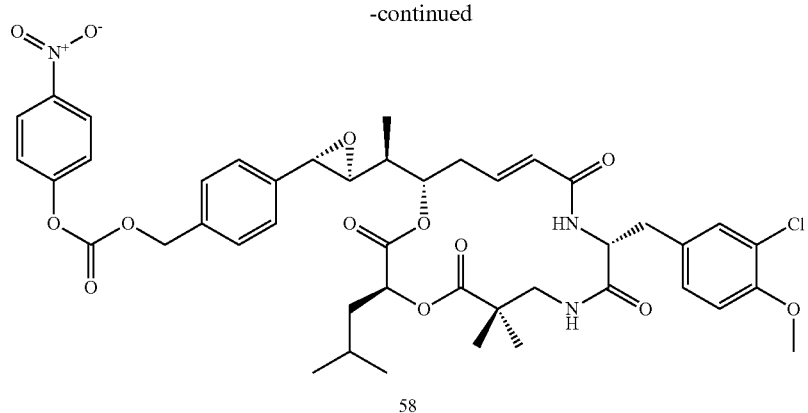

58

Derivative 57 (20 mg; 28.6 µmol, prepared according to Al-awar R. S., et al., *J. Med. Chem.* 2003, 46, 2985-3007) is dissolved in anhydrous DCM (0.3 ml) and the solution is purged with argon, followed by addition of TEA (40 µmol) and then 4-nitrophenyl chloroformate (32.32 µmol). After stirring for 3 hours 30 minutes at RT, the mixture is hydrolyzed and diluted in 7 ml of EtOAc. The organic phase is washed with water and then with saturated NaCl solution, dried over MgSO$_4$, filtered and evaporated to dryness to give compound 58 in the form of a white solid (23 mg, 93%).

LCMS (A3): ES m/z=864 [M+H]$^+$; m/z=908 [M+HCO$_2$H—H]$^-$; t$_R$=1.43 min.

Compound 59

3-(2-{2-[2-(2-{4-[(2S,3S)-3-((S)-1-{(E)-(3S,10R,16S)-10-[3-Chloro-4-methoxy-benzyl]-3-isobutyl-6,6-dimethyl-2,5,9,12-tetraoxo-1,4-dioxa-8,11-diaza-cyclohexadec-13-en-16-yl}-ethyl)oxiranyl]benzyloxycarbonylamino}ethoxy)ethoxy]ethoxy}ethoxy)propanoic acid

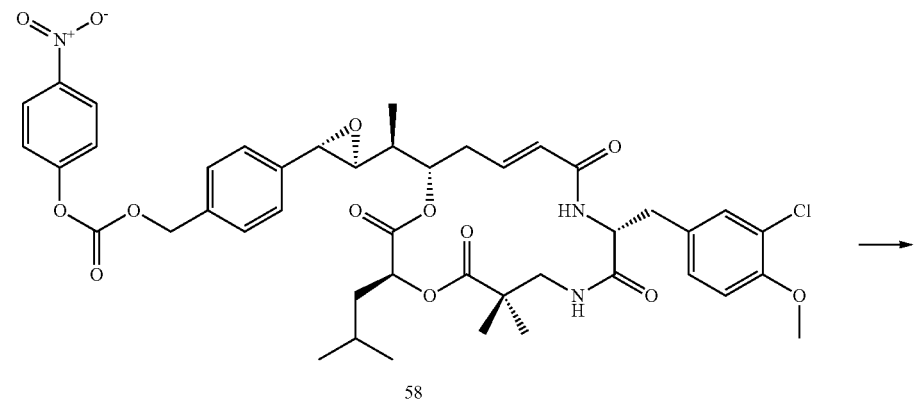

58

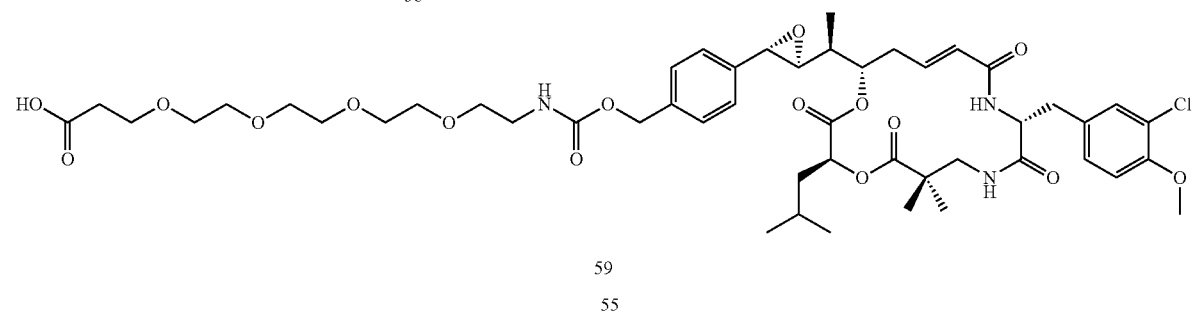

59

To a solution, purged with argon, of compound 58 (23 mg, 26.6 µmol) in anhydrous acetonitrile (1.6 ml) are successively added 3-(2-{2-[2-(2-aminoethoxy)ethoxy]ethoxy}ethoxy)propionic acid (39.9 µmol) and TEA (53.2 µmol). After stirring for 24 hours at RT, the mixture is diluted in 10 ml of EtOAc. The organic phase is washed with 10 ml of water containing 250 µl of 0.1N HCl (pH≈4). The aqueous phase is extracted with 10 ml of EtOAc (2×); the organic phases are combined, washed with 10 ml of water and then with 10 ml of saturated NaCl solution, dried over MgSO$_4$, filtered and evaporated to dryness to give compound 59 in the form of a very pale yellow solid (18.5 mg, 70%). LCMS (A3): ES m/z=990 [M+H]$^+$; m/z=988 [M−H]$^-$; t$_R$=1.32 min.

Example 18

2,5-Dioxopyrrolidin-1-yl 3-(2-{2-[2-(2-{4-[(2S,3S)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclo-hexadec-13-en-16-yl}ethyl)oxiranyl]benzyloxycarbonylamino}ethoxy)ethoxy]ethoxy}ethoxy)-propanoate

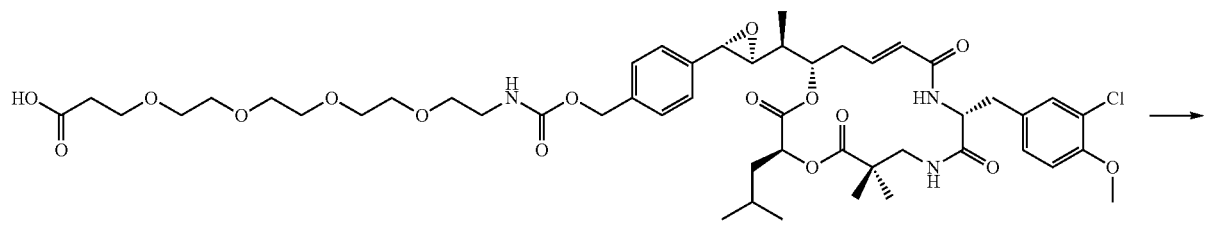

59

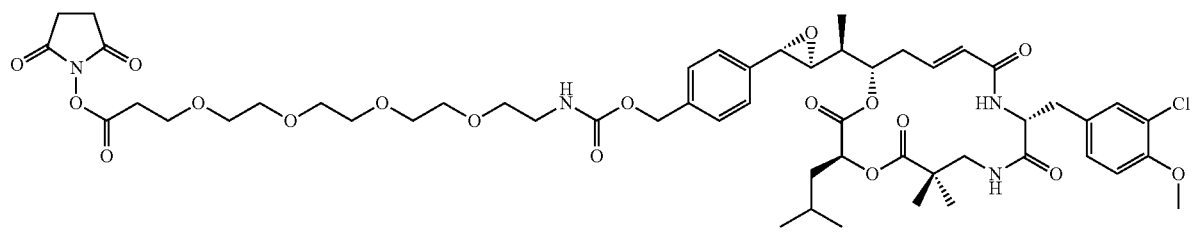

Ex 18

To a solution, purged with argon, of compound 59 (18.5 mg, 18.6 µmol) in THF (1.5 ml) are successively added DIPEA (55.8 µmol) and N,N'-disuccinimidyl carbonate (37.2 µmol). After stirring for 19 hours at RT, the mixture is diluted in 10 ml of EtOAc, washed with 10 ml of water (twice) and then with 10 ml of saturated NaCl solution, dried over MgSO$_4$ and evaporated to dryness. The crude product is purified by chromatography on silica gel, eluting with a 100/0 to 0/100 heptane/EtOAc mixture containing 10% isopropanol. The product Ex. 17 is obtained in the form of a white solid (6.08 mg; 30%). $^1$H NMR (500 MHz, DMSO-d$_6$): 0.83 to 0.88 (m, 6H); 0.97 (d, J=7.1 Hz, 3H); 1.02 (s, 3H); 1.15 (s, 3H); 1.47 to 1.56 (m, 1H); 1.58 to 1.68 (m, 2H); 1.82 to 1.90 (m, 1H); 2.39 to 2.47 (m, 1H); 2.60 to 2.66 (m, 1H); 2.71 (dd, J=11.5 and 14.4 Hz, 1H); 2.80 (s, 4H); 2.91 (t, J=6.0 Hz, 2H); 2.94 to 3.07 (m, 3H); 3.14 (q, J=6.0 Hz, 2H); 3.37 to 3.56 (partially masked m, 15H); 3.71 (t, J=6.0 Hz, 2H); 3.79 (m, 1H); 3.81 (s, 3H); 4.27 (ddd, J=3.8 and 8.0 and 11.3 Hz, 1H); 4.96 to 5.05 (m, 3H); 5.11 (m, 1H); 5.88 (d, J=15.4 Hz, 1H); 6.48 (ddd, J=3.8 and 11.3 and 15.4 Hz, 1H); 7.05 (d, J=8.8 Hz, 1H); 7.14 to 7.39 (m, 8H); 8.40 (d, J=8.0 Hz, 1H). LCMS (A2): ES m/z=1087 [M+H]$^+$; m/z=1085 [M−H]$^−$; t$_R$=1.09 min.

Example 19

2,5-Dioxopyrrolidin-1-yl (1-(4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexa-dec-13-en-16-yl}ethyl)oxiranyl]benzyl}-1H-1,2,3-triazol-4-yl)butanoate

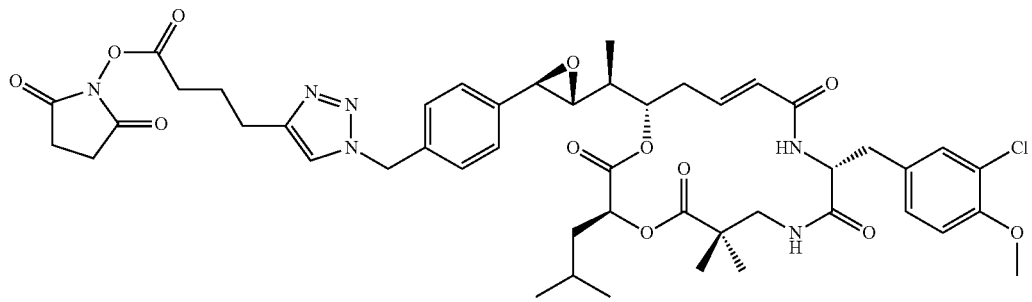

Compound 60

(E)-(3S,10R,16S)-16-{(S)-1-[(2R,3R)-3-(4-Azidomethylphenyl)oxiranyl]ethyl}-10-(3-chloro-4-methoxybenzyl)-3-isobutyl-6,6-dimethyl-1,4-dioxa-8,11-diazacyclohexadec-13-ene-2,5,9,12-tetraone

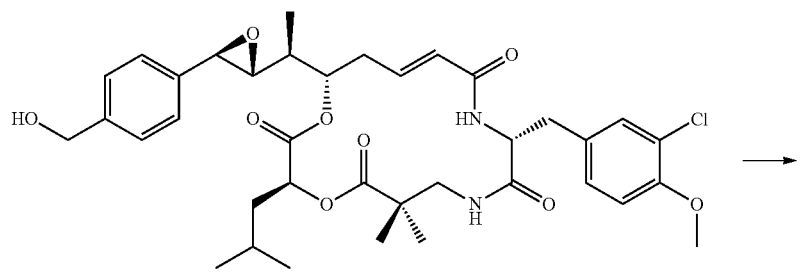

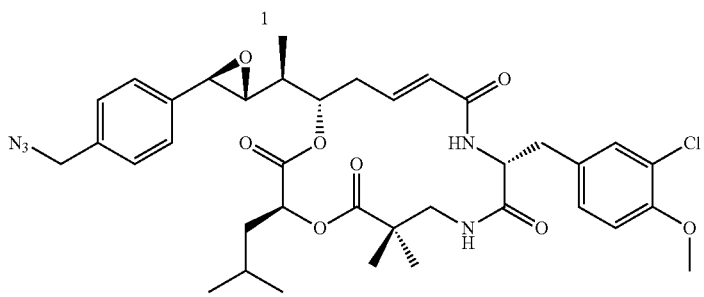

To a solution, purged with argon, of 60 mg (85.8 μmol) of compound 1 in 9 ml of anhydrous THF are added 25.9 μl (120 μmol) of diphenylphosphorazide. The mixture is stirred at RT for 10 minutes and then cooled to 0° C., followed by addition of 18.0 μl (120 μmol) of DBU. Stirring is continued at RT for 15 hours. The reaction is incomplete: 25.9 μl (120 μmol) of diphenylphosphorazide and 18.0 μl (120 μmol) of DBU are added and stirring is continued for 24 hours. Some starting compound 1 remains: 25.9 μl (120 μmol) of diphenylphosphorazide and 18.0 μl (120 μmol) of DBU are added and stirring is continued for 24 hours. The reaction mixture is hydrolyzed by addition of 6 ml of water and is then extracted with DCM (3×6 ml). The organic phases are combined, washed with saturated NaCl solution (8 ml) and dried over MgSO$_4$. After filtering and concentrating under reduced pressure, the crude product is purified by chromatography on silica gel, using a 100/0 to 90/10 DCM/methanol mixture as eluent. Compound 60 is obtained in the form of a white solid (46 mg, 74%). $^1$H NMR (500 MHz, DMSO-d$_6$): 0.76 (d, J=6.3 Hz, 3H); 0.78 (d, J=6.3 Hz, 3H); 1.00 (s, 3H); 1.05 (d, J=6.9 Hz, 3H); 1.12 (s, 3H); 1.30 (m, 1H); 1.49 to 1.63 (m, 2H); 1.82 (m, 1H); 2.27 (m, 1H); 2.63 to 2.74 (m, 2H); 2.95 to 3.05 (m, 3H); 3.25 to 3.38 (partially masked m, 1H); 3.81 (s, 3H); 3.92 (d, J=1.9 Hz, 1H); 4.25 (ddd, J=3.6 and 8.0 and 11.5 Hz, 1H); 4.46 (s, 2H); 4.92 (dd, J=3.6 and 9.6 Hz, 1H); 5.11 (ddd, J=1.5 and 5.7 and 11.3 Hz, 1H); 5.80 (dd, J=1.5 and 15.1 Hz, 1H); 6.48 (ddd, J=3.8 and 11.3 and 15.1 Hz, 1H); 7.05 (d, J=8.6 Hz, 1H); 7.17 (dd, J=2.2 and 8.6 Hz, 1H); 7.22 (dd, J=2.6 and 9.5 Hz, 1H); 7.28 (d, J=2.2 Hz, 1H); 7.34 (d, J=8.3 Hz, 2H); 7.38 (d, J=8.3 Hz, 2H); 8.34 (d, J=8.0 Hz, 1H). LCMS (A2): ES m/z=724 [M+H]$^+$; m/z=722 [M−H]$^−$; m/z=768 [M−H+HCO$_2$H]$^−$ base peak; t$_R$=1.18 min.

Compound 61

(1-{4-[(2R,3R)-3-((S)-1-{(E)-(3S,10R,16S)-10-[3-Chloro-4-methoxybenzyl]-3-isobutyl-6,6-dimethyl-2,5,9,12-tetraoxo-1,4-dioxa-8,11-diazacyclohexadec-13-en-16-yl}ethyl)-oxiranyl]benzyl}-1H-1,2,3-triazol-4-yl)butanoic acid

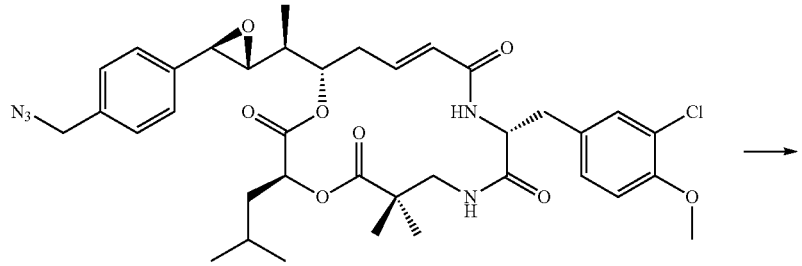

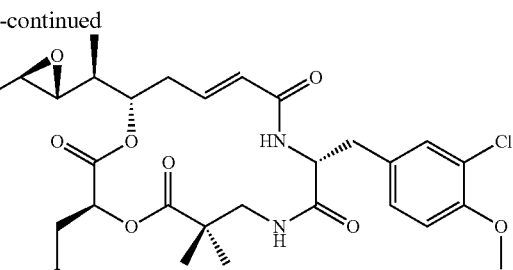

61

To a suspension of 22 mg (30.4 µmol) of compound 60 in 500 µl of water is added a solution of 6.8 mg (60.8 µmol) of 5-hexynoic acid in 500 µl of THF. 122 µl (12.2 µmol) of aqueous 0.1M copper sulfate solution and 122 µl (24.3 µmol) of aqueous 0.2M sodium ascorbate solution are then added. Stirring is continued for 2 hours at RT. The mixture is hydrolyzed by adding 2 ml of water and is then extracted with EtOAc (3×2 ml). The organic phases are combined, washed with saturated NaCl solution (3 ml) and dried over MgSO$_4$. After filtering and concentrating under reduced pressure, the crude product is purified by chromatography on silica gel, using a 98/2 to 90/10 DCM/methanol mixture as eluent. Compound 61 is obtained in the form of a white solid (19.4 mg, 76%). $^1$H NMR (500 MHz, DMSO-d$_6$): 0.73 (d, J=6.4 Hz, 3H); 0.75 (d, J=6.4 Hz, 3H); 1.00 (s, 3H); 1.04 (d, J=6.9 Hz, 3H); 1.11 (s, 3H); 1.29 (m, 1H); 1.50 to 1.59 (m, 2H); 1.76 to 1.85 (m, 3H); 2.20 to 2.30 (m, 3H); 2.62 (t, J=7.7 Hz, 2H); 2.65 to 2.72 (m, 2H); 2.94 to 3.04 (m, 3H); 3.28 to 3.38 (partially masked m, 1H); 3.81 (s, 3H); 3.89 (d, J=1.6 Hz, 1H); 4.25 (ddd, J=3.6 and 8.0 and 11.5 Hz, 1H); 4.90 (dd, J=3.6 and 9.6 Hz, 1H); 5.10 (ddd, J=1.6 and 5.2 and 11.2 Hz, 1H); 5.53 (s, 2H); 5.78 (dd, J=1.6 and 15.0 Hz, 1H); 6.46 (ddd, J=3.7 and 11.2 and 15.0 Hz, 1H); 7.05 (d, J=8.5 Hz, 1H); 7.17 (dd, J=1.9 and 8.5 Hz, 1H); 7.22 (dd, J=2.3 and 9.5 Hz, 1H); 7.28 (d, J=1.9 Hz, 1H); 7.31 (s, 4H); 7.92 (s, 1H); 8.37 (broad d, J=8.0 Hz, 1H); 12.03 (very broad m, 1H). LCMS (A2): ES m/z=836 [M+H]$^+$; m/z=418.5 [M+2H]$^{2+}$ base peak; m/z=834 [M−H]$^−$; t$_R$=1.04 min.

Compound 62

Methyl (1-{4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexadec-13-en-16-yl}ethyl)-oxiranyl]benzyl}-1H-1,2,3-triazol-4-yl)butanoate

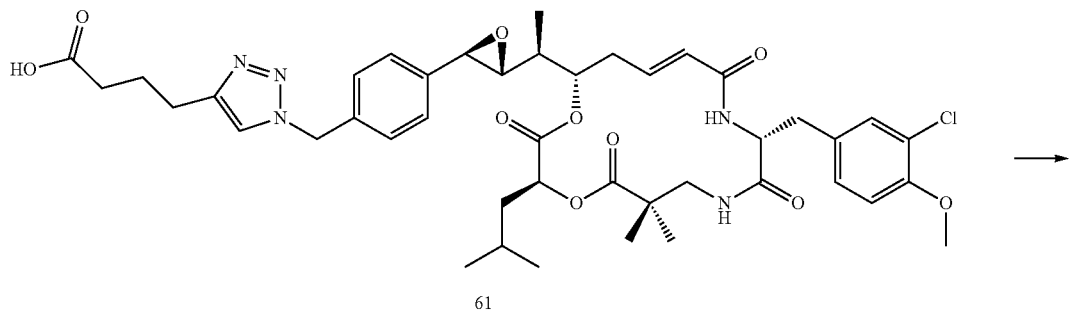

61

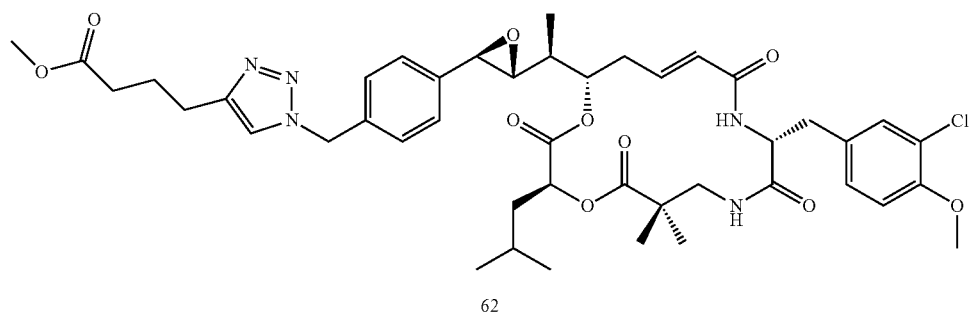

62

To a solution of 5 mg (6 μmol) of compound 61 in 500 μl of DCM and 200 μl of methanol are added 4.5 μl (9.0 μmol) of a 2M solution of trimethylsilyldiazomethane in hexane. Stirring is continued for 30 minutes. The mixture is concentrated under reduced pressure and purified by filtration on silica gel, eluting with a 98/2 DCM/methanol mixture. Compound 62 is obtained in the form of a white solid (5 mg, 98%). $^1$H NMR (500 MHz, DMSO-d$_6$): 0.72 (d, J=6.4 Hz, 3H); 0.75 (d, J=6.4 Hz, 3H); 0.99 (s, 3H); 1.04 (d, J=6.8 Hz, 3H); 1.11 (s, 3H); 1.28 (m, 1H); 1.50 to 1.59 (m, 2H); 1.79 (m, 1H); 1.83 (m, 2H); 2.25 (m, 1H); 2.35 (t, J=7.6 Hz, 2H); 2.62 (t, J=7.6 Hz, 2H); 2.65 to 2.72 (m, 2H); 2.94 to 3.05 (m, 3H); 3.25 to 3.38 (partially masked m, 1H); 3.57 (s, 3H); 3.81 (s, 3H); 3.89 (d, J=1.5 Hz, 1H); 4.25 (ddd, J=3.7 and 8.3 and 11.4 Hz, 1H); 4.89 (dd, J=3.4 and 9.8 Hz, 1H); 5.09 (ddd, J=1.5 and 5.4 and 11.4 Hz, 1H); 5.53 (s, 2H); 5.78 (dd, J=1.5 and 15.2 Hz, 1H); 6.46 (ddd, J=3.4 and 11.4 and 15.2 Hz, 1H); 7.05 (d, J=8.8 Hz, 1H); 7.17 (dd, J=2.0 and 8.8 Hz, 1H); 7.22 (dd, J=2.5 and 9.8 Hz, 1H); 7.28 (d, J=2.0 Hz, 1H); 7.31 (s, 4H); 7.92 (s, 1H); 8.34 (d, J=8.3 Hz, 1H). LCMS (A2): ES m/z=850 [M+H]$^+$; m/z=425.5 [M+2H]$^{2+}$ base peak; m/z=848 [M−H]$^-$; m/z=894 [M−H+HCO$_2$H]$^-$ base peak; $t_R$=1.11 min.

Example 19

2,5-Dioxopyrrolidin-1-yl (1-{4-[(2R,3R)-3-((S)-1-{(E)-(3S,10R,16S)-10-[3-chloro-4-methoxybenzyl]-3-isobutyl-6,6-dimethyl-2,5,9,12-tetraoxo-1,4-dioxa-8,11-diazacyclohexadec-13-en-16-yl}ethyl)oxiranyl]benzyl}-1H-1,2,3-triazol-4-yl)butanoate

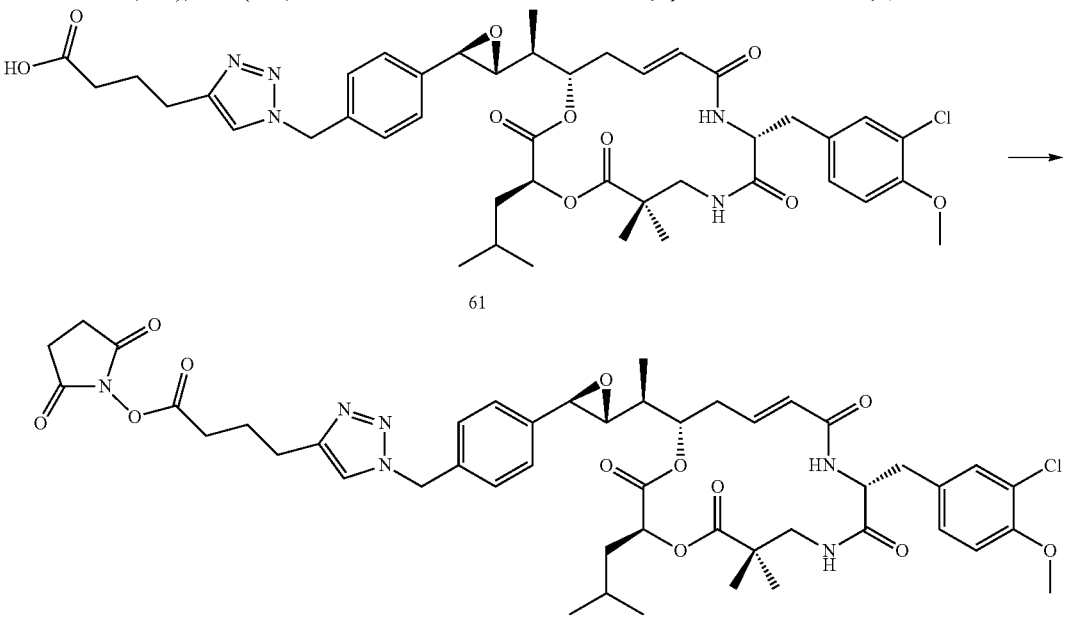

To a solution, purged with argon, of 13.4 mg (16 μmol) of compound 61 in 1.2 ml of THF are successively added 8.4 μl (48.1 μmol) of DIPEA and 8.21 mg (32.04 μmol) of N,N'-disuccinimidyl carbonate. Stirring is continued at RT for 26 hours. The mixture is hydrolyzed by addition of 2 ml of water and is then extracted with 2×2 ml of EtOAc. The organic phases are combined and dried over MgSO$_4$. After filtering and concentrating under reduced pressure, the crude product is purified by filtration on silica gel, eluting with a 98/2 DCM/methanol mixture. The product obtained contains 0.15 mol of NHS. It is taken up in 2 ml of DCM and washed with water (2×3 ml) and then dried over MgSO$_4$. After filtering and concentrating to dryness, compound Ex. 19 is obtained in the form of a white solid (12.56 mg, 84%). $^1$H NMR (500 MHz, DMSO-d$_6$): 0.73 (d, J=6.3 Hz, 3H); 0.75 (d, J=6.6 Hz, 3H); 1.00 (s, 3H); 1.04 (d, J=6.9 Hz, 3H); 1.11 (s, 3H); 1.30 (m, 1H); 1.49 to 1.60 (m, 2H); 1.79 (m, 1H); 1.95 (quin, J=7.5 Hz, 2H); 2.26 (m, 1H); 2.65 to 2.77 (m, 6H); 2.81 (broad s, 4H); 2.92 to 3.05 (m, 3H); 3.34 (partially masked m, 1H); 3.81 (s, 3H); 3.89 (d, J=1.9 Hz, 1H); 4.25 (ddd, J=3.7 and 8.1 and 11.5 Hz, 1H); 4.90 (dd, J=3.6 and 9.6 Hz, 1H); 5.09 (ddd, J=1.4 and 5.5 and 11.3 Hz, 1H); 5.54 (s, 2H); 5.79 (dd, J=1.4 and 15.1 Hz, 1H); 6.46 (ddd, J=3.8 and 11.3 and 15.1 Hz, 1H); 7.05 (d, J=8.5 Hz, 1H); 7.17 (dd, J=2.2 and 8.5 Hz, 1H); 7.21 (dd, J=2.5 and 9.6 Hz, 1H); 7.28 (d, J=2.2 Hz, 1H); 7.31 (s, 4H); 7.95 (s, 1H); 8.33 (d, J=8.1 Hz, 1H). LCMS (A2): ES m/z=933 [M+H]$^+$; m/z=467 [M+2H]$^{2+}$ base peak; m/z=977 [M−H+HCO$_2$H]$^-$ base peak; $t_R$=1.08 min.

Example 20

2,5-Dioxapyrrolidin-1-yl 3-(2-{2-[2-(2-{1-[1-(4-{(2R,3R)-3-[(S)-1-((E)-(10R,16S)-10-(3-chloro-4-methoxybenzyl)-3-isobutyl-6,6-dimethyl-2,5,9,12-tetraoxo-1,4-dioxa-8,11-diazacyclohexadec-13-en-16-yl)ethyl]oxiranyl}benzyl)-1,2,3-triazol-1-yl]methoxy}ethoxy)-ethoxy]ethoxy}ethoxy)propanoate

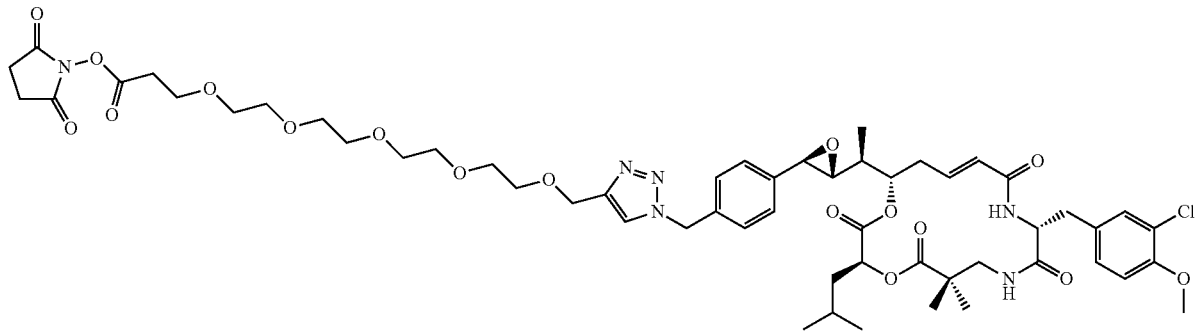

Compound 63

2-{2-[2-(2-Prop-2-ynyloxyethoxy)ethoxy]ethoxy}ethanol

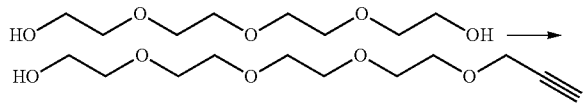

To a solution, purged with argon and cooled to 0° C., of 1 g (5.15 mmol) of tetraethylene glycol in 25 ml of anhydrous THF are added 144 mg (3.60 mmol) of NaH as a 60% dispersion in a mineral oil. Stirring is continued for 30 minutes at 0° C., and 194 µl (2.58 mmol) of propargyl bromide are then added. Stirring is continued at RT for 15 hours. The mixture is concentrated under reduced pressure and the crude product is then purified by chromatography on silica gel, using a 98/2 to 90/10 DCM/methanol mixture as eluent. Compound 63 is obtained in the form of a colourless oil (789 mg, 65%). $^1$H NMR (400 MHz, DMSO-$d_6$): 3.40 (t, J=2.4 Hz, 1H); 3.42 (t, J=5.5 Hz, 2H); 3.48 (q, J=5.5 Hz, 2H); 3.51 to 3.58 (m, 12H); 4.14 (d, J=2.4 Hz, 2H); 4.53 (t, J=5.5 Hz, 1H). LCMS (A2): ES m/z=233 [M+H]$^+$; $t_R$=0.38 min.

Compound 64 tert-Butyl 3-(2-{2-[2-(2-prop-2-ynyloxyethoxy)ethoxy]ethoxy}ethoxy)propanoate

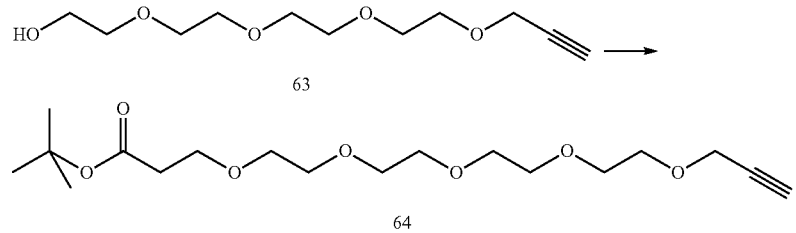

To a solution, purged with argon, of 790 mg (3.40 mmol) of compound 63 in 8.8 ml of anhydrous THF are added 4.4 mg (190 µmol) of sodium. The mixture is heated at 40° C. for 2 hours to fully dissolve it; after cooling to RT, 740 µl (5.09 mmol) of tert-butyl acrylate are added to the mixture. Stirring is continued for 15 hours at RT and the mixture is then concentrated under reduced pressure and the crude product is purified by chromatography on silica gel, using a 98/2 to 90/10 DCM/methanol mixture as eluent. Compound 64 is obtained in the form of a colourless oil (944 mg, 77%). $^1$H NMR (400 MHz, DMSO-$d_6$): 1.44 (s, 9H); 2.41 (t, J=6.2 Hz, 2H); 3.38 (t, J=2.4 Hz, 1H); 3.46 to 3.62 (m, 16H); 3.59 (t, J=6.2 Hz, 2H); 4.14 (d, J=2.4 Hz, 2H). LCMS (A1): ES m/z=361 [M+H]$^+$; m/z=383 [M+Na]$^+$; $t_R$=3.79 min.

Compound 65

3-(2-{2-[2-(2-prop-2-ynyloxyethoxy)ethoxy]ethoxy}ethoxy)propanoic acid

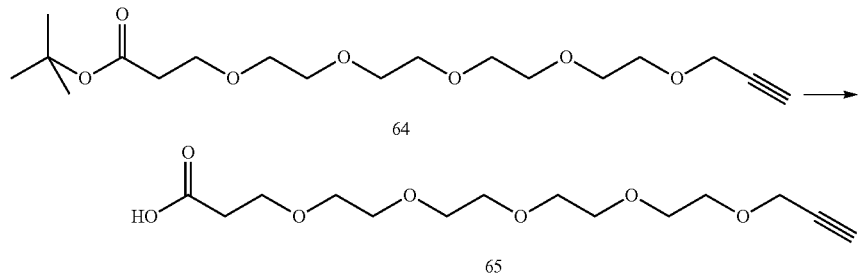

To a solution of 944 mg (2.62 mmol) of compound 64 are added 2 ml (52.4 mmol) of TFA. The mixture is stirred for 6 hours at RT and then concentrated to dryness, taken up in a minimum amount of DCM and entrained several times with toluene. Compound 65 is obtained in the form of a colourless oil (722 mg, 91%). $^1$H NMR (400 MHz, DMSO-d$_6$): 2.44 (t, J=6.4 Hz, 2H); 3.39 (t, J=2.4 Hz, 1H); 3.46 to 3.56 (m, 16H); 3.60 (t, J=6.4 Hz, 2H); 4.14 (d, J=2.4 Hz, 2H); 7.44 to 9.73 (very broad m, 1H). LCMS (A2): ES m/z=305 [M+H]$^+$; m/z=303 [M−H]$^-$; t$_R$=0.48 min.

Example 20

2,5-Dioxapyrrolidin-1-yl 3-(2-{2-[2-(2-{1-[1-(4-{(2R,3R)-3-[(S)-1-((E)-(10R,16S)-10-(3-chloro-4-methoxybenzyl)-3-isobutyl-6,6-dimethyl-2,5,9,12-tetraoxo-1,4-dioxa-8,11-diazacyclo-hexadec-13-en-16-yl)ethyl]oxiranyl}benzyl)-1,2,3-triazol-1-yl]methog}ethoxy)ethoxy]ethoxy}-ethoxy)propanoate

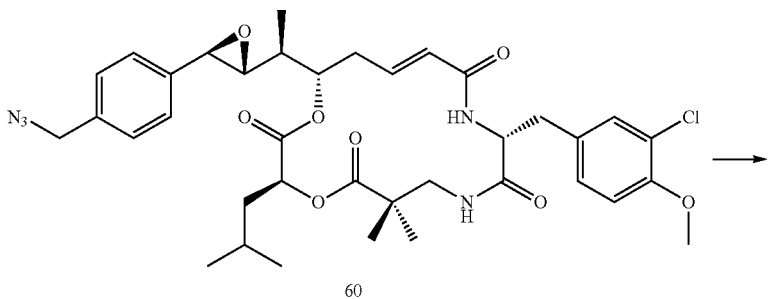

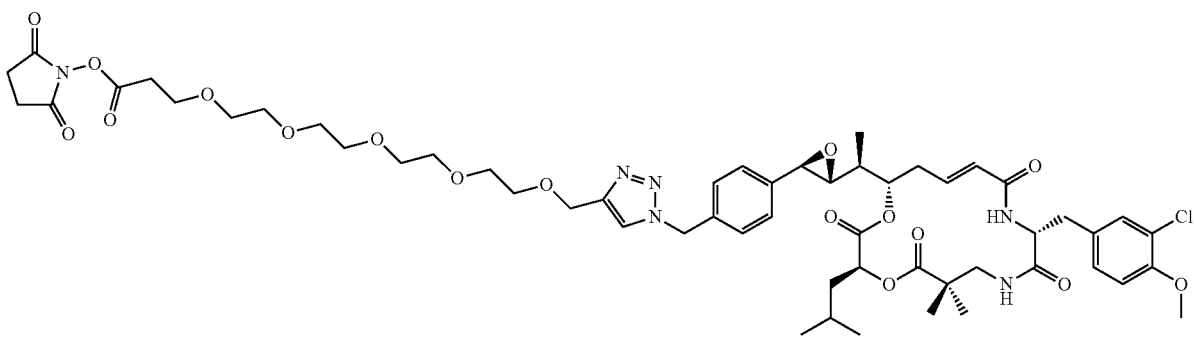

Example 20 may be obtained from compounds 60 and 65 according to the method described for compound 61, followed by activating the acid according to the method described for Example 19.

Example 21

2,5-Dioxopyrrolidin-1-yl (4-{1-[(4-{(2R,3R)-3-[(S)-1-((E)-(3S,10R,16S)-10-{3-chloro-4-methoxybenzyl}-3-isobutyl-6,6-dimethyl-2,5,9,12-tetraoxo-1,4-dioxa-8,11-diaza-cyclohexadec-13-en-16-yl)ethyl]oxiranyl}benzyl)methylamino]methyl}-1,2,3-triazol-1-yl)-butanoate

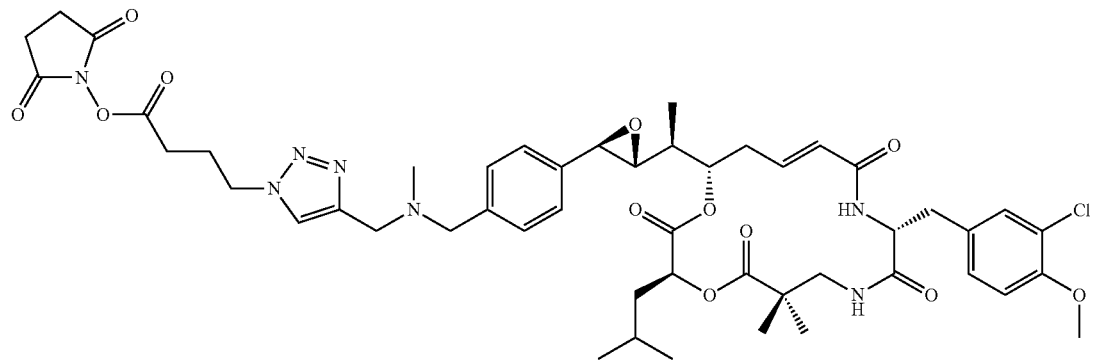

Compound 66

(E)-(3S,10R,16S)-10-(3-Chloro-4-methoxybenzyl)-3-isobutyl-6,6-dimethyl-16-[(S)-1-((2R,3R)-3-{4-[(methylprop-2-ynylamino)methyl]phenyl}oxiranyl)ethyl]-1,4-dioxa-8,11-diaza-cyclohexadec-13-ene-2,5,9,12-tetraone

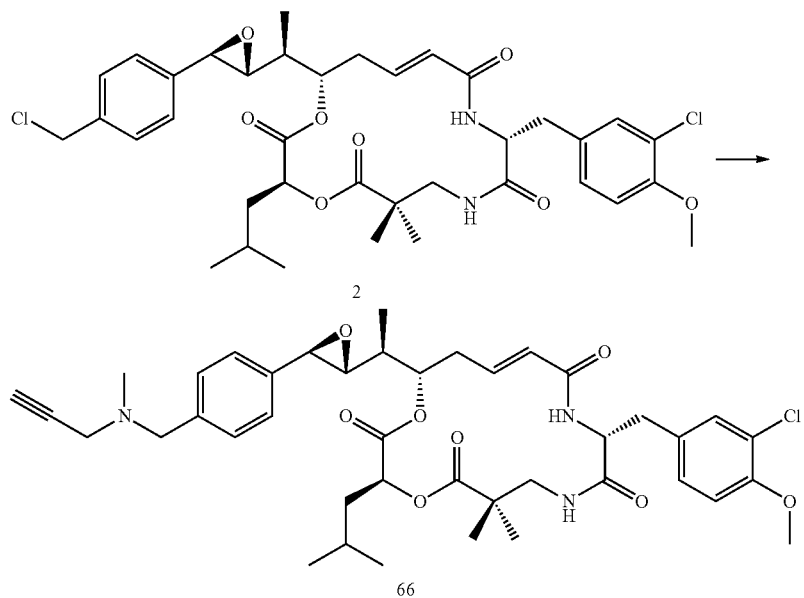

To a solution, purged with argon, of 40 mg (55.7 μmol) of compound 2 in 5 ml of anhydrous acetonitrile are successively added 48.5 μl (279 μmol) of DIPEA and 13.9 μl (167 μmol) of N-methylpropargylamine. The mixture is heated at 40° C. for 15 hours. Some starting compound 2 remains: a further 48.5 μl (279 μmol) of DIPEA and 13.9 μl (167 μmol) of N-methylpropargylamine are added. After stirring for 24 hours at 40° C., the mixture is diluted with 5 ml of EtOAc and then washed with 5 ml of water. The aqueous phase is extracted with 3×5 ml of EtOAc and the organic phases are combined, washed with saturated NaHCO$_3$ solution (10 ml) and with saturated NaCl solution (10 ml) and dried over MgSO$_4$. After filtering and concentrating under reduced pressure, the crude product is purified by chromatography on silica gel, using a 98/2 to 90/10 DCM/methanol mixture as eluent. Compound 66 is obtained in the form of a white solid (45 mg, quant.). $^1$H NMR (400 MHz, DMSO-d$_6$): 0.78 (m, 6H); 1.00 (s, 3H); 1.05 (d, J=6.8 Hz, 3H); 1.12 (s, 3H); 1.30 (m, 1H); 1.49 to 1.61 (m, 2H); 1.81 (m, 1H); 2.20 (s, 3H); 2.28 (m, 1H); 2.63 to 2.76 (m, 2H); 2.92 to 3.07 (m, 3H); 3.17 (t, J=2.4 Hz, 1H); 3.27 (d, J=2.4 Hz, 2H); 3.33 (partially masked m, 1H); 3.50 (s, 2H); 3.81 (s, 3H); 3.88 (d, J=1.7 Hz, 1H); 4.25 (ddd, J=3.4 and 7.8 and 11.4 Hz, 1H); 4.92 (dd, J=3.5 and 9.7 Hz, 1H); 5.11 (ddd, J=1.5 and 5.5 and 11.2 Hz, 1H); 5.80 (dd, J=1.5 and 15.0 Hz, 1H); 6.47 (ddd, J=3.9 and 11.2 and 15.0 Hz, 1H); 7.05 (d, J=8.6 Hz, 1H); 7.17 (dd, J=2.1 and 8.6 Hz, 1H); 7.22 (dd, J=2.1 and 9.4 Hz, 1H); 7.25 to 7.33 (m, 5H); 8.33 (d, J=7.8 Hz, 1H). LCMS (A2): ES m/z=750 [M+H]$^+$;

ES m/z=375.5 [M+2H]$^{2+}$ base peak; ES m/z=748 [M−H]$^-$; m/z=794 [M−H+HCO$_2$H]$^-$; $t_R$=0.91 min.

Compound 67

Ethyl 4-azidobutyrate

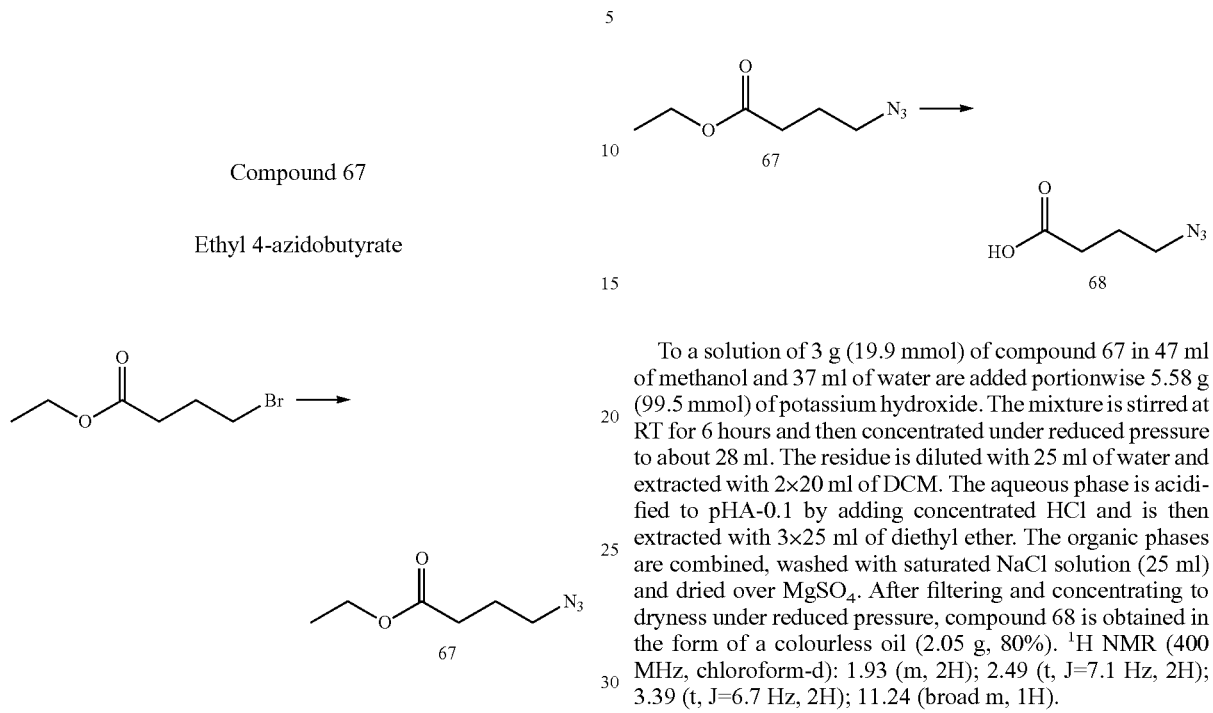

Compound 68

4-Azidobutanoic Acid 2.86 ml (20 mmol) of ethyl 4-bromobutanoate and 2.6 g (40 mmol) of NaN$_3$ are dissolved in 30 ml of a 2/1 acetone/water mixture. The mixture is refluxed for 7 hours. After cooling to RT and concentrating under reduced pressure, the residue is taken up in 50 ml of water. The aqueous phase is extracted with 3×30 ml of DCM. The organic phases are combined, dried over MgSO$_4$, filtered and concentrated under reduced pressure to give compound 67 in the form of a colourless oil (3 g, 95%). $^1$H NMR (400 MHz, chloroform-d): 1.27 (t, J=7.2 Hz, 3H); 1.92 (m, 2H); 2.41 (t, J=7.2 Hz, 2H); 3.36 (t, J=6.7 Hz, 2H); 4.15 (q, J=7.2 Hz, 2H).

To a solution of 3 g (19.9 mmol) of compound 67 in 47 ml of methanol and 37 ml of water are added portionwise 5.58 g (99.5 mmol) of potassium hydroxide. The mixture is stirred at RT for 6 hours and then concentrated under reduced pressure to about 28 ml. The residue is diluted with 25 ml of water and extracted with 2×20 ml of DCM. The aqueous phase is acidified to pHA-0.1 by adding concentrated HCl and is then extracted with 3×25 ml of diethyl ether. The organic phases are combined, washed with saturated NaCl solution (25 ml) and dried over MgSO$_4$. After filtering and concentrating to dryness under reduced pressure, compound 68 is obtained in the form of a colourless oil (2.05 g, 80%). $^1$H NMR (400 MHz, chloroform-d): 1.93 (m, 2H); 2.49 (t, J=7.1 Hz, 2H); 3.39 (t, J=6.7 Hz, 2H); 11.24 (broad m, 1H).

Compound 69

(4-{1-[(4-{(2R,3R)-3-[(S)-1-((E)-(3S,10R,16S)-10-{3-Chloro-4-methoxybenzyl}-3-isobutyl-6,6-dimethyl-2,5,9,12-tetraoxo-1,4-dioxa-8,11-diazacyclohexadec-13-en-16-yl)ethyl]-oxiranyl}benzyl) methylamino]methyl}-1,2,3-triazol-1-yl)butanoic acid

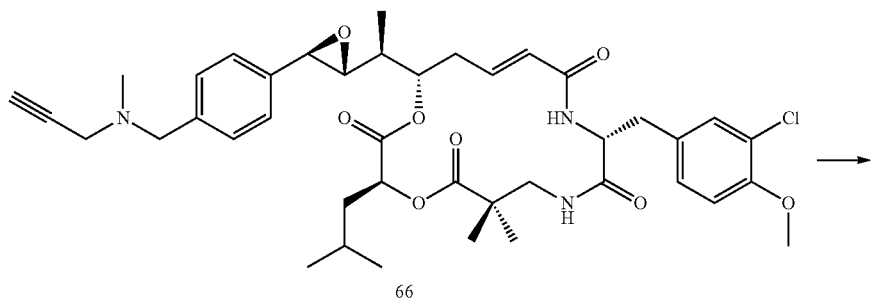

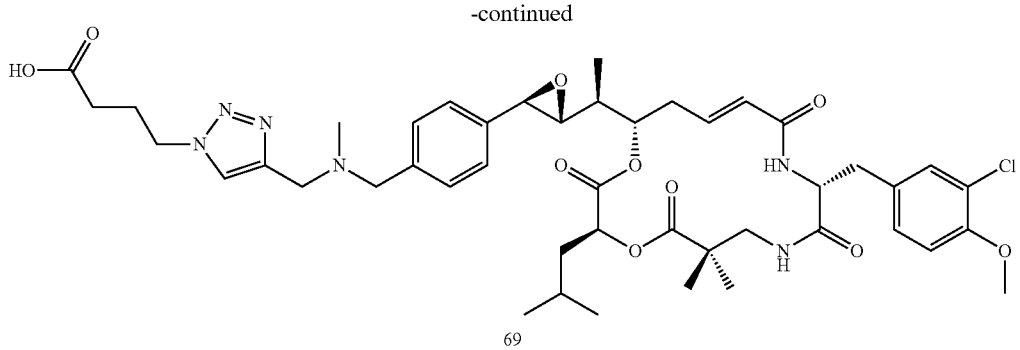

69

To a solution of 24 mg (32 µmol) of compound 66 in 545 µl of THF are successively added 8.3 mg (13 µmol) of compound 68, 545 µl of water, 128 µl of an aqueous 0.1M solution of copper sulfate and 128 µl of aqueous 0.2M sodium ascorbate solution. The mixture is stirred for 45 minutes at RT and then diluted with 2 ml of water. The aqueous phase is extracted with 3×2 ml of EtOAc. The organic phases are combined, washed with saturated NaCl solution (2 ml) and filtered through MgSO$_4$. After filtering and concentrating under reduced pressure, the crude product is purified by chromatography on diol-grafted silica gel, using a 98/2 to 90/10 DCM/methanol mixture as eluent. Compound 69 is obtained in the form of a white solid (22.6 mg, 80%). $^1$H NMR (500 MHz, DMSO-d$_6$): 0.76 (d, J=6.6 Hz, 3H); 0.78 (d, J=6.6 Hz, 3H); 1.00 (s, 3H); 1.05 (d, J=6.9 Hz, 3H); 1.11 (s, 3H); 1.30 (m, 1H); 1.50 to 1.62 (m, 2H); 1.81 (m, 1H); 2.03 (m, 2H); 2.10 (s, 3H); 2.20 (t, J=7.0 Hz, 2H); 2.30 (m, 1H); 2.64 to 2.74 (m, 2H); 2.94 to 3.03 (m, 3H); 3.35 (partially masked m, 1H); 3.48 (s, 2H); 3.61 (s, 2H); 3.81 (s, 3H); 3.87 (d, J=1.6 Hz, 1H); 4.25 (ddd, J=3.7 and 7.7 and 11.5 Hz, 1H); 4.37 (t, J=7.0 Hz, 2H); 4.91 (dd, J=3.6 and 9.6 Hz, 1H); 5.11 (ddd, J=1.5 and 5.5 and 11.3 Hz, 1H); 5.80 (dd, J=1.5 and 15.1 Hz, 1H); 6.47 (ddd, J=3.7 and 11.3 and 15.1 Hz, 1H); 7.05 (d, J=8.5 Hz, 1H); 7.17 (dd, J=2.2 and 8.5 Hz, 1H); 7.23 (dd, J=2.5 and 9.8 Hz, 1H); 7.26 (d, J=8.5 Hz, 2H); 7.28 (d, J=2.2 Hz, 1H); 7.34 (d, J=8.5 Hz, 2H); 8.02 (s, 1H); 8.39 (broad d, J=7.7 Hz, 1H); 12.14 (broad m, 1H). LCMS (A2): ES m/z=879 [M+H]$^+$; m/z=877 [M−H]$^−$; t$_R$=0.86 min.

Compound 70

Methyl (4-{1-[(4-{(2R,3R)-3-[(S)-1-((E)-(3S,10R,16S)-10-{3-chloro-4-methoxy-benzyl}-3-isobutyl-6,6-dimethyl-2,5,9,12-tetraoxo-1,4-dioxa-8,11-diaza-cyclohexadec-13-en-16-yl)ethyl]oxiranyl}benzyl) methylamino]methyl}-1,2,3-triazol-1-yl)butanoate

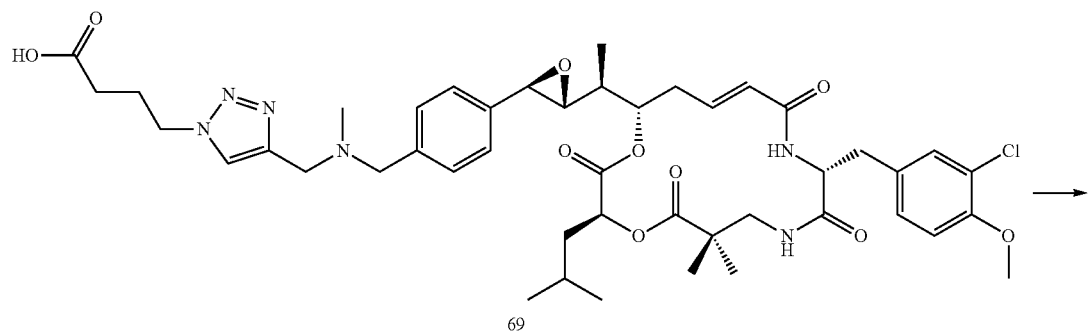

69

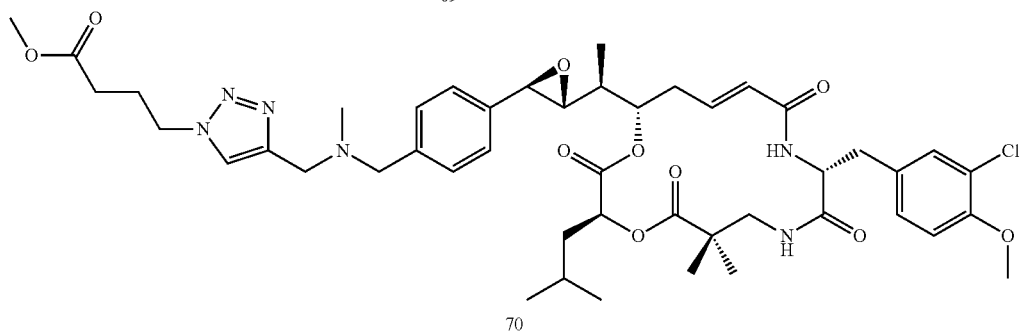

70

To a solution, purged with argon, of 5.5 mg (6.2 µmol) of compound 69 in 0.5 ml of DCM and 0.2 ml of methanol are added 4.7 µl (9.3 µmol) of trimethylsilyldiazomethane. The mixture is stirred for 45 minutes at RT and then concentrated to dryness. The crude product is purified by chromatography on silica gel, using a 98/2 to 95/5 DCM/methanol mixture as eluent. Compound 70 is obtained in the form of a white solid (3.4 mg, 62%). $^1$H NMR (500 MHz, DMSO-$d_6$): 0.75 (d, J=6.6 Hz, 3H); 0.77 (d, J=6.6 Hz, 3H); 1.00 (s, 3H); 1.05 (d, J=6.9 Hz, 3H); 1.11 (s, 3H); 1.28 (m, 1H); 1.49 to 1.61 (m, 2H); 1.80 (m, 1H); 2.07 (m, 2H); 2.10 (m, 3H); 2.26 (m, 1H); 2.31 (t, J=7.0 Hz, 2H); 2.62 to 2.74 (m, 2H); 2.93 to 3.04 (m, 3H); 3.27 to 3.37 (partially masked m, 1H); 3.48 (s, 2H); 3.58 (s, 3H); 3.61 (s, 2H); 3.81 (s, 3H); 3.87 (d, J=2.0 Hz, 1H); 4.25 (ddd, J=3.7 and 8.2 and 11.6 Hz, 1H); 4.38 (t, J=7.0 Hz, 2H); 4.91 (dd, J=3.9 and 9.8 Hz, 1H); 5.11 (ddd, J=1.5 and 5.3 and 11.2 Hz, 1H); 5.79 (dd, J=1.5 and 15.2 Hz, 1H); 6.47 (ddd, J=3.9 and 11.2 and 15.2 Hz, 1H); 7.05 (d, J=8.6 Hz, 1H); 7.16 (dd, J=2.2 and 8.6 Hz, 1H); 7.22 (dd, J=2.4 and 9.8 Hz, 1H); 7.26 (d, J=8.6 Hz, 2H); 7.28 (d, J=2.2 Hz, 1H); 7.33 (d, J=8.6 Hz, 2H); 8.03 (s, 1H); 8.34 (d, J=8.2 Hz, 1H). LCMS (A2): ES m/z=893 [M+H]$^+$; m/z=447 [M+2H]$^{2+}$ base peak; m/z=891 [M−H]$^−$; m/z=937 [M−H+HCO$_2$H]$^−$ base peak; $t_R$=0.90 min.

Example 21

2,5-Dioxopyrrolidin-1-yl (4-{1-[(4-{(2R,3R)-3-[(S)-1-((E)-(3S,10R,16S)-10-{3-chloro-4-methoxybenzyl}-3-isobutyl-6,6-dimethyl-2,5,9,12-tetraoxo-1,4-dioxa-8,11-diazacyclohexadec-13-en-16-yl)ethyl]oxiranyl}benzyl)methylamino]methyl}-1,2,3-triazol-1-yl)butanoate

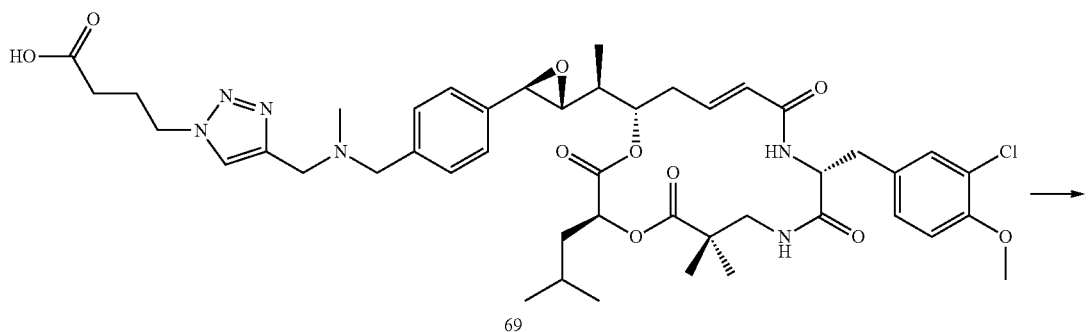
69

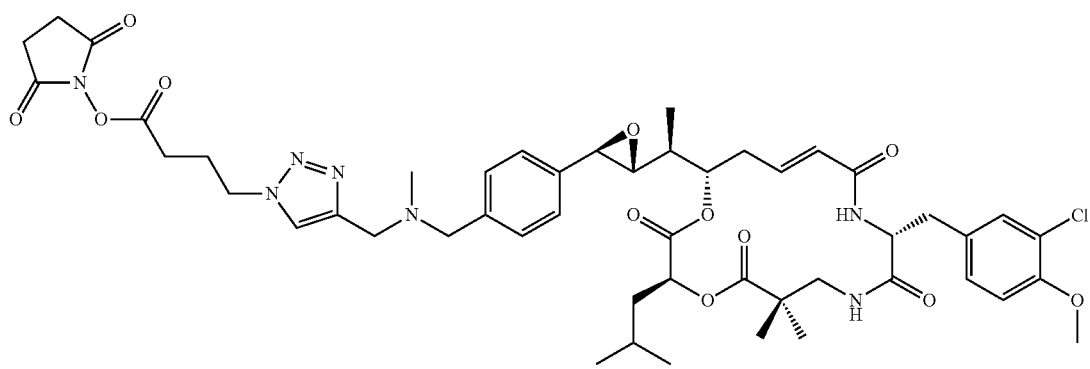
Ex21

Example 21 may be obtained by activating the acid 69 according to the method described for Example 19.

Example 22

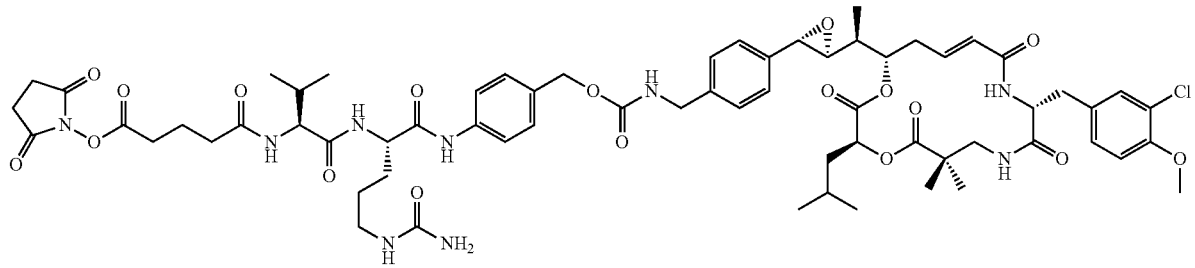

Compound 71

(E)-(3S,10R,16S)-16-{(S)-1-[(2S,3S)-3-(4-Azidomethylphenyl)oxiranyl]ethyl}-10-(3-chloro-4-methoxybenzyl)-3-isobutyl-6,6-dimethyl-1,4-dioxa-8,11-diazacyclohexadec-13-ene-2,5,9,12-tetraone

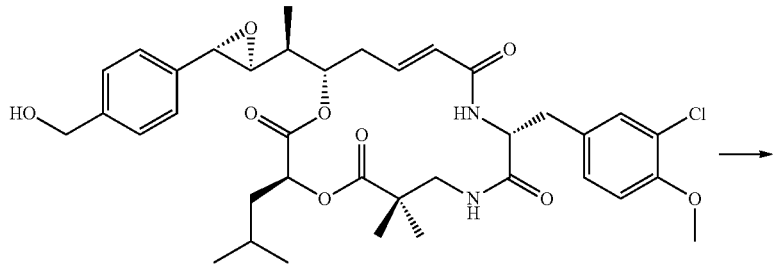

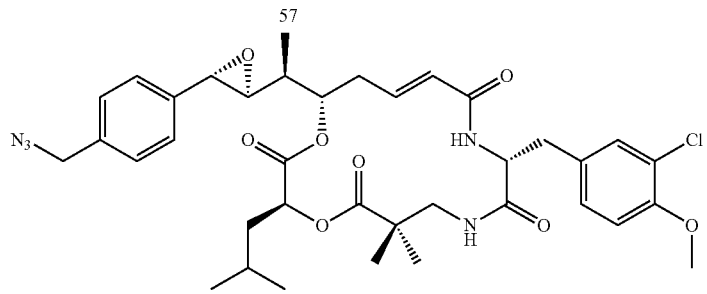

The alcohol 57 (36 mg; 51.48 μmol, prepared according to Al-awar R. S., et al., *J. Med. Chem.* 2003, 46, 2985-3007) is dissolved in anhydrous THF (2 ml). The solution is purged with argon and cooled in a bath of ice-cold water, followed by addition of DPPA (74 μmol) and then DBU (80 μmol). The mixture is allowed to warm to RT and stirring is continued overnight. The next day, the solution is again cooled in a bath of ice-cold water, followed by addition of a further 74 μmol of DPPA and 80 μmol of DBU. After reaction for 2 hours at 0° C. and 2 hours at RT, the mixture is hydrolyzed with 5 ml of water and then extracted 3 times with DCM. The combined organic phases are dried over $Na_2SO_4$, filtered and evaporated under reduced pressure. The crude product is then purified by chromatography on silica gel, eluting with a 100/0 to 95/5 DCM/methanol mixture. Compound 57 is obtained in the form of a colourless solid (24 mg; 64%). $^1$H NMR (500 MHz, DMSO-$d_6$) δ (ppm): 0.84 (d, J=6.3 Hz, 3H); 0.86 (d, J=6.3 Hz, 3H); 0.98 (d, J=7.1 Hz, 3H); 1.03 (s, 3H); 1.15 (s, 3H); 1.48 to 1.67 (m, 3H); 1.88 (m, 1H); 2.45 (m, 1H); 2.63 (m, 1H); 2.71 (dd, J=11.5 and 14.0 Hz, 1H); 2.97 to 3.08 (m, 3H); 3.36 (partially masked m, 1H); 3.82 (broad s, 4H); 4.28 (ddd, J=3.6 and 8.0 and 11.5 Hz, 1H); 4.44 (s, 2H); 4.99 (dd, J=3.7 and 9.5 Hz, 1H); 5.12 (ddd, J=1.4 and 5.7 and 11.4 Hz, 1H); 5.88 (dd, J=1.4 and 15.2 Hz, 1H); 6.49 (ddd, J=3.8 and 11.4 and 15.2 Hz, 1H); 7.05 (d, J=8.5 Hz, 1H); 7.18 (dd, J=2.2 and 8.5 Hz, 1H); 7.26 to 7.32 (m, 4H); 7.36 (d, J=8.5 Hz, 2H); 8.40 (d, J=8.0 Hz, 1H). LCMS (A2): ES m/z=722 [M−H]$^-$; m/z=724 [M+H]$^+$; m/z=768 [M+HCO$_2$H−H]$^-$; $t_R$=1.19 min.

Compound 72

(E)-(3S,10R,16S)-16-{(S)-1-[(2S,3S)-3-(4-Aminomethylphenyl)oxiranyl]ethyl}-10-(3-chloro-4-methoxybenzyl)-3-isobutyl-6,6-dimethyl-1,4-dioxa-8,11-diazacyclohexadec-13-ene-2,5,9,12-tetraone

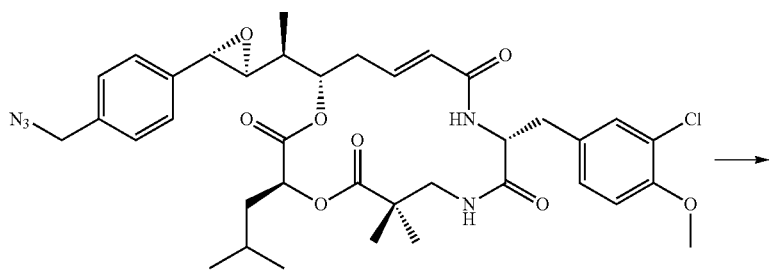

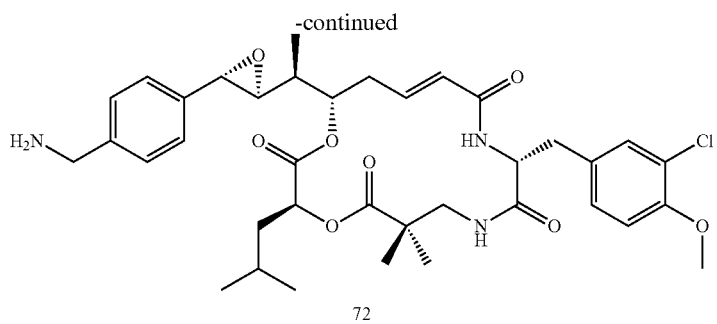

72

Compound 71 (22 mg, 30.38 μmol) is dissolved in a mixture of methanol (1 ml)/water (0.2 ml), followed by addition of TCEP (34.89 μmol). The solution obtained is stirred overnight at RT and then concentrated under reduced pressure. The residue is then taken up in saturated aqueous NaHCO$_3$ solution and extracted 3 times with DCM. The combined organic phases are dried over Na$_2$SO$_4$, filtered and concentrated under reduced pressure. The intermediate 72 is thus obtained in the form of a colourless solid (21 mg, 99%), which is used in crude form in the following step. LCMS (A5): ES m/z=696 [M−H]$^-$; m/z=698 [M+H]$^+$; m/z=742 [M+HCO$_2$H—H]$^-$; t$_R$=3.19 min.

Compound 74

FmocVal-Cit-PABAC-α-aminocryptophycin 72

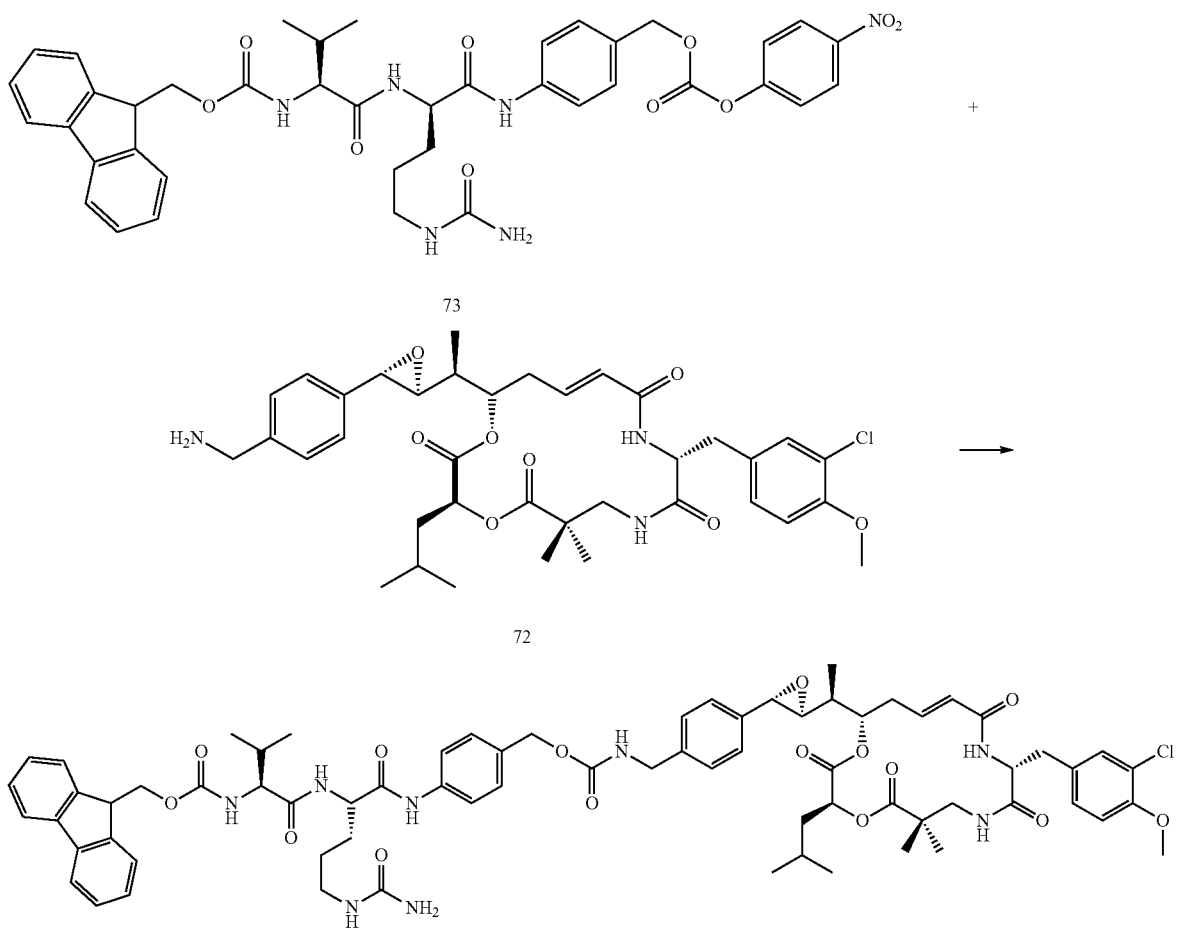

Compound 72 (21 mg, 30.08 µmol) is dissolved in a mixture of acetonitrile (2 ml)/anhydrous DMF (0.5 ml), followed by addition of a solution of compound 73 (23 mg, 30.1 µmol; prepared according to WO 2006/110 476) in acetonitrile (2 ml). The mixture is stirred for 22 hours at RT and then concentrated under reduced pressure. The residue is taken up in DCM and washed with saturated aqueous NaHCO$_3$ solution and then dried over Na$_2$SO$_4$, filtered and concentrated under reduced pressure. The crude product is then purified by chromatography on silica gel, eluting with a 100/0 to 90/10 DCM/methanol mixture. Compound 74 is obtained in the form of a white solid (22 mg), which is used in crude form in the following step. LCMS (A5): ES m/z=1325 [M+H]$^+$; m/z=1369 [M+HCO$_2$H—H]$^-$; t$_R$=4.30 min.

Compound 75

Val-Cit-PABAC-α-aminocryptophycin 72

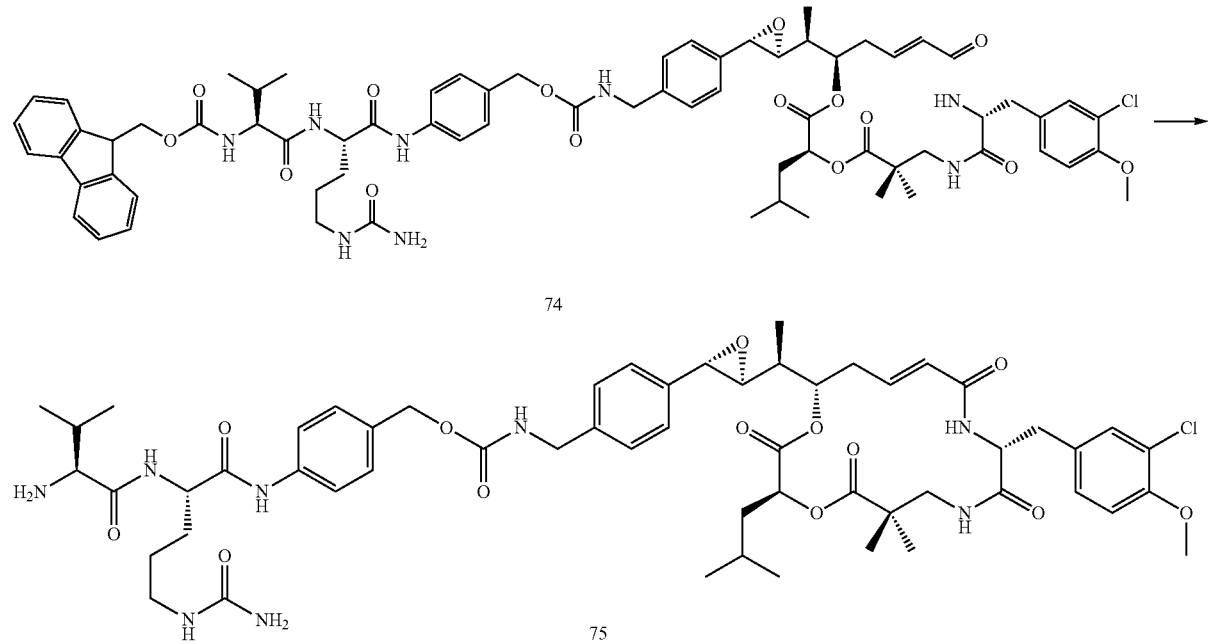

Compound 74 (22 mg, 16.59 µmol) is dissolved in DMF (3 ml), followed by addition of piperidine (150 µl, 1.51 mmol) and the mixture is stirred for 30 minutes at RT. The mixture is concentrated under reduced pressure; the residue is dissolved in a minimum amount of methanol and precipitated from ether. Compound 75 is thus obtained in the form of a white solid (15 mg, 82%). LCMS (A5): ES m/z=1103 [M+H]$^+$; m/z=1101 [M−H]$^-$; m/z=1148 [M+HCO$_2$H—H]$^-$; t$_R$=3.38 min.

Compound 76

Glutaric acid-Val-Cit-PABAC-α-aminocryptophycin 72

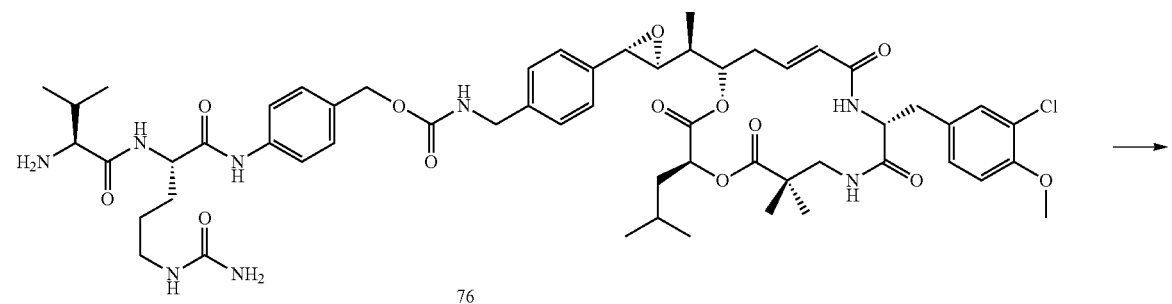

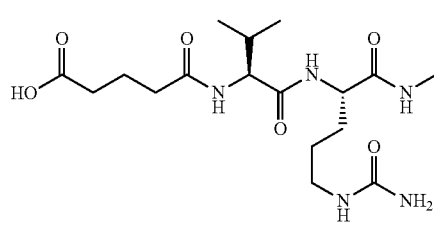 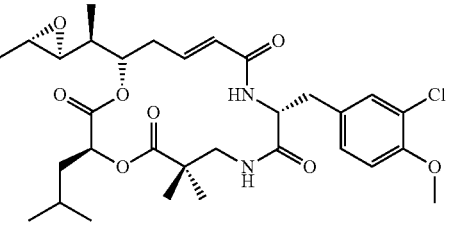

76

A solution of glutaric anhydride (8 mg, 70 μmol) in anhydrous DMF (200 μl) is added to compound 75 (15 mg, 13.59 μmol) conditioned under argon. The solution obtained is stirred overnight at RT, followed by addition of saturated aqueous NH₄Cl solution and extraction 3 times with DCM. The combined organic phases are dried over Na₂SO₄, filtered and concentrated under reduced pressure. The residue obtained is taken up in DCM and precipitated with ether. After filtering through a sinter funnel and washing with ether, compound 76 is obtained in the form of a beige-coloured solid (8 mg, 48%). ¹H NMR (500 MHz, DMSO-d₆) δ (ppm): 0.80 to 0.92 (m, 12H); 0.96 (d, J=7.1 Hz, 3H); 1.02 (s, 3H); 1.15 (s, 3H); 1.30 to 1.72 (m, 9H); 1.86 (m, 1H); 2.00 (m, 1H); 2.11 to 2.26 (m, 4H); 2.42 (m, 1H); 2.60 to 2.74 (m, 2H); 2.91 to 3.11 (m, 5H); 3.38 (partially masked m, 1H); 3.76 (d, J=1.8 Hz, 1H); 3.81 (s, 3H); 4.17 (m, 3H); 4.27 (m, 1H); 4.37 (m, 1H); 4.90 to 5.04 (m, 3H); 5.11 (m, 1H); 5.50 (broad m, 2H); 5.88 (broad d, J=15.2 Hz, 1H); 6.20 (broad m, 1H); 6.48 (m, 1H); 7.06 (d, J=8.3 Hz, 1H); 7.11 to 7.32 (m, 9H); 7.60 (m, 2H); 7.75 (m, 1H); 7.89 (m, 1H); 8.28 (broad m, 1H); 8.41 (d, J=7.8 Hz, 1H); 9.92 (broad s, 1H); 12.06 (broad m, 1H). LCMS (A2): ES m/z=1217 [M+H]⁺; m/z=1215 [M−H]⁻; $t_R$=1.05 min.

Example 22

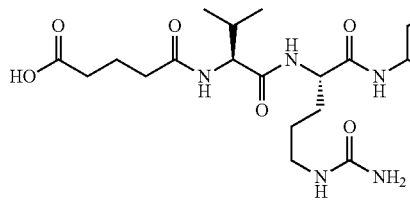 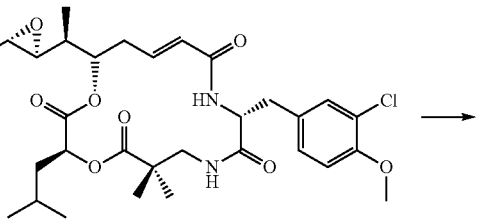

76

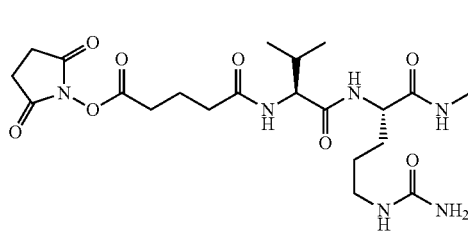

Ex 22

Compound 76 (6 mg, 4.93 μmol) is dissolved in a mixture of DCM (0.5 ml) and DMF (0.1 ml), followed by successive addition of N,N'-disuccinimidyl carbonate (6 mg, 23.42 μmol) and DIPEA (4 μl, 22.96 μmol). After reaction for 3 hours at RT, saturated aqueous NH₄Cl solution is added and the mixture is extracted 3 times with DCM. The combined organic phases are dried over Na₂SO₄, filtered and concentrated under reduced pressure. The crude product is purified by chromatography on silica gel, eluting with a 100/0 to 90/10 DCM/methanol mixture. Compound Ex. 22 is obtained in the form of a white solid (4 mg; 61%). ¹H NMR (500 MHz, DMSO-d$_6$) δ (ppm): 0.80 to 0.90 (m, 12H); 0.96 (d, J=7.3 Hz, 3H); 1.03 (s, 3H); 1.15 (s, 3H); 1.32 to 1.76 (m, 7H); 1.80 to 1.89 (m, 3H); 1.97 (m, 1H); 2.29 (m, 2H); 2.44 (m, 1H); 2.60 to 2.75 (m, 4H); 2.81 (s, 4H); 2.89 to 3.08 (m, 5H); 3.41 (partially masked m, 1H); 3.77 (d, J=2.0 Hz, 1H); 3.81 (s, 3H); 4.14 to 4.24 (m, 3H); 4.27 (ddd, J=3.9 and 8.3 and 11.5 Hz, 1H); 4.38 (m, 1H); 4.93 to 5.03 (m, 3H); 5.11 (m, 1H); 5.39 (broad s, 2H); 5.88 (broad d, J=15.2 Hz, 1H); 5.96 (t, J=5.9 Hz, 1H); 6.48 (ddd, J=3.7 and 11.1 and 15.2 Hz, 1H); 7.05 (d, J=8.3 Hz, 1H); 7.16 to 7.36 (m, 9H); 7.59 (d, J=7.8 Hz, 2H); 7.76 (t, J=6.1 Hz, 1H); 7.88 (d, J=8.8 Hz, 1H); 8.10 (d, J=7.3 Hz, 1H); 8.41 (d, J=8.3 Hz, 1H); 9.97 (broad s, 1H). LCMS (A2): ES m/z=1314 [M+H]$^+$; m/z=1358 [M+HCO$_2$H—H]$^-$; t$_R$=1.06 min.

Example 23

Compound 60 (23 mg, 31.76 μmol) is dissolved in a mixture of methanol (1 ml) and water (0.2 ml), folio wed by addition of TCEP (34.90 μmol) and DCM (an amount sufficient to dissolve it). The solution obtained is stirred overnight at RT and is then concentrated under reduced pressure. The residue is then taken up in saturated aqueous NaHCO$_3$ solution and extracted 3 times with DCM. The combined organic phases are dried over Na$_2$SO$_4$, filtered and concentrated under reduced pressure. The crude product is finally purified by chromatography on silica gel, eluting with a 100/0 to 90/10 DCM/methanol mixture. Compound 77 is thus obtained in the form of a white solid (12 mg, 59%). $^1$H NMR (500 MHz, DMSO-d$_6$) δ (ppm): 0.78 (d, J=6.4 Hz, 6H); 1.00 (s, 3H); 1.05 (d, J=6.9 Hz, 3H); 1.12 (s, 3H); 1.30 (m, 1H); 1.47 to 1.62 (m, 2H); 1.79 (m, 1H); 2.22 to 2.32 (m, 3H); 2.63 to 2.73 (m, 2H); 2.92 to 3.05 (m, 3H); 3.35 (partially masked m, 1H); 3.71 (s,

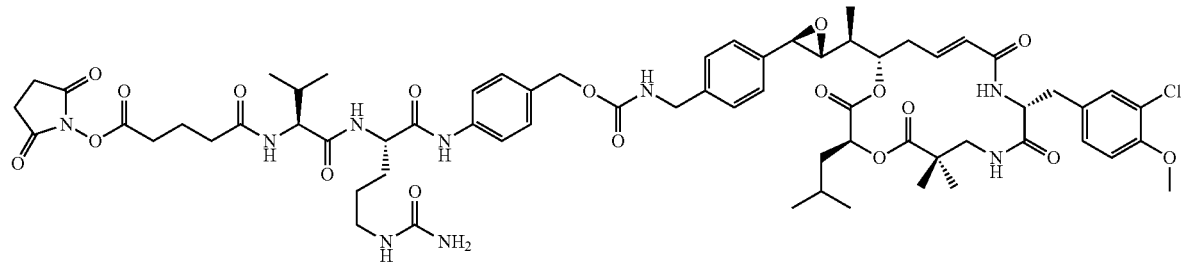

Compound 77

(E)-(3S,10R,16S)-16-{(S)-1-[(2R,3R)-3-(4-Aminomethylphenyl)oxiranyl]ethyl}-10-(3-chloro-4-methoxybenzyl)-3-isobutyl-6,6-dimethyl-1,4-dioxa-8,11-diazacyclohexadec-13-ene-2,5,9,12-tetraone 2H); 3.81 (s, 3H); 3.86 (d, J=1.6 Hz, 1H); 4.25 (ddd, J=3.6 and 8.0 and 11.3 Hz, 1H); 4.90 (dd, J=3.6 and 9.6 Hz, 1H); 5.11 (ddd, J=1.5 and 5.2 and 11.3 Hz, 1H); 5.79 (dd, J=1.5 and 15.0 Hz, 1H); 6.47 (ddd, J=3.6 and 11.3 and 15.0 Hz, 1H); 7.05 (d, J=8.5 Hz, 1H); 7.17 (dd, J=1.9 and 8.5 Hz, 1H); 7.19 to 7.26 (m, 3H); 7.28 (d, J=1.9 Hz, 1H); 7.34 (d, J=8.0 Hz, 2H); 8.34

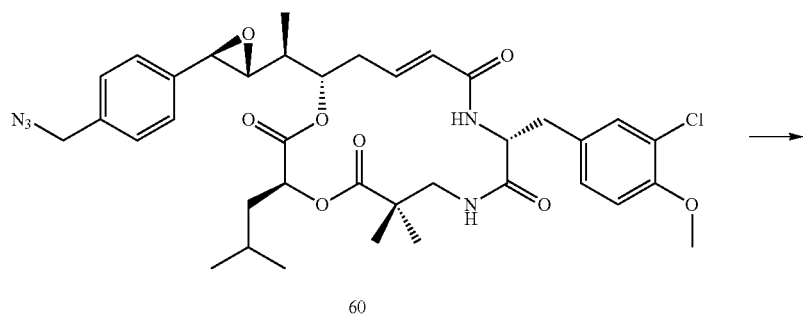

60

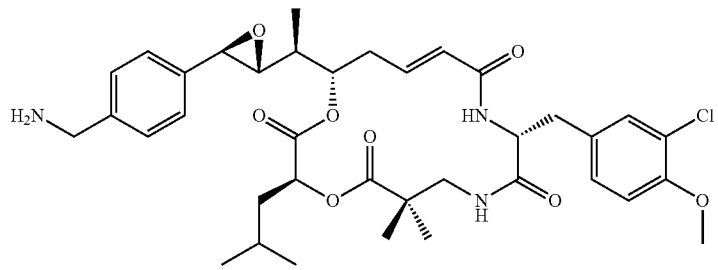

77

(d, J=8.0 Hz, 1H). LCMS (A2): ES m/z=698 [M+H]⁺; m/z=696 [M−H]⁻; m/z=742 [M+HCO₂H—H]⁻; $t_R$=0.87 min.

Compound 78

FmocVal-Cit-PABAC-α-aminocryptophycin 77

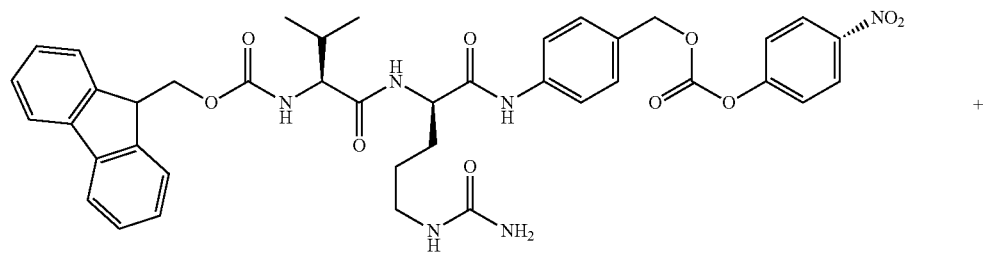

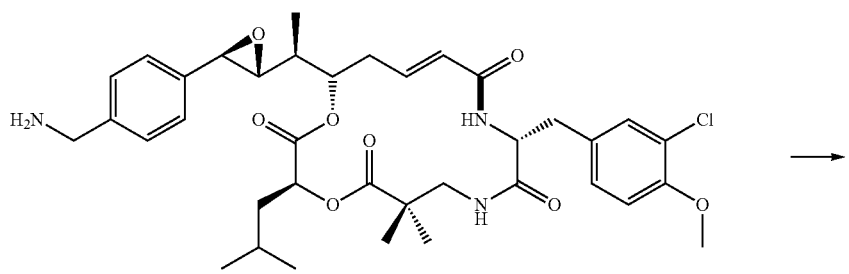

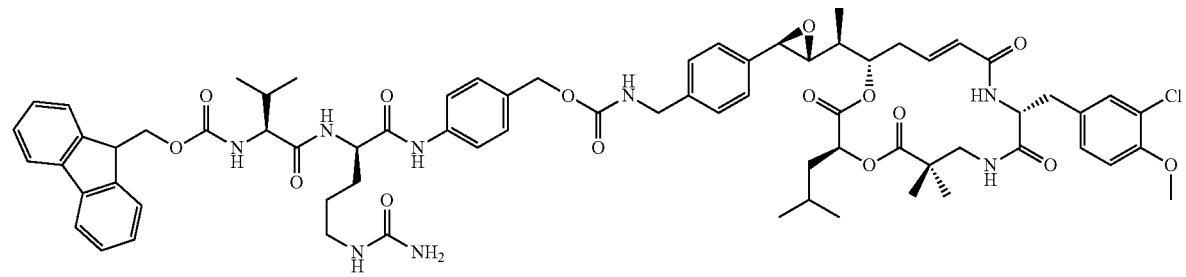

Compound 77 (10 mg, 14.32 µmol) is dissolved in anhydrous DMF (0.1 ml), followed by addition of a solution of the intermediate 73 (11 mg, 14.35 µmol; prepared according to WO 2006/110 476) in a mixture of acetonitrile (1 ml) and DMF (0.1 ml). The mixture is stirred for 3 hours at RT and then concentrated under reduced pressure. The residue is then purified by chromatography on silica gel, eluting with a 100/0 to 90/10 DCM/methanol mixture. Compound 78 is obtained in the form of a white solid (18 mg, 95%). LCMS (A5): ES m/z=1325 [M+H]⁺; m/z=1369 [M+HCO₂H—H]⁻; $t_R$=4.32 min.

Compound 79

Val-Cit-PABAC-α-aminocryptophycin 77

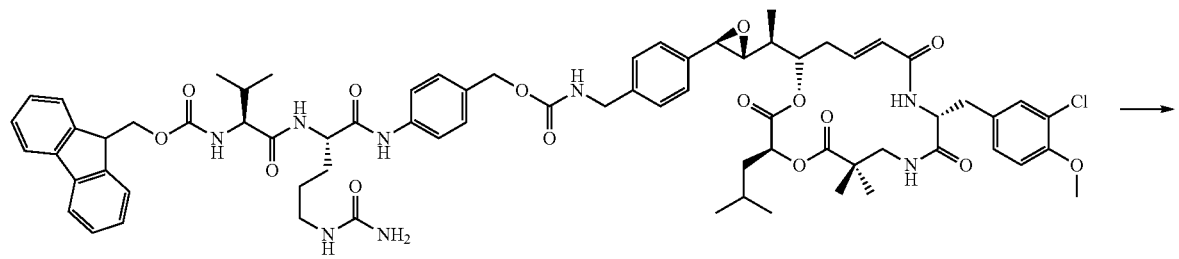

78

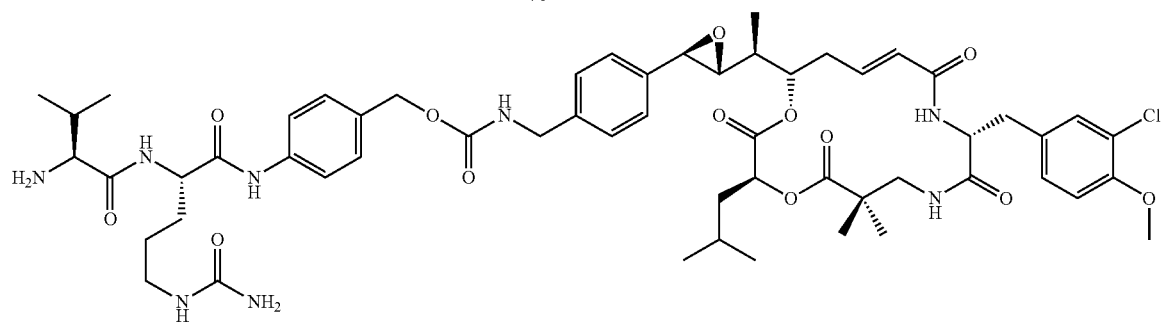

79

Compound 78 (42 mg, 31.68 μmol) is dissolved in DMF (5 ml), followed by addition of piperidine (150 μl, 1.51 mmol) and the mixture is stirred for 30 minutes at RT. The mixture is concentrated under reduced pressure and the residue is dissolved in a minimum amount of methanol and precipitated from ether. Compound 79 is thus obtained in the form of a white solid (21 mg, 60%). LCMS (A4): ES m/z=1103 [M+H]⁺; m/z=1101 [M−H]⁻; m/z=1147 [M+HCO₂H—H]⁻; $t_R$=3.67 min.

Compound 80

Glutaric acid-Val-Cit-PABAC-α-aminocryptophycin 77

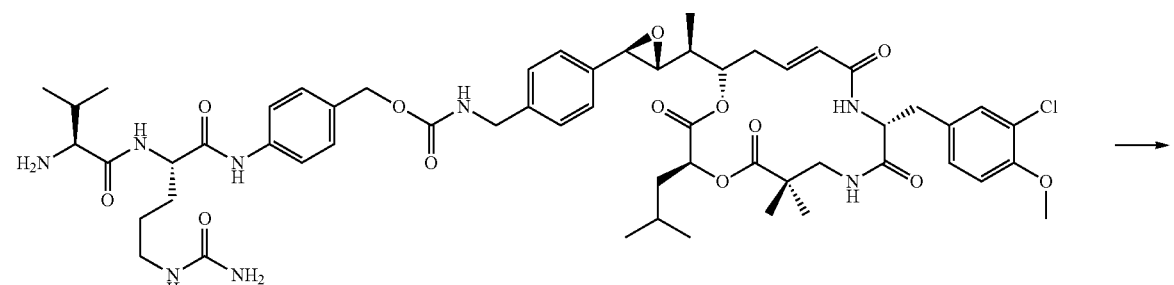

79

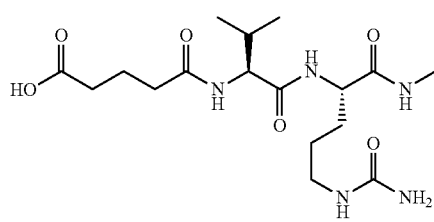
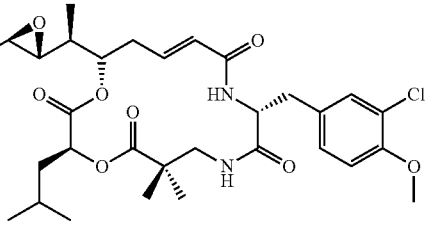

80

Compound 79 (20 mg, 18.12 µmol) is dissolved in a mixture of DMF (100 µl) and anhydrous DCM (500 µl), followed by addition of glutaric anhydride (4 mg, 35.06 µmol). The solution obtained is stirred overnight at RT and then concentrated under reduced pressure. The residue is taken up in a minimum amount of DCM and methanol, precipitated from a mixture of ether and pentane, and filtered on a sinter funnel. Compound 80 is thus obtained in the form of a white solid (23 mg, 104% crude), which is used in crude form in the following step. $^{1}$H NMR (500 MHz, DMSO-d$_{6}$): 0.78 (d, J=6.3 Hz, 6H); 0.84 (d, J=6.6 Hz, 3H); 0.86 (d, J=6.6 Hz, 3H); 1.00 (s, 3H); 1.04 (d, J=6.9 Hz, 3H); 1.12 (s, 3H); 1.22 to 1.47 (m, 3H); 1.51 to 1.64 (m, 3H); 1.72 (m, 3H); 1.80 (m, 1H); 1.99 (m, 1H); 2.20 (m, 4H); 2.28 (m, 1H); 2.59 to 2.73 (m, 2H); 2.90 to 3.07 (m, 5H); 3.32 (partially masked m, 1H); 3.81 (s, 3H); 3.87 (broad s, 1H); 4.19 (m, 3H); 4.24 (m, 1H); 4.38 (m, 1H); 4.91 (dd, J=3.3 and 9.6 Hz, 1H); 4.97 (broad s, 2H); 5.10 (dd, J=4.4 and 10.7 Hz, 1H); 5.40 (broad s, 2H); 5.79 (broad d, J=15.1 Hz, 1H); 5.99 (broad m, 1H); 6.47 (ddd, J=3.6 and 11.3 and 15.1 Hz, 1H); 7.05 (d, J=8.5 Hz, 1H); 7.17 (broad d, J=8.5 Hz, 1H); 7.20 to 7.34 (m, 8H); 7.60 (broad d, J=8.2 Hz, 2H); 7.76 (broad t, J=5.4 Hz, 1H); 7.83 (d, J=8.5 Hz, 1H); 8.09 (broad d, J=7.1 Hz, 1H); 8.34 (d, J=8.0 Hz, 1H); 9.95 (broad s, 1H); 11.98 (broad m, 1H). LCMS (A2): ES m/z=1217 [M+H]$^{+}$; m/z=1215 [M−H]$^{−}$; t$_{R}$=1.03 min.

Example 23

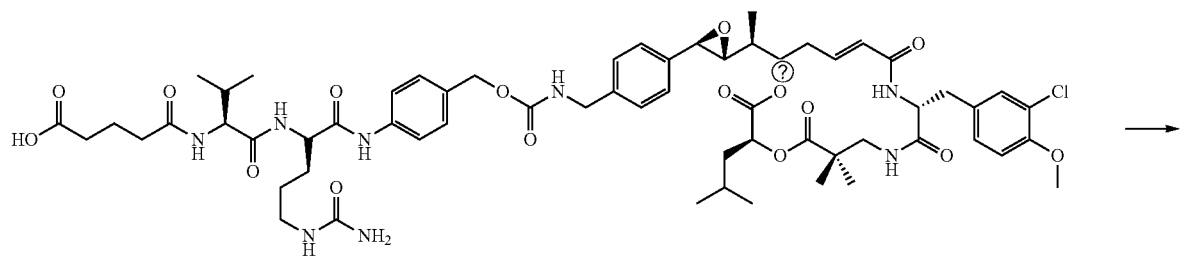

80

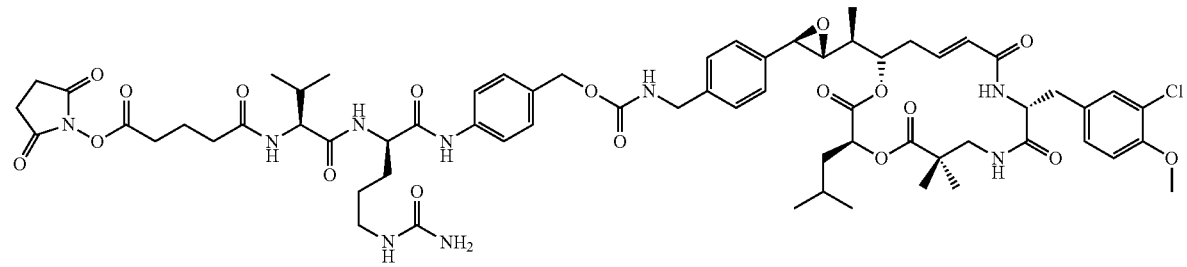

Ex 23

Example 23 may be obtained by activating the acid 80 according to the method described for Example 22.

Example 24

4-((2S,3S)-3-{(S)-1-[(E)-(3S,10R,16S)-10-(3-Chloro-4-methoxybenzyl)-3-isobutyl-6,6-dimethyl-2,5,9,12-tetraoxo-1,4-dioxa-8,11-diazacyclohexadec-13-en-16-yl]ethyl}oxiranyl)benzyl[2-methyl-2-(pyridin-2-yldisulfanyl)propyl]methylcarbamate

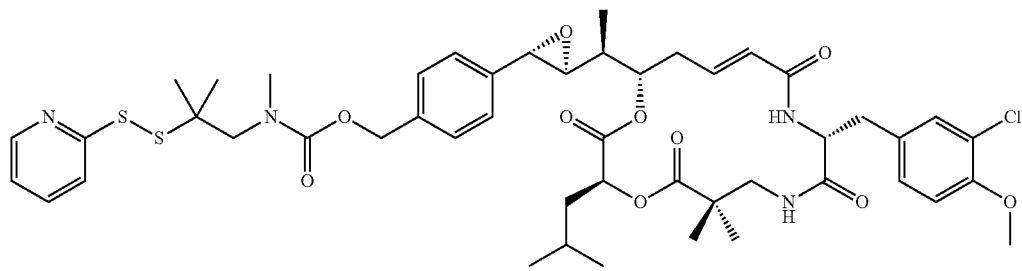

Compound 81

Methyl[2-methyl-2-(pyridin-2-yldisulfanyl)propyl]amine

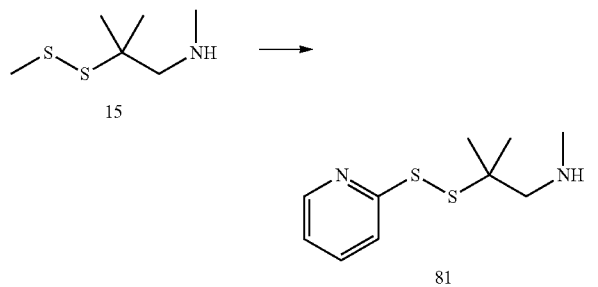

To a solution of the amine 15 (478 mg, 2.90 mmol) in MeOH (35 ml) is added TCEP (831 mg, 2.9 mmol). After reaction for 2 hours at RT, the solution obtained is added dropwise, under an argon atmosphere, to a solution of 2,2'-dipyridyl disulfide (960 mg, 4.36 mmol) in ethanol (70 ml). After reaction for a further 2 hours at RT, the mixture is concentrated under reduced pressure. The residue is taken up in DCM and washed with saturated aqueous NaHCO$_3$ solution. The organic phase is separated out and the aqueous phase is then extracted twice more with DCM. The combined organic phases are dried over Na$_2$SO$_4$, filtered and concentrated under reduced pressure. The crude product is purified by chromatography on silica gel, eluting with a 98/2 to 85/15 DCM/methanol mixture. Compound 81 is obtained in the form of a pale yellow oil (587 mg, 89%). $^1$H NMR (500 MHz, DMSO-d$_6$): 1.25 (s, 6H); 1.80 (broad m, 1H); 2.19 (s, 3H); 2.45 (s, 2H); 7.22 (ddd, J=1.5 and 5.0 and 7.0 Hz, 1H); 7.74 to 7.85 (m, 2H); 8.42 (ddd, J=1.1 and 1.5 and 5.0 Hz, 1H).

Example 24

4-((2S,3S)-3-{(S)-1-[(E)-(3S,10R,16S)-10-(3-Chloro-4-methoxybenzyl)-3-isobutyl-6,6-dimethyl-2,5,9,12-tetraoxo-1,4-dioxa-8,11-diazacyclohexadec-13-en-16-yl]ethyl}oxiranyl)-benzyl[2-methyl-2-(pyridin-2-yldisulfanyl)propyl]methylcarbamate

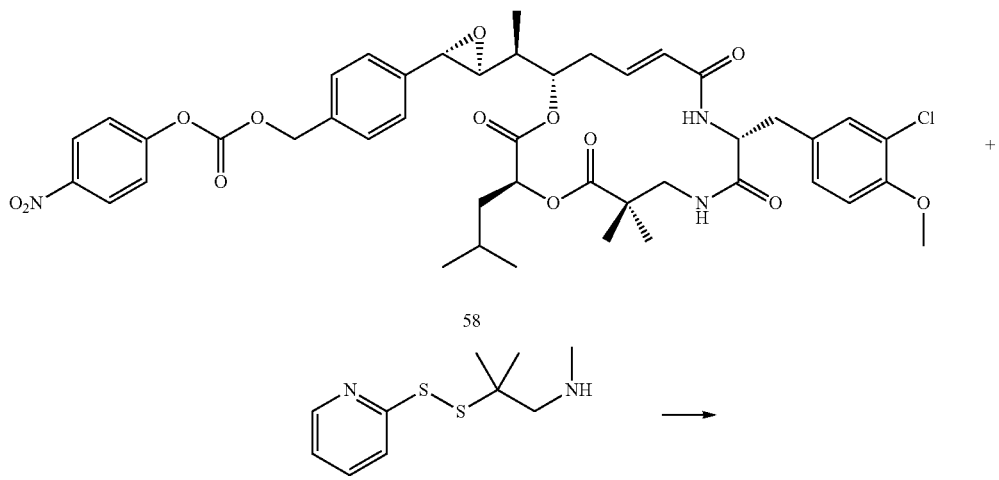

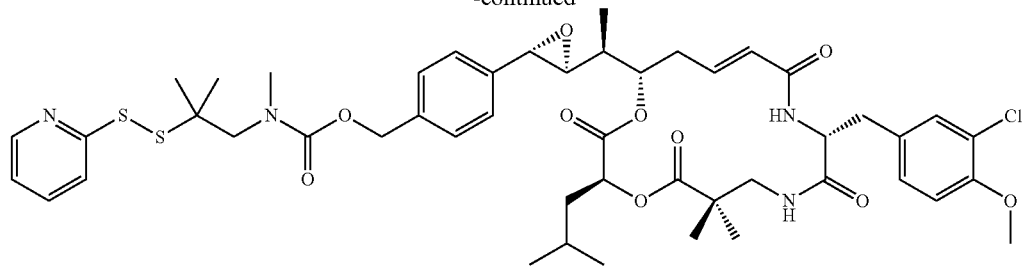

Ex 24

To a solution of the intermediate 58 (21 mg, 24.3 μmol) in anhydrous DCM are successively added the amine 81 (10 mg, 43.79 μmol) and DIPEA (8 μl, 45.43 μmol). After 24 hours at RT, saturated aqueous NaHCO$_3$ solution is added and the mixture is extracted 3 times with DCM. The combined organic phases are dried over Na$_2$SO$_4$, filtered and concentrated under reduced pressure. The crude product is purified by chromatography on silica gel, eluting with a 100/0 to 95/5 DCM/methanol mixture. Compound Ex. 24 is thus obtained in the form of a colourless solid (7 mg, 30%). $^1$H NMR (500 MHz, DMSO-d$_6$): 0.82 (d, J=6.0 Hz, 3H); 0.84 (d, J=6.0 Hz, 3H); 0.97 (d, J=6.8 Hz, 3H); 1.03 (s, 3H); 1.14 (s, 3H); 1.25 (broad s, 6H); 1.45 to 1.68 (m, 3H); 1.88 (m, 1H); 2.42 (partially masked m, 1H); 2.58 to 2.75 (m, 2H); 2.83 to 3.09 (m, 6H); 3.34 (partially masked m, 1H); 3.46 (broad s, 2H); 3.81 (broad s, 4H); 4.28 (m, 1H); 4.91 to 5.17 (m, 4H); 5.88 (broad d, J=15.2 Hz, 1H); 6.49 (m, 1H); 7.05 (d, J=8.6 Hz, 1H); 7.15 to 7.38 (m, 8H); 7.80 (broad m, 2H); 8.39 (d, J=7.8 Hz, 1H); 8.43 (broad d, J=4.6 Hz, 1H). LCMS (A2): ES m/z=953 [M+H]$^+$; m/z=477 [M+2H]$^{2+}$; m/z=997 [M+HCO$_2$H—H]$^-$; t$_R$=1.23 min.

Example 25 hu2H11-Ex17

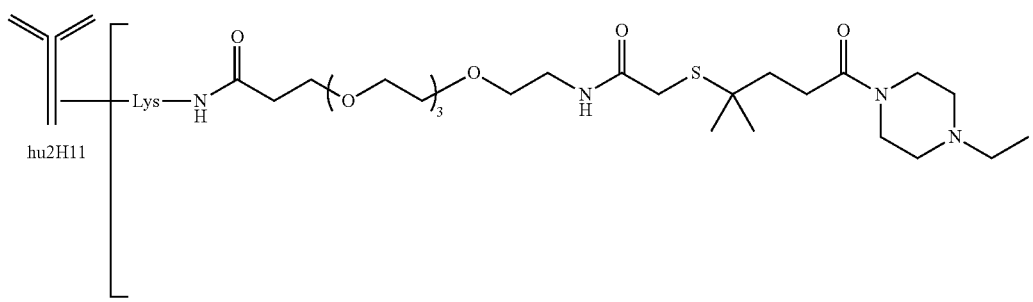

Ex 25

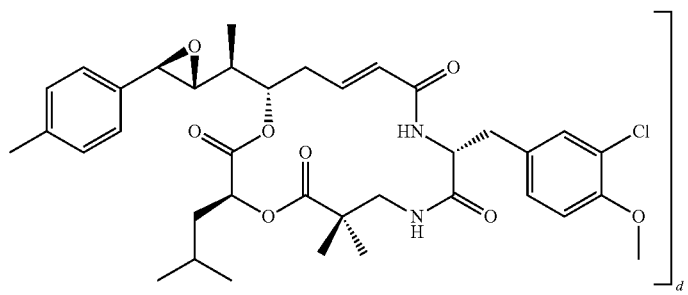

According to the general method, 8.31 mg (0.057 μmol, 1.468 ml) of naked antibody hu2H11 at a concentration of 5.66 mg/ml are treated with 5 eq. of compound Ex. 17 (0.442 mg, 0.340 μmol) dissolved in 37.3 pP of DMA, such that the final antibody concentration is 3 mg/ml in the mixture. After purifying on Superdex 200 pg and concentrating on Amicon Ultra-15 (Ultracel 50 k membrane, Millipore), 2.15 ml of conjugate are obtained at a concentration of 2.48 mg/ml with, on average, 2.2 cytotoxic units per antibody and a monomer purity of 99.7% in an aqueous pH 6.5 buffer containing 0.01 M of phosphate, 0.14 M of NaCl and 20% by volume of NMP. The final buffer change is performed in an aqueous pH 6.5 buffer containing 0.01 M of phosphate and 0.14 M of NaCl on 1 ml of conjugate. 1.5 ml of a solution of conjugate Ex. 25 at a concentration of 1.06 mg/ml with, on average, 2.8 cryptophycin derivatives (determined by UV) per antibody and a monomer purity of 99.7% are thus obtained.

Example 26 hu2H11-Ex18

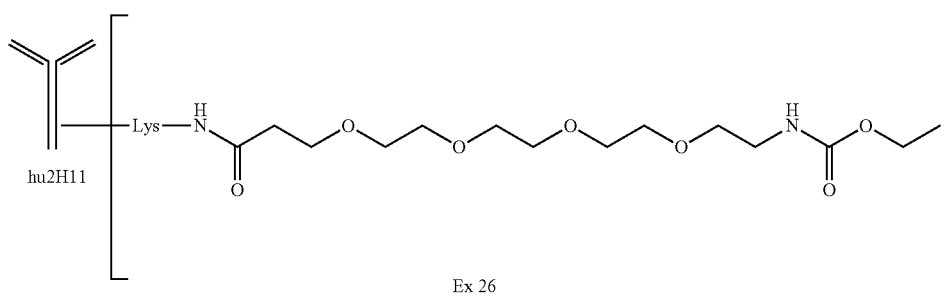

Ex 26

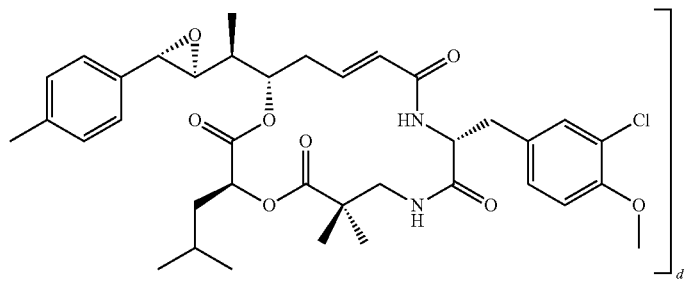

According to the general method, 7.8 mg (0.053 μmol, 1.458 ml) of naked antibody hu2H11 at a concentration of 5.35 mg/ml are treated with 6 eq. of compound Ex. 18 (0.578 mg, 0.531 μmol, purity 60%) dissolved in 272 μl of DMA, such that the final antibody concentration is 3 mg/ml in the mixture. After purifying on Superdex 200 pg and concentrating on Amicon Ultra-15 (Ultracel 50 k membrane, Millipore), 2.35 ml of conjugate are obtained at a concentration of 2.49 mg/ml with, on average, 2.5 cryptophycin derivatives per antibody and a monomer purity of 109% in an aqueous pH 6.5 buffer containing 0.01 M of phosphate, 0.14 M of NaCl and 20% by volume of NMP. The final buffer change is performed in an aqueous pH 6.5 buffer containing 0.01 M of phosphate and 0.14 M of sodium chloride on 1 ml of conjugate. 1.5 ml of a solution of conjugate Ex. 26 at a concentration of 0.84 mg/ml with, on average, 2.22 cryptophycin derivatives (determined by UV) per antibody and a monomer purity of 99.9% are thus obtained.

Example 27 hu2H11-Ex19

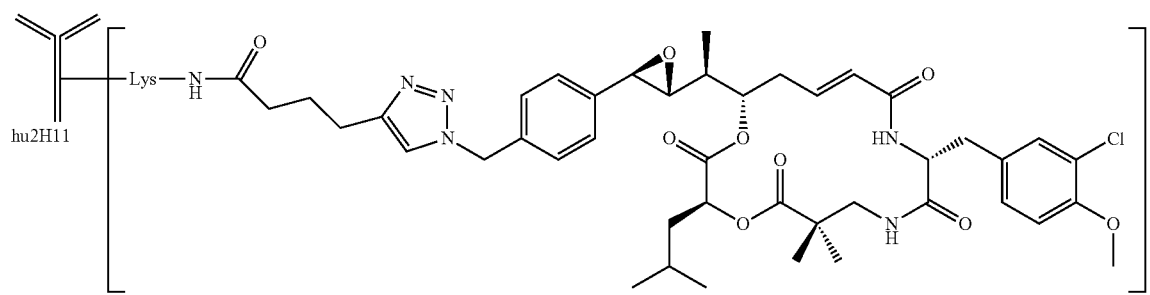

Ex27

According to the general method, 12 mg (81.7 µmol, 1.172 ml) of naked antibody hu2H11 at a concentration of 10.24 mg/ml are treated with 2×5 eq. of compound Ex. 19 (0.382 mg, 0.41 µmol) dissolved in 44.3 µl of DMA, such that the final antibody concentration is 3 mg/ml in the reaction medium. After purifying on Superdex 200 pg in the presence of 20% NMP and concentrating on Amicon Ultra-15 (Ultracel 50 k membrane, Millipore), 1.04 ml of conjugates are obtained in an aqueous pH 6.5 buffer containing 0.01 M of phosphate, 0.14 M of NaCl and 20% by volume of NMP. The final buffer change is performed in an aqueous pH 6.5 buffer containing 0.01 M of histidine, 10% of sucrose (w/v) and 5% of NMP (v/v). 1.5 ml of a solution of conjugate Ex. 27 at a concentration of 2.66 mg/ml with, on average, 1.4 cryptophycin derivatives (HRMS) per antibody and a monomer purity of 99.8% are thus obtained.

The examples given above were prepared with a particular cryptophycin derivative (often the derivative $D_1$), but may be applied to another derivative of the group $D_1$-$D_8$ or to the cryptophycin derivative of general formula (II). Similarly, the examples of conjugates in Examples 10, 11, 12, 25, 26 and 27 may be applied to antibodies other than hu2H11.

Note: in said examples, -Lys- means that the attachment takes place on the ε-amino groups of the lysines of the antibody.

Example 28

Evaluation of the inhibition of proliferation of MDA-MB-231, MDA-A1 and HCT116 cell lines by the cytotoxic agents, study performed on the compounds of formula (II) of the type $SZ_a$ with $Z_a$=SMe or of the type —C(=O)—$Z_b R_b$ with $Z_b R_b$=OMe or $OCH_2$—CH=$CH_2$ The MDA-MB-231, MDA-A1 or HCT116 cells in their exponential growth phase are trypsinized and resuspended in their respective culture medium (DMEM/F12 Gibco #21331, 10% FCS Gibco #10500-056, 2 nM glutamine Gibco #25030 for the MDA cells; DMEM Gibco #11960, 10% FCS Gibco #10500-056, 2 mM glutamine Gibco #25030 for the HCT116 cells). The cell suspension is seeded in Cytostar 96-well culture plates (GE Healthcare Europe, #RPNQ0163) in the whole culture medium containing serum at a density of 5000 cells/well (MDA-MB-231, MDA-A1, HCT116). After incubation for 4 hours, successive dilutions of the cryptophycin derivatives are added to the wells at concentrations decreasing from $10^{-7}$ to $10^{-12}$ M (in triplicate for each concentration). The cells are cultured for 3 days at 37° C. under an atmosphere containing 5% $CO_2$ in the presence of the cytotoxic agents. On the 4$^{th}$ day, 10 µl of a $^{14}$C-thymidine solution (0.1 µCi/well, Perkin Elmer #NEC56825000) are added to each well. The incorporation of $^{14}$C-thymidine is measured 96 hours after the start of the experiment using a microbeta radioactivity counter (Perkin Elmer). The data are expressed in the form of a percentage of survival by determining the ratio between the reduced count obtained with the cells treated with cytotoxic agent and the count obtained with the cells of the control wells (treated with the culture medium alone).

TABLE III

| | $IC_{50}$ (nM) | | |
|---|---|---|---|
| | HCT116 | MDA-MB-231 | MDA-A1 |
| Compound 1 | 0.032 | 0.041 | 1.07 |
| Compound 7 | 0.315 | 0.303 | 7.946 |
| Compound 8 | 0.052 | 0.104 | 0.828 |
| Compound 13 | 0.336 | 0.529 | 9.763 |
| Compound 19 | 0.152 | 0.149 | 2.705 |
| Compound 30 | 0.031 | 0.03 | 11.95 |
| Compound 40 | 0.12 | 0.293 | 1.579 |
| Compound 44 | 0.135 | 0.156 | 15.552 |
| Compound 57 | 1.131 | 1.185 | 29.01 |
| Compound 62 | 0.035 | 0.095 | 10.88 |
| Compound 77 | 0.105 | 0.170 | 15.06 |

Example 29

Evaluation of the inhibition of proliferation of the MDA-MB-231, MDA-A1 and HCT116 cell lines by the antibody-cytotoxic agent conjugates MDA-MB-231, MDA-A1 or HCT116 cells in their exponential growth phase are trypsinized and resuspended in their respective culture medium (DMEM/F12 Gibco #21331, 10% FCS Gibco #10500-056, 2 nM glutamine Gibco #25030 for the MDA cells; DMEM Gibco #11960, 10% FCS Gibco #10500-056, 2 mM glutamine Gibco #25030 for the HCT116 cells). The cell suspension is seeded in Cytostar 96-well culture plates (GE Healthcare Europe, #RPNQ0163) in the whole culture medium containing serum at a density of 5000 cells/well (MDA-MB-231, MDA-A1, HCT116). After incubation for 4 hours, successive dilutions of the cryptophycin derivatives are added to the wells at concentrations decreasing from $10^{-7}$ to $10^{-12}$ M (in triplicate for each concentration). The cells are cultured at 37° C. in an atmosphere containing 5% $CO_2$ in the presence of the antibody-cytotoxic agent immunoconjugates for 3 days. On the 4$^{th}$ day, 10 µl of a $^{14}$C-thymidine solution (0.1 µCi/well, Perkin Elmer

NEC56825000) are added to each well. The incorporation of $^{14}C$-thymidine is measured 96 hours after the start of the experiment with a microbeta radioactivity counter (Perkin Elmer). The data are expressed in the form of a percentage of survival by determining the ratio between the reduced count obtained with the cells treated with the immunoconjugate and the count obtained with the cells of the control wells (treated with the culture medium alone). In certain experiments, the naked antibody hu2H11 was added to the wells at a concentration of 1 μM at the start of the experiment and the inhibition of proliferation was measured as described previously.

TABLE IV

| | $IC_{50}$ (nM), MDA-MB-231 | |
| --- | --- | --- |
| | Conjugate alone | in the presence of naked antibody |
| Ex. 9 | 0.150 | 0.856 |
| Ex. 25 | 0.710 | 4.918 |

We claim:
1. A compound of formula (II):

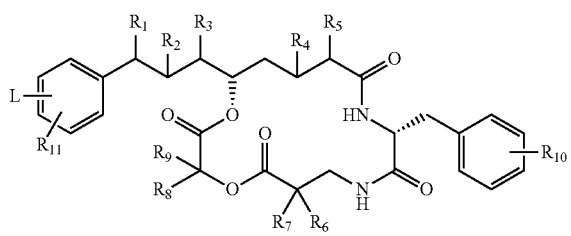

(II)

in which:
R$_1$ represents a halogen atom and R$_2$ represents an —OH, an acyl group derived from an amino acid AA, or a ($C_1$-$C_4$)alkanoyloxy group
or alternatively R$_1$ and R$_2$ form an epoxide unit;
AA denotes a natural or unnatural amino acid;
R$_3$ represents a ($C_1$-$C_6$)alkyl group;
R$_4$ and R$_5$ both represent H or together form a double bond CH=CH between C13 and C14;
R$_6$ and R$_7$ represent, independently of each other, H or a ($C_1$-$C_6$)alkyl group;
R$_8$ and R$_9$ represent, independently of each other, H or a ($C_1$-$C_6$)alkyl group;
R$_{10}$ represents at least one substituent of the phenyl nucleus chosen from: H, an OH, ($C_1$-$C_4$)alkoxy, a halogen atom, —NH$_2$, —NH($C_1$-$C_6$)alkyl or —N($C_1$-$C_6$)alkyl$_2$;
R$_{11}$ represents at least one substituent of the phenyl nucleus chosen from H and a ($C_1$-$C_4$)alkyl group;
L represents a linker in the ortho (O), meta (m) or para (p) position of the phenyl nucleus bearing the unit RCG$_1$ chosen from:
-G' X (CR$_{13}$R$_{14}$)$_t$(OCH$_2$CH$_2$)$_y$(CR$_{15}$R$_{16}$)$_u$ Q RCG$_1$;
-G' X (CR$_{13}$R$_{14}$)$_t$(OCH$_2$CH$_2$)$_y$—Y'—(CR$_{15}$R$_{16}$)$_u$ Q RCG$_1$;
-G' X (CR$_{13}$R$_{14}$)$_t$(CR$_{17}$=CR$_{18}$)(CR$_{15}$R$_{16}$)$_u$(OCH$_2$CH$_2$)$_y$ Q RCG$_1$;
-G' X (CR$_{13}$R$_{14}$)$_t$(OCH$_2$CH$_2$)$_y$(CR$_{17}$=CR$_{18}$)(CR$_{15}$R$_{16}$)$_u$ Q RCG$_1$;
-G' X (CR$_{13}$R$_{14}$)$_t$-phenyl-(CR$_{15}$R$_{16}$)$_u$ Y' Q RCG$_1$; -G' X (CR$_{13}$R$_{14}$)$_t$-furyl-(CR$_{15}$R$_{16}$)$_u$ Y' Q RCG$_1$;
-G' X (CR$_{13}$R$_{14}$)$_t$-oxazolyl-(CR$_{15}$R$_{16}$)$_u$ Y' Q RCG$_1$; -G' X (CR$_{13}$R$_{14}$)$_t$-thiazolyl-(CR$_{15}$R$_{16}$)$_u$ Y' Q RCG$_1$; -G' X (CR$_{13}$R$_{14}$)$_t$-thienyl-(CR$_{15}$R$_{16}$)$_u$ Y' Q RCG$_1$; -G' X (CR$_{13}$R$_{14}$)$_t$-imidazolyl-(CR$_{15}$R$_{16}$)$_u$ Y' Q RCG$_1$; -G' X (CR$_{13}$R$_{14}$)$_t$-piperazinyl-CO(CR$_{15}$R$_{16}$)$_u$ Y' Q RCG$_1$; -G' X (CR$_{13}$R$_{14}$)$_t$-piperidyl-methyl-NR$_{12}$—CO(CR$_{15}$R$_{16}$)$_u$ Y' Q RCG$_1$; -G' X (CR$_{13}$R$_{14}$)$_t$-piperidyl-(CR$_{15}$R$_{16}$)$_u$ Q RCG$_1$; -G' X (CR$_{13}$R$_{14}$)$_t$-piperidyl-NR$_{12}$—(CR$_{15}$R$_{16}$)$_u$ Y' Q RCG$_1$; -G' X (CR$_{13}$R$_{14}$)$_t$-triazolyl-(CR$_{15}$R$_{16}$)$_u$ Y' Q RCG$_1$; -G' X (CR$_{13}$R$_{14}$)$_t$-triazolyl-(CR$_{15}$R$_{16}$)$_u$ Y' Q RCG$_1$;
-G' X (CR$_{13}$R$_{14}$)$_t$-phenyl-(CR$_{15}$R$_{16}$)$_u$ Q RCG$_1$; -G' X (CR$_{13}$R$_{14}$)$_t$-furyl-(CR$_{15}$R$_{16}$)$_u$ Q RCG$_1$; -G' X (CR$_{13}$R$_{14}$)$_t$-oxazolyl-(CR$_{15}$R$_{16}$)$_u$ Q RCG$_1$; -G' X (CR$_{13}$R$_{14}$)$_t$-thiazolyl-(CR$_{15}$R$_{16}$)$_u$ Q RCG$_1$; -G' X (CR$_{13}$R$_{14}$)$_t$-thienyl-(CR$_{15}$R$_{16}$)$_u$ Q RCG$_1$; -G' X (CR$_{13}$R$_{14}$)$_t$-imidazolyl-(CR$_{15}$R$_{16}$)$_u$ Q RCG$_1$; -G' X (CR$_{13}$R$_{14}$)$_t$-piperazinyl-(CR$_{15}$R$_{16}$)$_u$ Q RCG$_1$; -G' X (CR$_{13}$R$_{14}$)$_t$-piperidyl-(CR$_{15}$R$_{16}$)$_u$ Q RCG$_1$; -G' X (CR$_{13}$R$_{14}$)$_t$-piperidyl-methyl-NR$_{12}$—(CR$_{15}$R$_{16}$)$_u$ Q RCG$_1$; -G' X (CR$_{13}$R$_{14}$)$_t$-piperidyl-NR$_{12}$—(CR$_{15}$R$_{16}$)$_u$ Q RCG$_1$; -G' X (CR$_{13}$R$_{14}$)$_t$-triazolyl-(CR$_{15}$R$_{16}$)$_u$ Q RCG$_1$;
-G" Y (CR$_{13}$R$_{14}$)$_t$(OCH$_2$CH$_2$)$_y$(CR$_{15}$R$_{16}$)$_u$ Q RCG$_1$;
-G" Y (CR$_{13}$R$_{14}$)$_t$(OCH$_2$CH$_2$)$_y$—Y'—(CR$_{15}$R$_{16}$)$_u$ Q RCG$_1$;
-G" Y (CR$_{13}$R$_{14}$)$_t$(CR$_{17}$=CR$_{18}$)(CR$_{15}$R$_{16}$)$_u$(OCH$_2$CH$_2$)$_y$ Q RCG$_1$;
-G" Y (CR$_{13}$R$_{14}$)$_t$(OCH$_2$CH$_2$)$_y$(CR$_{17}$=CR$_{18}$)(CR$_{15}$R$_{16}$)$_u$ Q RCG$_1$;
-G" Y (CR$_{13}$R$_{14}$)$_t$-phenyl-(CR$_{15}$R$_{16}$)$_u$ Y' Q RCG$_1$; -G" Y (CR$_{13}$R$_{14}$)$_t$-furyl-(CR$_{15}$R$_{16}$)$_u$ Y' Q RCG$_1$;
-G" Y (CR$_{13}$R$_{14}$)$_t$-oxazolyl-(CR$_{15}$R$_{16}$)$_u$ Y' Q RCG$_1$; -G" Y (CR$_{13}$R$_{14}$)$_t$-thiazolyl-(CR$_{15}$R$_{16}$)$_u$ Y' Q RCG$_1$; -G" Y (CR$_{13}$R$_{14}$)$_t$-thienyl-(CR$_{15}$R$_{16}$)$_u$ Y' Q RCG$_1$; -G" Y (CR$_{13}$R$_{14}$)$_t$-imidazolyl-(CR$_{15}$R$_{16}$)$_u$ Y' Q RCG$_1$; -G" Y (CR$_{13}$R$_{14}$)$_t$-piperazinyl-CO(CR$_{15}$R$_{16}$)$_u$ Y' Q RCG$_1$; -G" Y (CR$_{13}$R$_{14}$)$_t$-piperidyl-methyl-NR$_{12}$—CO(CR$_{15}$R$_{16}$)$_u$ Y' Q RCG$_1$; -G" Y (CR$_{13}$R$_{14}$)$_t$-piperidyl-(CR$_{15}$R$_{16}$)$_u$ Q RCG$_1$; -G" Y (CR$_{13}$R$_{14}$)$_t$-piperidyl-NR$_{12}$—(CR$_{15}$R$_{16}$)$_u$ Y' Q RCG$_1$; -G" Y (CR$_{13}$R$_{14}$)$_t$-triazolyl-(CR$_{15}$R$_{16}$)$_u$ Y' Q RCG$_1$;
-G" Y (CR$_{13}$R$_{14}$)$_t$-phenyl-(CR$_{15}$R$_{16}$)$_u$ Q RCG$_1$; -G" Y (CR$_{13}$R$_{14}$)$_t$-furyl-(CR$_{15}$R$_{16}$)$_u$ Q RCG$_1$;
-G" Y (CR$_{13}$R$_{14}$)$_t$-oxazolyl-(CR$_{15}$R$_{16}$)$_u$ Q RCG$_1$; -G" Y (CR$_{13}$R$_{14}$)$_t$-thiazolyl-(CR$_{15}$R$_{16}$)$_u$ Q RCG$_1$;
-G" Y (CR$_{13}$R$_{14}$)$_t$-thienyl-(CR$_{15}$R$_{16}$)$_u$ Q RCG$_1$; -G" Y (CR$_{13}$R$_{14}$)$_t$-imidazolyl-(CR$_{15}$R$_{16}$)$_u$ Q RCG$_1$;
-G" Y (CR$_{13}$R$_{14}$)$_t$-piperazinyl-(CR$_{15}$R$_{16}$)$_u$ Q RCG$_1$; -G" Y (CR$_{13}$R$_{14}$)$_t$-piperazinyl-(CR$_{15}$R$_{16}$)$_u$ Q CCR$_1$; G" Y (CR$_{13}$R$_{14}$)$_t$-piperidyl-(CR$_{15}$R$_{16}$)$_u$ Q RCG$_1$; -G" Y (CR$_{13}$R$_{14}$)$_t$-piperidyl-methyl-NR$_{12}$—(CR$_{15}$R$_{16}$)$_u$ Q RCG$_1$; -G" Y (CR$_{13}$R$_{14}$)$_t$-piperidyl-NR$_{12}$—(CR$_{15}$R$_{16}$)$_u$ Q RCG$_1$; or -G" Y (CR$_{13}$R$_{14}$)$_t$-triazolyl-(CR$_{15}$R$_{16}$)$_u$ Q RCG$_1$;
in which formulae:
G' represents a —CH=CH— or —(CH$_2$)$_n$— group;
G" represents a —(CH$_2$)$_n$— group;
n represents an integer ranging from 1 to 6;
X represents a single bond or a —CO—, —COO— or —CONR$_{12}$—, wherein the CO is attached to G';
Y represents a —O—, —OCO—, —OCOO—, —OCONR$_{12}$—, —NR$_{12}$—, —NR$_{12}$CO—, —NR$_{12}$CONR'$_{12}$—, —NR$_{12}$COO— or —S(O)$_q$—, wherein the O and the NR$_{12}$ are attached to G";
q represents an integer that may be 0, 1 or 2;

Y' represents a —O—, —OCO—, —OCOO—, —OCONR$_{12}$—, —NR$_{12}$—, —NR$_{12}$CO—, —NR$_{12}$CONR'$_{12}$—, —NR$_{12}$COO—, —S(O)$_q$—, —CO—, —OCO—, or —CONR$_{12}$—;

R$_{12}$, R'$_{12}$, R$_{13}$, R$_{14}$, R$_{15}$, R$_{16}$, R$_{17}$ and R$_{18}$ represent, independently of each other, H or a (C$_1$-C$_6$)alkyl group;

t, u and y represent integers that may range from 0 to 20 and such that t+u+y is greater than or equal to 1;

in the case of the linker of formula -G"Y(CR$_{13}$R$_{14}$)$_t$ (OCH$_2$CH$_2$)$_y$—Y'—(CR$_{15}$R$_{16}$)$_u$ Q RCG$_1$, if y is 0 and Q represents a single bond, then u cannot be 0;

Q represents a single bond, a (C$_1$-C$_{10}$)alkylene group or a (OCH$_2$CH$_2$)$_i$ group, wherein i is an integer ranging from 1 to 20;

RCG1 represents —SZ$_a$, —C(=O)—Z$_b$R$_b$,

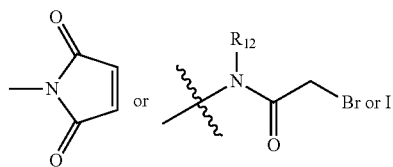

with R$_{12}$ representing H or (C$_1$-C$_6$)alkyl;
or L is chosen from:

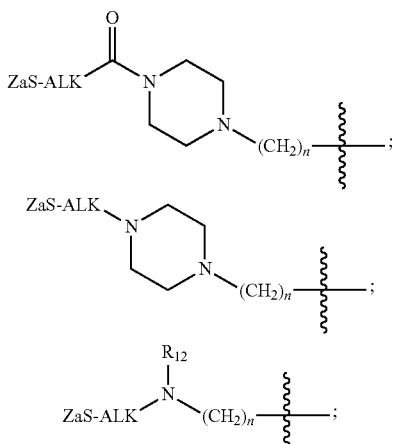

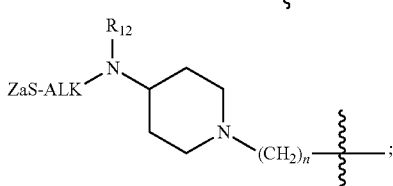

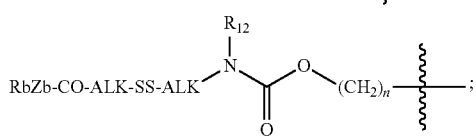

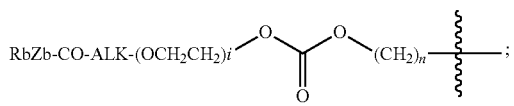

-continued

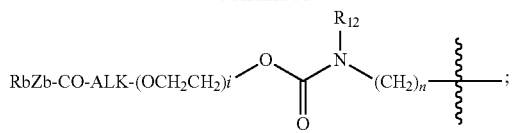

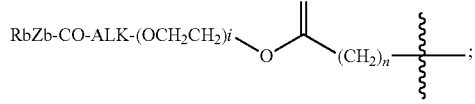

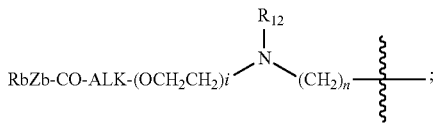

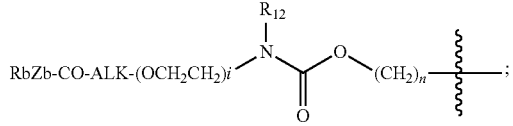

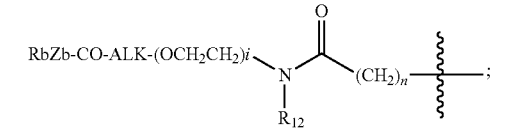

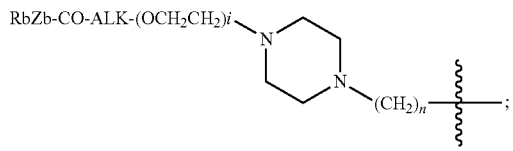

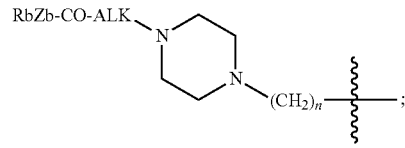

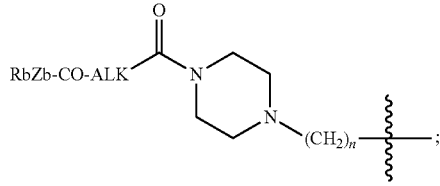

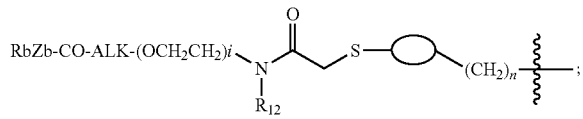

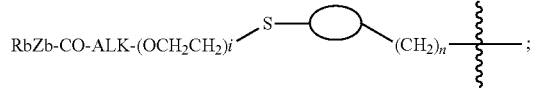

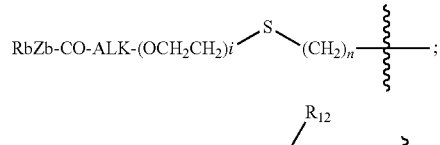

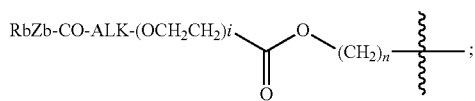

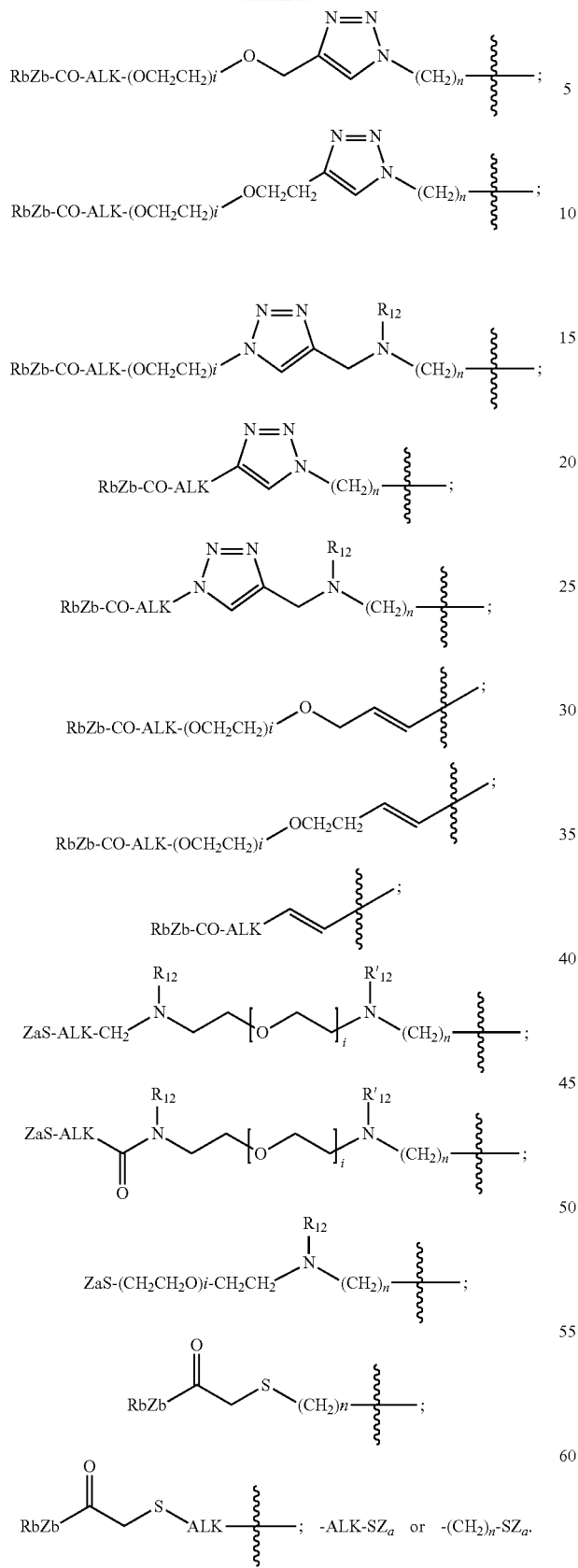
in which formulae:
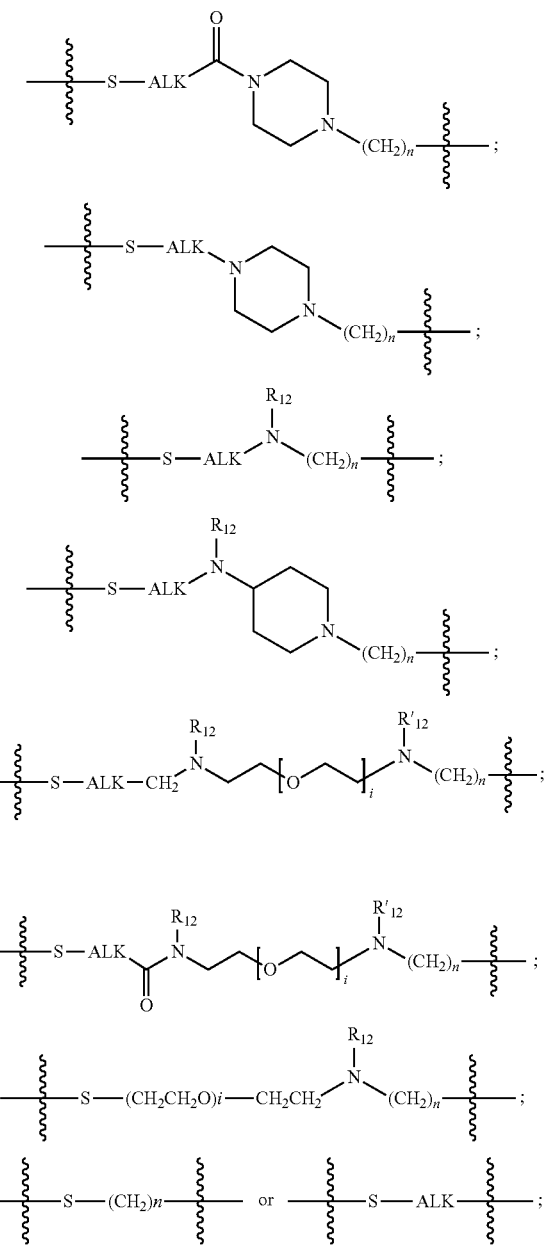
represents one of the following 9 groups:
n represents an integer ranging from 1 to 6;
ALK represents a group $(C_1-C_{12})$alkylene;
$R_{12}$ and $R'_{12}$ represent, independently of each other, H or a group $(C_1-C_6)$alkyl;
i represents an integer ranging from 1 to 20;
or alternatively L is a linker of formula (IV):

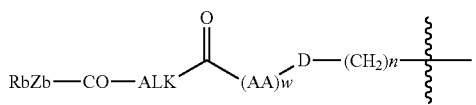
(IV)

in which:
(AA)$_w$ represents a sequence of w amino acids AA connected together via peptide bonds;
w represents an integer ranging from 1 to 12;
n represents an integer ranging from 1 to 6;
D represents one of the following units:

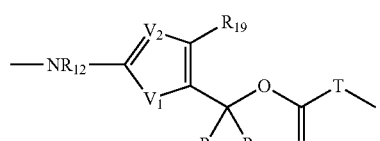
(D1)

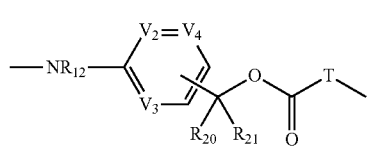
(D2)

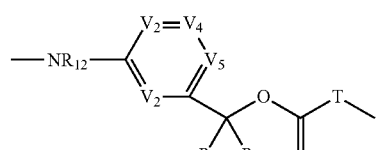
(D3)

for which:
R$_{12}$ represents H or a (C$_1$-C$_6$)alkyl group;
R$_{19}$, R$_{20}$, R$_{21}$ and R$_{22}$ represent, independently of each other, H, a halogen atom, —OH, CN or a (C$_1$-C$_4$)alkyl group;
T attached to (CH$_2$), represents NR$_{12}$ or O;
V$_1$ represents O, S or NR$_{12}$;
V$_2$ represents CR$_{22}$ or N;
V$_3$, V$_4$ and V$_5$ are chosen, independently of each other, from CR$_{22}$ and N;
Z$_a$ represents H or the group —SR$_a$, wherein R$_a$ represents a (C$_1$-C$_6$)alkyl, (C$_3$-C$_7$)cycloalkyl, aryl, heteroaryl or (C$_3$-C$_7$)heterocycloalkyl;
Z$_b$ represents a single bond, —O— or —NH—, wherein R$_b$ represents H, (C$_1$-C$_6$)alkyl, (C$_3$-C$_7$)cycloalkyl, aryl, heteroaryl or (C$_3$-C$_7$)heterocycloalkyl.

2. The compound according to claim 1, in which R$_{10}$ represents at least one substituent on the phenyl nucleus chosen from: H, an OH, (C$_1$-C$_4$)alkoxy, or a halogen atom.

3. The compound according to claim 1, in which RCG1 represents —SZ, or —C(=O)—Z$_b$R$_b$.

4. The compound according to claim 1, in which

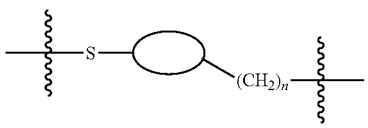

represents one of the following 7 groups:

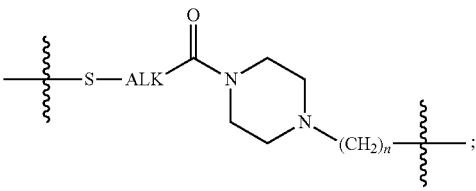
;

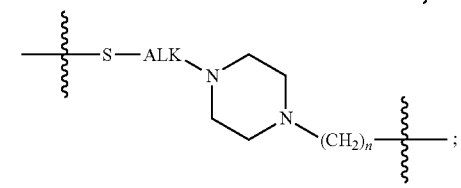
;

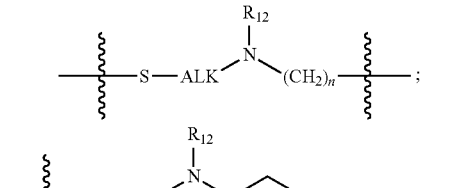
;

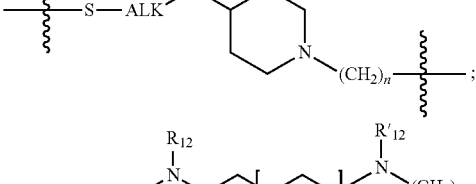
;

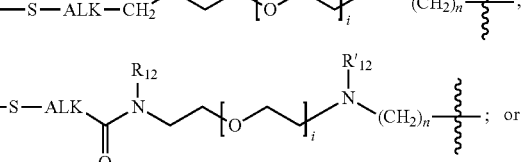
; or

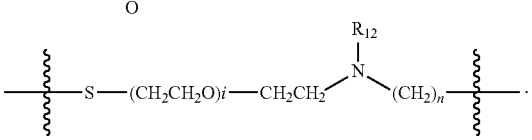
.

5. The compound according to claim 1, in which n is 1.

6. The compound according to claim 1, in which L is chosen from:

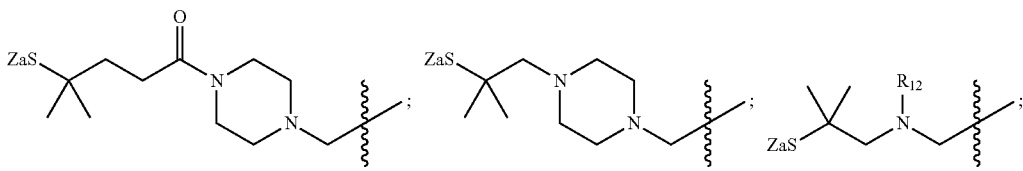

-continued
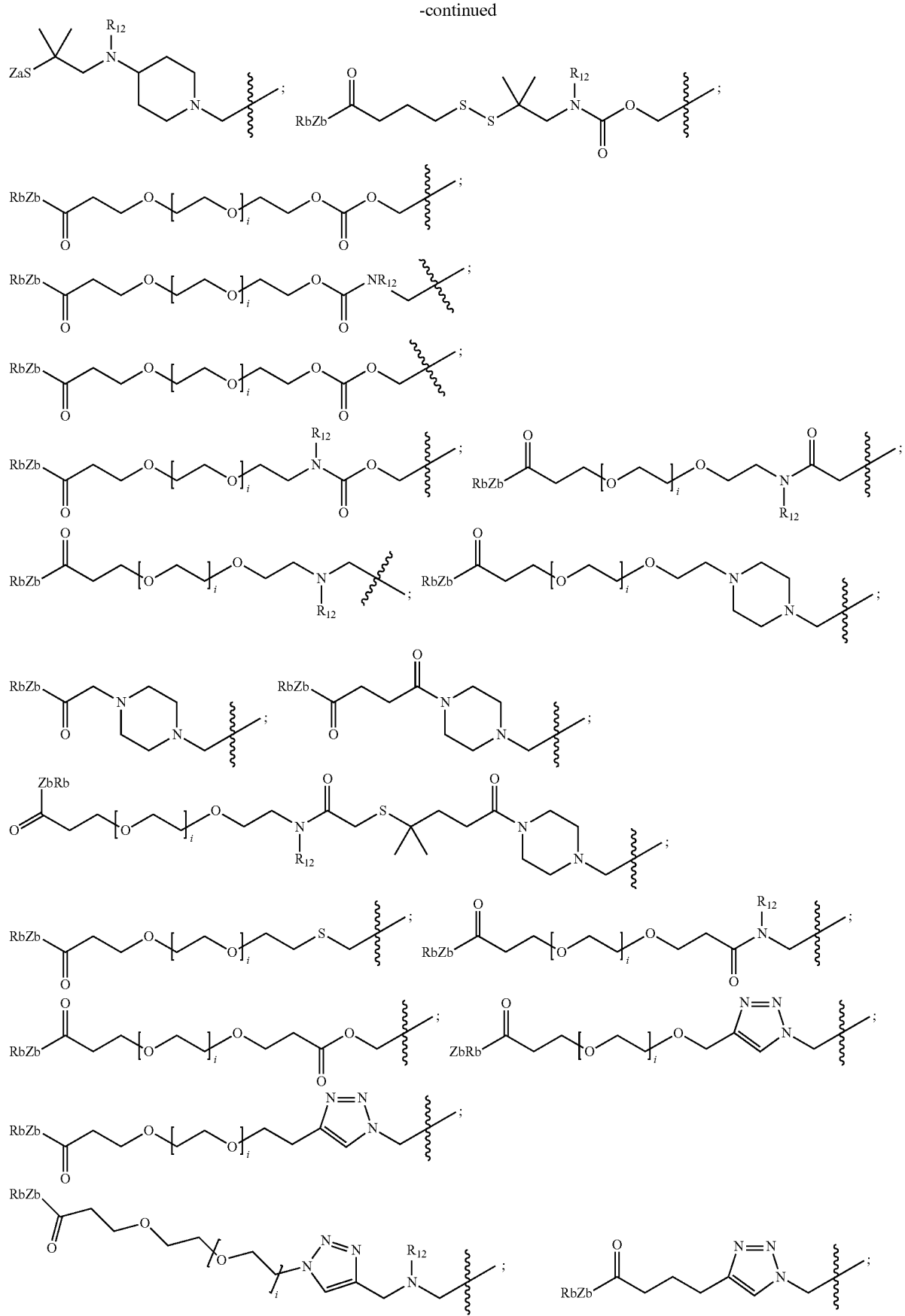

-continued
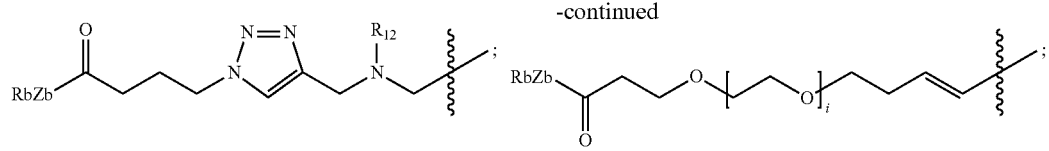
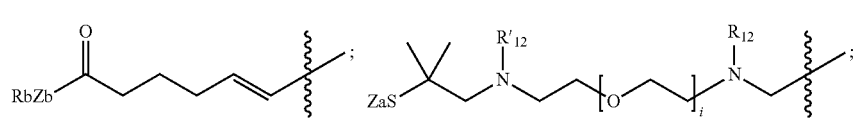
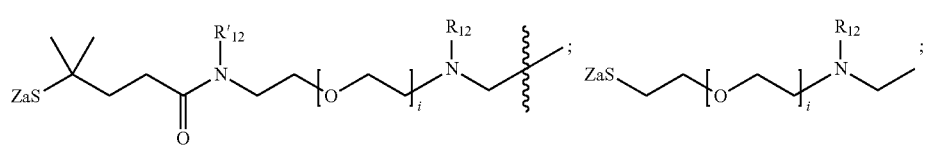
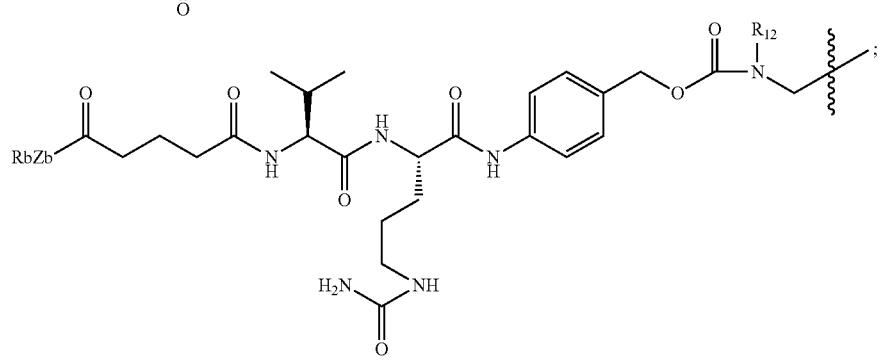
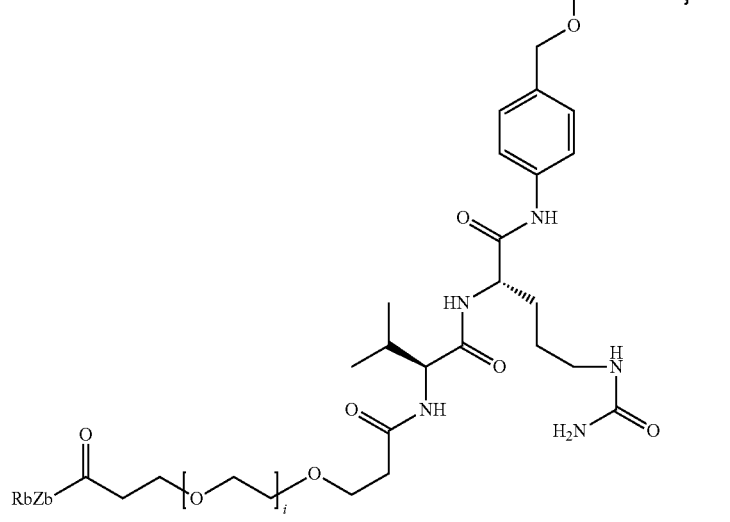
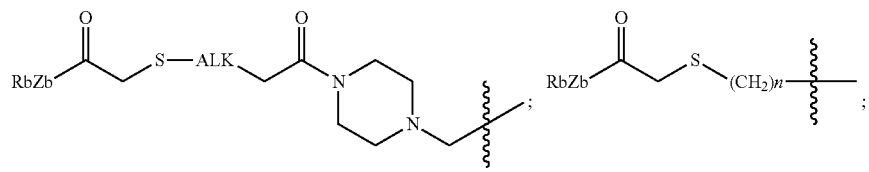
—CH$_2$SZ$_a$;  or  —ALK—SZ$_a$.

7. The compound according to claim 1, in which L is chosen from:
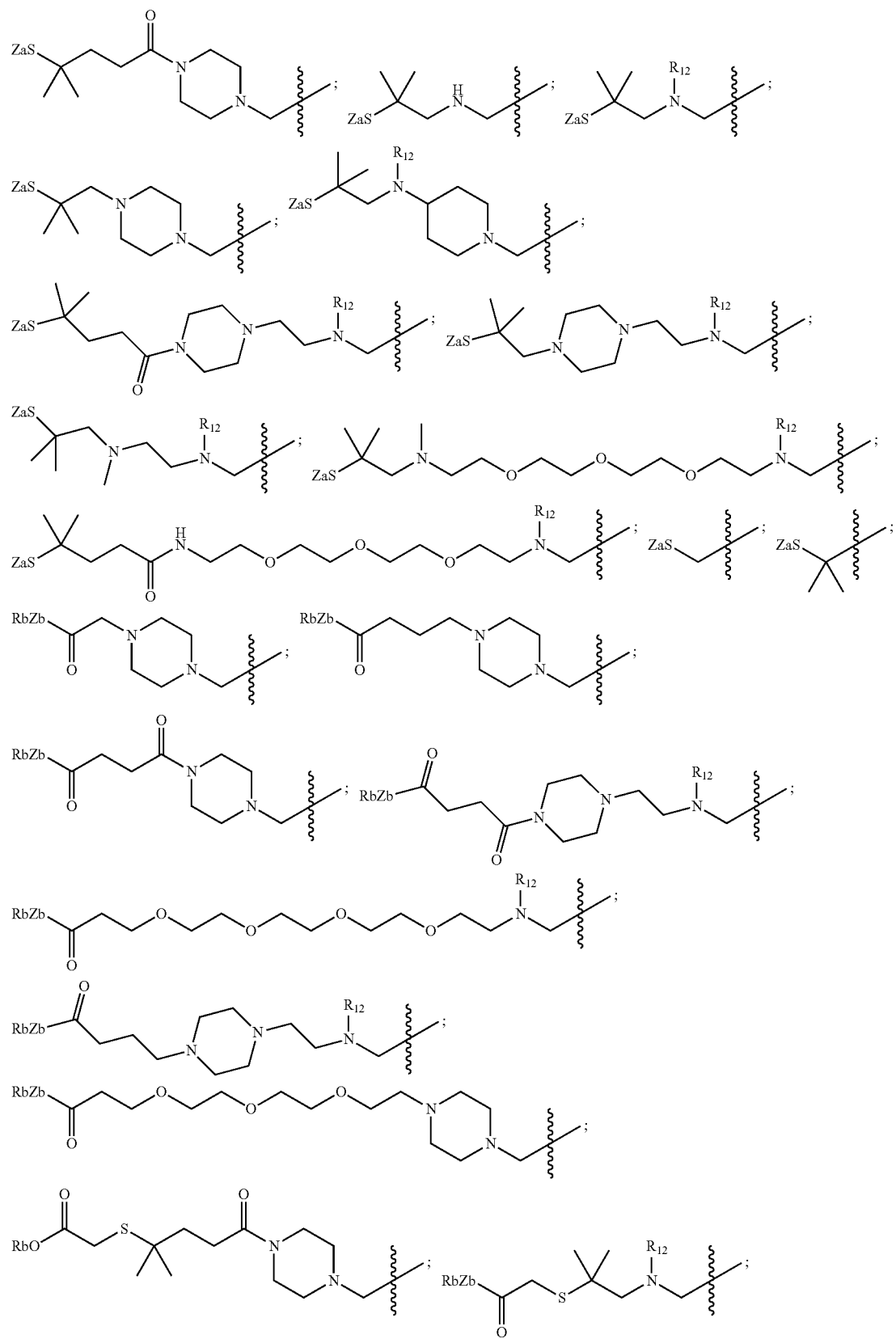

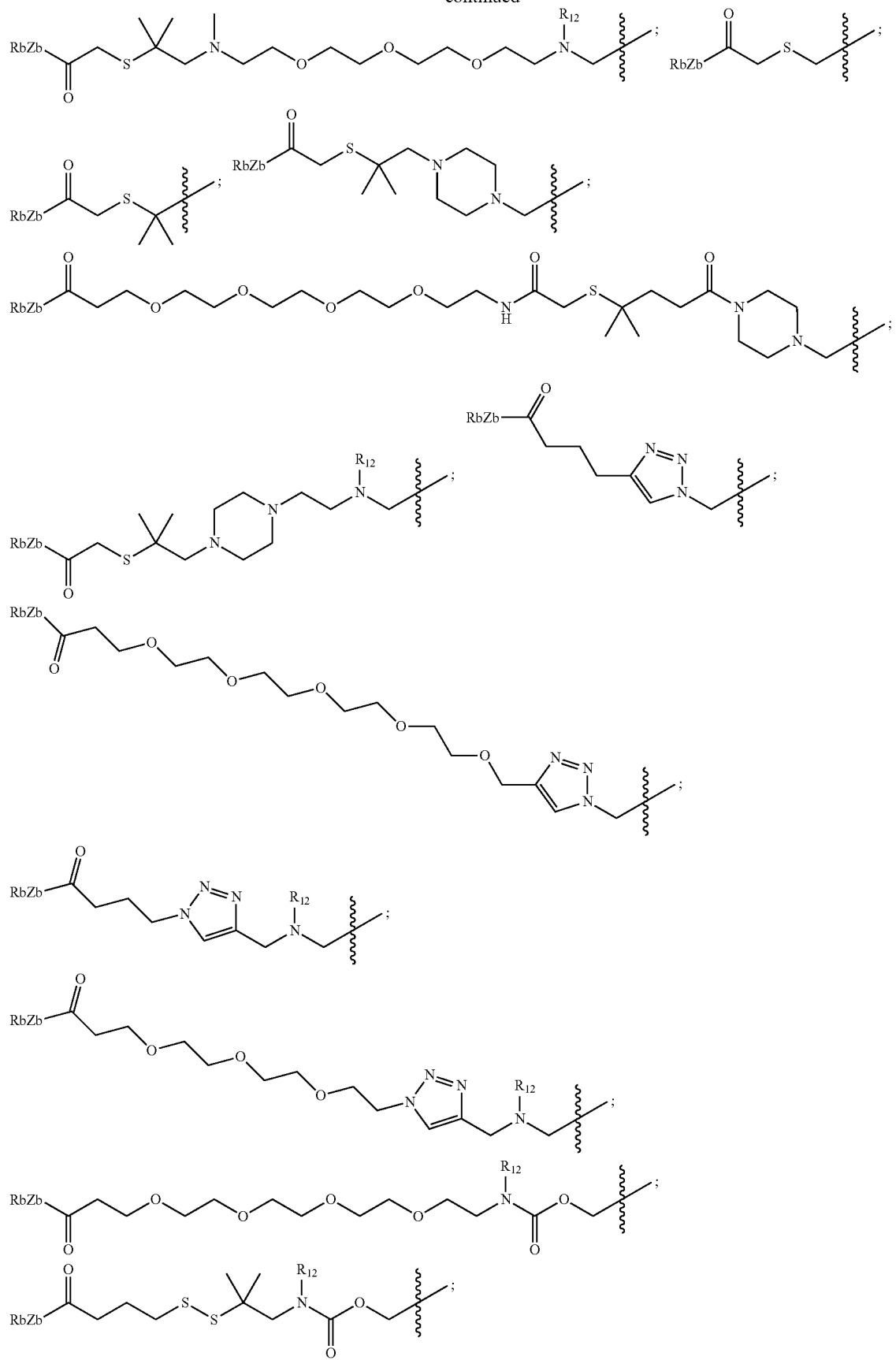

-continued
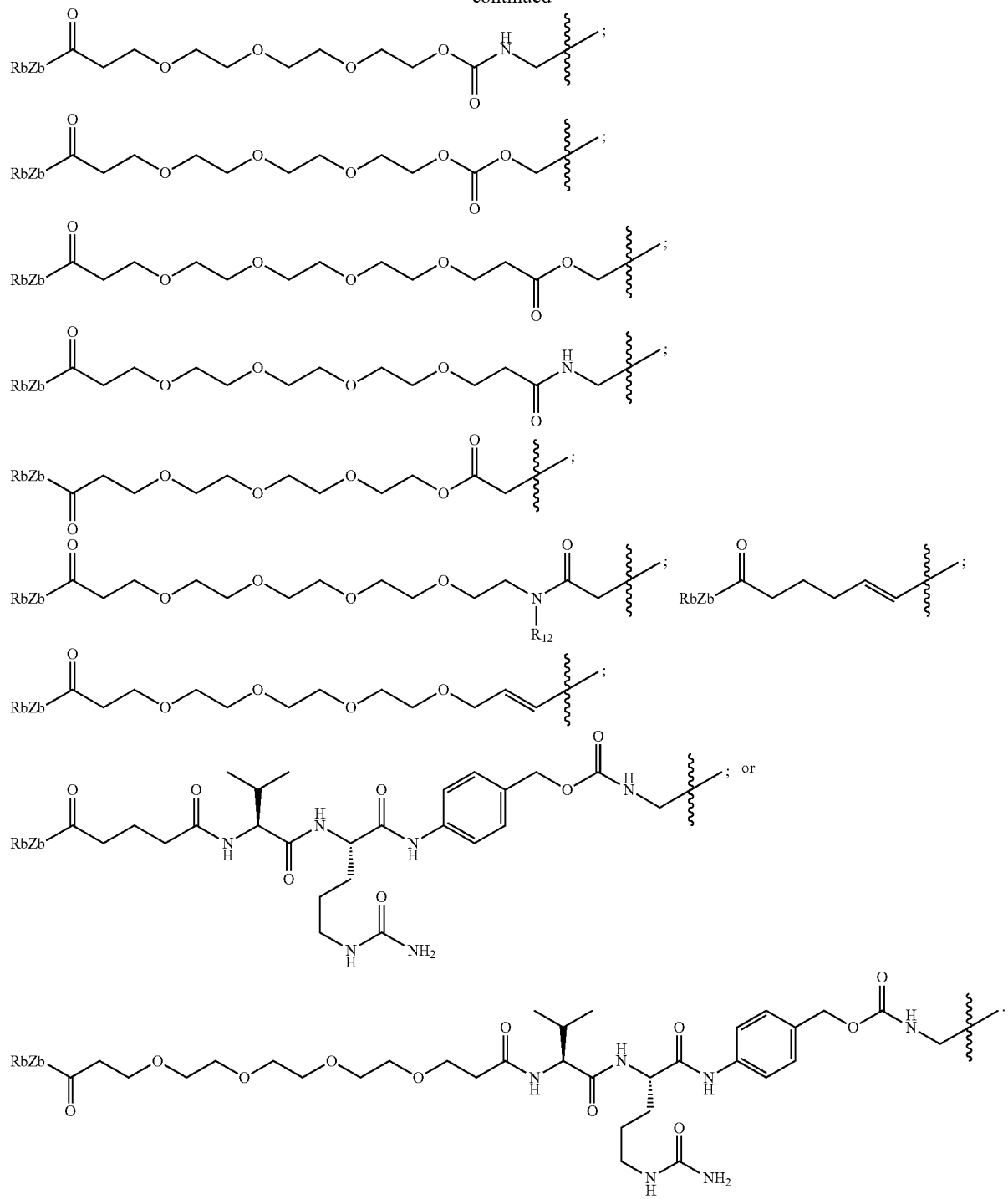
8. The compound according to claim 7, in which $R_{12}$ represents H.
9. The compound according to claim 7, in which $R_{12}$ represents $(C_1-C_6)$alkyl.
10. The compound according to claim 1, in which $Z_a$ represents H, —S$(C_1-C_6)$alkyl, or —S-heteroaryl; or $Z_bR_b$ represents —O$(C_1-C_6)$alkyl, —OH, —OCH$_3$, —OCH$_2$CH=CH$_2$,
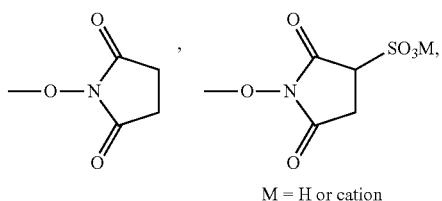
M = H or cation

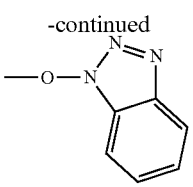
or the group
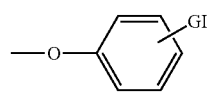
in which GI represents at least one electroinductive group; or alternatively in which —C(=O)$Z_b R_b$ represents
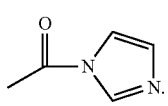
11. The compound according to claim 1 defined according to one of the following formulae:
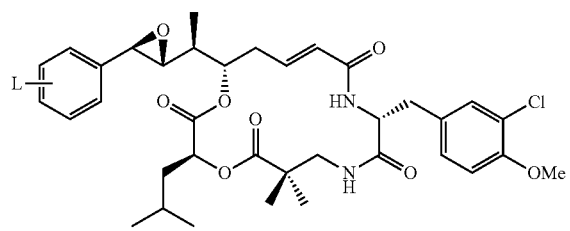
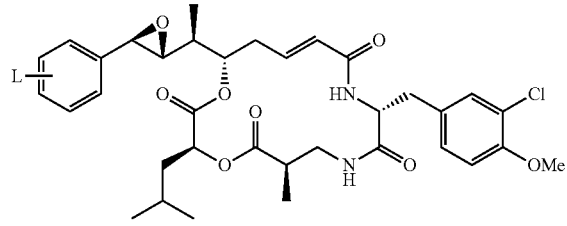
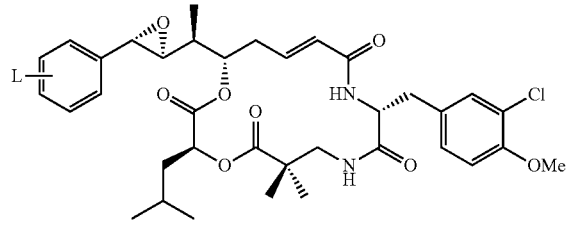
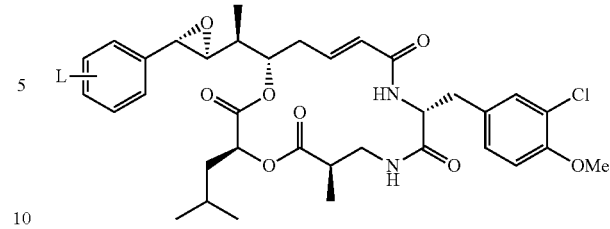
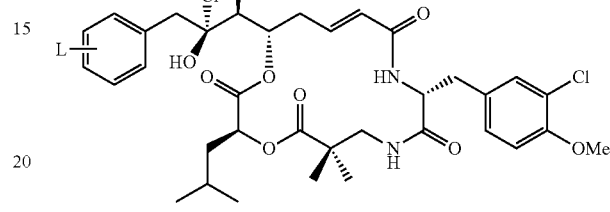
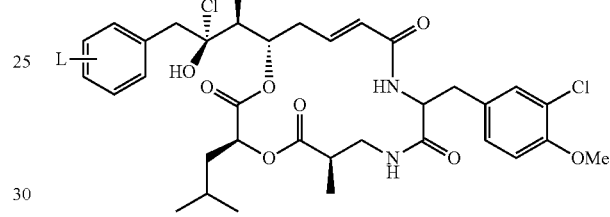
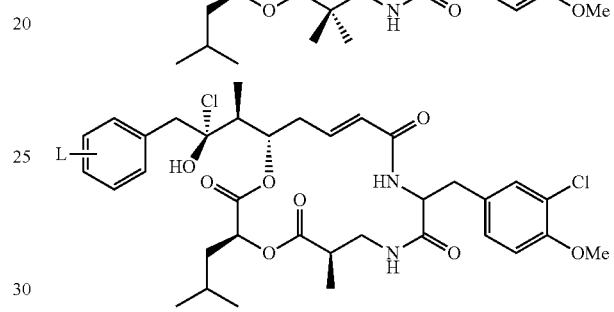
Gly = glycinate
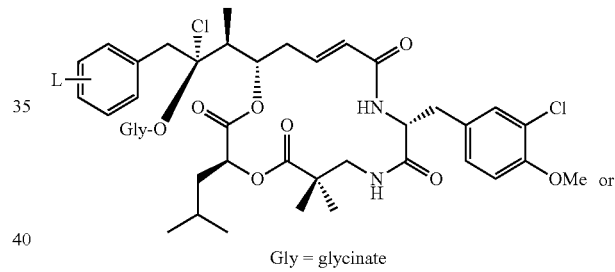
Gly = glycinate
12. The compound according to claim 1, chosen from:
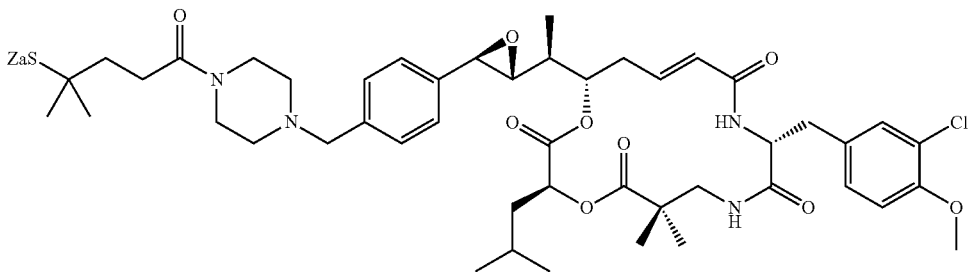

305
-continued
306
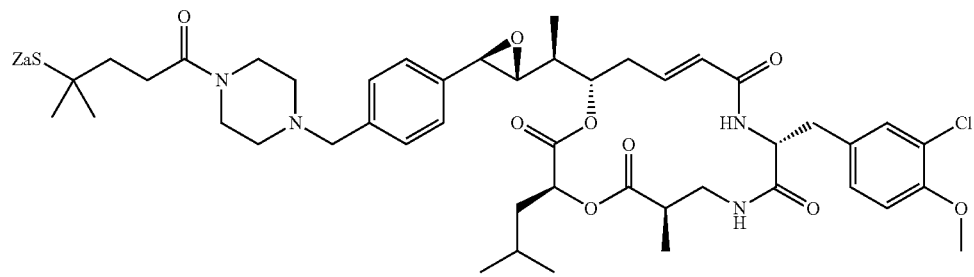
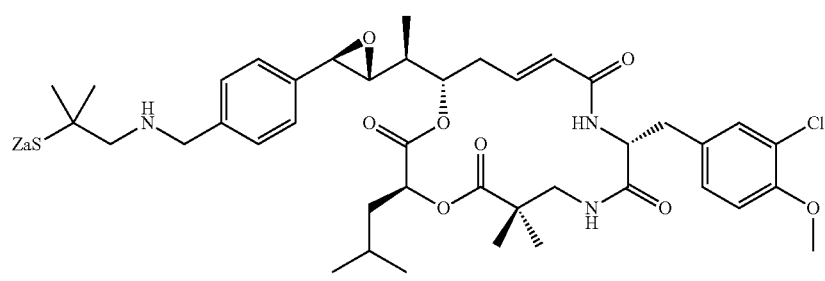
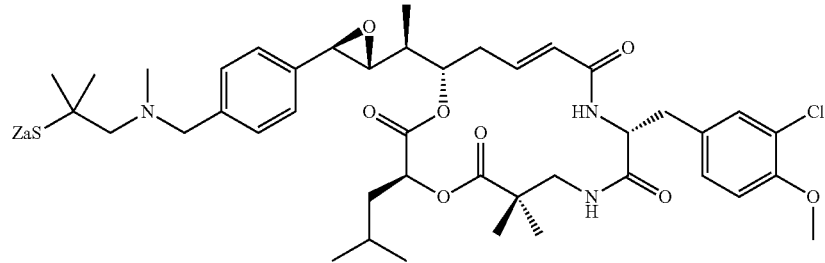
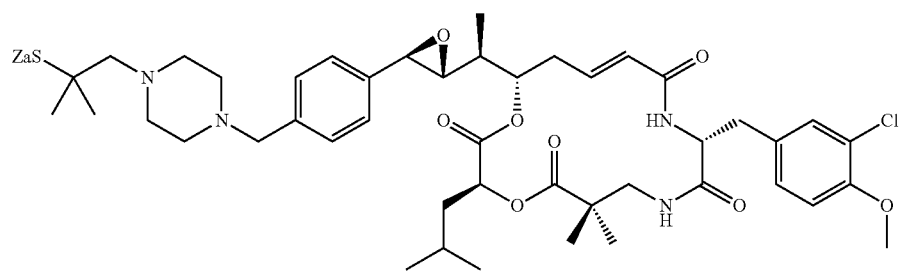
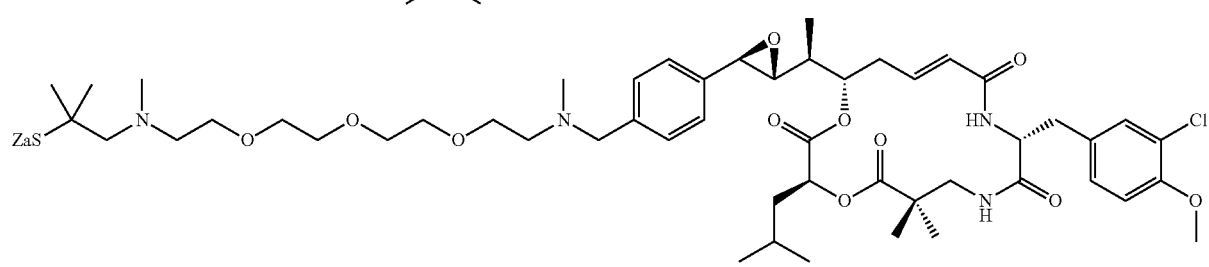
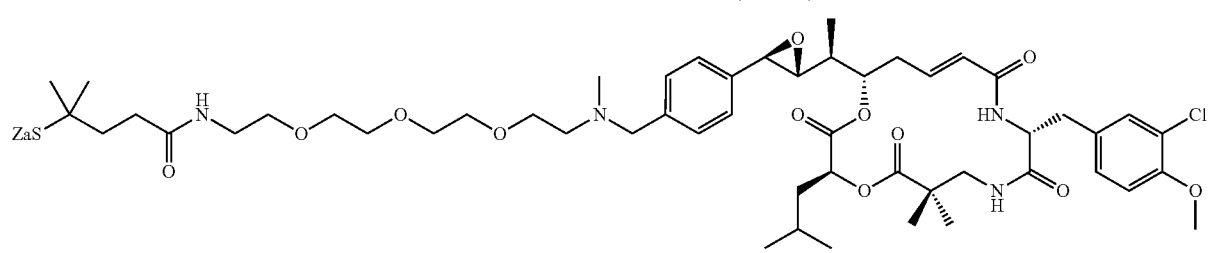

307 308
-continued
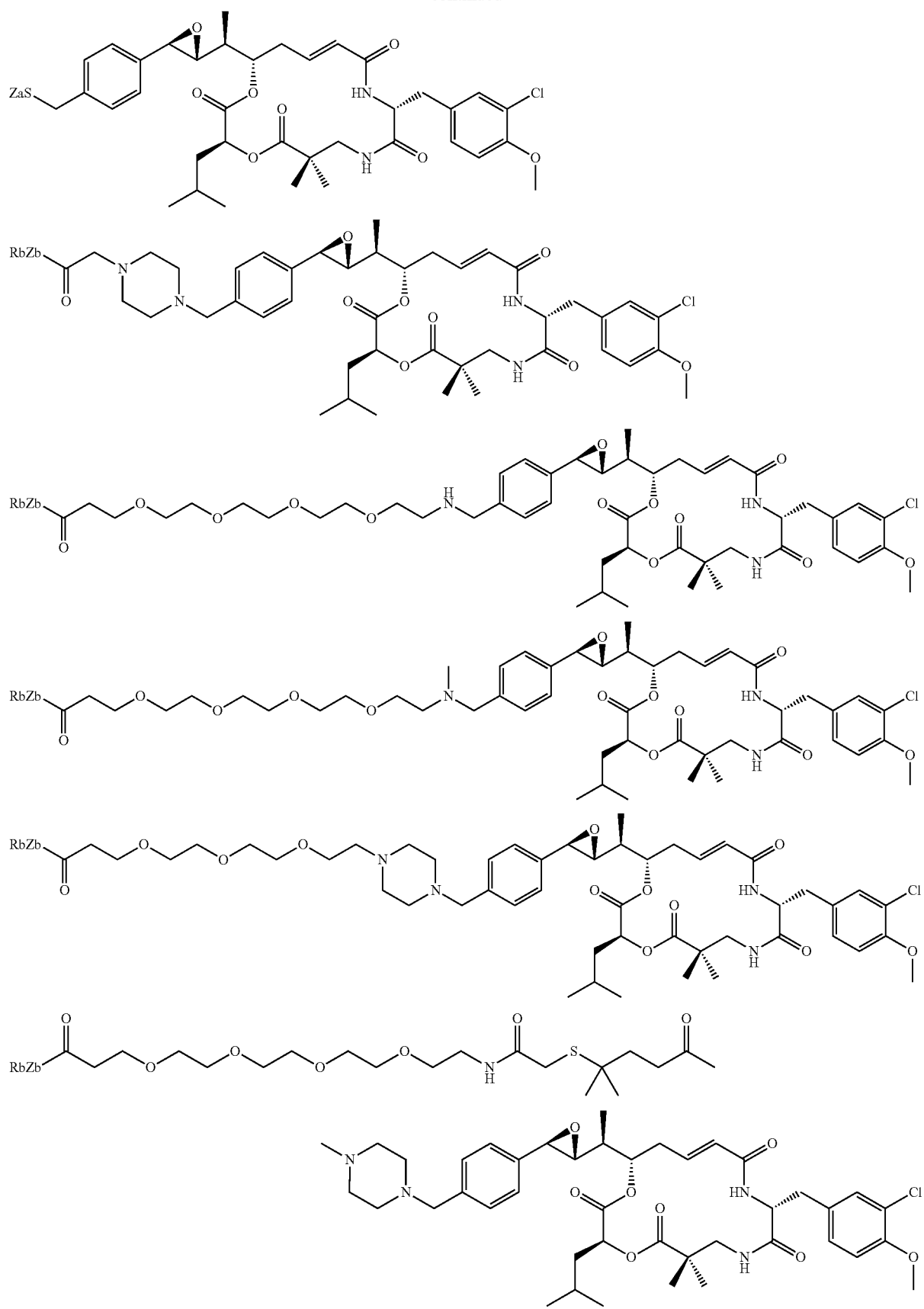

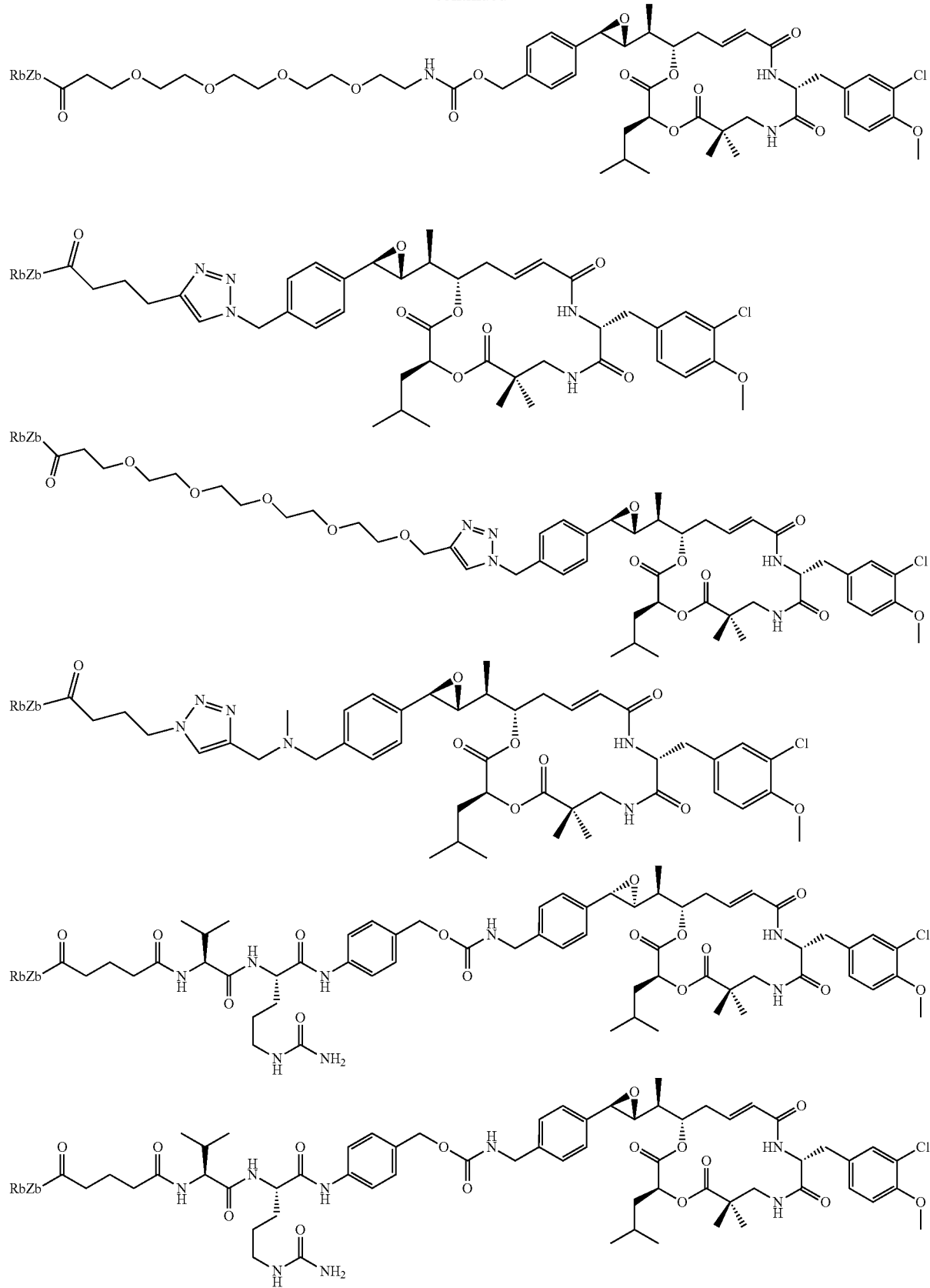
or

-continued

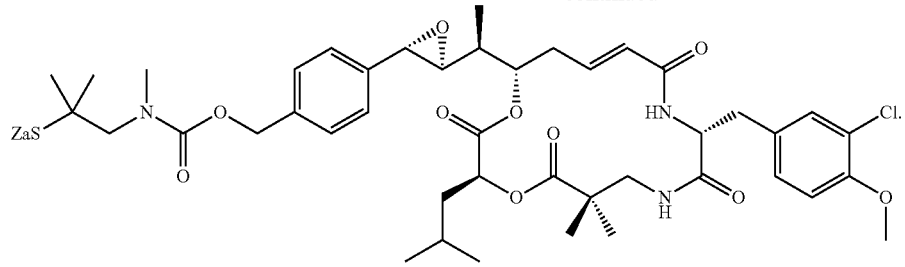

13. The compound according to claim 12, in which $Z_a$ represents H, —S($C_1$-$C_6$)alkyl, or —S-heteroaryl; or $Z_bR_b$ represents —O($C_1$-$C_6$)alkyl, —OH, —OCH$_3$, —OCH$_2$CH=CH$_2$,

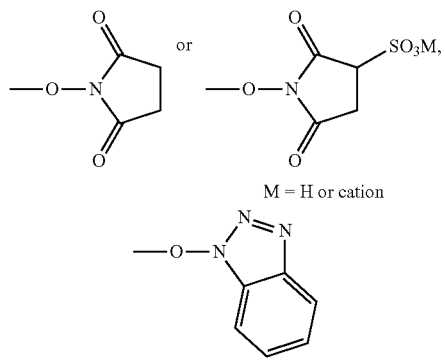

M = H or cation or the group

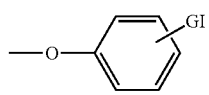

in which GI represents at least one electroinductive group; or alternatively in which —C(=O)$Z_bR_b$ represents

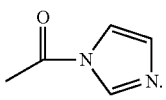

14. A compound of formula (III):

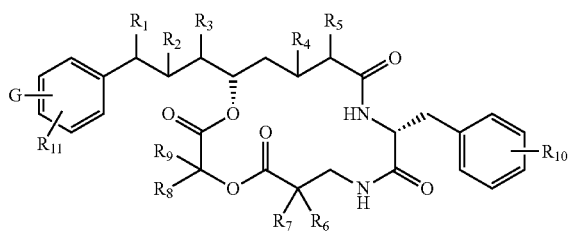

in which:
$R_1$ represents a halogen atom and $R_2$ represents an —OH, an acyl group derived from an amino acid AA, or a ($C_1$-$C_4$)alkanoyloxy group;

or alternatively $R_1$ and $R_2$ form an epoxide unit;
AA denotes a natural or unnatural amino acid;
$R_3$ represents a ($C_1$-$C_6$)alkyl group;
$R_4$ and $R_5$ both represent H or together form a double bond CH=CH between C13 and C14;
$R_6$ and $R_7$ represent, independently of each other, H or a ($C_1$-$C_6$)alkyl group;
$R_8$ and $R_9$ represent, independently of each other, H or a ($C_1$-$C_6$)alkyl group;
$R_{10}$ represents at least one substituent of the phenyl nucleus chosen from: H, an OH, ($C_1$-$C_4$)alkoxy, a halogen atom, —NH$_2$, —NH($C_1$-$C_6$)alkyl or —N($C_1$-$C_6$)alkyl$_2$;
$R_{11}$ represents at least one substituent of the phenyl nucleus chosen from H and a ($C_1$-$C_4$)alkyl group; and
G represents a group —(CH$_2$)$_n$Y, which is in an ortho (o), meta (m) or para (p) position on the phenyl nucleus bearing the unit CR$_1$,
n is an integer ranging from 1 to 6, and Y denoting Cl, —N$_3$, OH, NH$_2$, —NR$_{12}$—CH$_2$—C≡CH in which R$_{12}$ represents H; ($C_1$-$C_6$)alkyl; —OMs; —OC(=O)—O-(4-nitrophenyl);

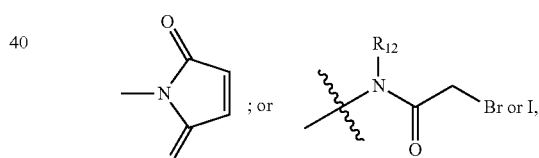

wherein $R_{12}$ represents H or ($C_1$-$C_6$)alkyl.

15. The compound according to claim 14, in which Y represents —N$_3$; —NR$_{12}$—CH$_2$—C≡CH, in which R$_{12}$ represents H; ($C_1$-$C_6$)alkyl; —OMs or —OC(=O)—O-(4-nitrophenyl).

16. The compound according to claim 14, wherein G is —(CH$_2$)$_n$Y with Y is —Cl, —N$_3$, —OH, —NH$_2$, maleimido or haloacetamido.

17. The compound according to claim 1 wherein said compound is conjugated to a binding agent.

18. The compound according to claim 14 wherein said compound is conjugated to a binding agent.

19. The compound according to claim 17, in which the binding agent is a ligand, a protein, an antibody, a protein or antibody fragment, a peptide, an oligonucleotide, or an oligosaccharide.

20. The compound according to claim 18, in which the binding agent is a ligand, a protein, an antibody, a protein or antibody fragment, a peptide, an oligonucleotide, or an oligosaccharide.

21. A process for preparing a cryptophycin conjugate, said process comprising:
   (i) placing in contact and leaving to react an aqueous solution of an optionally buffered binding agent and a solution of a compound of claim 1;
   (ii) and then optionally separating the conjugate formed in step (i) from the cryptophycin derivative or the unreacted binding agent or any aggregates formed, or any combination thereof.

22. The process according to claim 21, wherein
   when the compound comprises a reactive chemical group RCG1 of the type —$SZ_a$, the binding agent comprises:
      disulfide chemical groups in the case where RCG1 represents —SH;
      thiol chemical groups in the case where RCG1 represents —SZ, with $Z_a$H; or
      maleimido or iodoacetamido chemical groups in the case where RCG1 represents —SH;
   when the compound comprises a reactive chemical group RCG1 of the type —C(=O)—$Z_bR_b$, the compound is reacted with the amino functions of the binding agent; or
   when the compound comprises a reactive chemical group RCG1 of maleimido or haloacetamido type, the binding agent comprises thiol chemical groups.

23. A process for preparing a cryptophycin conjugate, said process comprising:
   (i) placing in contact and leaving to react an aqueous solution of an optionally buffered binding agent and a solution of a compound of claim 14;
   (ii) and then optionally separating the conjugate formed in step (i) from the cryptophycin derivative or the unreacted binding agent or any aggregates formed, or any combination thereof.

24. The process according to claim 23, wherein when G is —$(CH_2)_n$Y, the binding agent comprises —SH when Y is —Cl or -maleimido, —C≡CH when Y is —$N_3$, or carboxylic acid groups when Y is —OH or —$NH_2$.

25. The process according to claim 21, in which:
   when the compound comprises a reactive chemical group RCG1 of the type —$SZ_a$, the binding agent is modified with a modifying agent chosen from a compound of formula:

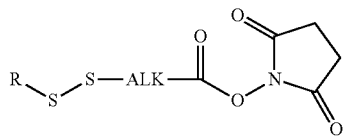

in which R represents a ($C_1$-$C_6$)alkyl, aryl, heteroaryl, ($C_3$-$C_7$)cycloalkyl, or ($C_3$-$C_7$)heterocycloalkyl, wherein ALK represents a ($C_1$-$C_6$)alkylene;

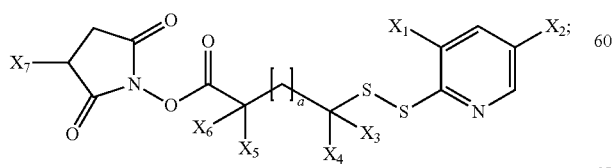

a pegylated analogue of formula:

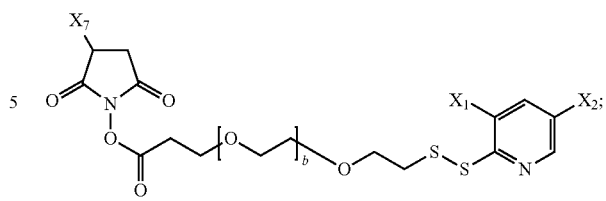

or a sulfonic analogue of formula

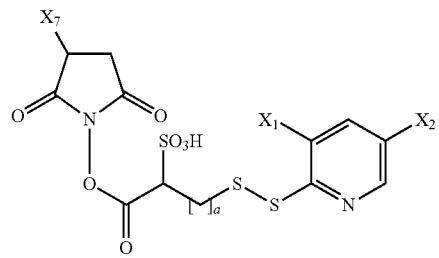

in which:
   $X_3$, $X_4$, $X_6$ and $X_6$ represent H or a ($C_1$-$C_6$)alkyl; $X_1$ and $X_2$ represent —H, —$CONX_8X_9$, or —$NO_2$; $X_8$ and $X_9$ representing H or a ($C_1$-$C_6$)alkyl, $X_7$ represents —$SO_3^-M^+$, H, or a quaternary ammonium group; a denotes an integer ranging from 0 to 4; and b denotes an integer ranging from 0 to 2000; and

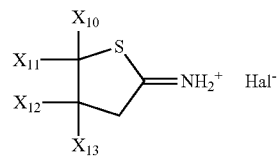

in which:
   Hal represents a halogen atom;
   each of the $X_{11}$, $X_{12}$ and $X_{13}$ independently represents a hydrogen atom or may represent $X_3$;
   $X_{10}$ represents a halogen atom, $COOX_{14}$, nitro, unsubstituted or halogenated ($C_1$-$C_8$)alkyl, unsubstituted or halogenated ($C_1$-$C_8$)alkoxy, unsubstituted or halogenated ($C_2$-$C_8$)alkenyl, unsubstituted or halogenated ($C_2$-$C_8$)alkynyl, unsubstituted ($C_3$-$C_8$)cycloalkyl, aryl that is unsubstituted or substituted with one to three substituents selected from amino, halogen atom, unsubstituted or halogenated ($C_1$-$C_8$)alkyl group, or unsubstituted or halogenated ($C_1$-$C_8$)alkoxy;
   or $X_{10}$ and $X_{11}$ together form a ring ($C_2$-$C_5$)alkylene, which is unsubstituted or substituted with one to five ($C_1$-$C_4$)alkyl groups;
   or $X_{10}$ and $X_{11}$ form, together with $X_{12}$, a ($C_1$-$C_5$) alkylene ring, which is unsubstituted or substituted with one to five ($C_1$-$C_4$)alkyl groups; and
   $X_{14}$ is —H or a ($C_1$-$C_8$)alkyl group; or
when the compound comprises a reactive chemical group RCG1 of the type —SH, the binding agent is modified with a modifying agent chosen from succinimidyl-4-(N-maleimidomethyl)cyclohexane-1-carboxylate; sulfosuccinimidyl 4-(N-maleimidomethyl)cyclohexane-1-carboxylate;

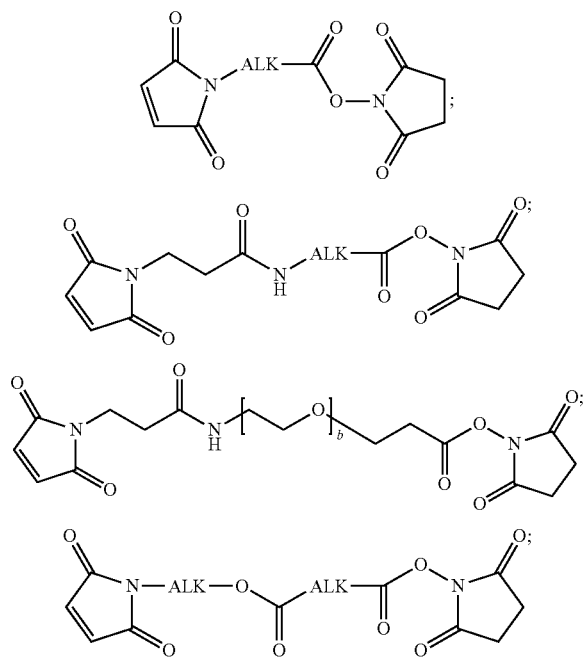

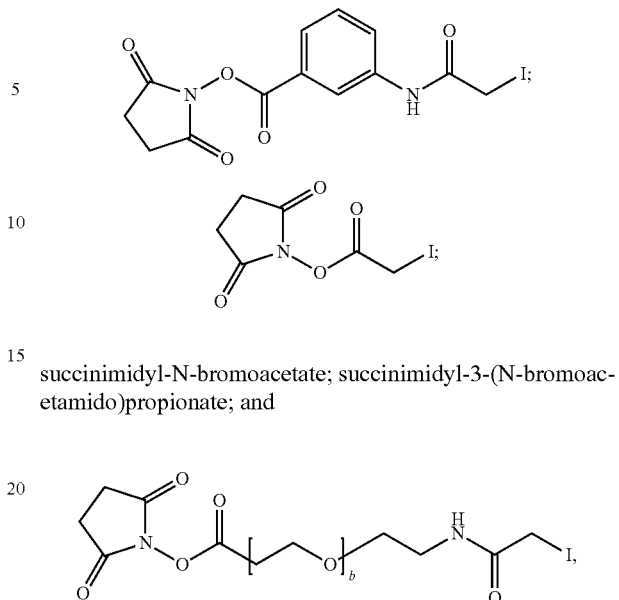

succinimidyl-N-bromoacetate; succinimidyl-3-(N-bromoacetamido)propionate; and

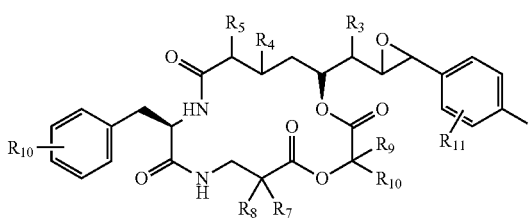

wherein b is an integer between 0 and 2000.

26. A compound of formula:

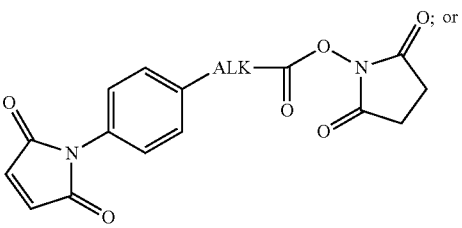

in which:
R₁ represents a halogen atom and R₂ represents an —OH, an acyl group derived from an amino acid AA, or a group ($C_1$-$C_4$)alkanoyloxy;
or alternatively R₁ and R₂ form an epoxide unit;
AA denotes a natural or unnatural amino acid;
R₃ represents a ($C_1$-$C_6$)alkyl group;
R₄ and R₅ both represent H or together form a double bond CH=CH between C13 and C14;
R₆ and R₇ represent, independently of each other, H or a ($C_1$-$C_6$)alkyl group;
R₈ and R₉ represent, independently of each other, H or a ($C_1$-$C_6$)alkyl group;
R₁₀ represents at least one substituent of the phenyl nucleus chosen from: H, an OH, ($C_1$-$C_4$)alkoxy, a halogen atom, —NH₂, —NH($C_1$-$C_6$)alkyl or —N($C_1$-$C_6$)alkyl₂;
R₁₁ represents at least one substituent of the phenyl nucleus chosen from H and a ($C_1$-$C_4$)alkyl group; and
n is an integer ranging from 1 to 6.

27. The compound according to claim 1, in which L represents a linker in the para position, of the phenyl nucleus bearing the unit RCG₁.

28. The compound according to claim 1, in which i is an integer ranging from 1 to 6.

29. The compound according to claim 28, in which i is an integer ranging from 2 to 5.

-continued

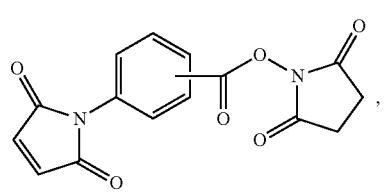

wherein ALK represents a ($C_1$-$C_{12}$)alkylene group and b is an integer between 0 and 2000;

30. The compound according to claim 1, in which $R_{12}$ and $R'_{12}$ represent, independently of each other, H or a methyl group.

31. The compound according to claim 1, in which w represents an integer ranging from 1 to 6.

32. The compound according to claim 9, in which $R_{12}$ represents a methyl group.

33. The compound according to claim 1, in which $Z_a$ represents H, —SMe, or

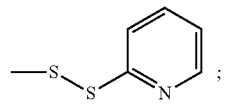

;

or $Z_b R_b$ represents —O($C_1$-$C_6$)alkyl, —OH, —OCH$_3$, —OCH$_2$CH=CH$_2$,

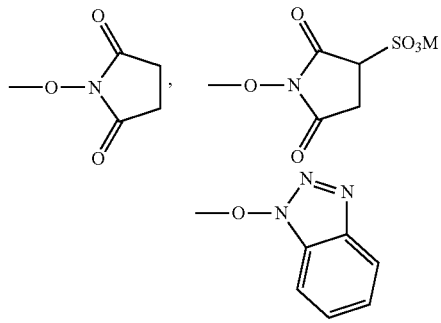

M = H or cation, or the group

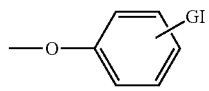

in which GI represents at least one electroinductive group; or alternatively in which —C(=O)$Z_b R_b$ represents

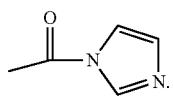

34. The compound according to claim 12, in which $Z_a$ represents H, —SMe, or

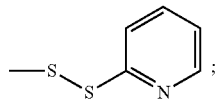

;

or $Z_b R_b$ represents —O($C_1$-$C_6$)alkyl, —OH, —OCH$_3$, —OCH$_2$CH=CH$_2$,

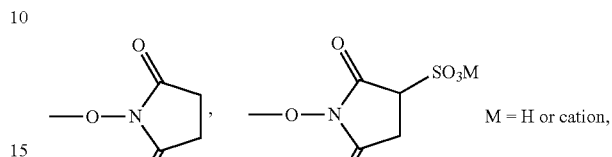

M = H or cation, or the group

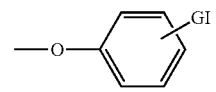

in which GI represents at least one electroinductive group; or alternatively in which —C(=O)$Z_b R_b$ represents

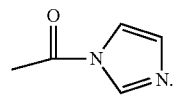

35. The compound according to claim 11 wherein L is in the para position.

36. The compound according to claim 14, wherein G represents a group —(CH$_2$)$_n$Y, which is para (p) position on the phenyl nucleus bearing the unit $CR_1$.

37. The compound according to claim 14, wherein $R_{12}$ is a methyl group.

38. The compound according to claim 19, wherein the antibody is a monoclonal antibody.

39. The compound according to claim 20, wherein the antibody is a monoclonal antibody.

* * * * *